(12) United States Patent
Naini et al.

(10) Patent No.: US 11,891,413 B2
(45) Date of Patent: Feb. 6, 2024

(54) **VACCINE AGAINST *KLEBSIELLA PNEUMONIAE***

(71) Applicant: Idorsia Pharmaceuticals Ltd, Allschwil (CH)

(72) Inventors: Arun Naini, Berlin (DE); Daniel Knopp, Storkow (DE); Bopanna Monnanda, Berlin (DE); Arne Von Bonin, Basel (CH); Claney Lebev Pereira, Berlin (DE)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 134 days.

(21) Appl. No.: 16/768,350

(22) PCT Filed: Nov. 30, 2018

(86) PCT No.: PCT/EP2018/083245
§ 371 (c)(1),
(2) Date: May 29, 2020

(87) PCT Pub. No.: WO2019/106200
PCT Pub. Date: Jun. 6, 2019

(65) Prior Publication Data
US 2021/0386845 A1 Dec. 16, 2021

(30) Foreign Application Priority Data
Nov. 30, 2017 (EP) .................................... 17204806

(51) Int. Cl.
| | | |
|---|---|---|
| *C07H 3/06* | (2006.01) | |
| *A61K 47/54* | (2017.01) | |
| *A61K 31/33* | (2006.01) | |
| *A61K 31/335* | (2006.01) | |
| *A61K 31/702* | (2006.01) | |
| *A61K 39/108* | (2006.01) | |
| *C07H 15/20* | (2006.01) | |
| *G01N 33/569* | (2006.01) | |
| *A61K 39/00* | (2006.01) | |
| *C07H 15/04* | (2006.01) | |
| *C07H 15/08* | (2006.01) | |

(52) U.S. Cl.
CPC .............. *C07H 3/06* (2013.01); *A61K 31/33* (2013.01); *A61K 31/335* (2013.01); *A61K 31/702* (2013.01); *A61K 39/0266* (2013.01); *A61K 47/549* (2017.08); *C07H 15/20* (2013.01); *G01N 33/56916* (2013.01); *A61K 2039/6037* (2013.01); *C07H 15/04* (2013.01); *C07H 15/08* (2013.01); *G01N 2333/26* (2013.01)

(58) Field of Classification Search
CPC .............. A61K 31/702; A61K 39/0266; A61K 47/549; A61K 2039/6037; C07H 3/06; C07H 15/04; C07H 15/08
See application file for complete search history.

(56) References Cited

U.S. PATENT DOCUMENTS
8,273,357 B2 9/2012 Hacohen et al.
9,238,669 B2 1/2016 Seeberger et al.

FOREIGN PATENT DOCUMENTS
| | | |
|---|---|---|
| JP | 2014-111609 A | 6/2014 |
| JP | 2017-532321 A | 11/2017 |
| WO | WO 2009/049370 A1 | 4/2009 |
| WO | WO 2013/038375 A2 | 3/2013 |
| WO | WO 2013/041732 A1 | 3/2013 |
| WO | WO 2014/080251 | 5/2014 |
| WO | WO 2016/044773 | 3/2016 |
| WO | WO 2016/046420 A1 | 3/2016 |
| WO | WO 2016/156338 | 10/2016 |
| WO | WO 2017/071835 | 5/2017 |

OTHER PUBLICATIONS

Trautmann et al., Clinical Diagnostic Laboratory Immunology, 1997, vol. 4, No. 5, p. 550-555. (Year: 1997).*
Chen et al., Carbohydrate Research, 2002, 337, p. 383-390. (Year: 2002).*
Guachalla et al., Scientific Reports, 2017, 7, 6635, 13 pages, published online Jul. 26, 2017. (Year: 2017).*
Jansson et al., Carbohydrate Research, 1985, 145, p. 59-66. (Year: 1985).*
Ahmad et al., Infectious Disease Reports, 2012; 4:e33, p. 128-133 (Year: 2012).*
Adamo et al., "Rapid assembly of gp120 oligosaccharide moieties via one-pot glycosidation-deprotection sequences" Carb. Res. (2010) 345(10):1316-1323.
Adamo, R.,"Advancing Homogeneous Antimicrobial Glycoconjugate Vaccines " Acc Chem Res (2017) 50:1270-1279.
Adamo et al., "Antimicrobial glycoconjugate vaccines: an overview of classic and modern approaches for protein modification" Chem. Soc. Rev. (2018) 47:9015-9025.
Alonso Develasco, et al., "*Streptococcus pneumoniae*: virulence factors, pathogenesis, and vaccines" Microbiological Reviews (1995) 59(4):591-603.
Anish, et al., "Chemical Biology approaches to Designing Defined Carbohydrate Vaccines" Chemistry and Biology (2014) 21(1):38-50.
Arcuri et al., "The influence of conjugation variables on the design and immunogenicity of a glycoconjugate vaccine against *Salmonella typhi*" PLoS ONE (2017) 12(12):e0189100.

(Continued)

*Primary Examiner* — Jonathan S Lau
(74) *Attorney, Agent, or Firm* — Hoxie & Associates LLC

(57) ABSTRACT

The present invention relates to a synthetic oligosaccharide of general formula (I): T*-[(—$U_{x+4}$—$U_{x+3}$—$U_{x+2}$—$U_{x+1}$—$U_x$)$_m$—($V_{x+2}$—$V_{x+1}$—$V_x$)$_{1-m}$-T-O-L-E that is related to *Klebsiella pneumoniae* serotype O3, O3b and/or O5 lipopolysaccharide and conjugate thereof. Said synthetic oligosaccharide, said conjugate and pharmaceutical composition containing said synthetic oligosaccharide or said conjugate are useful for prevention and/or treatment of diseases associated with *Klebsiella pneumoniae*. Furthermore, the synthetic oligosaccharide of general formula (I) is useful as marker in immunological assays for detection of antibodies against *Klebsiella pneumoniae* serotype O3, O3b and/or O5 bacteria.

32 Claims, 7 Drawing Sheets

(56) References Cited

OTHER PUBLICATIONS

Figure 3:
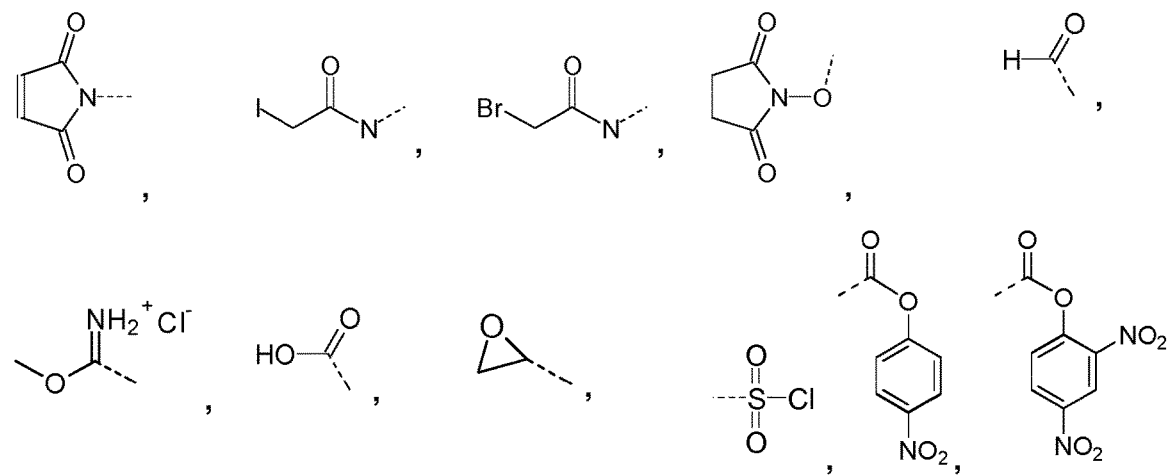

Boeckler et al., "Immunogenicity of new heterobifunctional cross-linking reagents used in the conjugation of synthetic peptides to liposomes" J. Immun. Meth. (1996) 191:1-10.
Cryz, et al., "Safety and immunogenicity of a polyvalent *Klebsiella* capsular polysaccharide vaccine in humans" Vaccine (1986) 4(1):15-20.
De Jong et al., "Exploring and Exploiting the Reactivity of Glucuronic Acid Donors" J. Org. Chem. (2012) 77(1):108-125.
Gagarinov et al. "Chemoenzymatic Approach for the Preparation of Asymmetric Bi-, Tri-, and Tetra-Antennary N-Glycans from a Common Precursor" J. Am. Chem. Soc. (2017) 1392:1011-1018.
Heukkendorff et al., "Dissection of the effects that govern thioglucoside and thiomannoside reactivity" Org. Biomol. Chem. (2018) 16(13):2277-2288.
Huang et al., "PEG as a spacer arm markedly increases the immunogenicity of meningococcal group Y polysaccharide conjugate vaccine" Journal of Controlled Release (2013) 172:382-389.
Kawano et al., "Natural killer-like nonspecific tumor cell lysis mediated by specific ligand-activated Vα14 NKT cells" Proc. Natl Acad. Sci. USA (1998) 95 (10):5690-5693.
Knirel, Y.A. "Structure of O-Antigens" Bacterial Lipopolysaccharides (2011) 41, 54-56 (DOI 10.1007/978-3-7091-0733-1_3).
Ovodov, Y.S., "Bacterial Capsular Antigens. Structural Patterns of Capsular Antigens" Biochemistry (Moscow) (2006) 71(9):937-954.
Peeters et al., Preparation of Polysaccharide-Conjugate Vaccines. In: Robinson A., Hudson M.J., Cranage M.P. (eds) Vaccine Protocols. Methods in Molecular Medicine™ (2003) vol. 87. Humana Press. https://doi.org/10.1385/1-59259-399-2:153.
"Remington's Pharmaceutical Sciences" Mack Publishing Co., Easton PA (Cover and Table of Contents Only).
Sanapala et al., "Chemical Synthesis of Asparagine-Linked Archaeal N-Glycan from *Methanothermus fervidus*" Chem. Eur. J. (2014) 20(13):3578-3583 & Supplemental Information.
Seeberger, P., "Automated carbohydrate synthesis as platform to address fundamental aspects of glycobiology—current status and future challenges" Carbohydrate Research (2008) 343(12):1889-1896.
Serna et al. "Construction of N-Glycan Microarrays by Using Modular Synthesis and On-Chip Nanoscale Enzymatic Glycosylation", Chemistry Chem. Eur. J. (2010) 16(44):13163-13175.
Smoot et al., "Development of an Arming Participating Group for Stereoselective Glycosylation and Chemoselective Oligosaccharide Synthesis" J. Org. Chem. (2005) 70(18):7123-7126.
Vinogradov et al., "Structural analysis of the core region of the lipopolysaccharides from eight serotypes of *Klesbiella pneumoniae*" Carbohydrate Research (2001) 335:291-296.
Vinogradov et al., "Structures of Lipopolysaccharides from *Klebsiella pneumoniae*" Journal of Biological Chemistry (2002) 277(28):25070-25081.
International Search Report and Written Opinion dated Jan. 3, 2019 for PCT Application No. PCT/EP2018/083245, filed Nov. 30, 2018.
International Preliminary Report on Patentability completed on Feb. 10, 2020 for PCT Application No. PCT/EP2018/083245, filed Nov. 30, 2018.
Extended European Search Report dated May 24, 2018 for EP Application 17204806.8, filed Nov. 30, 2018.
Grandjean, C. et al., "On the Preparation of Carbohydrate-Protein Conjugates Using the Traceless Staudinger Ligation," Journal of Organic Chemistry, 2005, 70, 7123-7132.
Pastore, A. et al., "Rapid Assembly of gp120 Oligosaccharide Moieties via One-pot Glycosidation-deprotection Sequences," Carbohydrate Research, 2010, 345, 1316-1323.
Smoot, J. et al., "Development of an Arming Participating Group for Stereoselective Glycosylation and Chemoselective Oligosaccharide Synthesis," Angewandte Chemie International Edition, 2005, 44, 7123-7126.
Abronina, P. et al., "Synthesis of a Derivative of a Pentasaccharide Repeating Unit of the O-antigenic Polysaccharide of the Bacterium *Klebsiella pneumoniae* O3 as a Benzolyated 2-Methoxycarbonylethyl Thioglycoside," Russian Chemical Bulletin, International Edition, 2009, 58 (2), 457-467.
Chen, L. et al., "Synthesis of α-Manp-(1→2)-α-Manp-(1→3)-α-Manp-(1→3)-Manp, the Tetrasaccharide Repeating Unit of *Escherichia coli* O9a, and α-Manp-(1→2)-α-Manp-(1→2)-α-Manp-(1→3)-α-Manp-(1→3)-Manp, the Pentasaccharide Repeating Unit of *E. coli* O9 and *Klebsiella* O3," Carbohydrate Research, 2002, 337, 383-390.
Doores, K. et al., "Reagent Switchable Stereoselective β(1,2) Mannoside Mannosylation: OH-2 of Mannose is a Privileged Acceptor," Organic & Biomolecular Chemistry, 2008, 6, 2692-2969.
Fairweather, J. et al., "Synthesis and heparanase inhibitory activity of sulfated mannooligosaccharides related to the antiangiogenic agent PI-88," Bioorganic & Medical Chemistry, 2008, 16 (2), 699-709.
Parameswarappa, S. et al., "A Semi-synthetic Oligosaccharide Conjugate Vaccine Candidate Confers Protection against *Streptococcus pneumoniae* Serotype 3 Infection," Cell Chemical Biology, 2016, 23, 1407-1416.
Reinhardt, A. et al., "Antigenic Potential of a Highly Conserved *Neisseria meningitidis* Lipopolysaccharide Inner Core Structure Defined by Chemical Synthesis," Chemistry & Biology, 2015, 22, 38-49.
Seeberger, P. et al., "A Semi-Synthetic Glycoconjugate Vaccine Candidate for Carbapenem-Resistant *Klebsiella pneumoniae*," Angewandte Chemie International Edition, 2017, 56, 13973-13978.
Seeberger, P., "Discovery of Semi- and Fully-Synthetic Carbohydrate Vaccines Against Bacterial Infections Using a Medicinal Chemistry Approach," Chemical Reviews, 2021, 121, 3598-3626.
Shang, W. et al., "Chemical synthesis of the outer core oligosaccharide of *Escherichia coli* R3 and immunological evaluation," Organic & Biomolecular Chemistry, 2015, 13, 4321-4330.

* cited by examiner

Figure 1
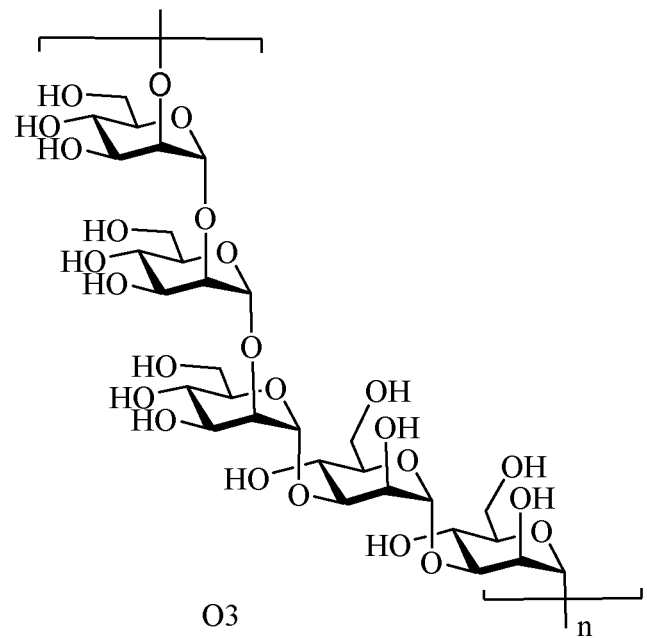
O3
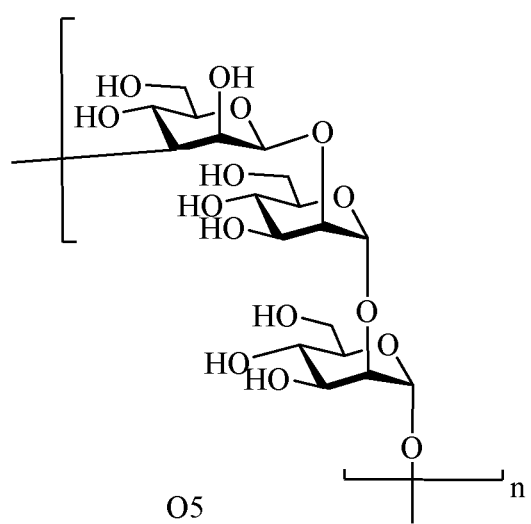
O5

Figure 2

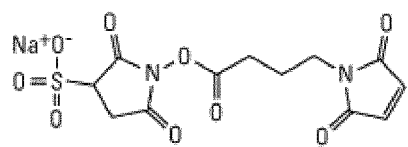

Sulfo-GMBS
N-(γ-Maleimidobutyryloxy) sulfosuccinimide ester
MW 382.28
Spacer Arm 7.3 Å

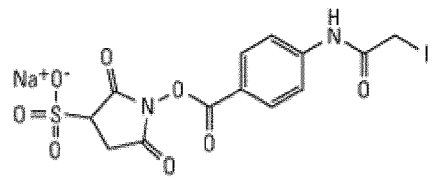

Sulfo-SIAB
Sulfosuccinimidyl (4-iodoacetyl) aminobenzoate
MW 504.19
Spacer Arm 10.6 Å

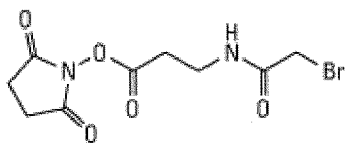

SBAP
Succinimidyl-3-(bromoacetamido)propionate
MW 307.10
Spacer Arm 6.2 Å

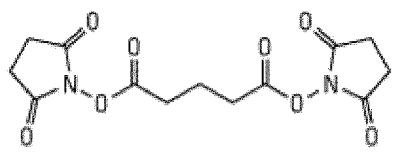

DSG
Disuccinimidyl glutarate
MW 326.26
Spacer Arm 7.7 Å

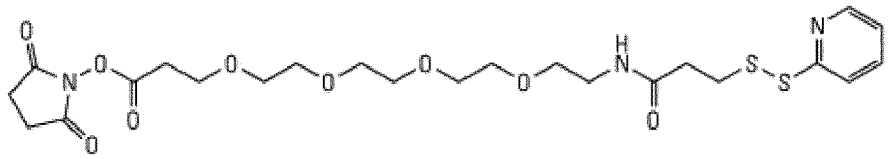

PEG4-SPDP
2-Pyridyldithiol-tetraoxatetradecane-N-hydroxysuccinimide
MW 559.17
Spacer Arm 25.7 Å

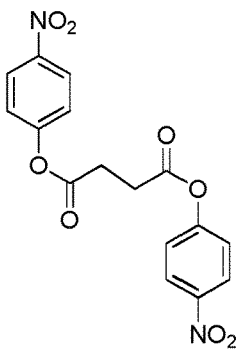

Bis-(4-nitrophenyl)succinate

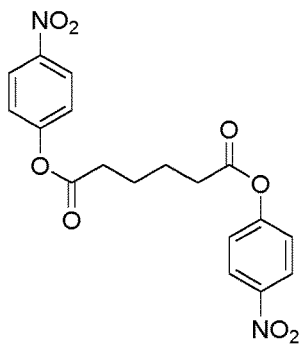

Bis-(4-nitrophenyl) adipate

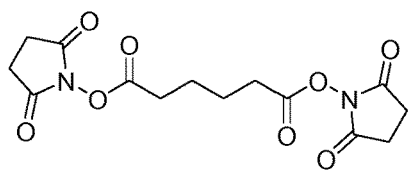

DSA
Disuccinimidyl adipate

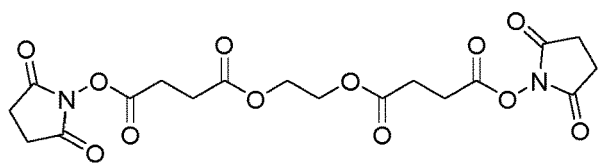

Ethylene glycol-bis(succinic acid
N-hydroxysuccinimide ester)

A

Figure 4:
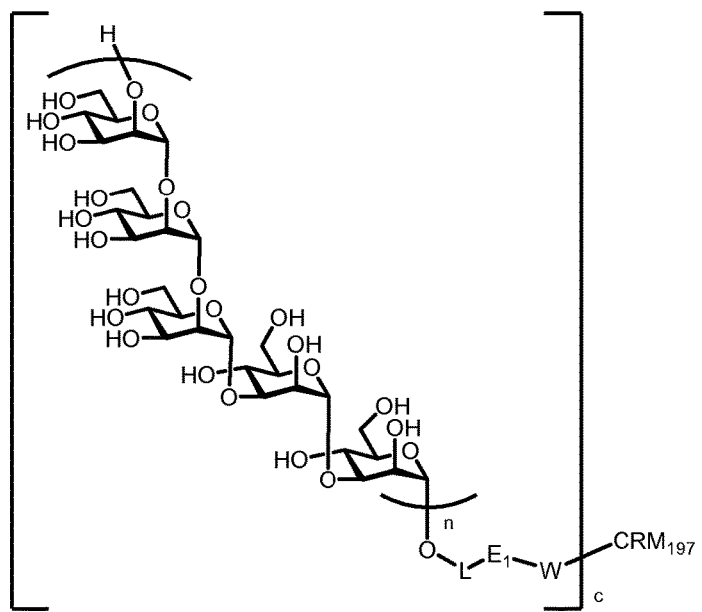

Figure 4 cont.
B
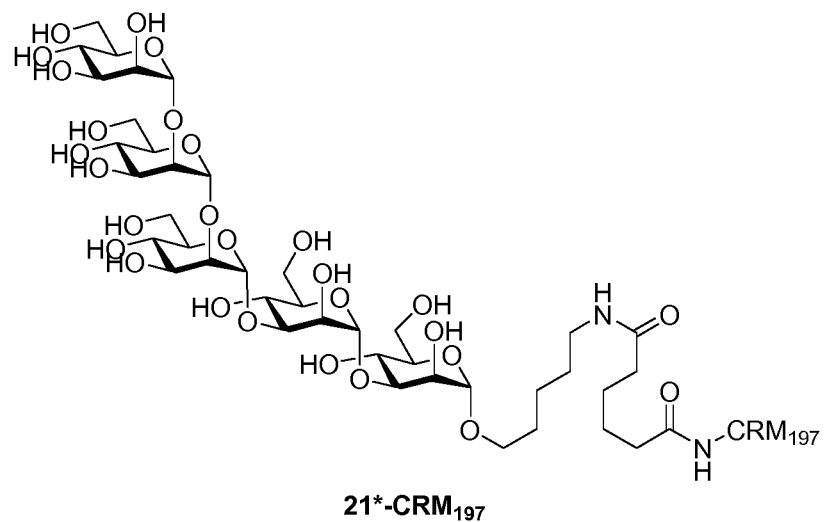
21*-CRM$_{197}$
C
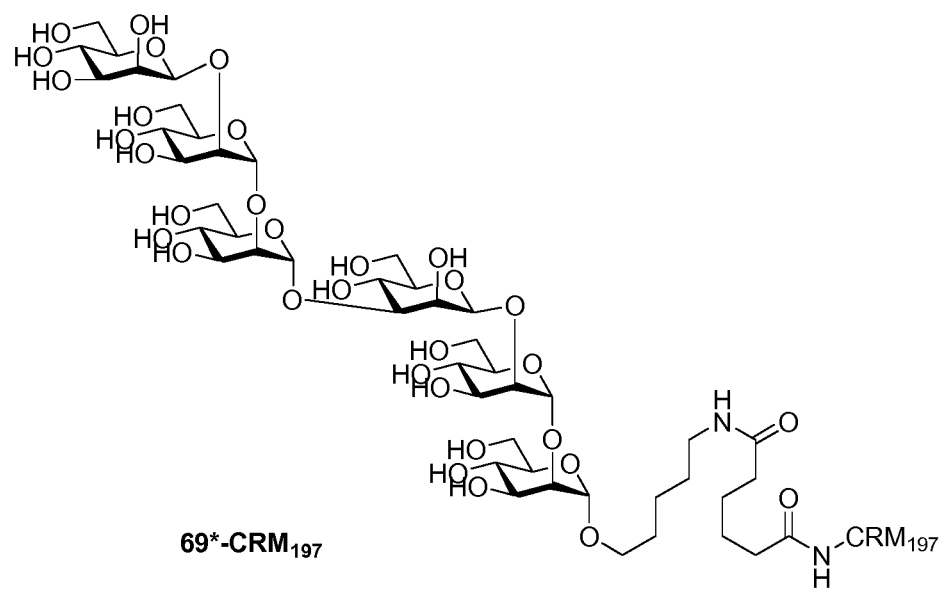
69*-CRM$_{197}$

VACCINE AGAINST *KLEBSIELLA PNEUMONIAE*

CROSS REFERENCE TO RELATED APPLICATIONS

This application is a U.S. National Phase Application of PCT International Application No. PCT/EP2018/083245, filed on Nov. 30, 2018, designating the United States of America and published in the English language, which claims priority to EP Application No. 17204806.8, filed Nov. 30, 2017. The disclosures of the above-referenced applications are hereby expressly incorporated by reference in their entireties.

FIELD OF THE INVENTION

The present invention relates to a synthetic oligosaccharide of general formula (I) that is related to *Klebsiella pneumoniae* serotype O3, O3b and/or O5 lipopolyoligosaccharide specifically the O-antigens and conjugate thereof. Said synthetic oligosaccharide, said conjugate and pharmaceutical composition containing said synthetic oligosaccharide or said conjugate are useful for prevention and/or treatment of diseases associated with *Klebsiella pneumoniae*, more specifically of diseases associated with *Klebsiella pneumoniae* serotype O3, O3b and/or O5. Furthermore, the synthetic oligosaccharide of general formula (I) is useful as marker in immunological assays for detection of antibodies against *Klebsiella pneumoniae* bacteria.

BACKGROUND OF THE INVENTION

*Klebsiella pneumoniae* is a gram-negative, facultative anaerobic, rod-shaped bacterium colonizing mostly the respiratory and urinary tracts and causing *K. pneumoniae* infections (KPIs). KPI is the main cause of nosocomial infections, primarily affecting immunocompromised patients. In the last ten years, infections caused by *K. pneumoniae* are becoming an important challenge in healthcare settings due to the emergence of strains resistant to almost all available antimicrobial agents and their worldwide dissemination. Infections caused by *Klebsiella pneumoniae* are responsible for high rates of morbidity and mortality. Thus, prevention of infections caused by *K. pneumoniae* is highly desirable, and vaccination of risk groups is the most cost-efficient and the most powerful means.

*K. pneumoniae* bacteria typically express two types of antigens on their cell surfaces. The first, O-antigen, is a component of the lipopolyoligosaccharide (LPS), of which 9 serogroups exist. The second is K antigen, a capsular polysaccharide/oligosaccharide with more than 80 serotypes. The O-antigen is the most variable portion of the LPS and provides serological specificity, which together with the K antigen is used for serotyping. Both antigens are composed of complex polysaccharide/oligosaccharides on the bacterial surface, which are highly immunogenic and non-toxic. In comparison with proteins, carbohydrates are evolutionarily more stable. When covalently connected to a carrier protein, oligosaccharide antigens can elicit long lasting, T-cell-dependent protection (*Microbiol Rev* 1995, 591). For a review on current development of carbohydrate vaccines see *Chem. & Biol.* 2014, 21, 38-50. For a review on automated carbohydrate synthesis and its application in the development of carbohydrate-based vaccines see *Carbohydr. Res.* 2008, 343, 1889-1896.

WO 2016/156338 A1 discloses synthetic carbapenem-resistant *Klebsiella pneumoniae* oligosaccharides and conjugates thereof for the treatment of diseases caused by *Klebsiella pneumoniae* bacteria.

The article Vaccine 1986, 4, 15 reports on a hexavalent *Klebsiella* vaccine composed of the capsular polysaccharide derived from K2, K3, K10, K21, K30 and K55 serotypes. The tested vaccine was found to be highly protective against fatal experimental *Klebsiella* K2 burn wound sepsis, thus indicating that functional antibody is elicited following vaccination.

The repeating unit of the O-antigens, i.e. O-polysaccharides of *K. pneumoniae* was elucidated (*The Journal of Biological Chemistry*, 2002, 277 (28), 25070-25081) (see FIG. 1).

The repeating unit of the O-polysaccharide of *K. pneumoniae* serotype O3 consists of:

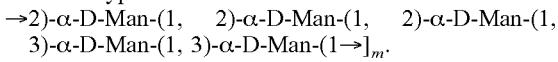

The repeating unit of the O-polysaccharide of *K. pneumoniae* serotype O3b consists of:

The repeating unit of the O-polysaccharide of *K. pneumoniae* serotype O5 consists of:

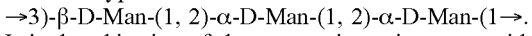

It is the objective of the present invention to provide a well-defined synthetic oligosaccharide of general formula (I) that is related to *Klebsiella pneumoniae* serotype O3, O3b and O5 lipopolysaccharide and contains a protective immunogenic O-antigen epitope i.e. a O-antigen epitope that elicits antibodies which protect against diseases caused by *Klebsiella pneumoniae* serotype O3, O3b and serotype O5. Said oligosaccharide can be conjugated to an immunogenic carrier to provide a conjugate and pharmaceutical composition thereof that are useful for prevention and/or treatment of diseases associated with *Klebsiella pneumoniae* serotype O3, O3b and serotype O5. Furthermore, the synthetic oligosaccharide of general formula (I) is useful as marker in immunological assays for detection of antibodies against *Klebsiella pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of an oligosaccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. By keeping a certain distance between the oligosaccharide and the immunogenic carrier the shielding of immunogenic oligosaccharide epitopes by the structure of the immunogenic carrier (e.g. secondary structure of a carrier protein) is avoided. In addition, the linker provides greater efficiency of coupling with oligosaccharides by reducing steric hindrance of reactive groups (Methods in Molecular Medicine 2003, 87, 153-174). More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

Any linker for oligosaccharide conjugates (e.g. polysaccharide and oligosaccharide-carrier protein conjugate, antibody-drug conjugate) known in the art can be used within the present invention. From the large number of publications directed to polysaccharide and oligosaccharide carrier protein conjugates the person skilled in the art can readily envision suitable linkers for the herein disclosed oligosaccharides and conjugates (see "Antimicrobial glycoconjugate vaccines: an overview of classic and modern approaches for protein modification" in Chem Soc Rev. 2018, Advance Article, DOI: 10.1039/C8CS00495A; Acc Chem Res 2017, 50, 1270-1279) since the used linker, i.e. its length and linkage type, does not significantly influence the immunogenicity of a oligosaccharide conjugate (see PLoS ONE 2017, 12(12): e0189100, J. Immun. Meth. 1996, 191, 1-10). Such suitable linkers are harmless (i.e. non-toxic) and non-immunogenic (i.e. do not lead to the formation of nonprotective antibodies on immunization with a conjugate) and include but are not restricted to commercially available bifunctional polyethylene glycol (Journal of Controlled Release 2013, 172, 382-389, J. Immun. Meth. 1996, 191, 1-10), glutaric acid derivatives (J. Org. Chem. 2005, 70(18), 7123-7132), adipic acid derivatives, squarate derivatives, alkynes, N-hydroxysuccinimides, such as the commercially available MFCO-NHS (monofluoro-substituted cyclooctyne N-hydroxysuccinimide ester), maleimides (as disclosed in Acc Chem Res 2017, 50, 1270-1279), or hydrophilic alkyl phosphinates and sulfonyls (as described in WO2014080251A1).

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 3 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:

mineral-containing compositions, including calcium salts and aluminium salts (or mixtures thereof). Calcium salts include calcium phosphate. Aluminium salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminium hydroxide and aluminium phosphate may be also used. The invention can use any of the "hydroxide" or "phosphate" adjuvants that are in general used as adjuvants. The adjuvants known as "aluminium hydroxide" are typically aluminium oxyhydroxide salts, which are usually at least partially crystalline.

The adjuvants known as "aluminium phosphate" are typically aluminium hydroxyphosphates, often also containing a small amount of sulfate (i. e. aluminium hydroxyphosphate sulfate). They may be obtained by precipitation, and the reaction conditions and concentrations during precipitation influence the degree of substitution of phosphate for hydroxyl in the salt. Mixtures of both an aluminium hydroxide and an aluminium phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaparilla), *Gypsophila paniculata* (brides veil), and *Saponaria officinalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS 7, QS 17, QS 18, QS21, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly(α-hydroxy acid), polyhydroxybutyric acid, polyorthoester, polyanhydride, polycaprolactone;

CD1d ligands, such as an α-glycosylceramide, phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-sulfo-galactosyl-ceramide; 7DW8-5 (Funakoshi Co., Ltd.)

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant), outer membrane vesicles (OMVs).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can:

direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and—blocking the rapid dispersal of the antigen challenge.

Polysaccharides and oligosaccharides are known by the person skilled in the art as TI-2 (T cell independent-2) antigens and poor immunogens, if they are not zwitterionic. Therefore, to produce a poly-,oligosaccharide-based vaccine, said poly-, oligosaccharides are conjugated to an immunogenic carrier to provide a conjugate, which presents an increased immunogenicity in comparison with the poly- or oligosaccharide. In this context the term "immunogenic carrier" is defined as a structure, which is conjugated to the poly-, oligosaccharide to form a conjugate that presents an increased immunity in comparison with the poly-, oligosaccharide per se. Thus, the conjugation of the oligosaccharides to the immunogenic carrier, preferably protein carrier, has an effect of stimulating the immune response against said oligosaccharide, without inducing an immune response against the said immunogenic carrier.

Hence, the present invention is directed to an oligosaccharide of general formula (I)

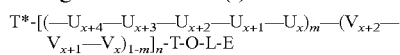

(I)

wherein m is an integer selected from 0 and 1;

x is an integer selected from 1 to 2×m+3;

n is an integer selected from 1, 2, 3, 4, 5, 6, 7, 8, 9 and 10;

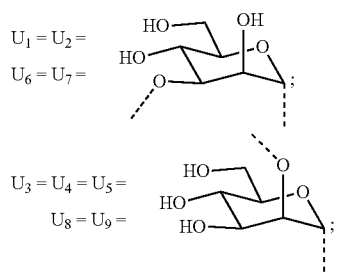

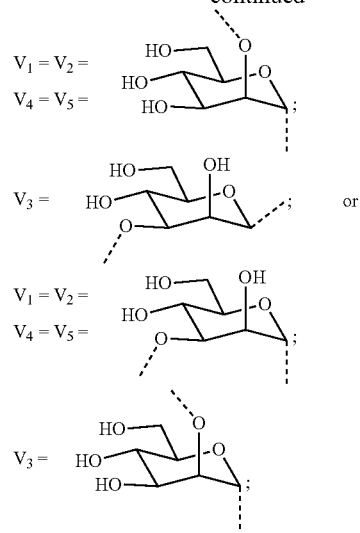

T- represents a bond, $-(U_{x+4})_m-(V_{x+2})_{1-m}-$, $-(U_{x+4}-U_{x+3})_m-(V_{x+2}-V_{x+1})_{1-m}-$, $-(U_{x+4}-U_{x+3}-U_{x+2})_m-$ or $-(U_{x+4}-U_{x+3}-U_{x+2}-U_{x+1})_m-$;

T*- represents H—, $H-(U_x)_m-(V_x)_{1-m}-$, $H-(U_{x+1}-U_x)_m-(V_{x+1}-V_x)_{1-m}-$, $H-(U_{x+2}-U_{x+1}-U_x)_m-$ or $H-(U_{x+3}-U_{x+2}-U_{x+1}-U_x)_m-$;

L represents a linker;

E represents $-NH_2$, $-N_3$, $-CN$, $-O-NH_2$, $-CH=CH_2$, $-C\equiv CH$, $-Br$, $-Cl$, $-I$, $-CO_2R'$, $-COR'$, $-CONH-NH_2$, $-SH$, or $-SAc$;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

or a diastereoisomer or a pharmaceutically acceptable salt thereof.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms.

The shortest atom chain between the oxygen atom (i.e. the oxygen of —O-L-E) and the E-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the $NH_2$-group) consists of 2 to 6 atoms, these are preferably carbon atoms. In case the shortest chain consists of 4 to 8 atoms, the chain may contain 1 or 2 heteroatoms selected from O, N and S. In case the shortest chain consists of 9 to 14 atoms, the chain may contain 1, 2, 3, or 4 heteroatoms selected from O, N and S.

It is also preferred that the linker -L-, or the shortest chain is fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle.

The linker -L- may also contain amide (—NH—CO—, —CO—NH—) and/or urea (—NH—CO—NH—) residues and preferably only one amide or urea residue. The linker may also contain substituents and preferably two substituents such as $R^{10}$ and $R^{11}$ or four substituents such as $R^{10}$, $R^{11}$, $R^{15}$ and $R^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$.

In case the linker -L- is fluorinated, more than two substituents —F are preferred.

Preferably the linker -L- is selected from: —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -$L^a$-, -$L^a$-$L^e$-, -$L^a$-$L^b$-$L^e$-, -$L^a$-$L^b$-$L^d$-$L^c$-$L^e$-, -$L^a$-$L^d$-$L^e$-;

wherein

-$L^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—.

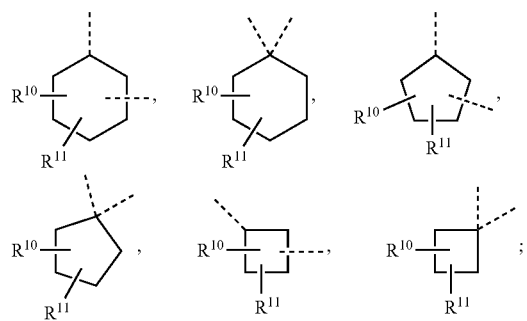

-$L^b$- and -$L^c$- are independently of each other selected from: —O—, —NH—C(O)—NH—, —NH—C(S)—NH—, —NH—C(O)—, —C(O)—NH—, —NH—C(O)—O—, —NR$^9$—, —NR$^{18}$—, —SO$_2$—, —NH—CO—CH$_2$—NH—,

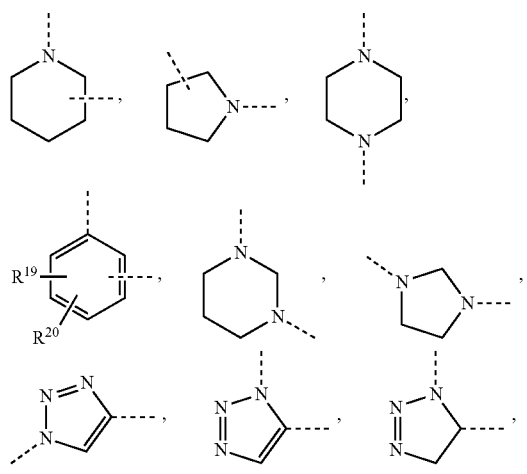

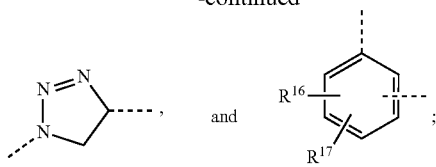

-$L^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

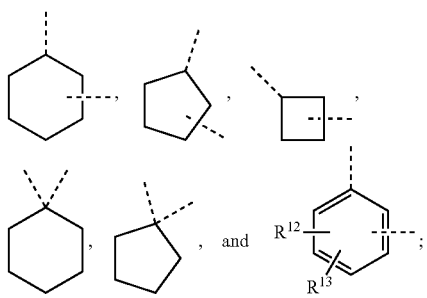

-$L^e$- is selected from: —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$—, —(CH$_2$)$_{p1}$—O—(CH$_2$)$_{p2}$—, —(CR$^{14}$R$^{15}$)$_{p1}$—, —(CR$^{14}$R$^{15}$)$_{p1}$—O—(CR$^{21}$R$^{22}$)$_{p2}$—,

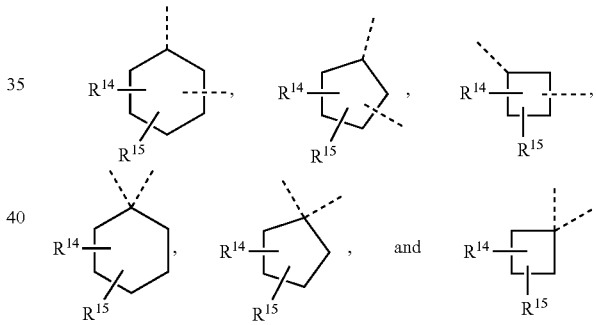

$R^9$ and $R^{18}$ are independently of each other selected from: —CH$_3$, —C$_2$H$_5$, —C$_3$H$_7$ and —C(O)CH$_3$;

$R^{10}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$ and —N(C$_2$H$_5$)$_2$;

o, q, p1 and p2 are independently of each other an integer selected from 1, 2, 3, 4, 5, 6, 7, 8, 9, and 10.

More preferred, -L- represents -$L^a$-, -$L^a$-$L^e$-, -$L^a$-$L^b$-$L^e$-, or -$L^a$-$L^d$-$L^e$-;

-$L^a$- represents —(CH$_2$)$_o$—, —(CH$_2$—CH$_2$—O)$_o$—C$_2$H$_4$—, or —(CH$_2$—CH$_2$—O)$_o$—CH$_2$;

-$L^b$- represents —O—, —NH—CO—NH—, —NH—CO—CH$_2$—NH—, —NH—CO—;

-$L^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;

-$L^e$- represents —(CH$_2$)$_{p1}$—, —(CF$_2$)$_{p1}$—, —C2H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6; preferably an integer selected from 1, 2, 3, and 4.

Most preferred, the oligosaccharide of the formula (I) has the group —O-L-E selected from the group consisting of:

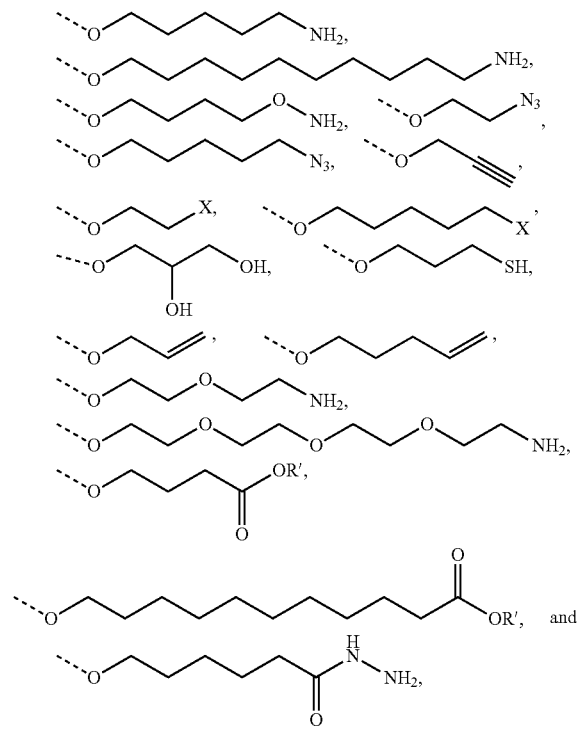

wherein R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

X represents —Br, —Cl, —I, —CO$_2$H, or —SAc.

Thus, preferred are oligosaccharides of general formula (I)

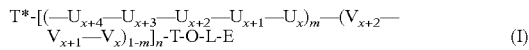

wherein m is an integer selected from 0 and 1;
x is an integer selected from 1 to 2×m+3;
n is an integer selected from 1, 2, 3, 4, 5, 6, 7, 8, 9 and 10; preferably n is an integer selected from 1, 2, 3, 4, 5, 6, 7, and 8; more preferably n is an integer selected from 1, 2, 3, 4, 5, and 6; still more preferably n is an integer selected from 1, 2, 3, and 4; still more preferably n is an integer selected from 1, 2, and 3; still more preferably n is an integer selected from 1 and 2;

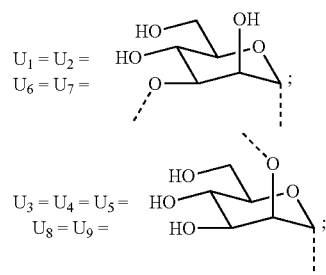

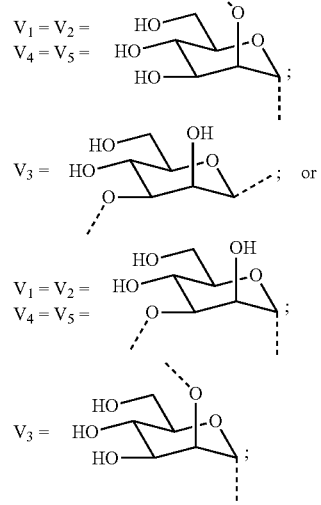

T- represents a bond, —(U$_{x+4}$)$_m$—(V$_{x+2}$)$_{1-m}$—, —(U$_{x+4}$—U$_{x+3}$)$_m$—(V$_{x+2}$—V$_{x+1}$)$_{1-m}$—, —(U$_{x+4}$—U$_{x+3}$—U$_{x+2}$)$_m$— or —(U$_{x+4}$—U$_{x+3}$—U$_{x+2}$—U$_{x+1}$)$_m$—;

T*- represents H—, H—(U$_x$)$_m$—(V$_x$)$_{1-m}$—, H—(U$_{x+1}$—U$_x$)$_m$—(V$_{x+1}$—V$_x$)$_{1-m}$—, H—(U$_{x+2}$—U$_{x+1}$—U$_x$)$_m$— or H—(U$_{x+3}$—U$_{x+2}$—U$_{x+1}$—U$_x$)$_m$—;

-L represents -L$^a$-, -L$^a$-L$^e$-, -L$^a$-L$^b$-L$^e$-, or -L$^a$-L$^d$-L$^e$-;

-L$^a$- represents —(CH$_2$)$_o$—, —(CH$_2$—CH$_2$—O)$_o$—C$_2$H$_4$—, or —(CH$_2$—CH$_2$—O)$_o$—CH$_2$;

L$^b$- represents —O—, —NH—CO—NH—, —NH—CO—CH$_2$—NH—, —NH—CO—;

-L$^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;

-L$^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6; preferably an integer selected from 1, 2, 3, and 4.

E represents —NH$_2$, —N$_3$, —CN, —O—NH$_2$, —CH═CH$_2$, —C≡CH, —Br, —Cl, —I, —CO$_2$R', —COR', —CONH—NH$_2$, —SH, or —SAc;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

or a diastereoisomer or a pharmaceutically acceptable salt thereof.

The anomers of oligosaccharides of the present invention mean the α/β-anomers at C-1-position to which the group —O-L-E is bounded. It is clear for the skilled person in the art of carbohydrate chemistry that the stereochemistry of the glycosidic bond is defined by the stereochemistry indicated for the anomeric center of the sugar fragments U$_1$, U$_2$, U$_3$, U$_4$, U$_5$, U$_6$, U$_7$, U$_8$, U$_9$, V$_1$, V$_2$, V$_3$, V$_4$, and V$_5$, in the general formula (I).

The oligosaccharides of the present invention can be hygroscopic and thus can build various hydrates thereof. Preferred, molar ratio of water molecule to the oligosaccharide is in the range of 1 to 20, more preferred, 1 to 10, most preferred, 5-10.

The oligosaccharides of the present invention may bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

It is clear for the skilled person in the art of carbohydrate chemistry that the oligosaccharides of general (I) are not containing —O—O— bonds and or sugar fragments ($U_x$, $U_{x+1}$, $U_{x+2}$, $U_{x+3}$, $U_{x+4}$, $V_x$, $V_{x+1}$, $V_{x+2}$) connected or bound to each other via their anomeric or C-1 carbons.

Surprisingly, it was found that a oligosaccharide of general formula (I) contains an immunogenic protective epitope and is able to induce a protective immune response against *K. pneumoniae* serotype O3, O3b and/or O5 bacteria in a human and/or animal host. The oligosaccharide of general formula (I) elicits antibodies that are cross-reacting with the natural *K. pneumoniae* serotype O3, O3b and/or O5 O-antigen of the lipopolysaccharide, recognize specifically *K. pneumoniae* serotype O3, O3b and/or O5 bacteria and opsonize them for killing by phagocytes, thus conferring protection against *K. pneumoniae* serotype O3, O3b and/or O5 bacteria.

The oligosaccharides of the present invention overcome all the problems associated with the poly-, oligosaccharides produced from bacterial sources and conjugates thereof in terms of purity and easiness of production. It is well known that the isolation and purification of pure oligosaccharides of defined length and structure from the O-antigen of lipopolysaccharides of pathogenic bacteria is a tedious and sometimes not feasible process. Firstly, the production of the O-antigens of lipopolysaccharides requires optimization of the growth conditions. Secondly, depolymerization conditions under which the structural integrity of the constituting monosaccharides is maintained need to be found. Finally, purification conditions enabling the isolation of the pure poly-, oligosaccharide of defined length and structure need to be determined. Besides usual contaminants, such as cellular polysaccharides, nucleic acids, lipids and proteins, also the undesired oligosaccharides obtained through the depolymerization process, must be excluded. Thus, the production of pure oligosaccharides of defined structure and length from bacterial sources is a tedious, almost impossible process.

Preferred are synthetic oligosaccharides of general formula (II)

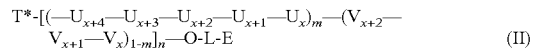
(II)

wherein m, n, x, L, E, $U_{x+1}$, $U_{x+2}$, $U_{x+3}$, $U_{x+4}$, $V_x$, $V_{x+1}$, $V_{x+2}$ and T* have the meanings as defined herein.

Preferred are the general formulae (Ia) and (IIa),

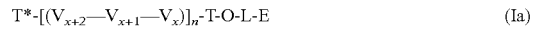
(Ia)

(IIa)

wherein x is an integer selected from 1, 2 or 3;

n is an integer selected from 1, 2, 3, 4, 5, 6, 7, 8, 9 and 10; preferably n is an integer selected from 1, 2, 3, 4, 5, 6, 7, and 8; more preferably n is an integer selected from 1, 2, 3, 4, 5, and 6; still more preferably n is an integer selected from 1, 2, 3, and 4; still more preferably n is an integer selected from 1, 2, and 3; still more preferably n is an 3 integer selected from 1 and 2;

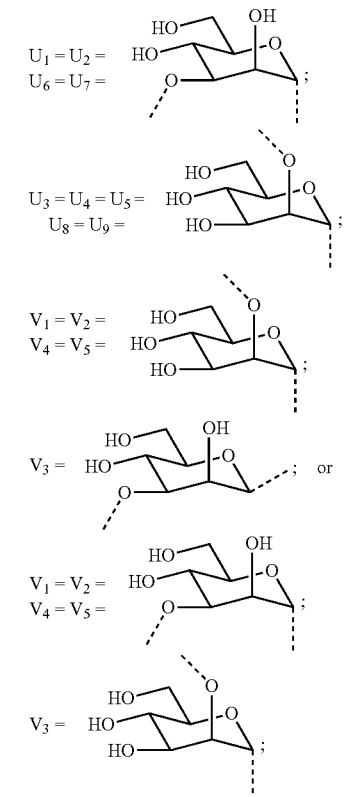

-T- represents a bond, $-(U_{x+4})_m-(V_{x+2})_{1-m}-$, $-(U_{x+4}-U_{x+3})_m-(V_{x+2}-V_{x+1})_{1-m}-$, $-(U_{x+4}-U_{x+3}-U_{x+2})_m-$ or $-(U_{x+4}-U_{x+3}-U_{x+2}-U_{x+1})_m-$;

T*- represents H—, $H-(U_x)_m-(V_x)_{1-m}-$, $H-(U_{x+1}-U_x)_m-(V_{x+1}-V_x)_{1-m}-$, $H-(U_{x+2}-U_{x+1}-U_x)_m-$ or $H-(U_{x+3}-U_{x+2}-U_{x+1}-U_x)_m-$;

L represents -$L^a$-, -$L^a$-$L^e$-, -$L^a$-$L^b$-$L^e$-, or -$L^a$-$L^d$-$L^e$-;

-$L^a$- represents —(CH$_2$)$_o$—, —(CH$_2$—CH$_2$—O)$_o$—C$_2$H$_4$—, or —(CH$_2$—CH$_2$—O)$_o$—CH$_2$;

-$L^b$- represents —O—, —NH—CO—NH—, —NH—CO—CH$_2$—NH—, —NH—CO—;

-$L^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;

-$L^e$- represents —$(CH_2)_{p1}$—, —$(CF_2)_{p1}$—, —$C_2H_4$—$(O-CH_2-CH_2)_{p1}$-, —$CH_2$—$(O-CH_2-CH_2)_{p1}$ or $(CH_2)_{p1}$—$O$—$(CH_2)_{p2}$—; and o, q, p1 and p2 are independently of each other an integer selected from 1, 2, 3, 4, 5, and 6; preferably an integer selected from 1, 2, 3, and 4.

E represents —$NH_2$, —$N_3$, —CN, —$O$—$NH_2$, —$CH=CH_2$, —$C\equiv CH$, —Br, —Cl, —I, —$CO_2R'$, —$COR'$, —$CONH$—$NH_2$, —SH, or —SAc;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

or a diastereoisomer or a pharmaceutically acceptable salt thereof.

Also preferred are the general formulae (Ib) and (IIb),

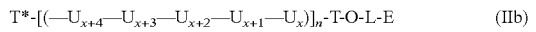

$$T^*-[(-U_{x+4}-U_{x+3}-U_{x+2}-U_{x+1}-U_x)]_n\text{-T-O-L-E} \quad (IIb)$$

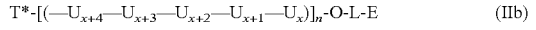

$$T^*-[(-U_{x+4}-U_{x+3}-U_{x+2}-U_{x+1}-U_x)]_n\text{-O-L-E} \quad (IIb)$$

wherein x is an integer selected from 1, 2, 3, 4 or 5;

n is an integer selected from 1, 2, 3, 4, 5, 6, 7, 8, 9 and 10; preferably n is an integer selected from 1, 2, 3, 4, 5, 6, 7, and 8; more preferably n is an integer selected from 1, 2, 3, 4, 5, and 6; still more preferably n is an integer selected from 1, 2, 3, and 4; still more preferably n is an integer selected from 1, 2, and 3; still more preferably n is an integer selected from 1 and 2;

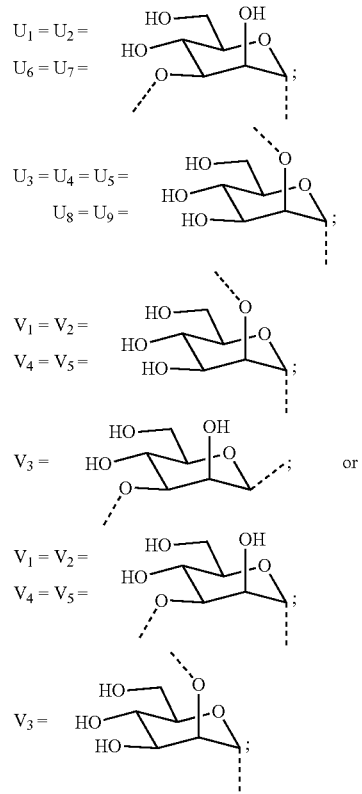

-T- represents a bond, —$(U_{x+4})_m$—$(V_{x+2})_{1-m}$—, —$(U_{x+4}-U_{x+3})_m$—$(V_{x+2}-V_{x+1})_{1-m}$—, —$(U_{x+4}-U_{x+3}-U_{x+2})_m$— or —$(U_{x+4}-U_{x+3}-U_{x+2}-U_{x+1})_m$—;

$T^*$- represents H—, H—$(U_x)_m$—$(V_x)_{1-m}$—, H—$(U_{x+1}-U_x)_m$—$(V_{x+1}-V_x)_{1-m}$—, H—$(U_{x+2}-U_{x+1}-U_x)_m$— or H—$(U_{x+3}-U_{x+2}-U_{x+1}-U_x)_m$—;

L represents -$L^a$-, -$L^a$-$L^e$-, -$L^a$-$L^b$-$L^e$-, or -$L^a$-$L^d$-$L^e$-;

-$L^a$- represents —$(CH_2)_o$—, —$(CH_2-CH_2-O)_o$—$C_2H_4$—, or —$(CH_2-CH_2-O)_o$—$CH_2$;

-$L^b$- represents —O—, —NH—CO—NH—, —NH—CO—$CH_2$—NH—, —NH—CO—;

-$L^d$- represents —$(CH_2)_q$—, —$(CH(OH))_q$—, —$(CF_2)_q$—, —$(CH_2-CH_2-O)_q$—$C_2H_4$—, or —$(CH_2-CH_2-O)_q$—$CH_2$—;

-$L^e$- represents —$(CH_2)_{p1}$—, —$(CF_2)_{p1}$—, —$C_2H_4$—$(O-CH_2-CH_2)_{p1}$-, —$CH_2$—$(O-CH_2-CH_2)_{p1}$ or $(CH_2)_{p1}$—$O$—$(CH_2)_{p2}$—; and o, q, p1 and p2 are independently of each other an integer selected from 1, 2, 3, 4, 5, and 6; preferably an integer selected from 1, 2, 3, and 4.

E represents —$NH_2$, —$N_3$, —CN, —$O$—$NH_2$, —$CH=CH_2$, —$C\equiv CH$, —Br, —Cl, —I, —$CO_2R'$, —$COR'$, —$CONH$—$NH_2$, —SH, or —SAc;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

or a diastereoisomer or a pharmaceutically acceptable salt thereof.

Also preferred are oligosaccharides of general formula (Ic)

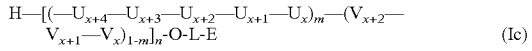

$$H-[(-U_{x+4}-U_{x+3}-U_{x+2}-U_{x+1}-U_x)_m-(V_{x+2}-V_{x+1}-V_x)_{1-m}]_n\text{-O-L-E} \quad (Ic)$$

wherein m is an integer selected from 0 and 1;

x is an integer selected from 1 to 2×m+3;

n is an integer selected from 1, 2, 3, 4, 5, 6, 7, 8, 9 and 10; preferably n is an integer selected from 1, 2, 3, 4, 5, 6, 7, and 8; more preferably n is an integer selected from 1, 2, 3, 4, 5, and 6; still more preferably n is an integer selected from 1, 2, 3, and 4; still more preferably n is an integer selected from 1, 2, and 3; still more preferably n is an integer selected from 1 and 2;

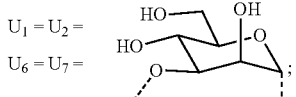

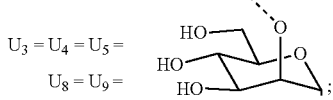

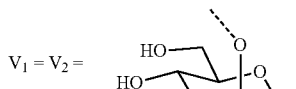

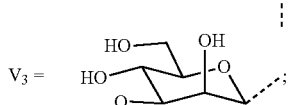

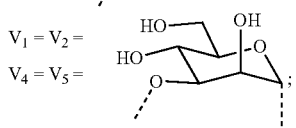

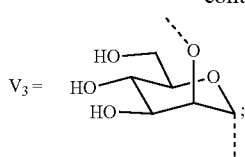

- -L represents -$L^a$-, -$L^a$-$L^e$-, -$L^a$-$L^b$-$L^e$-, or -$L^a$-$L^d$-$L^e$-;
- -$L^a$- represents —$(CH_2)_o$—, —$(CH_2$—$CH_2$—$O)_o$— $C_2H_4$—, or —$(CH_2$—$CH_2$—$O)_o$—$CH_2$;
- -$L^b$- represents —O—, —NH—CO—NH—, —NH—CO—$CH_2$—NH—, —NH—CO—;
- -$L^d$- represents —$(CH_2)_q$—, —$(CH(OH))_q$—, —$(CF_2)_q$—, —$(CH_2$—$CH_2$—$O)_q$—$C_2H_4$—, or —$(CH_2$—$CH_2$—$O)_q$—$CH_2$—;
- -$L^e$- represents —$(CH_2)_{p1}$—, —$(CF_2)_{p1}$—, —$C_2H_4$—(O—$CH_2$—$CH_2)_{p1}$—, —$CH_2$—(O—$CH_2$—$CH_2)_{p1}$— or —$(CH_2)_{p1}$—O—$(CH_2)_{p2}$—; and
- o, q, p1 and p2 are independently of each other an integer selected from 1, 2, 3, 4, 5, and 6; preferably an integer selected from 1, 2, 3, and 4.
- E represents —$NH_2$, —$N_3$, —CN, —O—$NH_2$, —CH=$CH_2$, —C≡CH, —Br, —Cl, —I, —$CO_2R'$, —COR', —CONH—$NH_2$, —SH, or —SAc;
- R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);
- or a diastereoisomer or a pharmaceutically acceptable salt thereof.

Thus, a oligosaccharide of general formula (II-a), (II-b), (II-c), (II-d), (II-e), (II-f), (II-g), (II-h), (II-i), (II-j) or (II-k) wherein n, L, E and T* have the meanings defined herein is especially preferred.

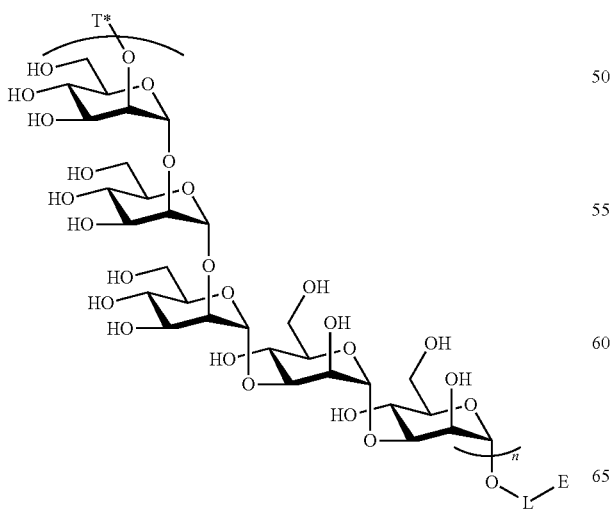

II-a

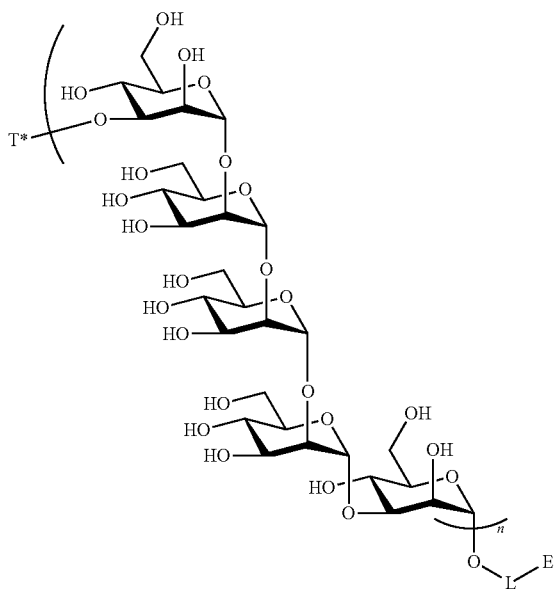

II-b

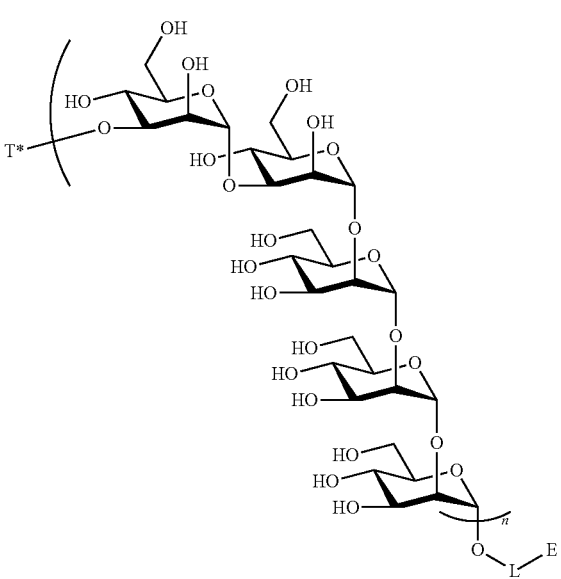

II-c

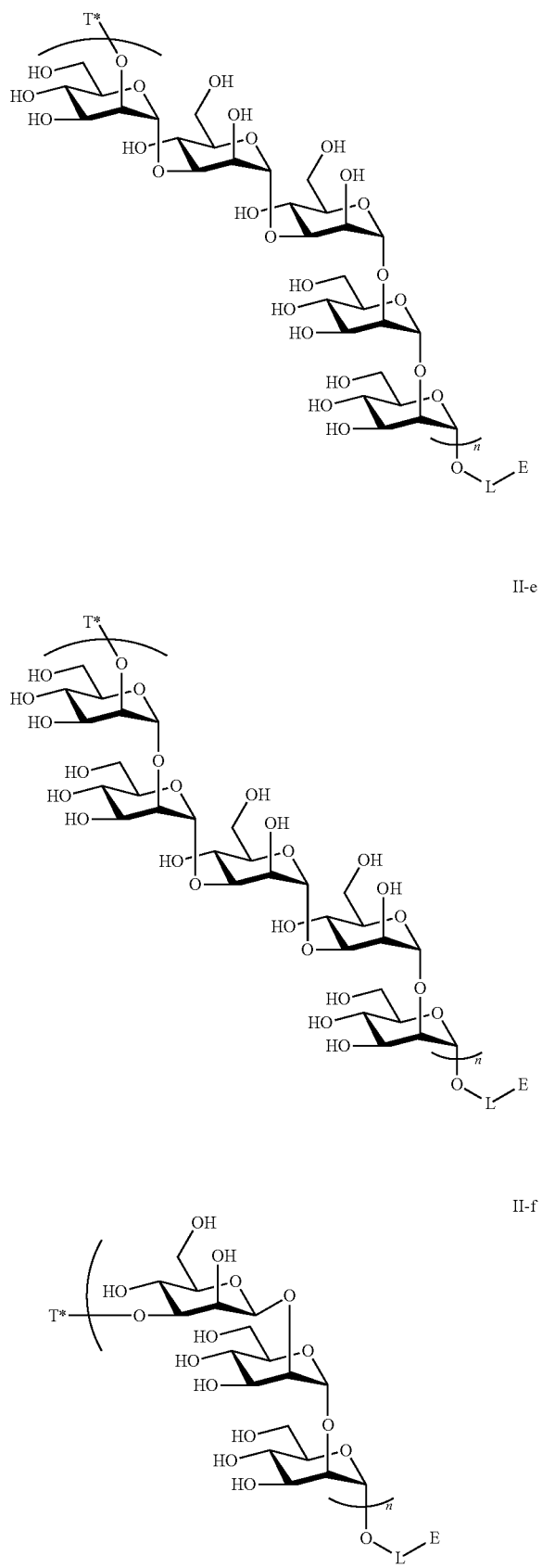
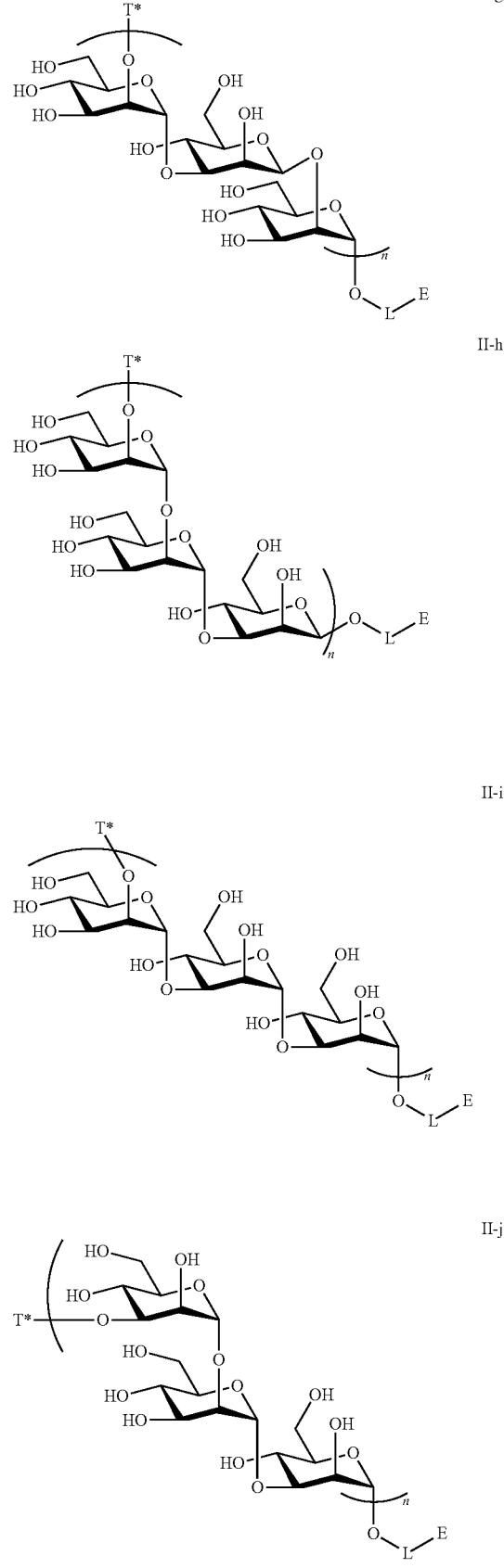

II-k

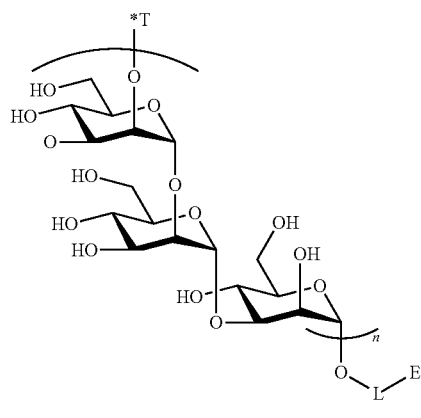

Also preferred are synthetic oligosaccharides of general formula (III)

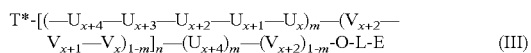

wherein m, n, x, L, E, $U_{x+1}$, $U_{x+2}$, $U_{x+3}$, $U_{x+4}$, $V_x$, $V_{x+1}$, $V_{x+2}$ and T* have the meanings as defined herein.

Thus, an oligosaccharide of general formula (III-a), (III-b), (III-c), (III-d), (III-e), (III-f), (III-g), (III-h), (III-i), (III-j) and (III-k) wherein n, L, E and T* have the meanings defined herein is especially preferred.

III-b

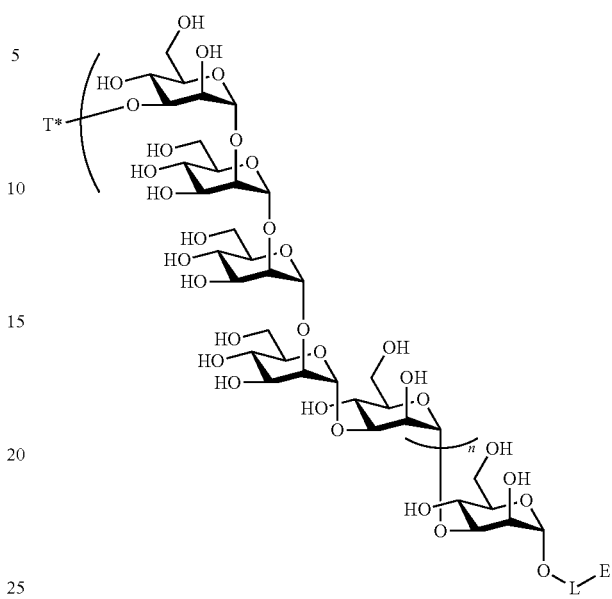

III-a

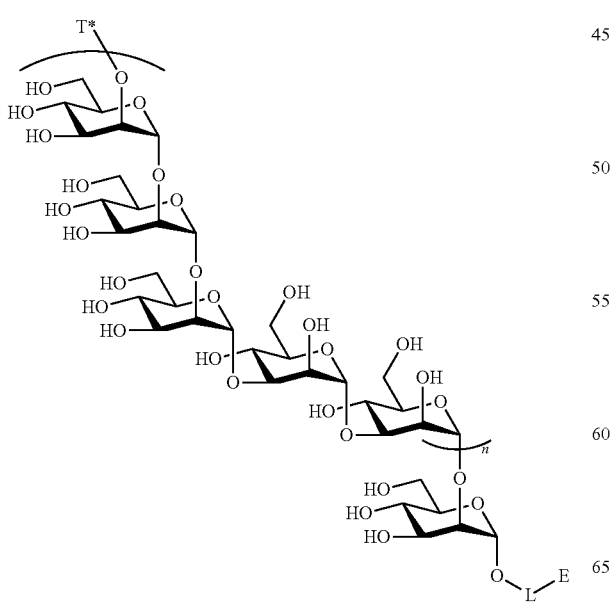

III-c

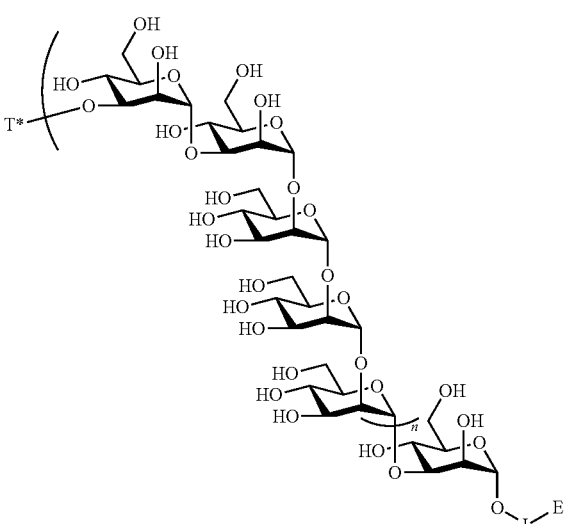

III-d
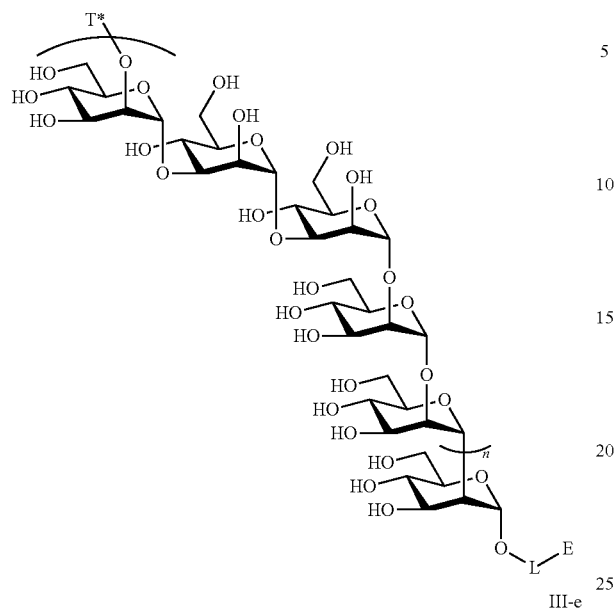
III-e
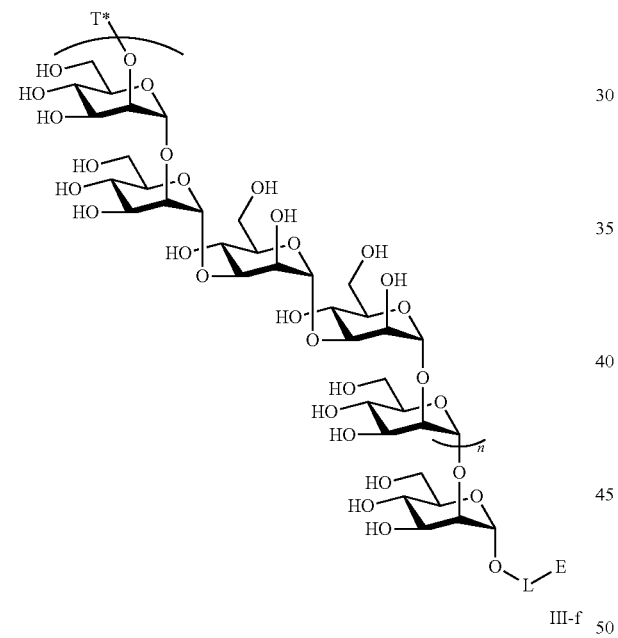
III-f
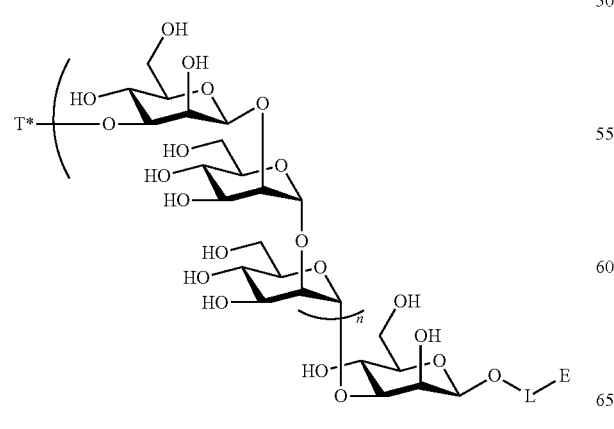
III-g
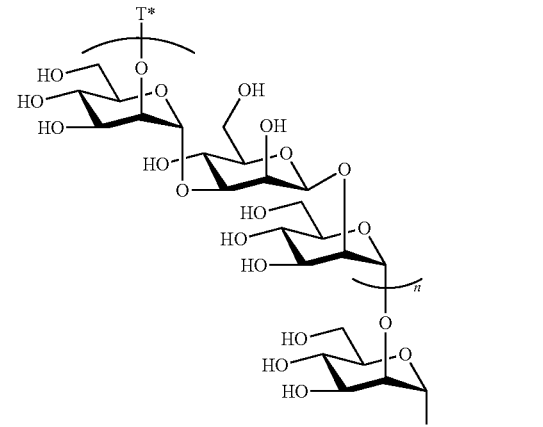
III-h
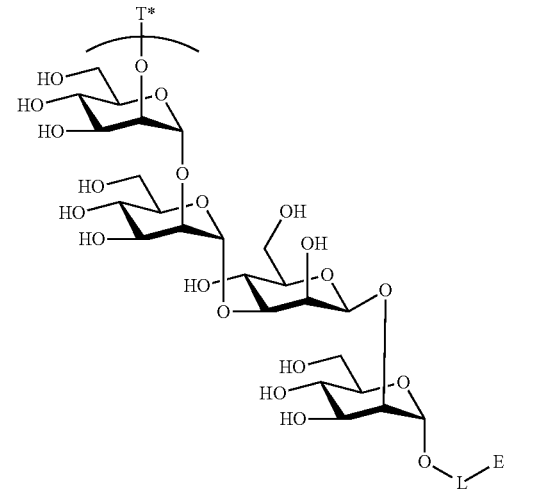
III-i

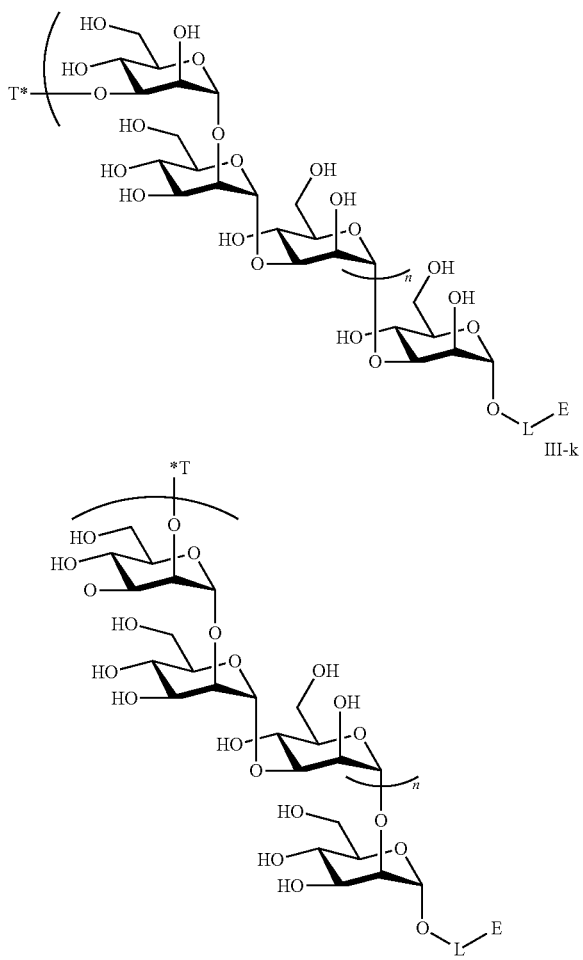

wherein n, L and E have the meanings as defined herein.

Preferably, the integer x represents 1, Therefore, a compound of general formula (I), (II) or (III), wherein x represents 1 is especially preferred. Even more preferred is a compound of general formula (I), (II) or (III), wherein x represents 1 and T* represents H—. A compound of general formula (I), (II) or (III), wherein T* represents H— is also preferred.

Preferably, n represents an integer selected from 2 to 10, preferably from 1 to 8, more preferably from 1 to 6, still more preferably from 1 to 4, still more preferably from 1 to 3, still more preferably 1 or 2. Hence, an oligosaccharide of general formula (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein n represents an integer selected from 2 to 10 is especially preferred. In an alternative embodiment, the integer is preferably 1. Hence, an oligosaccharide of general formula (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein n represents 1 is also preferred.

Preferably the linker -L- represents -$L^a$-, -$L^a$-$L^e$-, -$L^a$-$L^b$-$L^e$-, or -$L^a$-$L^d$-$L^e$-;

-$L^a$- represents —$(CH_2)_o$—, —$(CH_2$—$CH_2$—$O)_o$—$C_2H_4$—, or —$(CH_2$—$CH_2$—$O)_o$—$CH_2$;

-$L^b$- represents —O—, —NH—CO—NH—, —NH—CO—$CH_2$—NH—, —NH—CO—;

-$L^d$- represents —$(CH_2)_q$—, —$(CH(OH))_q$—, —$(CF_2)_q$—, —$(CH_2$—$CH_2$—$O)_q$—$C_2H_4$—, or —$(CH_2$—$CH_2$—$O)_q$—$CH_2$—;

-$L^e$- represents —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— or —$(CH_2)_{p1}$—O—$(CH_2)_{p2}$—; and o, q, p1 and p2 are independently of each other an integer selected from 1, 2, 3, 4, 5, and 6; preferably an integer selected from 1, 2, 3, and 4.

Therefore, an oligosaccharide of any one of general formulae (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein -L- represents -$L^a$-, -$L^a$-$L^e$-, -$L^a$-$L^b$-$L^e$-, or -$L^a$-$L^d$-$L^e$-;

-$L^a$- represents —$(CH_2)_o$—, —$(CH_2$—$CH_2$—$O)_o$—$C_2H_4$—, or —$(CH_2$—$CH_2$—$O)_o$—$CH_2$;

-$L^b$- represents —O—, —NH—CO—NH—, —NH—CO—$CH_2$—NH—, —NH—CO—;

-$L^d$- represents —$(CH_2)_q$—, —$(CH(OH))_q$—, —$(CF_2)_q$—, —$(CH_2$—$CH_2$—$O)_q$—$C_2H_4$—, or —$(CH_2$—$CH_2$—$O)_q$—$CH_2$—;

-$L^e$- represents —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— or —$(CH_2)_{p1}$—O—$(CH_2)_{p2}$—; and o, q, p1 and p2 are independently of each other an integer selected from 1, 2, 3, 4, 5, and 6 and preferably an integer selected from 1, 2, 3, and 4 is especially preferred.

A oligosaccharide of any one of general formulae (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein -L- is selected from: -$L^a$-, -$L^a$-$L^e$-, -$L^a$-$L^b$-$L^e$-, and -$L^a$-$L^d$-$L^e$-;

-$L^a$- is selected from: —$(CH_2)_o$—, —$(CH_2$—$CH_2$—$O)_o$—$C_2H_4$—, —$(CH_2$—$CH_2$—$O)_o$—$CH_2$;

-$L^b$- represents —O—, —NH—CO—NH—, —NH—CO—$CH_2$—NH—, —NH—CO—;

-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

-$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

o, q, p1 and p2 are independently of each other an integer selected from 1, 2, 3, 4, 5, and 6; preferably an integer selected from 1, 2, 3, and 4; and n represents 1 is also preferred.

Even more preferred is a oligosaccharide of general formula (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein -L- represents —$(CH_2)_o$— and o is an integer selected from 2, 3, 4, 5 and 6.

Also preferred is a oligosaccharide of general (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein -L- represents —$(CH_2)_o$—, o is an integer selected from 2, 3, 4, 5 and 6, and n represents 1.

In a more preferred embodiment, —O-L-E is selected from the group consisting of:

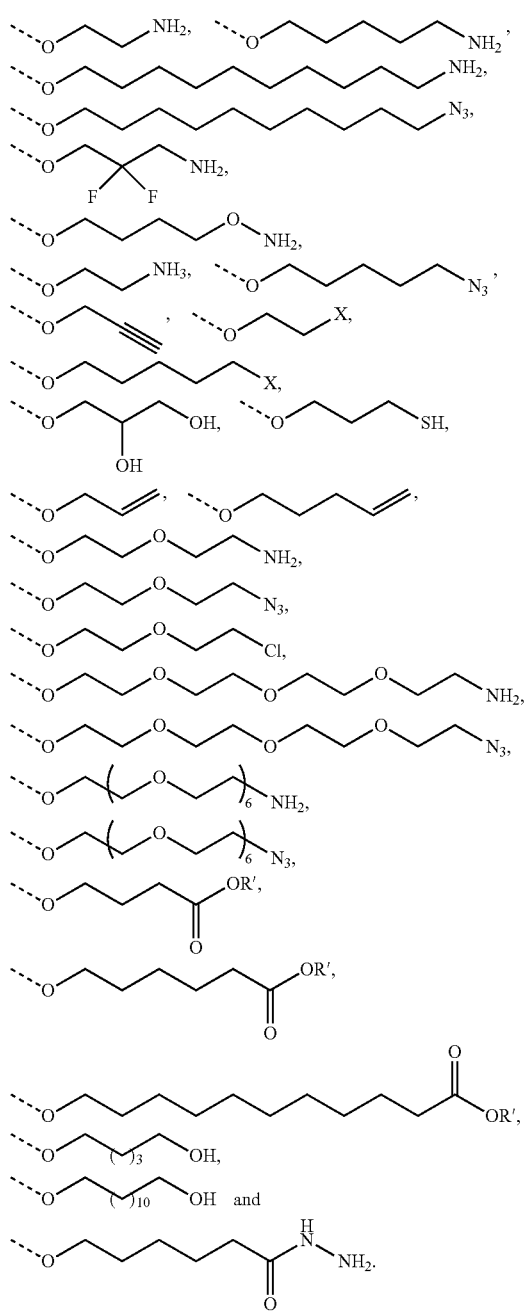

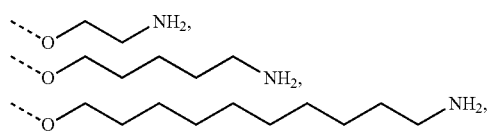

wherein R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

X represents —Br, —Cl, —I, —CO$_2$H, or —SAc.

Particularly preferred, —O-L-E is selected from the group consisting of:

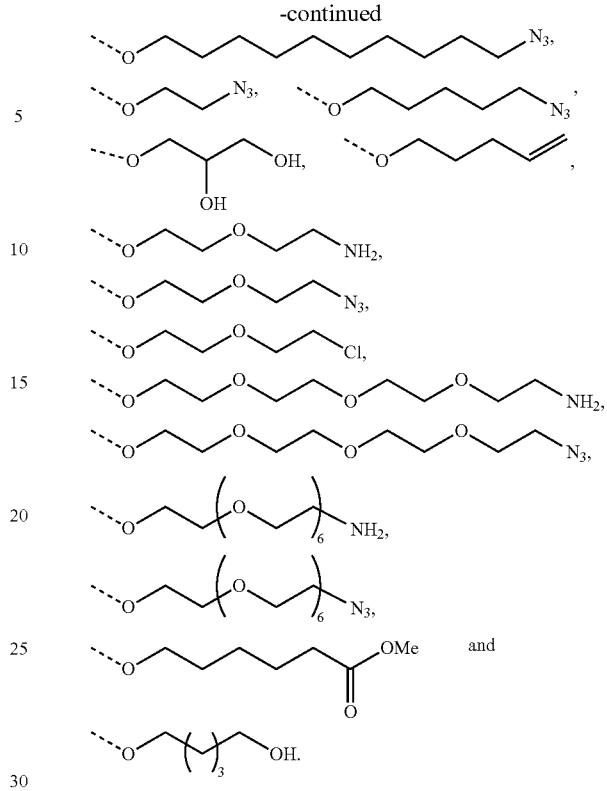

Particularly preferred is a oligosaccharide of general formula (II-a), wherein T* represents —H and —O-L-E is selected from the group consisting of:

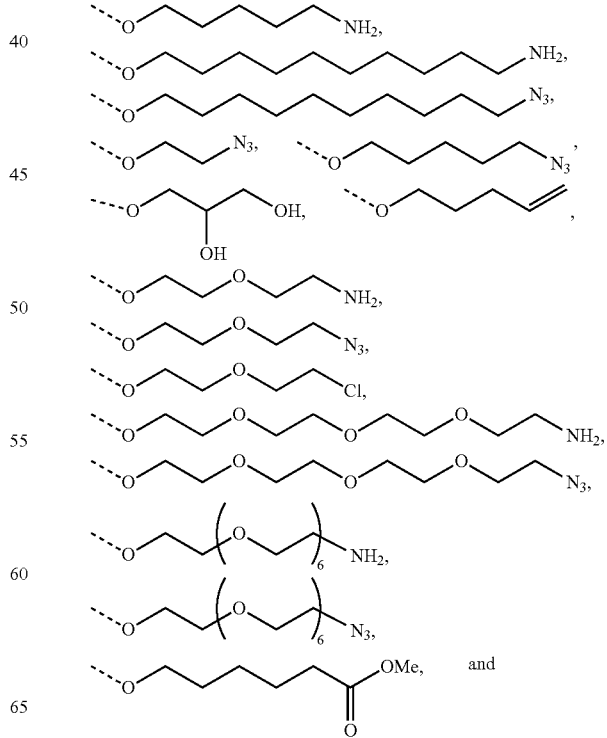

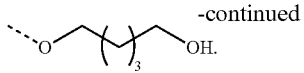

Particularly preferred is a oligosaccharide of general formula (II-f), wherein T* represents —H and —O-L-E is selected from the group consisting of:

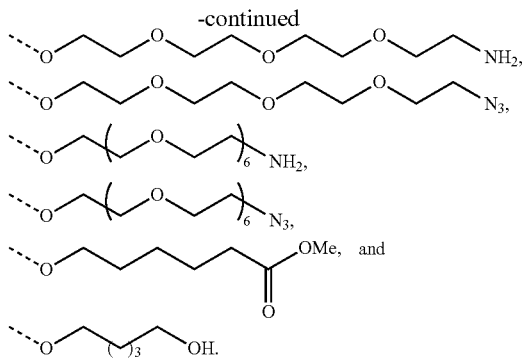

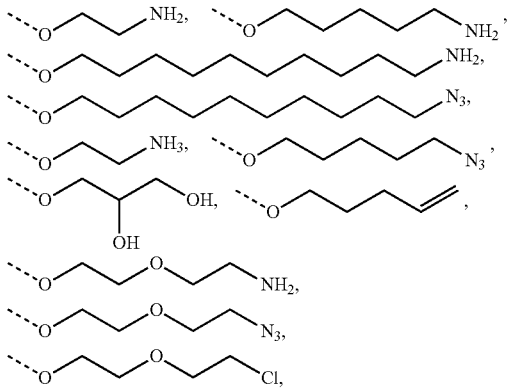

Also preferred is a oligosaccharide of general formula (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein -L- represents —$(CH_2)_o$—, o is an integer selected from 2, 3, 4, 5 and 6 E represents an amino group.

In yet another preferred embodiment, the oligosaccharide according to the present invention is selected from the group consisting of:

(I'a-1)

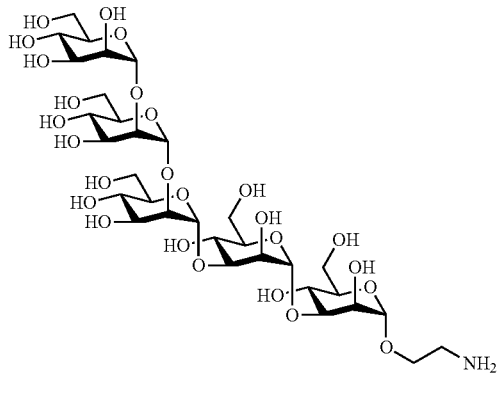

(I'a-2)

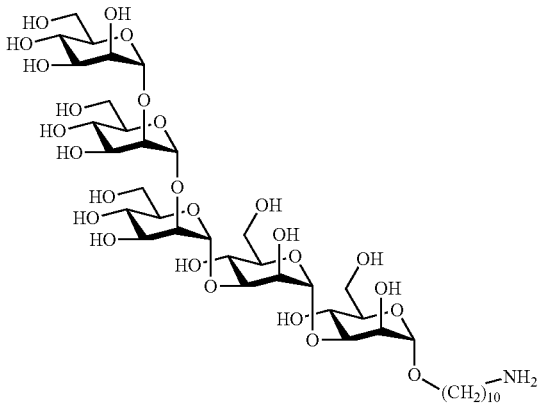

(I'a-3)

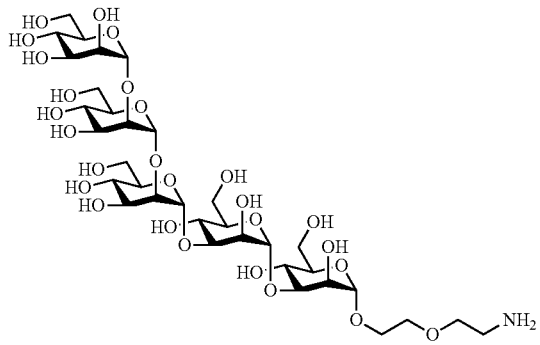

(I'a-4)

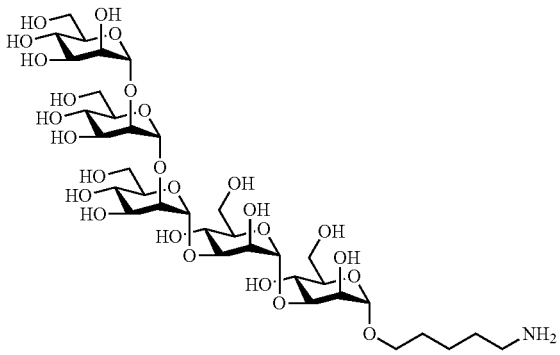

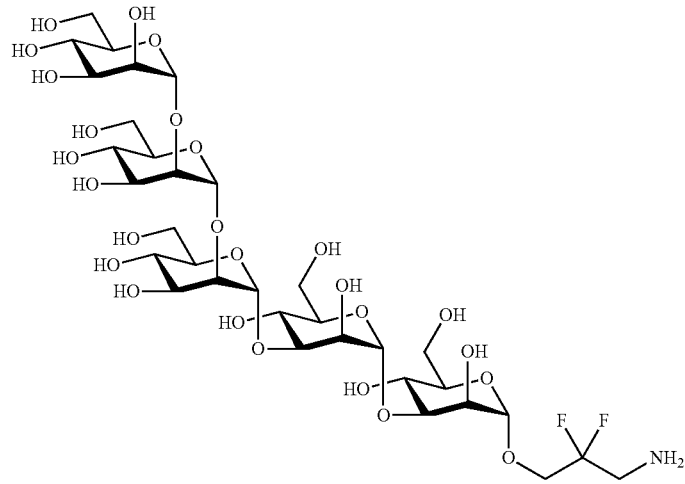
(I'a-5)
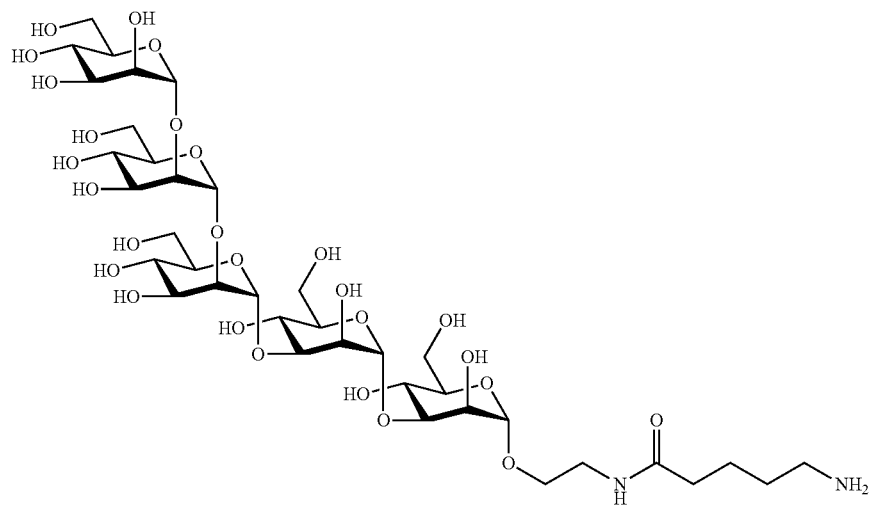
(I'a-6)
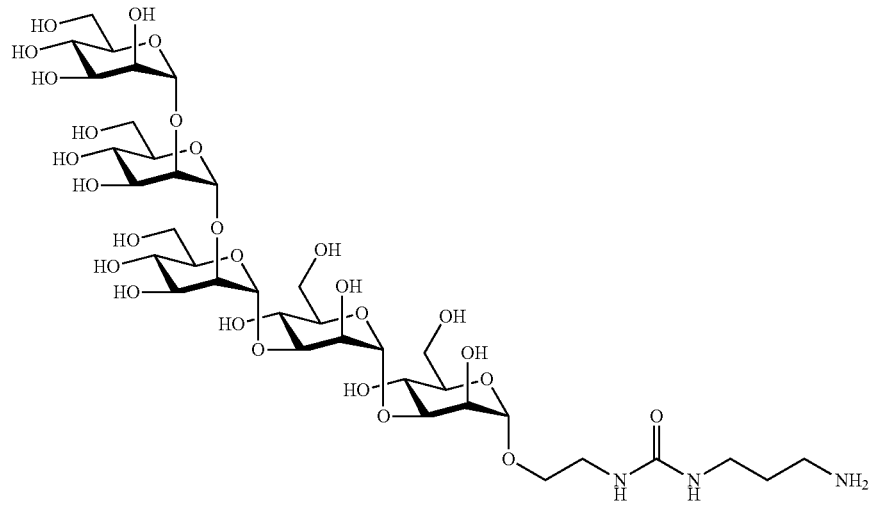
(I'a-7)

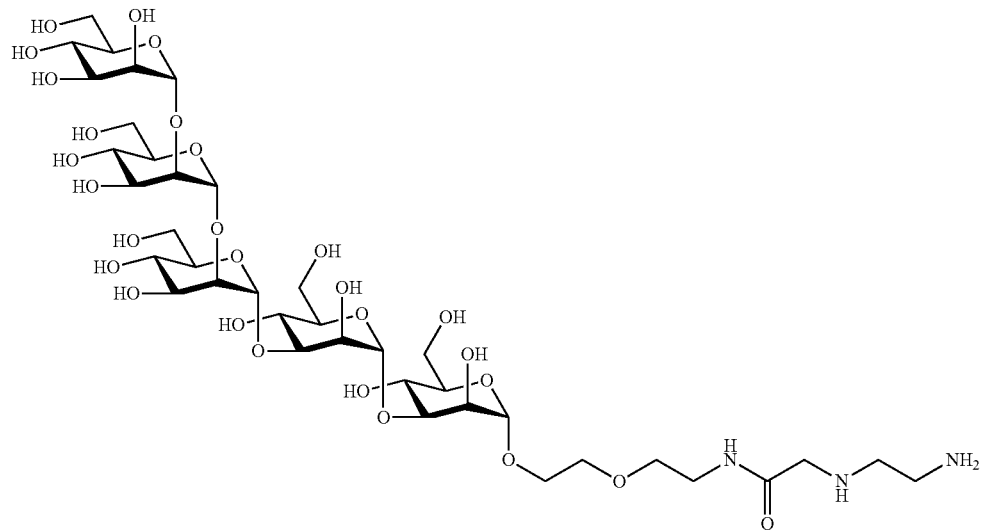
(I'a-8)
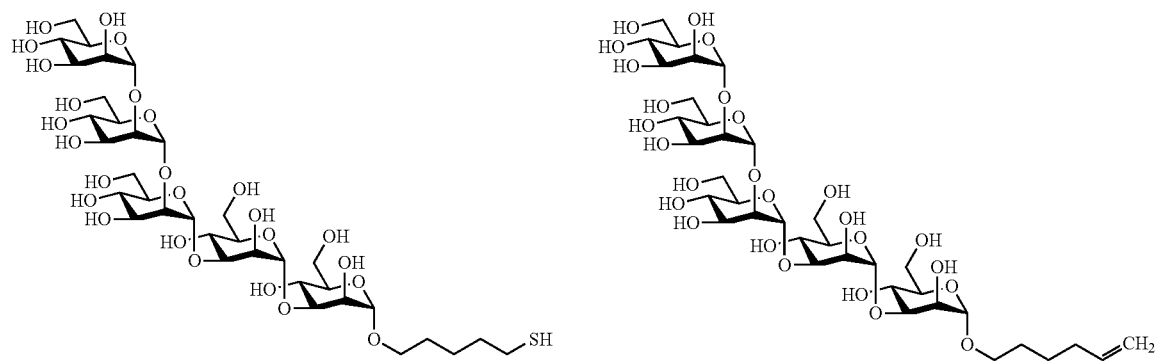
(I'a-9) (I'a-10)
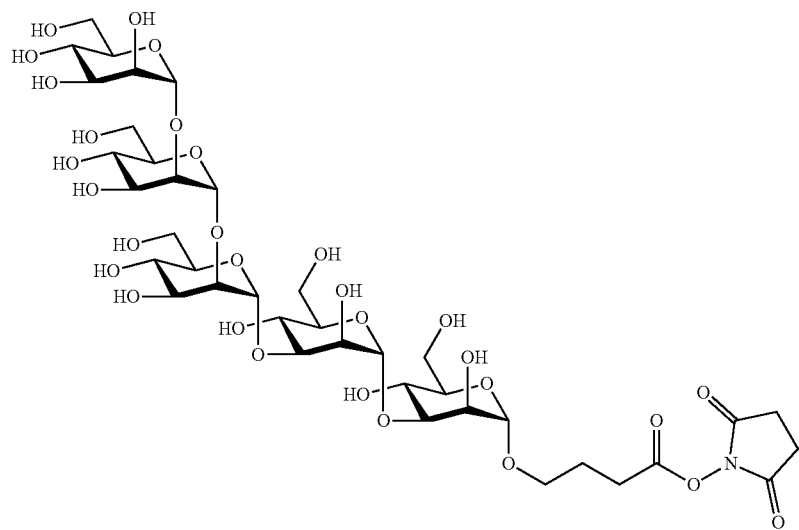
(I'a-11)

-continued
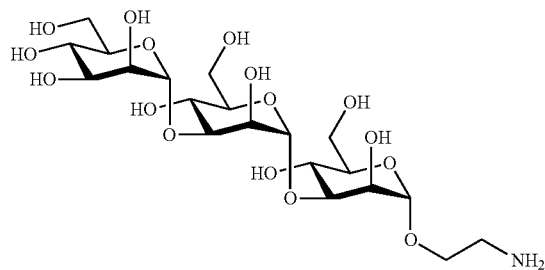
(I'b-1)
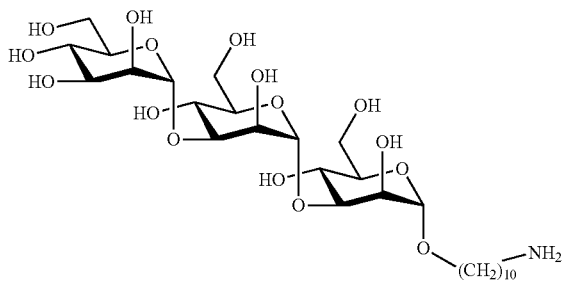
(I'b-2)
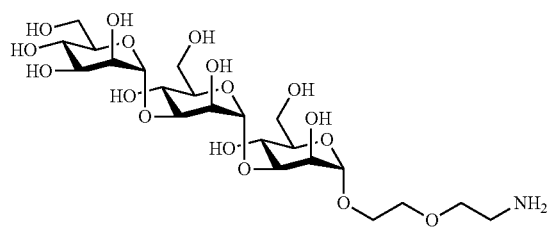
(I'b-3)
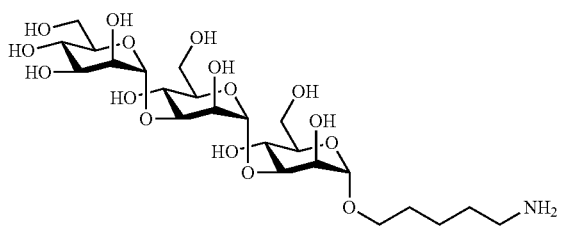
(I'b-4)
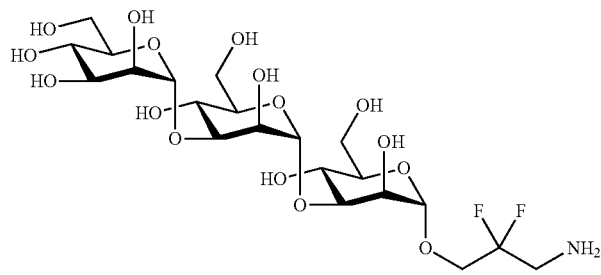
(I'b-5)
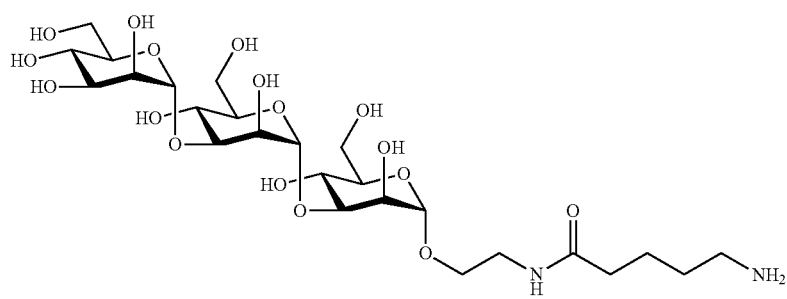
(I'b-6)
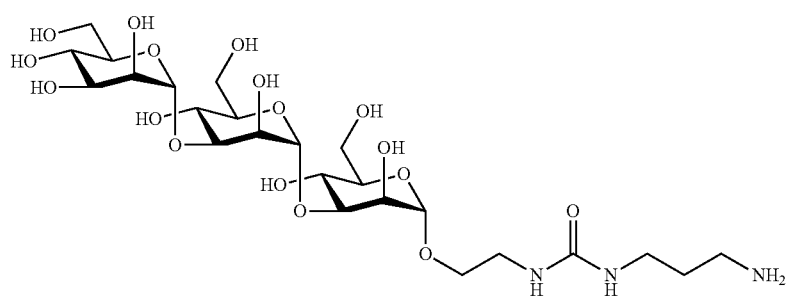
(I'b-7)

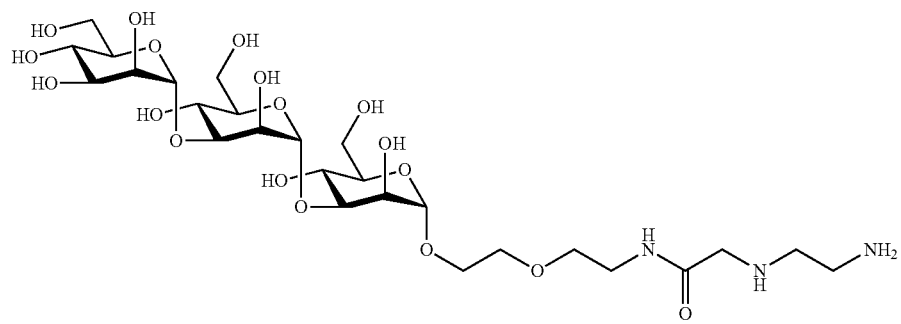
(I'b-8)
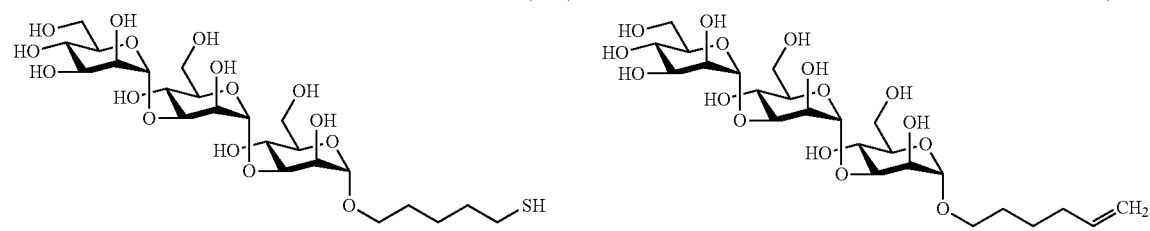
(I'b-9) (I'b-10)
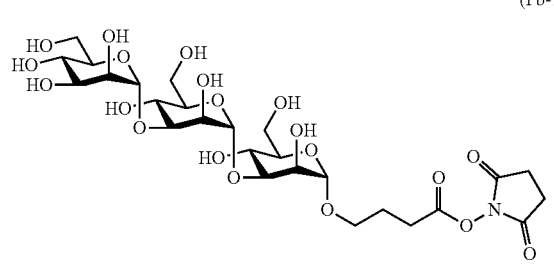
(I'b-11)
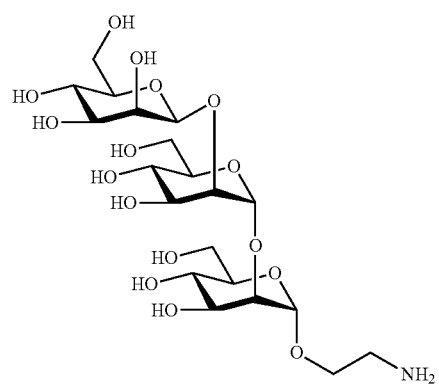
(I'c-1)
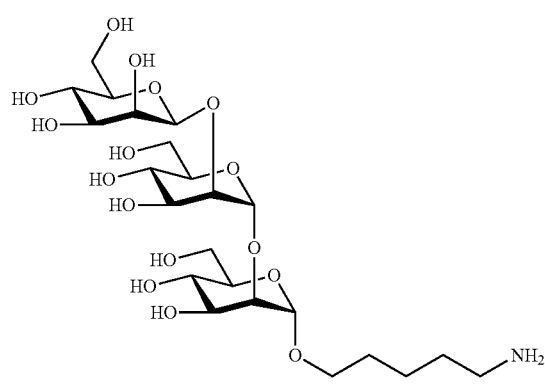
(I'c-2) (I'c-3)

-continued
(I'c-4)
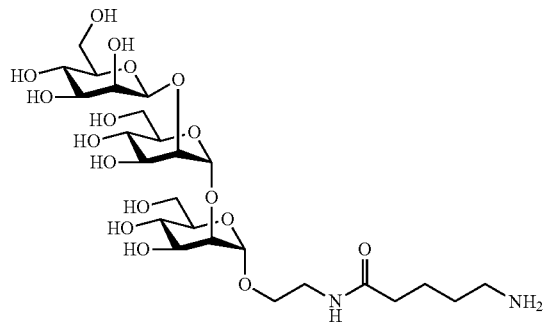
(I'c-5)
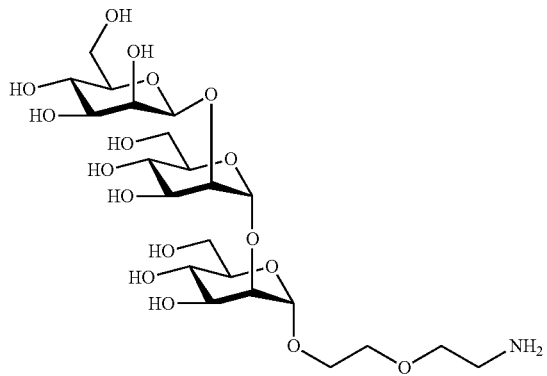
(I'c-6)
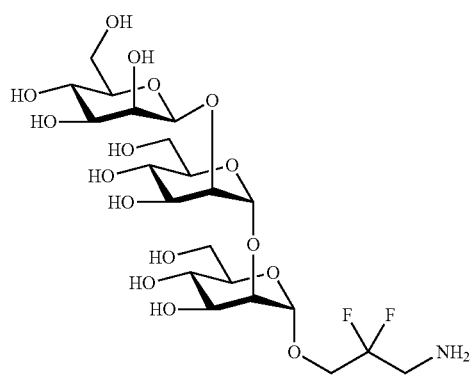
(I'c-7)
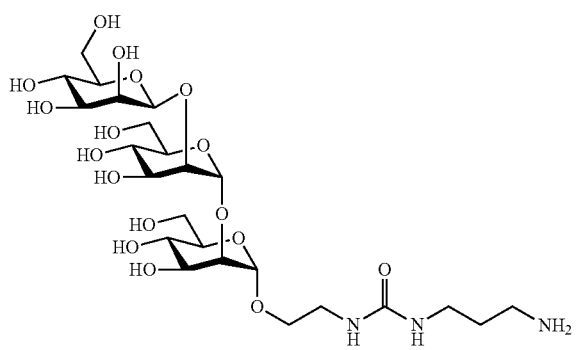
(I'c-8)
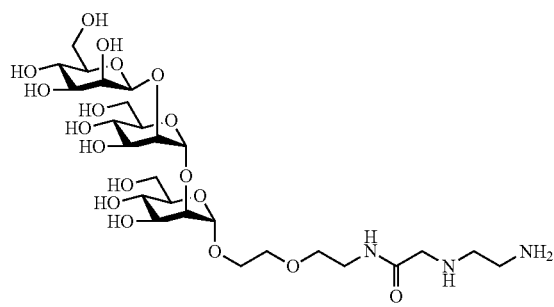
(I'c-9)
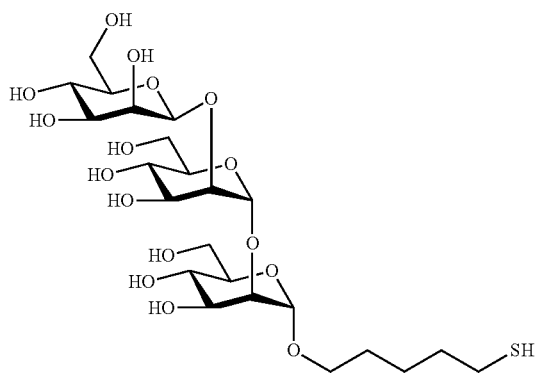
(I'c-10)
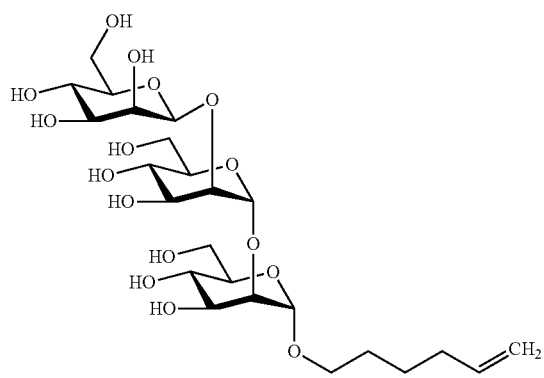
(I'c-11)
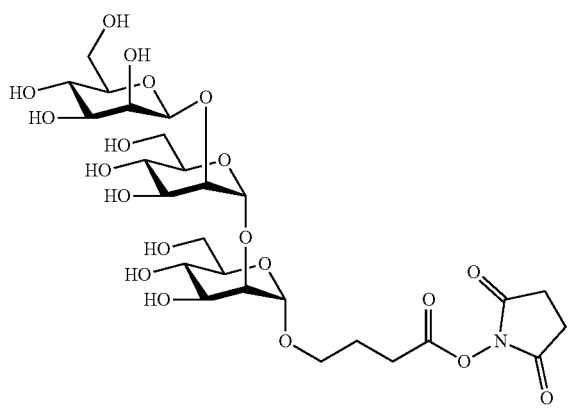

-continued
(I'd-1)
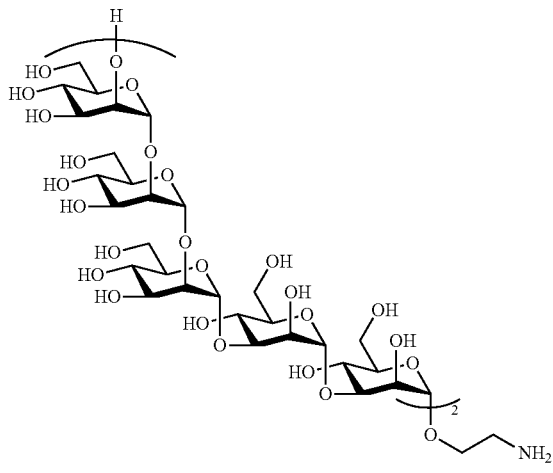
(I'd-2)
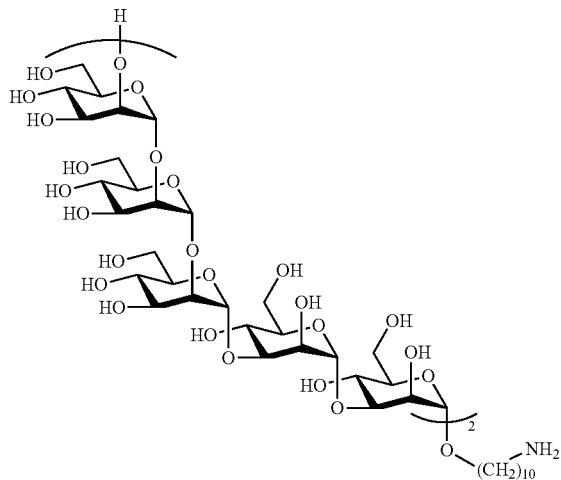
(I'd-3)
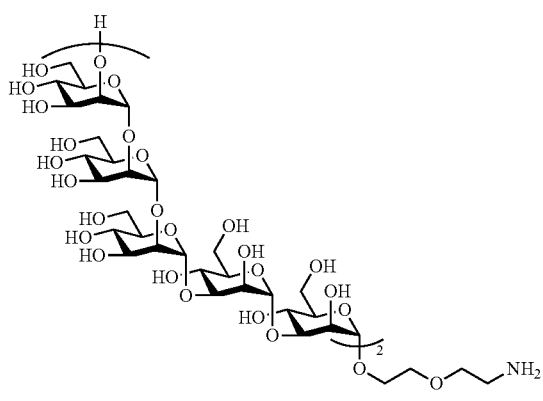
(I'd-4)
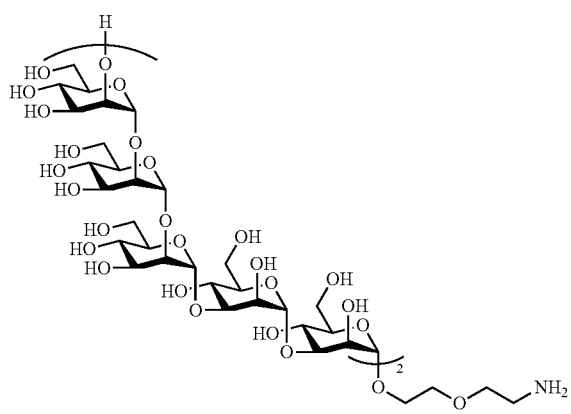
(I'd-5)
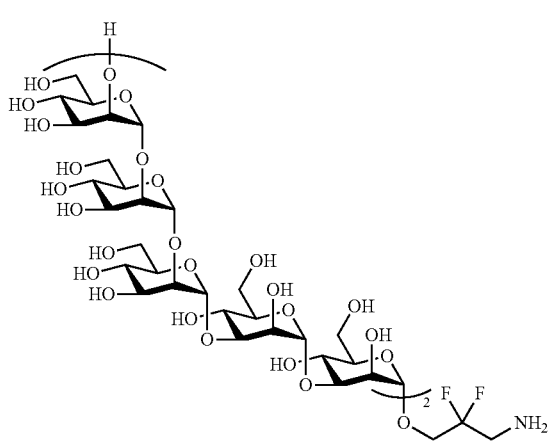

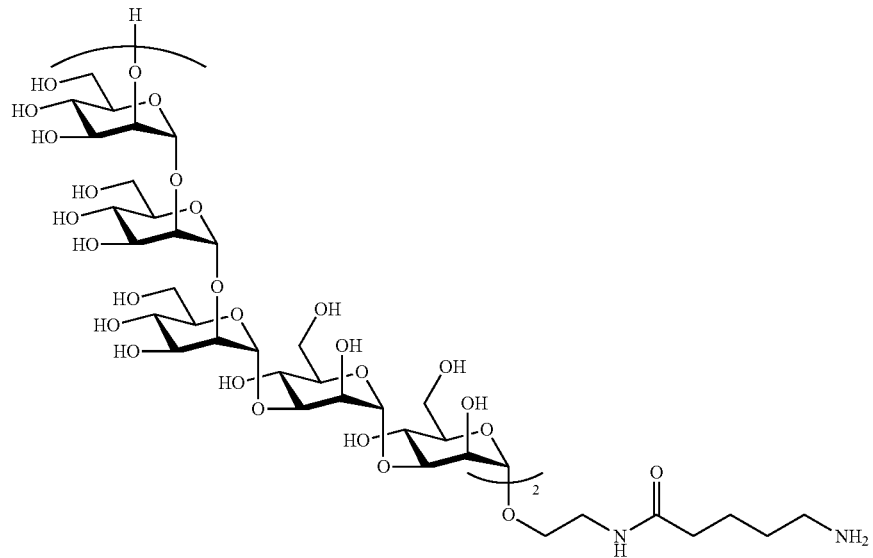
(I′d-6)
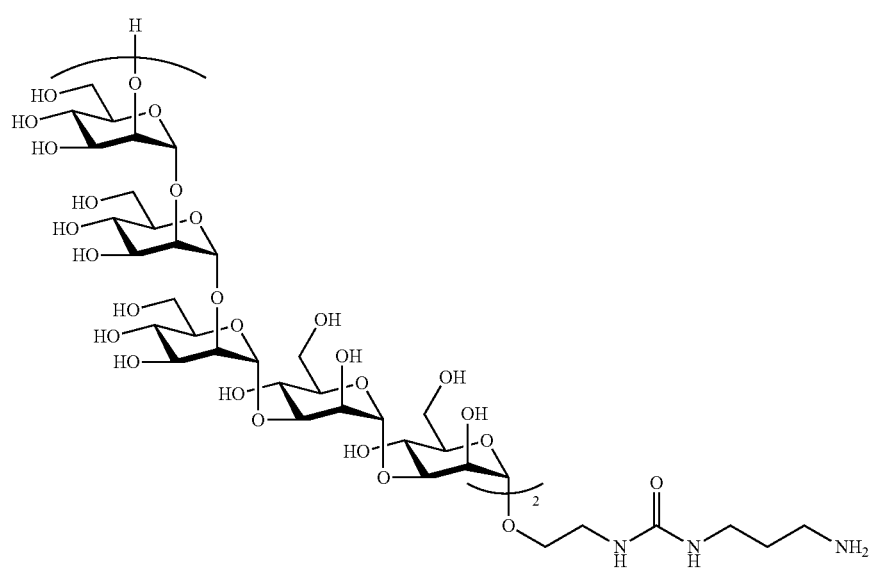
(I′d-7)

-continued
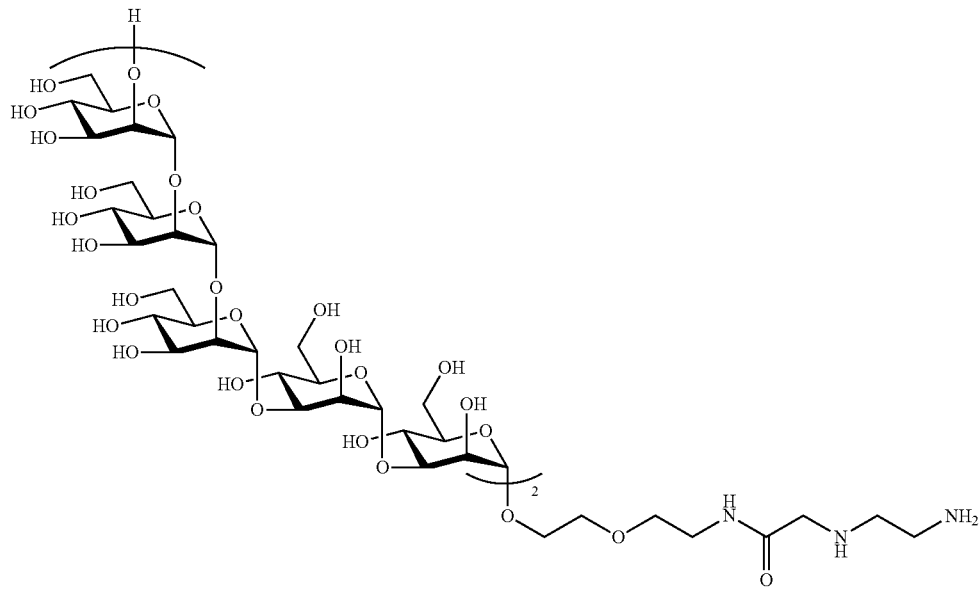
(I'd-8)
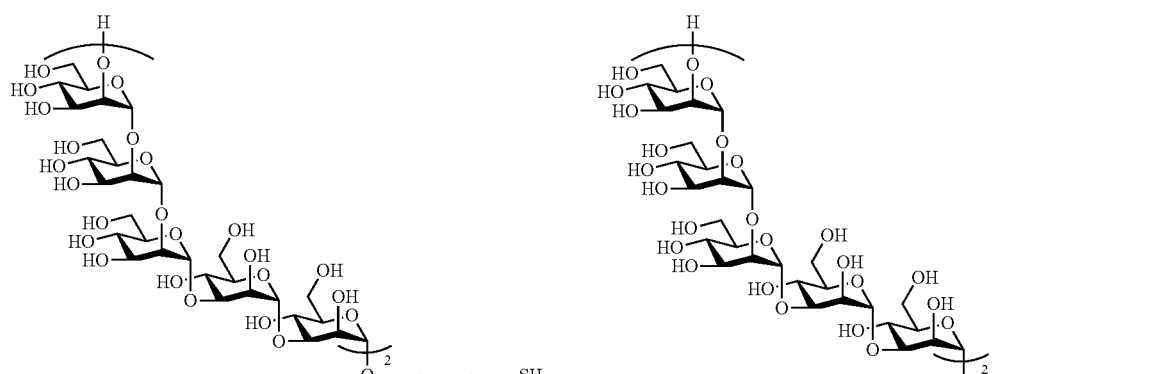
(I'd-9) (I'd-10)
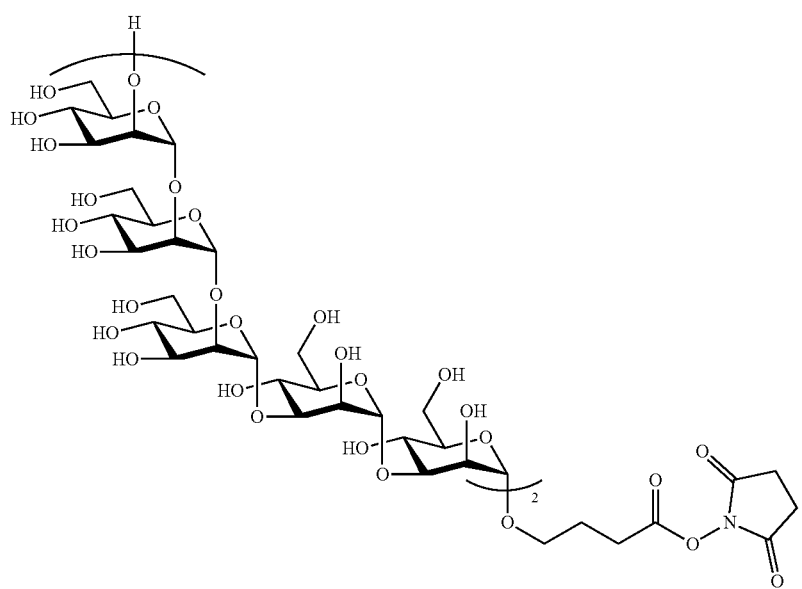
(I'd-11)

-continued
(I'e-1)
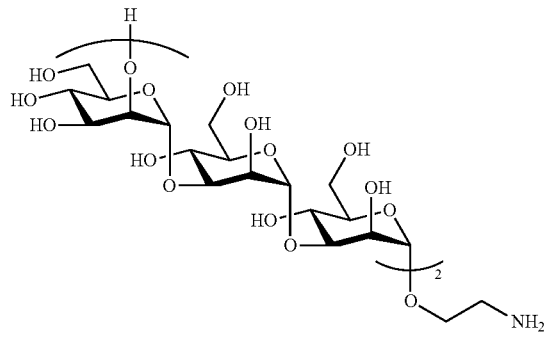
(I'e-2)
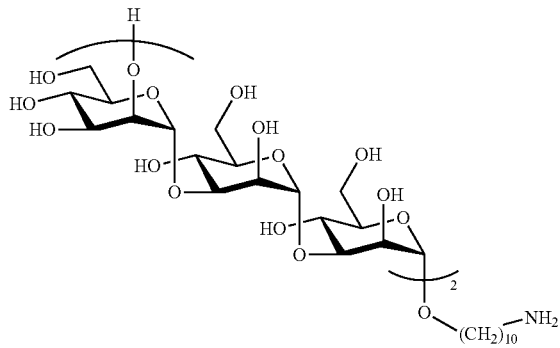
(I'e-3)
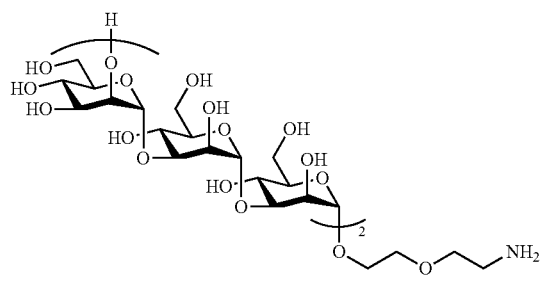
(I'e-4)
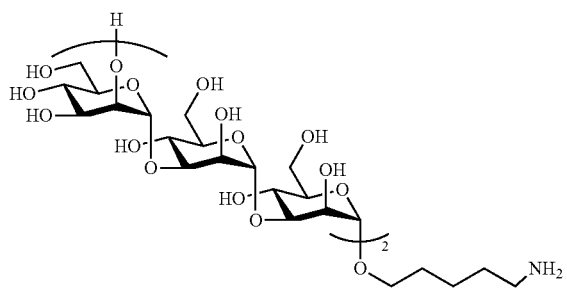
(I'e-5)
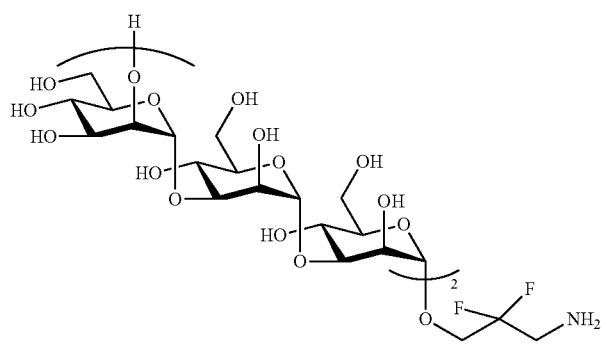
(I'e-6)
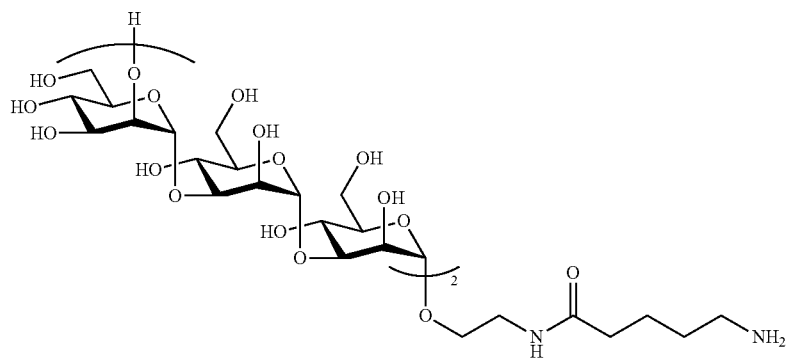

-continued
(I'e-7)
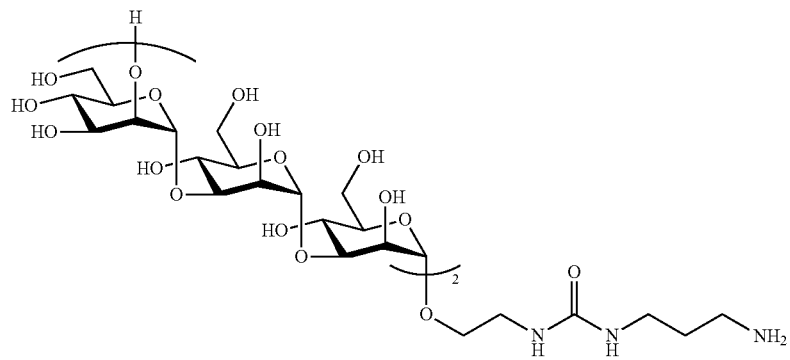
(I'e-8)
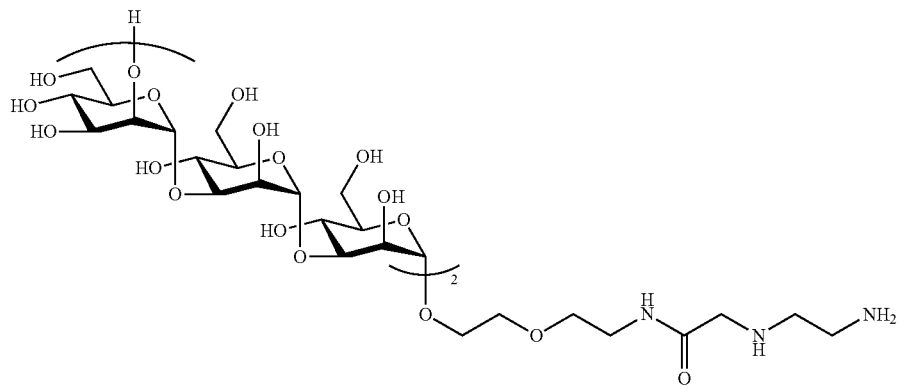
(I'e-9)
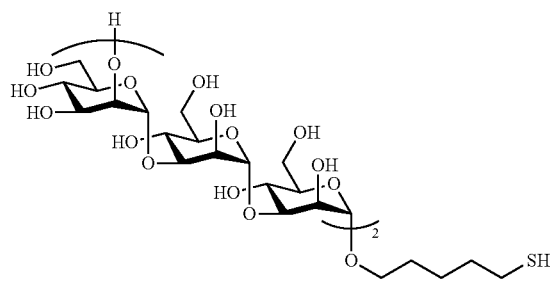
(I'e-10)
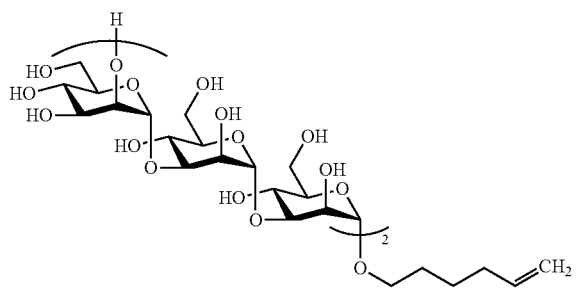
(I'e-11)
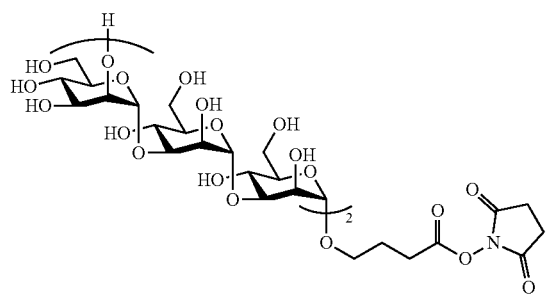
(I'f-1)
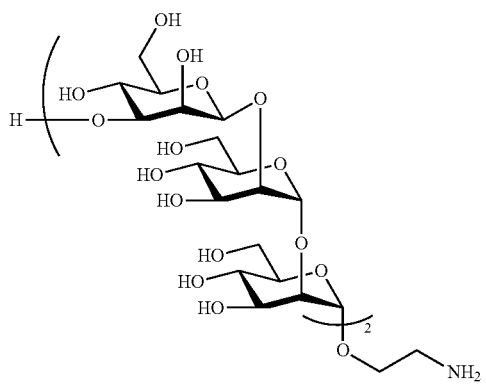

-continued
(I'f-2)
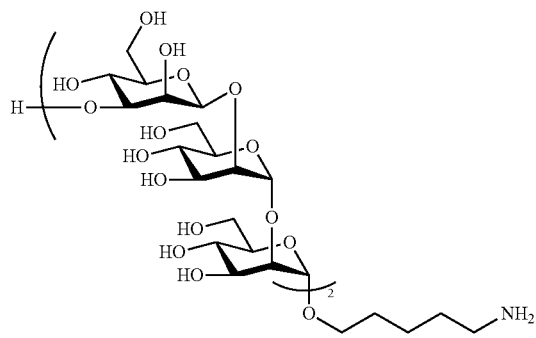
(I'f-3)
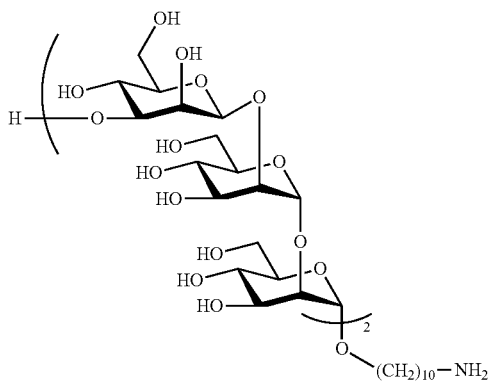
(I'f-4)
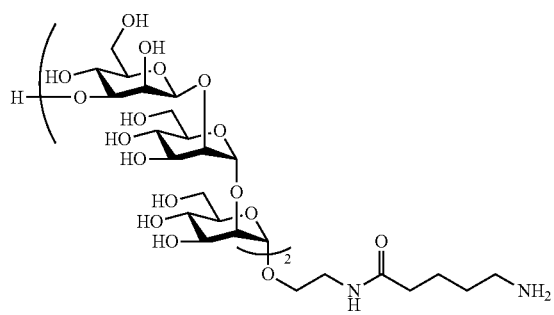
(I'f-5)
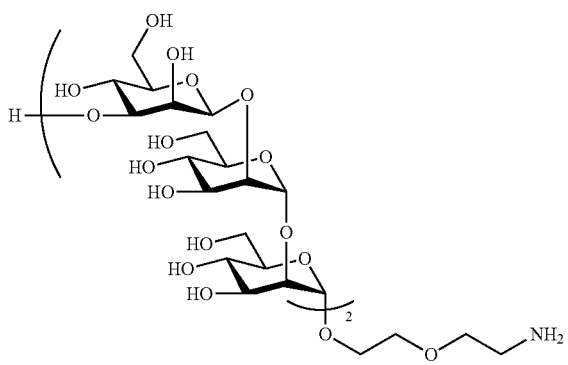
(I'f-6)
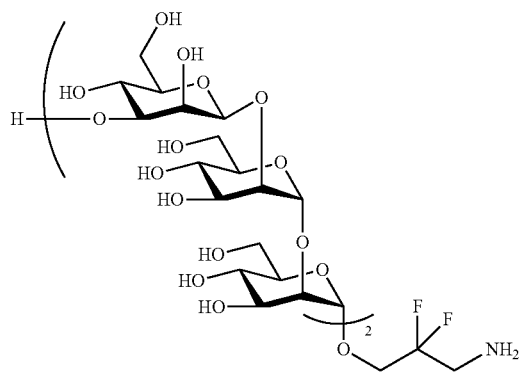
(I'f-7)
(I'f-8)
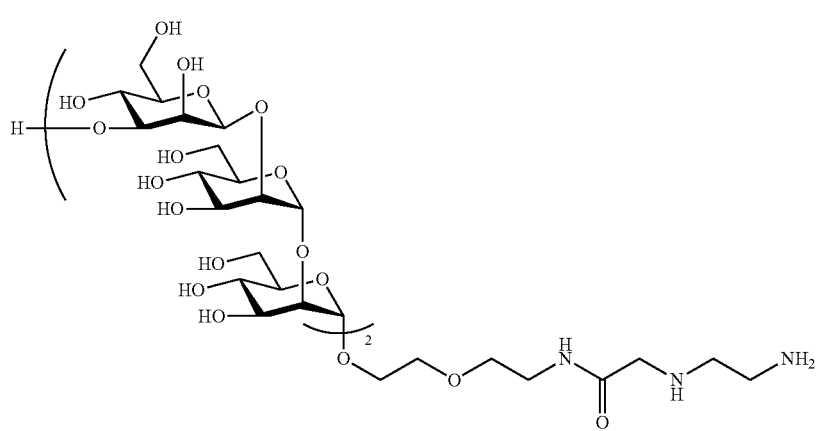

(I'f-9)

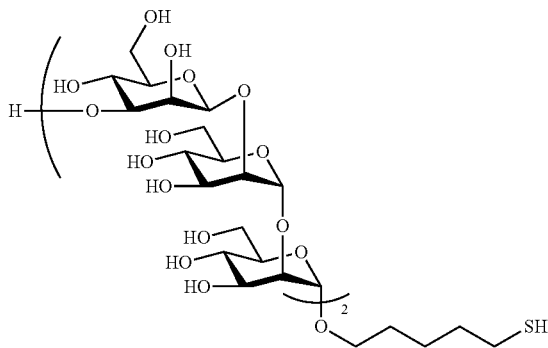

(I'f-10)

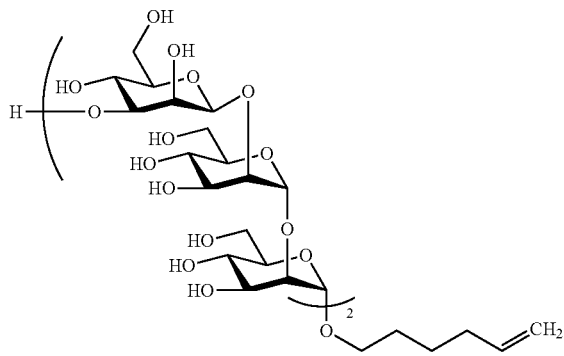

(I'f-11)

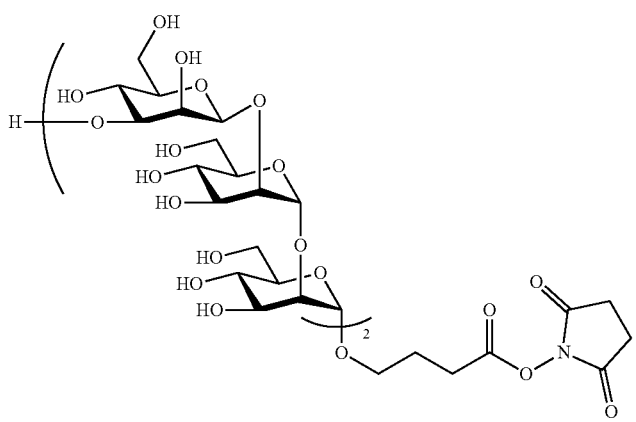

Chemical Synthesis

Another aspect of the present invention is directed to a method of synthesis of an oligosaccharide of general formula (I)

$$T^*\text{-}[(\text{—}U_{x+4}\text{—}U_{x+3}\text{—}U_{x+2}\text{—}U_{x+1}\text{—}U_x)_m\text{—}(V_{x+2}\text{—}V_{x+1}\text{—}V_x)_{1\text{-}m}]_n\text{-}T\text{-}O\text{-}L\text{-}E \quad (I)$$

wherein m is 1;

x is an integer selected from 1 to 2×m+3;

n is an integer selected from 1, 2, 3, 4, 5, 6, 7, 8, 9 and 10;

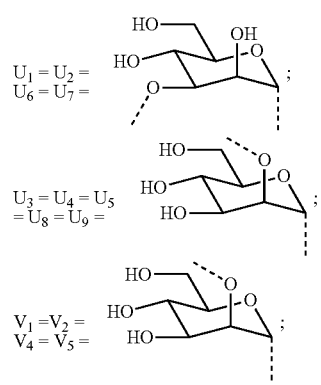

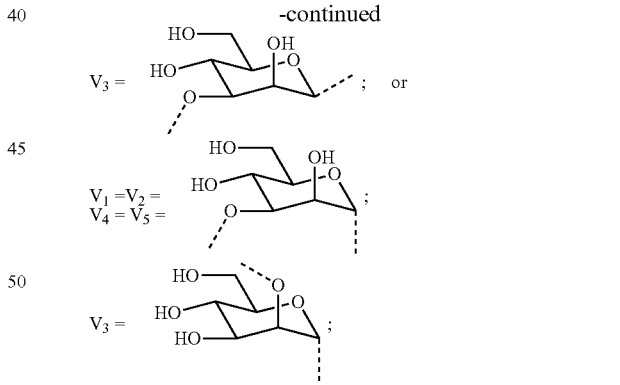

-T- represents a bond;

T*- represents H;

L represents a linker;

E represents —NH$_2$, —N$_3$, —CN, —O—NH$_2$, —CH=CH$_2$, —C≡CH, —Br, —Cl, —I, —CO$_2$R', —COR', —CONH—NH$_2$, —SH, or —SAc;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

comprising the following steps:

A1) providing a monosaccharide 1

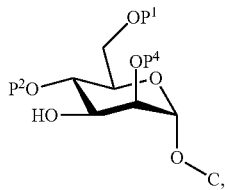

(1)

wherein $P^1$, $P^2$ and $P^4$ represent protecting groups and C represents -L-$E_p$ with $E_p$ being a solid support or a protected end group E, wherein E and L have the meanings as defined herein;

A2) treating monosaccharide 1 with a building block 2 in presence of an activating agent

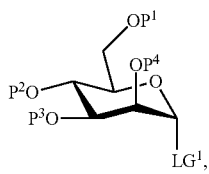

(2)

wherein $P^1$-$P^4$ represent protecting groups and $LG^1$ represents a leaving group;

A3) performing removal of protecting group $P^3$;

A4) treating the product of step A3) with a building block 3 in presence of an activating agent

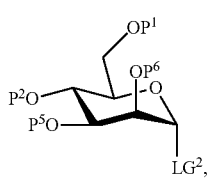

(3)

wherein $P^1$, $P^2$, $P^5$ and $P^6$ represent protecting groups and $LG^2$ represents a leaving group;

A5) performing removal of protecting group $P^6$;

A6) repeating steps A4) and A5) two times to obtain intermediate compound 4a;

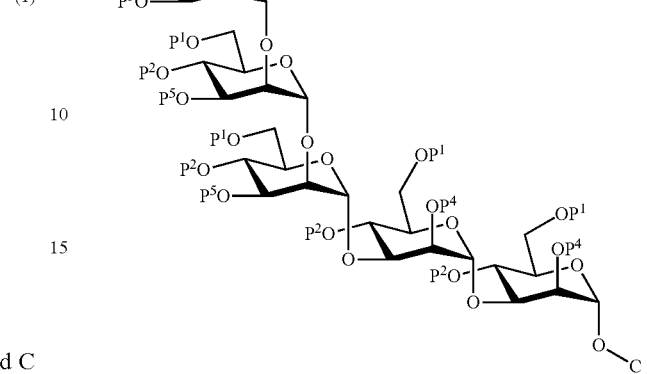

(4a)

wherein $P^1$, $P^2$, $P^4$ and $P^5$ represent protecting groups and C represents -L-$E_p$ with $E_p$ being a solid support or a protected end group E, wherein E and L have the meanings as defined herein;

A7) optionally repeating steps A2)-A6) in the following order A2)→A3)→A2)→A3)→A4)→A5)→A6) n−1 times to obtain intermediate compound of formula 5a,

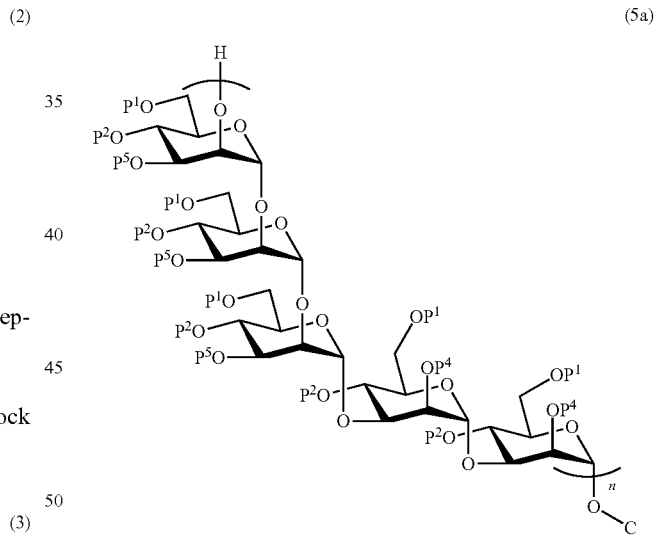

(5a)

wherein $P^1$, $P^2$, $P^4$ and $P^5$ represent protecting groups and C represents -L-$E_p$ with $E_p$ being a solid support or a protected end group E, wherein n, E and L have the meanings as defined herein;

A8) performing removal of all protecting groups to obtain an oligosaccharide of general formula (I).

A further method of the synthesis of an oligosaccharide of general formula (I) comprises the following steps:

B1) providing a monosaccharide 1

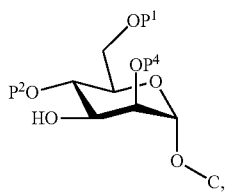
(1)

wherein $P^1$, $P^2$ and $P^4$ represent protecting groups and C represents -L-$E_p$ with $E_p$ being a solid support or a protected end group E, wherein E and L have the meanings as defined herein;

B2) treating monosaccharide 1 with a building block 3 in presence of an activating agent

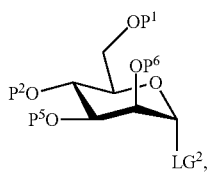
(3)

wherein $P^1$, $P^2$, $P^5$ and $P^6$ represent protecting groups and $LG^2$ represents a leaving group;

B3) performing removal of protecting group $P^6$;

B4) repeating steps B2) and B3) two times;

B5) treating the product of step B4) with building block 2 in presence of an activating agent

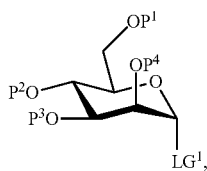
(2)

wherein $P^1$-$P^4$ represent protecting groups and $LG^1$ represents a leaving group;

B6) performing removal of protecting group $P^3$ to obtain intermediate compound 4b;

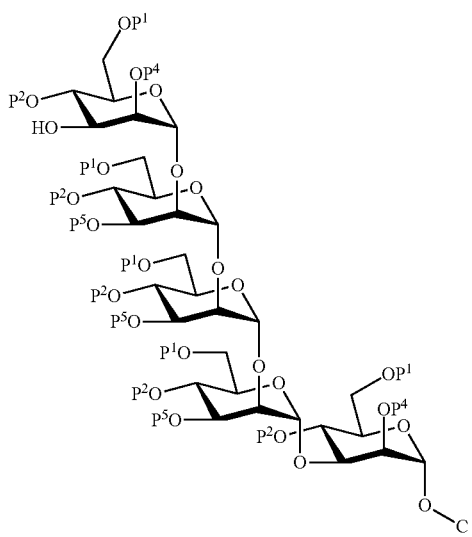
(4b)

wherein $P^1$, $P^2$, $P^4$ and $P^5$ represent protecting groups and C represents -L-$E_p$ with $E_p$ being a solid support or a protected end group E, wherein E and L have the meanings as defined herein;

B7) optionally repeating steps B2)-B6) in the following order B5)→B6)→B2)→B3)→B4)→B5)→B6) n−1 times to obtain intermediate compound of formula 5b

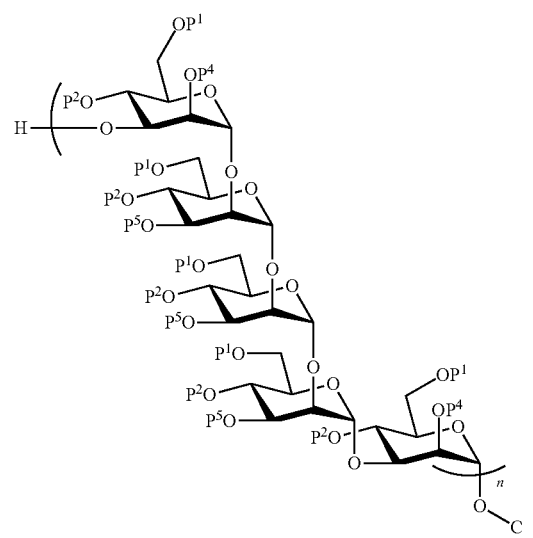
(5b)

wherein $P^1$, $P^2$, $P^4$ and $P^5$ represent protecting groups and C represents -L-$E_p$ with $E_p$ being a solid support or a protected end group E, wherein n, E and L have the meanings as defined herein;

B8) performing removal of all protecting groups to obtain an oligosaccharide of general formula (I).

A further method of the synthesis of an oligosaccharide of general formula (I) comprises the following steps:

C1) providing a monosaccharide 6

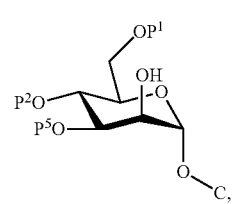
(6)

wherein $P^1$, $P^2$ and $P^5$ represent protecting groups and C represents -L-$E_p$ with $E_p$ being a solid support or a protected end group E, wherein E and L have the meanings as defined herein;

C2) treating monosaccharide 6 with a building block 3 in presence of an activating agent

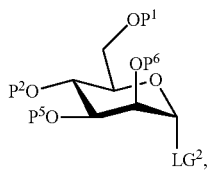

(3)

wherein $P^1$, $P^2$, $P^5$ and $P^6$ represent protecting groups and $LG^2$ represents a leaving group;

C3) performing removal of protecting group $P^6$;

C4) treating the product of step C3) with building block 2 in presence of an activating agent

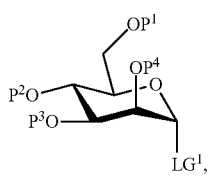

(2)

wherein $P^1$-$P^4$ represent protecting groups and $LG^1$ represents a leaving group;

C5) performing removal of protecting group $P^3$;

C6) repeating steps C4) and C5);

C7) repeating steps C2) and C3) to obtain intermediate compound 4d;

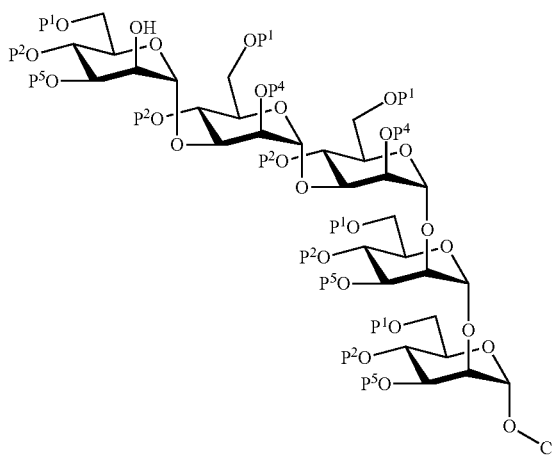

(4d)

wherein $P^1$, $P^2$, $P^4$ and $P^5$ represent protecting groups and C represents -L-$E_p$ with $E_p$ being a solid support or a protected end group E, wherein E and L have the meanings as defined herein;

C8) optionally repeating steps C2)-C7) in the following order C2)→C3)→C2)→C3)→C4)→C5)→C6)→C7) n−1 times to obtain intermediate compound of formula 5d

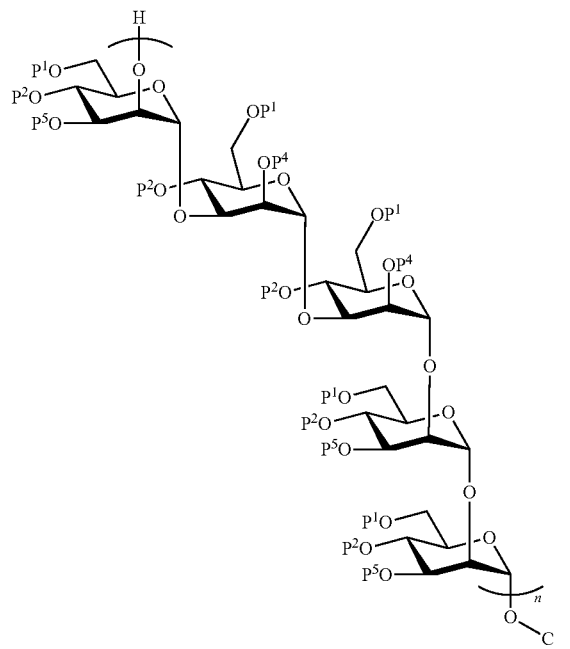

(5d)

wherein $P^1$, $P^2$, $P^4$ and $P^5$ represent protecting groups and C represents -L-$E_p$ with $E_p$ being a solid support or a protected end group E, wherein n, E and L have the meanings as defined herein;

C9) performing removal of all protecting groups to obtain an oligosaccharide of general formula (I).

A further method of the synthesis of an oligosaccharide of general formula (I) comprises the following steps:

D1) providing a monosaccharide 6

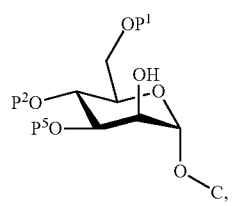

(6)

wherein $P^1$, $P^2$ and $P^5$ represent protecting groups and C represents -L-$E_p$ with Ep being a solid support or a protected end group E, wherein E and L have the meanings as defined herein;

D2) treating monosaccharide 6 with a building block 3 in presence of an activating agent

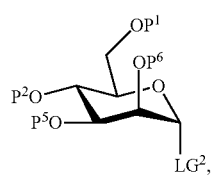

(3)

wherein $P^1$, $P^2$, $P^5$ and $P^6$ represent protecting groups and $LG^2$ represents a leaving group;

D3) performing removal of protecting group $P^6$;
D4) repeating steps D2) and D3);
D5) treating the product of step D4) with building block 2 in presence of an activating agent

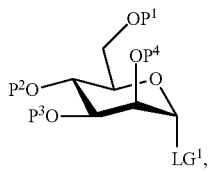

(2)

wherein $P^1$-$P^4$ represent protecting groups and $LG^1$ represents a leaving group;

D6) performing removal of protecting group $P^3$;

D7) repeating steps D5) and D6) to obtain intermediate compound 4c;

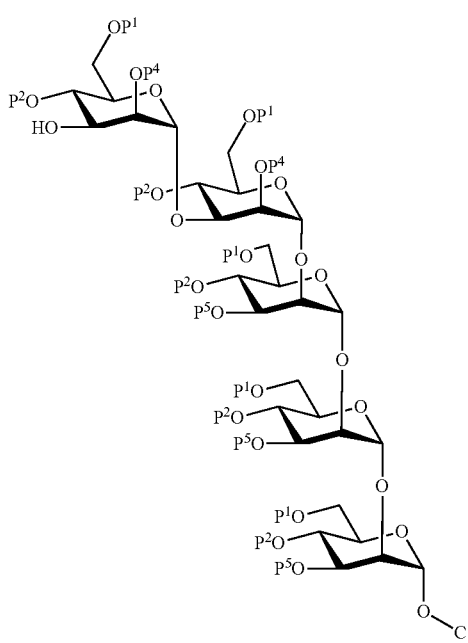

(4c)

wherein $P^1$, $P^2$, $P^4$ and $P^5$ represent protecting groups and C represents -L-$E_p$ with Ep being a solid support or a protected end group E, wherein E and L have the meanings as defined herein;

D8) optionally repeating steps D2)-D7) in the following order D2)→D3)→D4)→D4)→D5)→D6)→D7) n–1 times to obtain intermediate compound of formula 5c,

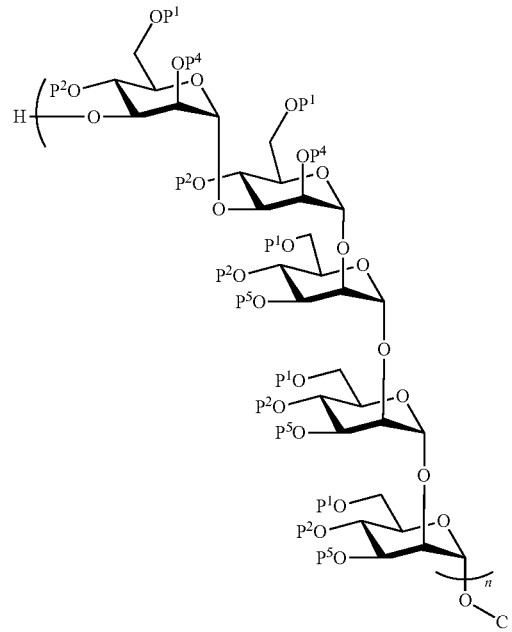

(5c)

wherein $P^1$, $P^2$, $P^4$ and $P^5$ represent protecting groups and C represents -L-$E_p$ with Ep being a solid support or a protected end group E, wherein n, E and L have the meanings as defined herein;

D9) performing removal of all protecting groups to obtain an oligosaccharide of general formula (I).

Another method of the synthesis of an oligosaccharide of general formula (I) comprises the following steps:

E1) providing a monosaccharide 6

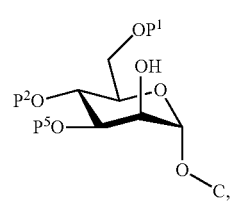

(6)

wherein $P^1$, $P^2$ and $P^5$ represent protecting groups and C represents -L-$E_p$ with Ep being a solid support or a protected end group E, wherein E and L have the meanings as defined herein;

E2) treating monosaccharide 6 with a building block 2 in presence of an activating agent

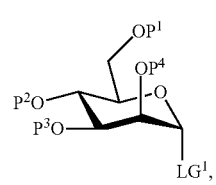

(2)

wherein $P^1$-$P^4$ represent protecting groups and LG represents a leaving group;

E3) performing removal of protecting group $P^3$;
E4) repeating steps E2) and E3);
E5) treating the product of step E4) with building block 3 in presence of an activating agent

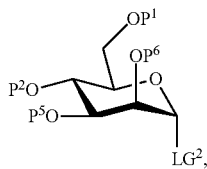

(3)

wherein $P^1$, $P^2$, $P^5$ and $P^6$ represent protecting groups and $LG^2$ represents a leaving group;

E6) performing removal of protecting group $P^6$;

E7) repeating steps E5) and E6) to obtain intermediate compound 4e;

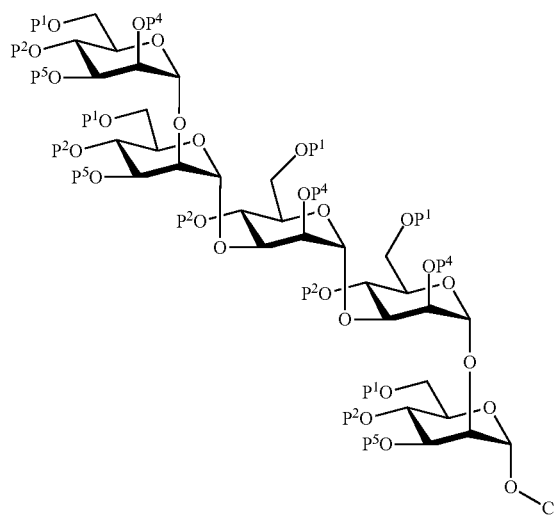

(4e)

wherein $P^1$, $P^2$, $P^4$ and $P^5$ represent protecting groups and C represents -L-$E_p$ with Ep being a solid support or a protected end group E, wherein E and L have the meanings as defined herein;

E8) optionally repeating steps E2)-E6) in the following order E5)→E6)→E2)→E3)→E4)→E5)→E6) n−1 times to obtain intermediate compound of formula 5e,

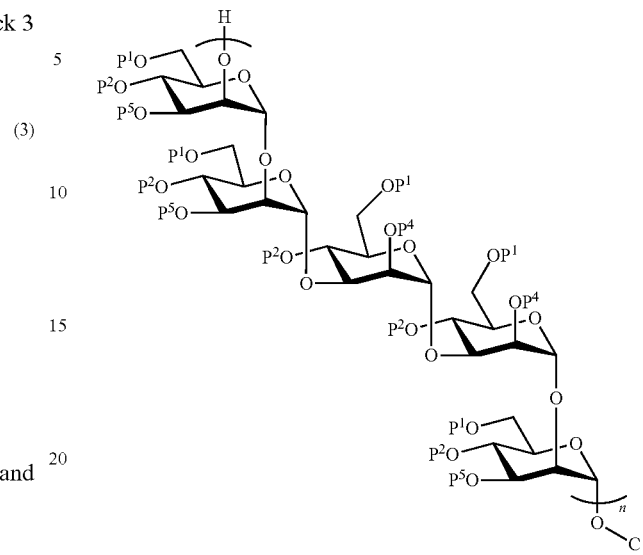

(5e)

wherein $P^1$, $P^2$, $P^4$ and $P^5$ represent protecting groups and C represents -L-$E_p$ with Ep being a solid support or a protected end group E, wherein n, E and L have the meanings as defined herein;

E8) performing removal of all protecting groups to obtain a oligosaccharide of general formula (I).

Another method of the synthesis of an oligosaccharide of general formula (I) comprises the following steps:

F1) providing a monosaccharide 7

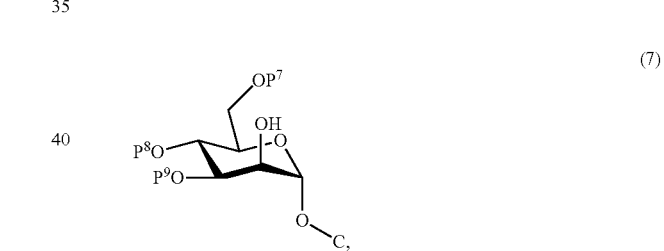

(7)

wherein $P^7$, $P^8$ and $P^9$ represent protecting groups and C represents -L-$E_p$ with $E_p$ being a solid support or a protected end group E, wherein E and L have the meanings as defined herein;

F2) treating monosaccharide 7 with a building block 8 in presence of an activating agent

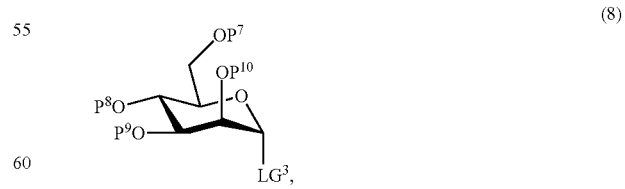

(8)

wherein $P^7$-$P^{10}$ represent protecting groups and $LG^3$ represents a leaving group;

F3) performing removal of protecting group $P^{10}$;

F4) treating the product of step F3) with building block 9 in presence of an activating agent

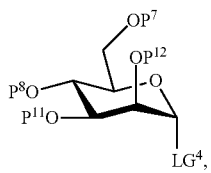

(9)

wherein $P^7$, $P^8$, $P^{11}$ and $P^{12}$ represent protecting groups and $LG^4$ represents a leaving group;

F5) performing removal of protecting group $P^{11}$ to obtain intermediate compound 4f;

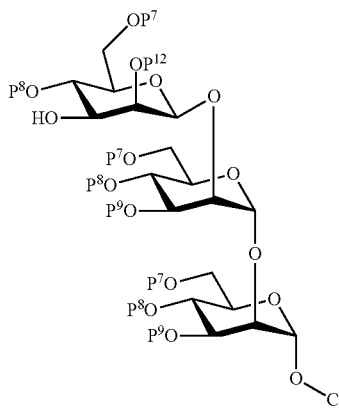

(4f)

wherein $P^7$-$P^9$ and $P^{12}$ represent protecting groups and C represents -L-$E_p$ with Ep being a solid support or a protected end group E, wherein E and L have the meanings as defined herein;

F6) optionally repeating steps F2)-F5) in the following order F2)→F3)→F2)→F4)→F5) n−1 times to obtain intermediate compound of formula 5f,

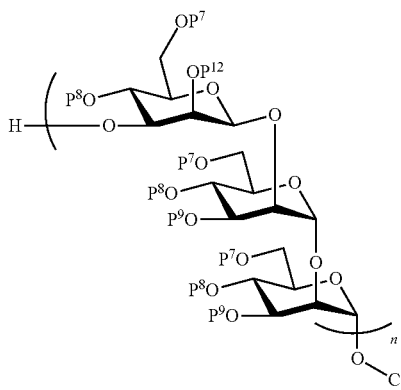

(5f)

wherein $P^7$-$P^9$ and $P^{12}$ represent protecting groups and C represents -L-$E_p$ with Ep being a solid support or a protected end group E, wherein n, E and L have the meanings as defined herein;

F7) performing removal of all protecting groups to obtain an oligosaccharide of general formula (I).

Another method of the synthesis of an oligosaccharide of general formula (I) comprises the following steps:

G1) providing a monosaccharide 7

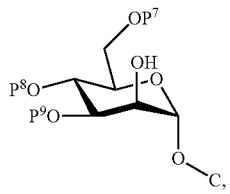

(7)

wherein $P^7$, $P^8$ and $P^9$ represent protecting groups and C represents -L-$E_p$ with Ep being a solid support or a protected end group E, wherein E and L have the meanings as defined herein;

G2) treating monosaccharide 7 with building block 9 in presence of an activating agent

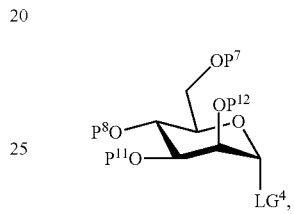

(9)

wherein $P^7$, $P^8$, $P^{11}$ and $P^{12}$ represent protecting groups and $LG^4$ represents a leaving group;

G3) performing removal of protecting group $P^{11}$;

G4) treating the product of step G3) with building block 8 in presence of an activating agent

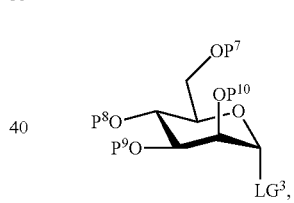

(8)

wherein $P^7$-$P^{10}$ represent protecting groups and $LG^3$ represents a leaving group;

G5) performing removal of protecting group $P^{10}$ to obtain intermediate compound 4g;

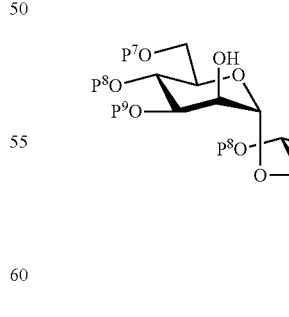

(4g)

wherein $P^7$-$P^9$ and $P^{12}$ represent protecting groups and C represents -L-$E_p$ with Ep being a solid support or a protected end group E, wherein E and L have the meanings as defined herein;

G6) optionally repeating steps G2)-G5) in the following order G4)→G5)→G2)→G3)→G4)→G5) n−1 times to obtain intermediate compound of formula 5g,

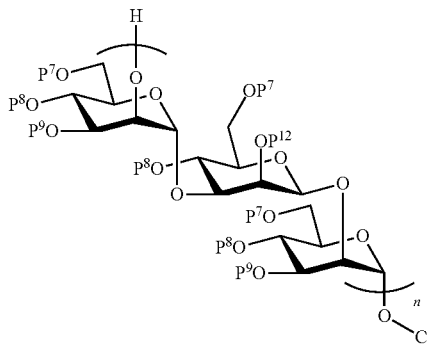
(5g)

wherein $P^7$-$P^9$ and $P^{12}$ represent protecting groups and C represents -L-$E_p$ with Ep being a solid support or a protected end group E, wherein n, E and L have the meanings as defined herein;

G7) performing removal of all protecting groups to obtain an oligosaccharide of general formula (I).

Another method of the synthesis of an oligosaccharide of general formula (I) comprises the following steps:

H1) providing a monosaccharide 10

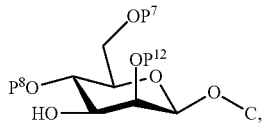
(10)

wherein $P^7$, $P^8$ and $P^{12}$ represent protecting groups and C represents -L-$E_p$ with Ep being a solid support or a protected end group E, wherein E and L have the meanings as defined herein;

H2) treating monosaccharide 10 with building block 8 in presence of an activating agent

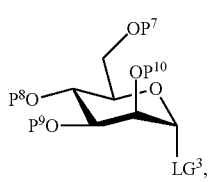
(8)

wherein $P^7$-$P^{10}$ represent protecting groups and $LG^3$ represents a leaving group;

H3) performing removal of protecting group $P^{10}$;

H4) repeating steps H2) and H3) to obtain intermediate compound 4h;

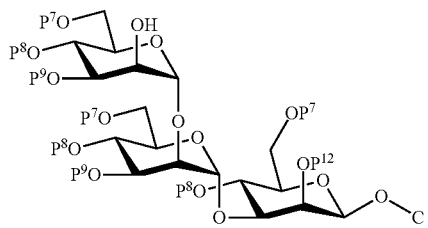
(4h)

wherein $P^7$-$P^9$ and $P^{12}$ represent protecting groups and C represents -L-$E_p$ with Ep being a solid support or a protected end group E, wherein E and L have the meanings as defined herein;

H5) optionally treating compound 4h with building block 9 in presence of an activating agent

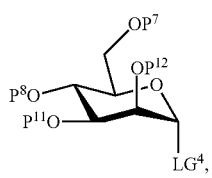
(9)

wherein $P^7$, $P^8$, $P^{11}$ and $P^{12}$ represent protecting groups and $LG^4$ represents a leaving group, performing removal of protecting group $P^{11}$, and performing steps H2)-H4) n−1 times to obtain intermediate compound of formula 5h

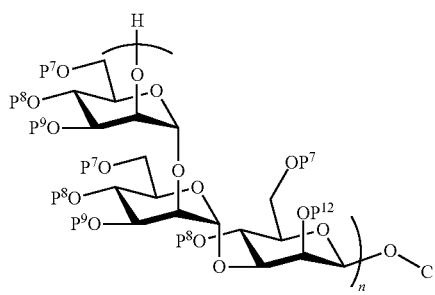
(5h)

wherein $P^7$-$P^9$ and $P^{12}$ represent protecting groups and C represents -L-$E_p$ with Ep being a solid support or a protected end group E, wherein n, E and L have the meanings as defined herein;

H6) performing removal of all protecting groups to obtain an oligosaccharide of general formula (I).

A further method of the synthesis of an oligosaccharide of general formula (I) comprises the following steps:

I1) providing a monosaccharide 1

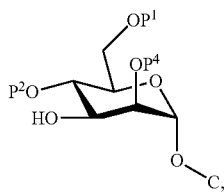
(1)

wherein $P^1$, $P^2$ and $P^4$ represent protecting groups and C represents -L-$E_p$ with Ep being a solid support or a protected end group E, wherein E and L have the meanings as defined herein;

I2) treating monosaccharide 1 with building block 2 in presence of an activating agent

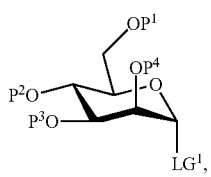
(2)

wherein $P^1$-$P^4$ represent protecting groups and $LG^1$ represents a leaving group;

I3) performing removal of protecting group $P^3$;

I4) treating the product of step I3) with building block 3 in presence of an activating agent

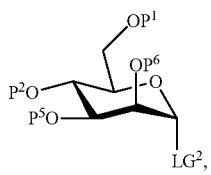
(3)

wherein $P^1$, $P^2$, $P^5$ and $P^6$ represent protecting groups and $LG^2$ represents a leaving group;

I5) performing removal of protecting group $P^6$ to obtain intermediate compound 4i;

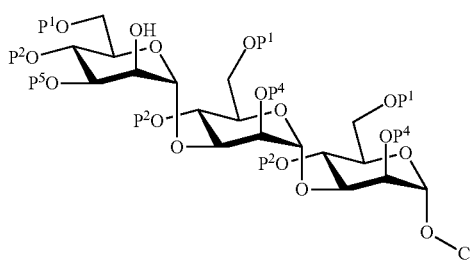
(4i)

wherein $P^1$, $P^2$, $P^4$ and $P^5$ represent protecting groups and C represents -L-$E_p$ with $E_p$ being a solid support or a protected end group E, wherein E and L have the meanings as defined herein;

I6) optionally repeating steps I2)-I5) in the following order I2)→I3)→I2)→I3)→I4)→I5) n−1 times to obtain intermediate compound of formula 5i

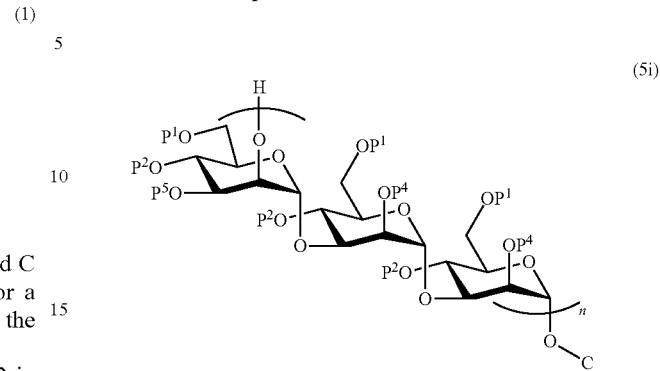
(5i)

wherein $P^1$, $P^2$, $P^4$ and $P^5$ represent protecting groups and C represents -L-$E_p$ with Ep being a solid support or a protected end group E, wherein n, E and L have the meanings as defined herein;

I7) performing removal of all protecting groups to obtain an oligosaccharide of general formula (I).

A further method of the synthesis of an oligosaccharide of general formula (I) comprises the following steps:

J1) providing a monosaccharide 1

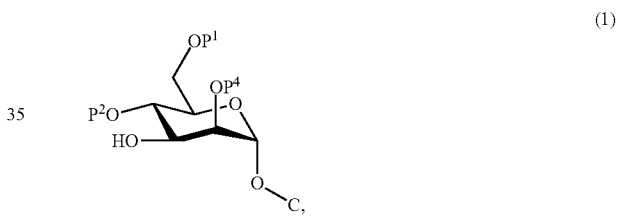
(1)

wherein $P^1$, $P^2$ and $P^4$ represent protecting groups and C represents -L-$E_p$ with Ep being a solid support or a protected end group E, wherein E and L have the meanings as defined herein;

J2) treating monosaccharide 1 with a building block 3 in presence of an activating agent

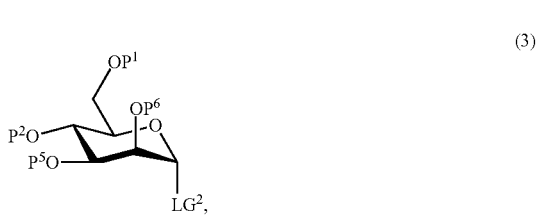
(3)

wherein $P^1$, $P^2$, $P^5$ and $P^6$ represent protecting groups and $LG^2$ represents a leaving group;

J3) performing removal of protecting group $P^6$

J4) treating the product of step J3) with building block 2 in presence of an activating agent

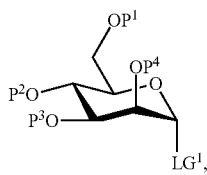
(2)

wherein P¹-P⁴ represent protecting groups and LG¹ represents a leaving group;

J5) performing removal of protecting group P³ to obtain intermediate compound 4j;

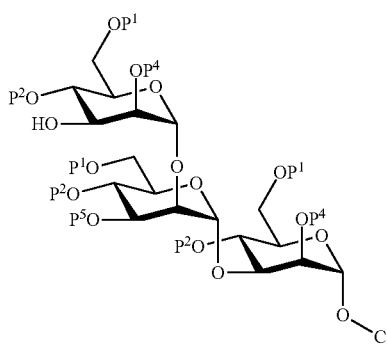
(4j)

wherein P¹, P², P⁴ and P⁵ represent protecting groups and C represents -L-$E_p$ with $E_p$ being a solid support or a protected end group E, wherein E and L have the meanings as defined herein;

J6) optionally repeating steps J2)-J5) in the following order J4)→J5)→J2)→J3)→J4)→J5) n−1 times to obtain intermediate compound of formula 5j

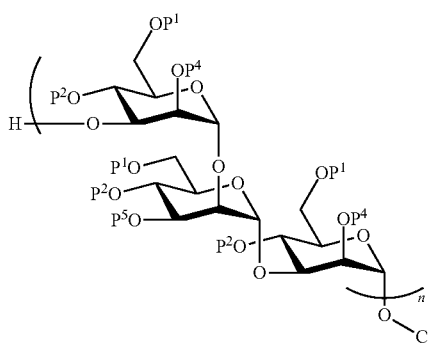
(5j)

wherein P¹, P², P⁴ and P⁵ represent protecting groups and C represents -L-$E_p$ with Ep being a solid support or a protected end group E, wherein n, E and L have the meanings as defined herein;

J7) performing removal of all protecting groups to obtain an oligosaccharide of general formula (I).

A further method of the synthesis of an oligosaccharide of general formula (I) comprises the following steps:

K1) providing a monosaccharide 6

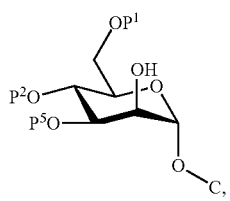
(6)

wherein P¹, P² and P⁵ represent protecting groups and C represents -L-$E_p$ with $E_p$ being a solid support or a protected end group E, wherein E and L have the meanings as defined herein;

K2) treating monosaccharide 6 with building block 2 in presence of an activating agent

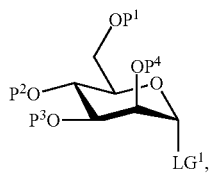
(2)

wherein P¹-P⁴ represent protecting groups and LG¹ represents a leaving group;

K3) performing removal of protecting group P³;

K4) repeating steps K2) and K3) to obtain intermediate compound 4k;

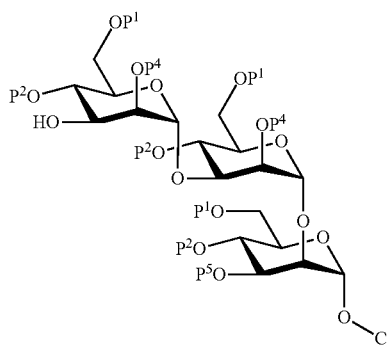
(4k)

wherein P¹, P², P⁴ and P⁵ represent protecting groups and C represents -L-$E_p$ with $E_p$ being a solid support or a protected end group E, wherein E and L have the meanings as defined herein;

K5) optionally treating compound 4k with a building block 3 in presence of an activating agent

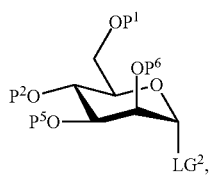
(3)

wherein P¹, P², P⁵, and P⁶ represent protecting groups and LG² represents a leaving group, performing removal of protecting group P⁶ and repeating steps K2)-K4) n−1 times to obtain intermediate compound of formula 5k

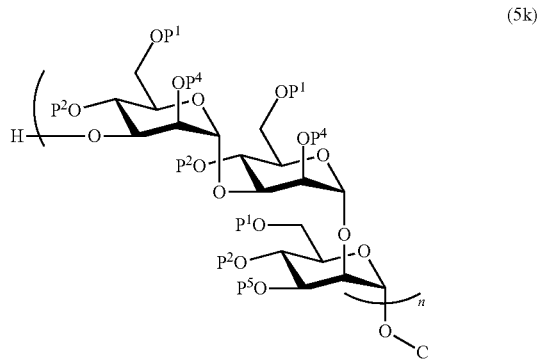

(5k)

wherein $P^1$, $P^2$, $P^4$ and $P^5$ represent protecting groups and C represents -L-$E_p$ with Ep being a solid support or a protected end group E, wherein n, E and L have the meanings as defined herein;

K7) performing removal of all protecting groups to obtain an oligosaccharide of general formula (I).

$E_p$ represents a solid support or a protected end group. E represents —NH₂, —N₃, —CN, —O—NH₂, —CH=CH₂, —C≡CH, —Br, —Cl, —I, —CO₂R', —CONHNH₂, —SH, or —SAc; and the corresponding protected end group $E_p$ represents —N($P^{13}$)($P^{14}$), —N₃, —CN, —O—N($P^{13}$)($P^{14}$), —CH=CH₂, —C≡CH, —Br, —Cl, —I, —CO₂R', —CONHN($P^{13}$)($P^{14}$), —SP$_s$, or —SAc $P^1$, $P^2$, $P^3$, $P^4$, $P^5$, $P^6$, $P^7$, $P^8$, $P^9$, $P^{10}$, $P^{11}$, $P^{12}$, $P^{13}$ and $P^{14}$ represent protecting groups. The term "protecting group" as used herein refers to commonly used groups in organic synthesis, preferably used for protection hydroxyl groups, and thiols. More preferably, $P^1$, $P^2$, $P^3$, $P^4$, $P^5$, $P^6$, $P^7$, $P^8$, $P^9$, $P^{10}$, $P^{11}$ and $P^{12}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzyledene, p-nitrophenyl, allyl, acetyl, isopropyl, p-bromobenzyl, dimethoxytrityl, trityl, 2-naphthylmethyl, pivaloyl, (2-nitrophenyl)acetyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl.

The protecting groups can be differentiated in permanent protecting groups and temporary protecting groups. Permanent protecting groups are protecting groups that are stable during the entire synthesis and that can be efficiently removed at the late stage of the synthesis. In this case, permanent protecting groups include $P^1$, $P^2$, $P^4$ $P^5$, $P^7$, $P^8$, $P^9$, $P^{12}$, $P^{13}$ and $P^{14}$. $P^1$, $P^2$, $P^4$ $P^5$, $P^7$, $P^8$, $P^9$ and $P^{12}$ are masking the hydroxyl groups during the entire synthesis, while protecting groups $P^{13}$ and $P^{14}$ are masking the terminal amino group present in the end group $E_p$. Preferably protecting groups $P^1$, $P^2$, $P^5$, $P^7$, $P^8$ and $P^9$ are benzyl groups, protecting group $P^4$ is a benzoyl group, protecting group $P^{12}$ is a benzyl group, protecting group $P^{13}$ is a benzyl group and protecting group $P^{14}$ is a benzyloxycarbonyl group (Cbz).

The temporary protecting groups are generally orthogonal protecting groups that can be selectively removed at different levels of the synthesis to free hydroxyl groups for subsequent introduction of different substituents, including monooligosaccharides, other protecting groups or other residues present on the molecule. In this case, temporary protecting groups include $P^3$, $P^6$, $P^{10}$ and $P^{11}$.

The ingenious choice of protecting groups allows expedient access to a library of oligosaccharides of general formulae (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k) functionalized with a terminal group for subsequent conjugation to an immunogenic carrier or a solid support. Moreover, the choice of leaving groups affects the stereochemical outcome of the glycosylation reactions in steps A2), A4), B2), B5), C2), C4), D2), D5), E2), E5), F2), F4), H2), H5), J2), J4), I2), I4), K2) and K5). From the prior art it is apparent for a skilled person to choose the protecting group and reaction conditions in order to obtain the desired mannose oligosaccharides of general formulae (I), (II), (II-a), (II-b), (II-c), (II-d), (II-e), (II-f), (II-g), (II-h), (II-i), (II-J), (II-k), (III), (III-a), (III-b), (III-c), (III-d), (III-e), (III-f), (III-g), (III-h), (III-i), (III-j) or (III-k) (see J. Chem. Soc., Perkin Trans. 1, 2000, 1471-1491 and Eur. J. Org. Chem. 2009, 870-888).

Temporary protecting groups $P^3$, $P^6$, $P^{10}$ and $P^{11}$ are preferably selected from, but are not restricted to: allyl, p-methoxybenzyl, 2-naphthylmethyl, tri-isopropylsilyl, tert-butyldimethylsilyl, tert-butylmethoxyphenylsilyl, triethylsilyl, trimethylsilyl, 2-trimethylsilylethoxymethyl, 9-fluorenylmethoxycarbonyl and levulinoyl. Preferably, protecting groups $P^3$, $P^6$, $P^{10}$ and $P^{11}$ can be selectively removed in presence of protecting groups $P^1$, $P^2$, $P^4$ $P^5$, $P^7$, $P^8$, $P^9$, $P^{12}$, $P^{13}$ and $P^{14}$. Preferably, $P^3$, $P^6$, $P^{10}$ and $P^{11}$ are 9-fluorenylmethoxycarbonyl or levulinoyl, and more preferably $P^3$ and $P^{11}$ are the same and $P^6$ and $P^{10}$ are the same. In a preferred embodiment, protecting groups $P^6$ and $P^{10}$ represent 9-fluorenylmethoxycarbonyl and protecting groups $P^3$ and $P^{11}$ represent -fluorenylmethoxycarbonyl or levulinoyl.

Building blocks 2, 3, 8 and 9 are glycosylating agents. As used herein, the term glycosylating agent refers to a monosaccharide functionalized at the anomeric position with a leaving group that upon activation with a suitable activating agent provide an oxocarbenium intermediate able to react with a nucleophile, such as a hydroxyl group. Hence, glycosylating agents 2, 3, 8 and 9 are functionalized at the anomeric position with leaving groups $LG^1$, $LG^2$, $LG^3$ and $LG^4$. Examples of leaving groups suitable for the present synthesis are well known to the person skilled in carbohydrate chemistry and include halides, thioethers, imidates, acetate, sulfoxide, pentenyl, and phosphate.

Preferably, leaving groups $LG^1$, $LG^2$, $LG^3$ and $LG^4$ are selected from the group of leaving groups consisting of:

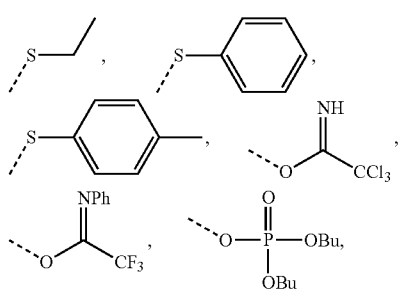

As mentioned, the provision of an oxocarbenium intermediate relies on the activation of the leaving group installed at the anomeric position of the glycosylating agent with an appropriate or suitable activating agent. It is common knowledge for the skilled person that suitable activating agents for phosphate (i.e. phosphate activating agents) and imidate (i.e. imidate activating agents) are Lewis acids, such as silyl triflate or silver triflate, while suitable activating agents for thioether i.e. thioether activating agents include, but are not restricted to: NIS/TfOH, NIS/TMSOTf, NIS/BF$_3$.Et$_2$O, NIS/AgOTf, DMTST/Tf$_2$O, IDPC, BSP/Tf$_2$O, Ph$_2$SO/Tf$_2$O. Examples of silyl triflate include, but are not restricted to trimethylsilyl trifluoromethanesulfonate, tert-butyl dimethyl trifluoromethanesulfonate, triiospropyl trifluoromethanesulfonate.

Preferably, LG$^1$, LG$^2$, LG$^3$ and LG$^4$ are thioethers and even more preferred is when LG$^1$, LG$^2$, LG$^3$ and LG$^4$ are selected from the group consisting of:

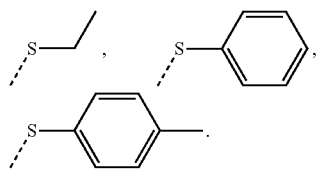

It is preferred that the coupling reaction between oligosaccharides in the steps A2), A4), B2), B5), C2), C4), D2), D5), E2), E5), F2), F4), G2), G4), H2), H5), J2), J4), I2), I4), K2) and K5) is performed by activation with NIS/TfOH or TMSOTf, in a mixture of apolar solvent and polar aprotic solvent at a temperature of between −78° C. or −50° C. to 0° C. or between −10° C. and +10° C. Even more preferred is that said reaction is performed in a mixture of apolar solvent and polar aprotic solvent, by treatment with NIS/TfOH at a temperature of about 0° C.

Preferred polar aprotic solvents are tetrahydrofuran, diethyl ether and dioxane. Preferred apolar solvents are toluene, halogenated solvents such as chloroform and methylene chloride. Preferred mixtures of apolar and polar aprotic solvent are: methylene chloride/tetrahydrofuran, methylene chloride/diethyl ether, toluene/diethyl ether, toluene/tetrahydrofuran.

The removal of protecting groups P$^1$, P$^2$, P$^4$ P$^5$, P$^7$, P$^8$, P$^9$, P$^{12}$, P$^{13}$ and P$^{14}$ performed at steps A8), B8), C9), D9), E8), F7), F4), G7), H8), I7), J7) and K7) involves:
  first cleavage of the base-labile protecting groups by treatment with a base optionally in presence of hydrogen peroxide in a mixture of solvents. Preferably, the base is NaOMe or LiOH; and
  second cleavage of the protecting groups sensitive to hydrogenation by subjecting the compound to hydrogen in presence of a palladium catalyst in a mixture of solvents.

A further aspect according to the present invention refers to an intermediate compound for preparing a oligosaccharide of the general formulae (I), (II), (II-a), (II-b), (II-c), (II-d), (II-e), (II-f), (II-g), (II-h), (II-i), (II-j), (II-k), (III), (III-a), (III-b), (III-c), (III-d), (III-e), (III-f), (III-g), (III-h), (III-i), (III-j) or (III-k), wherein the intermediate compound has any one of general formulae (I2a), (I2b), (I2c), (I2d), (I2e), (I2f), (I2g), (I2h), (I3a), (I3b), (I3c), (I3d), (I3e), (I3f), (I3g), (I3h), (I3i), (I3j), (I3k), (I3l), (I3m), (I3n), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i) or (I5j):

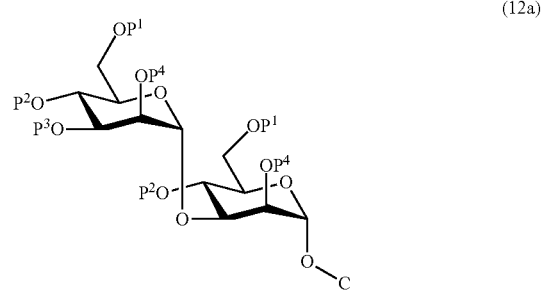
(12a)

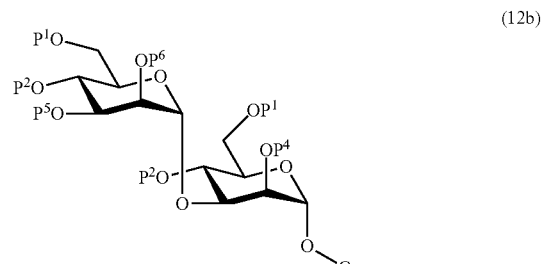
(12b)

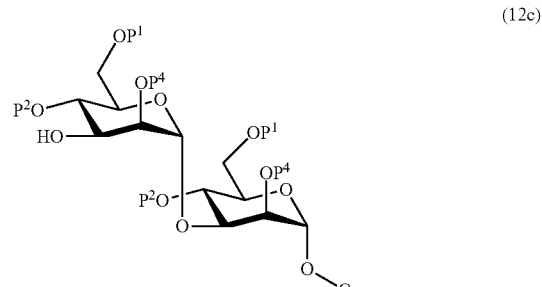
(12c)

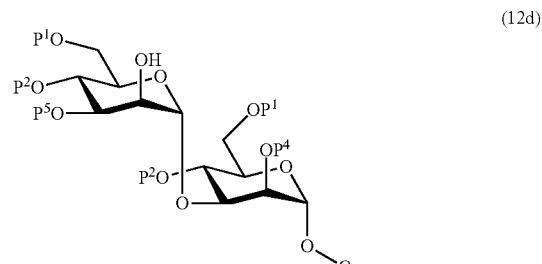
(12d)

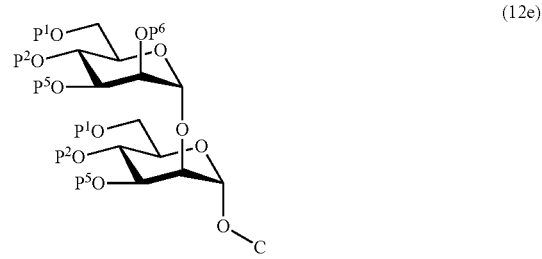
(12e)

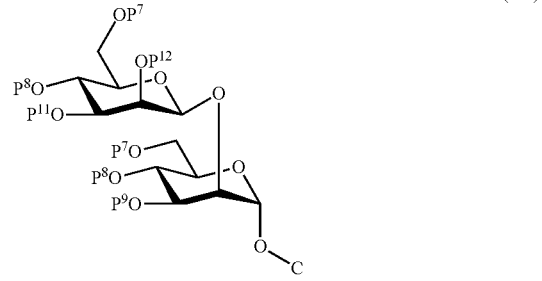
(12f)

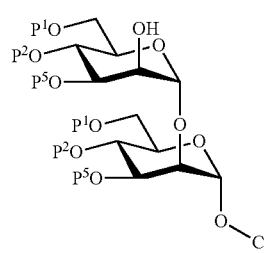
(12g)
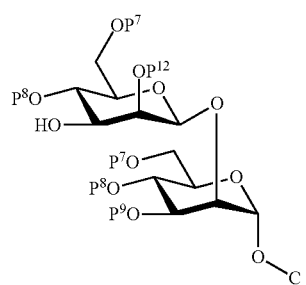
(12h)
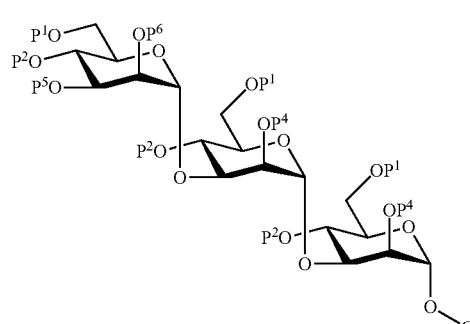
(13a)
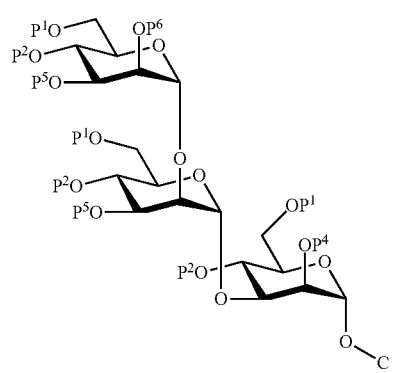
(13b)
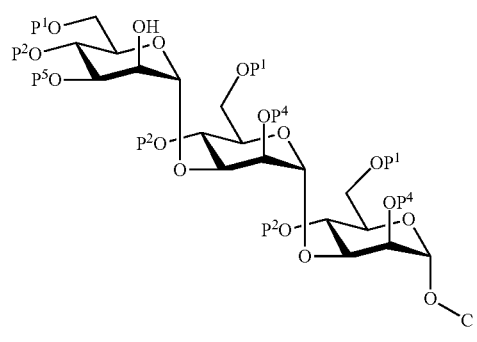
(13c)
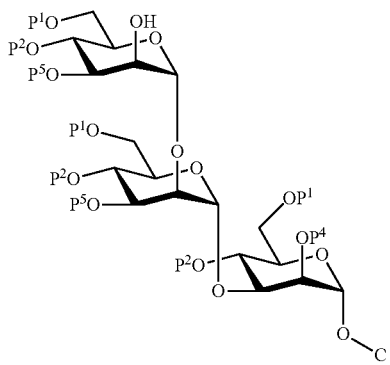
(13d)
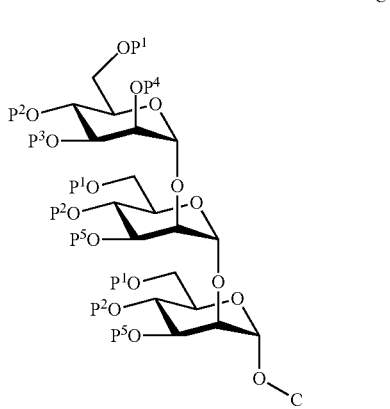
(13e)
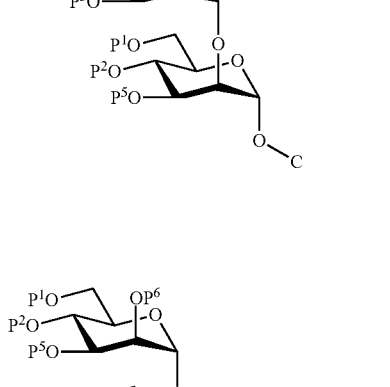
(13f)
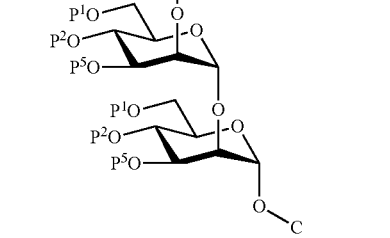
(13g)
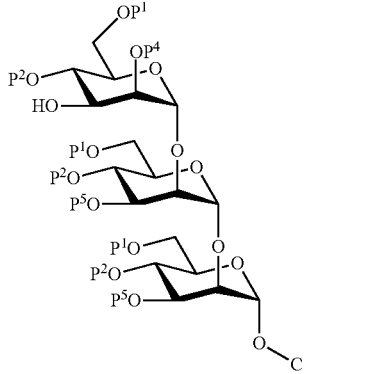

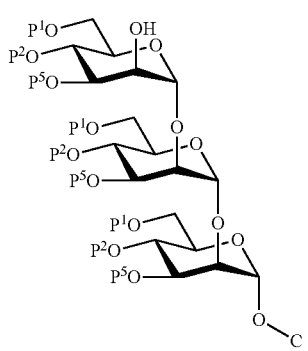
(13h)
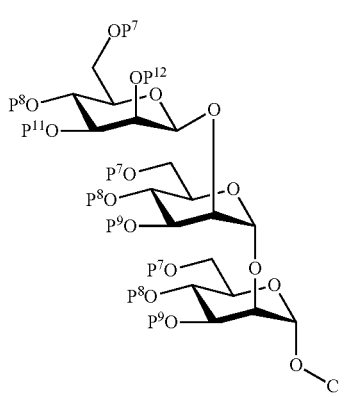
(13i)
(13j)
(13k)
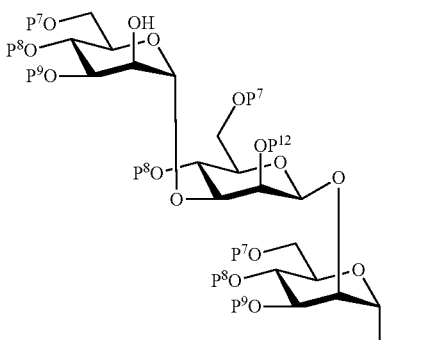
(13l)
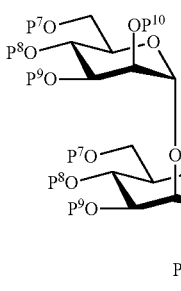
(13m)
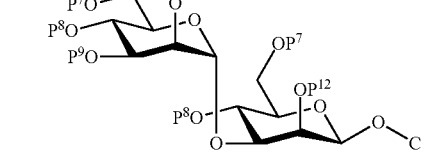
(13n)
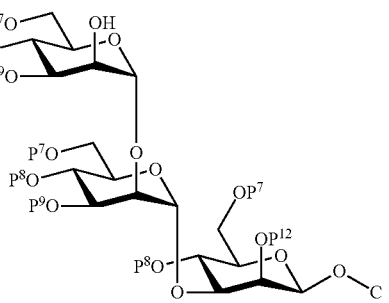
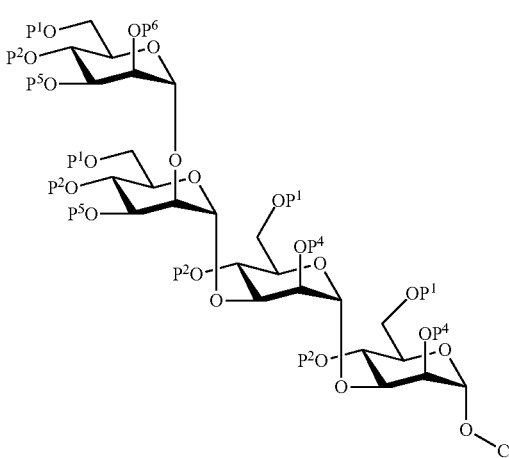
(14a)

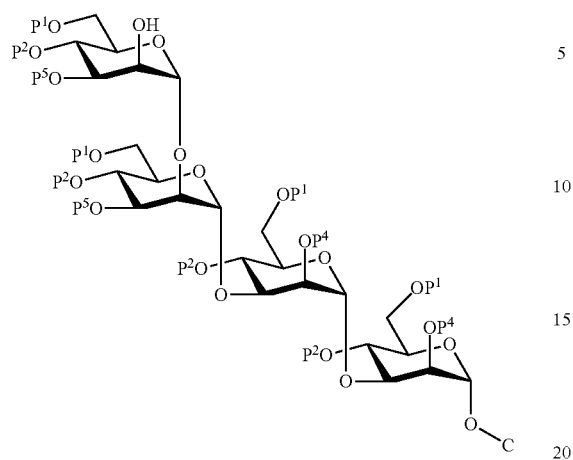
(14b)
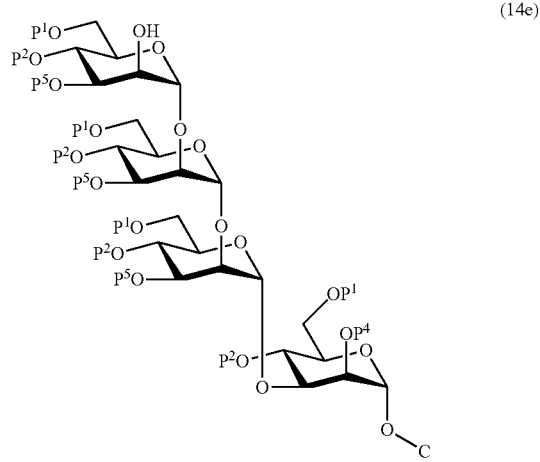
(14e)
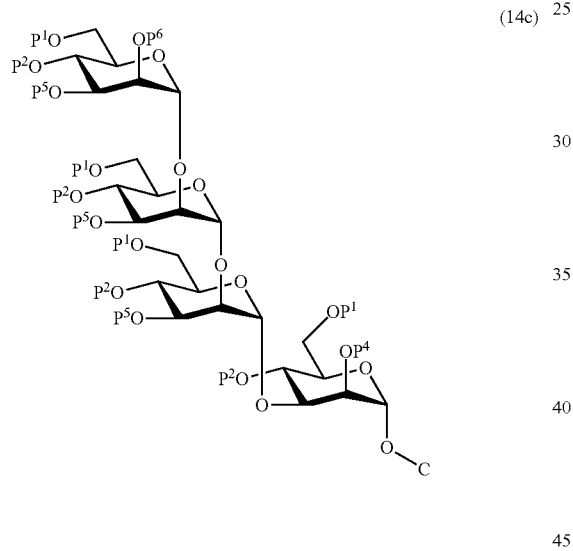
(14c)
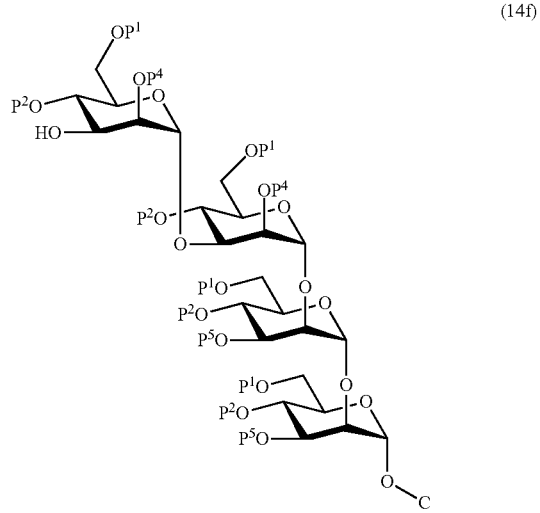
(14f)
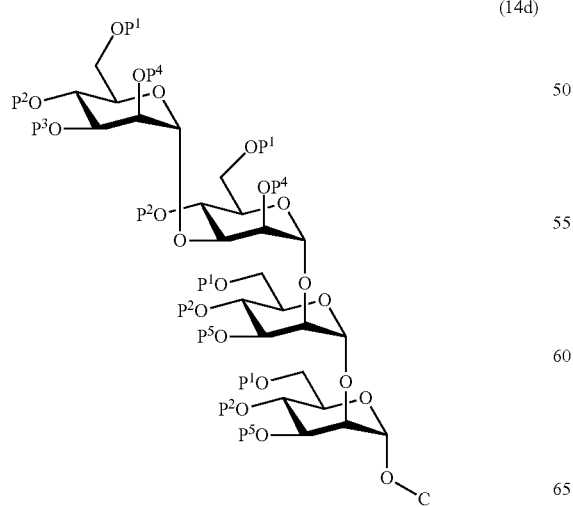
(14d)
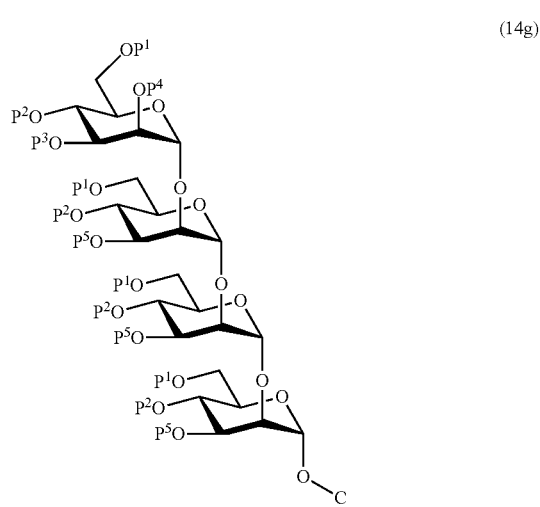
(14g)

(14h)
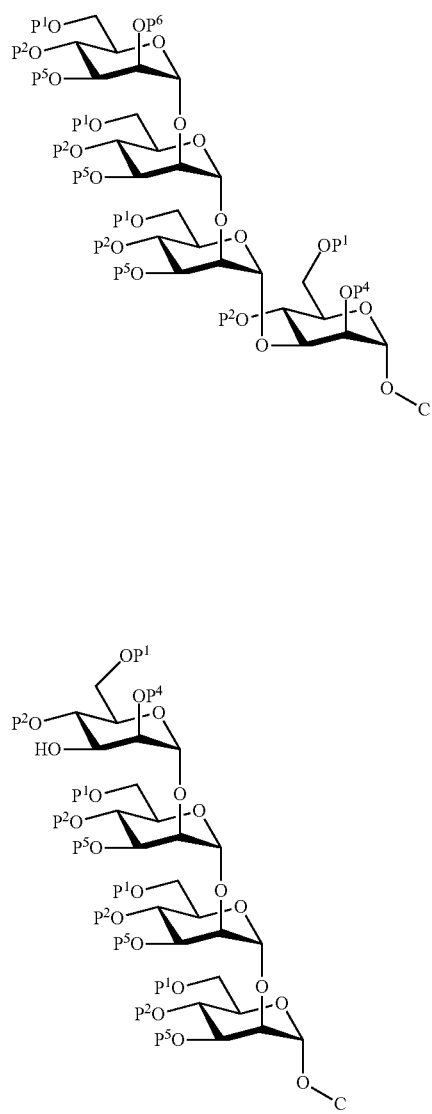
(14i)
(14j)
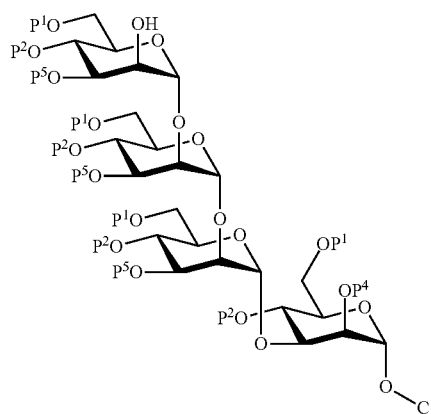
(15a)
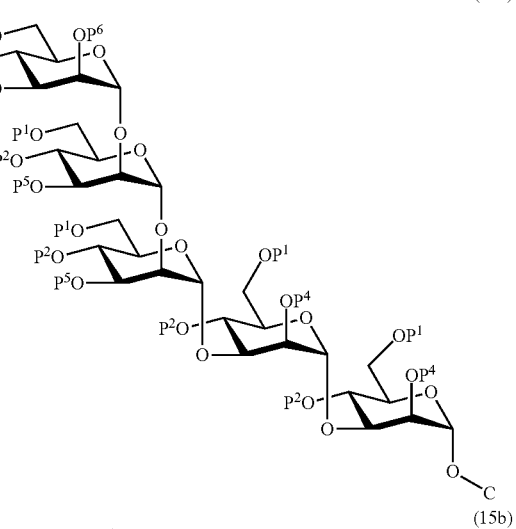
(15b)
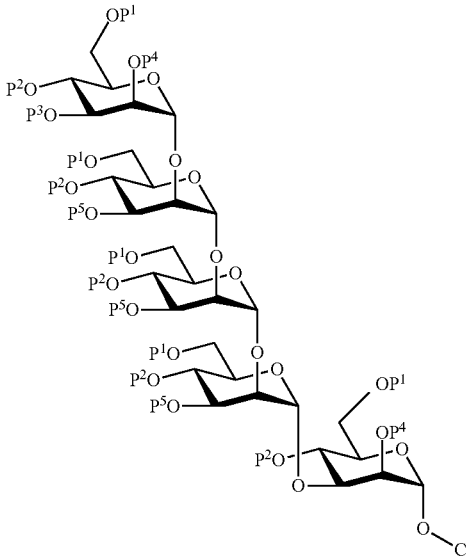
(15c)
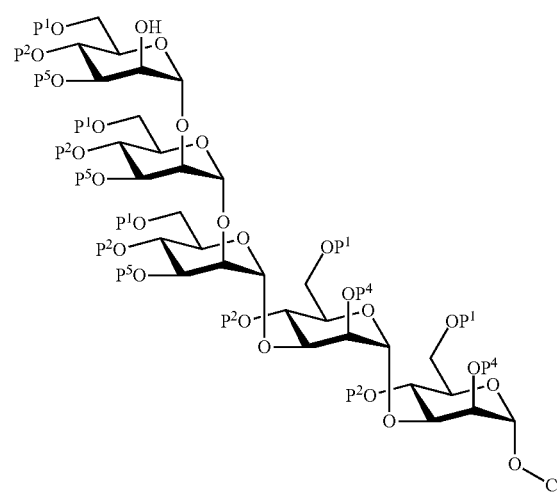

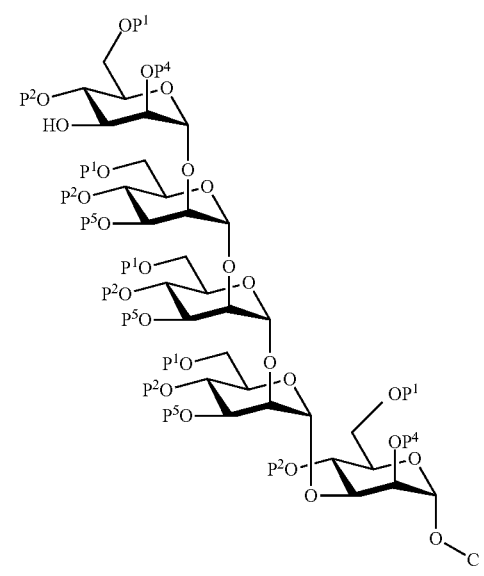

-continued (15j)

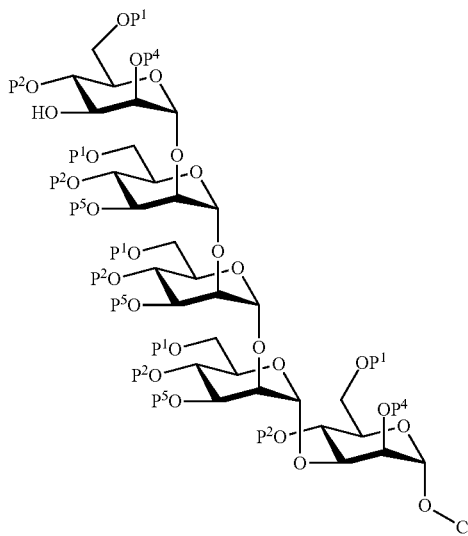

wherein C represents -L-$E_p$ with Ep being a solid support or a protected end group E, $P^1$, $P^2$, $P^3$, $P^4$, $P^5$, $P^6$, $P^7$, $P^8$, $P^9$, $P^{10}$, $P^{11}$ and $P^{12}$ represent protecting groups, and E and L have the same meanings as defined above.

In formulae (I2a), (I2b), (I2c), (I2d), (I2e), (I2f), (I2g), (I2h), (I3a), (I3b), (I3c), (I3d), (I3e), (I3f), (I3g), (I3h), (I3i), (I3j), (I3k), (I3l), (I3m), (I3n), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i) or (I5j), preferably the linker-L- represents -$L^a$-, -$L^a$-$L^e$-, -$L^a$-$L^b$-$L^e$-, or -$L^a$-$L^d$-$L^e$-;

-$L^a$- represents —$(CH_2)_o$—, —$(CH_2$—$CH_2$—$O)_o$— $C_2H_4$—, or —$(CH_2$—$CH_2$—$O)_o$—$CH_2$;

-$L^b$- represents —O—, —NH—CO—NH—, —NH—CO—$CH_2$—NH—, —NH—CO—;

-$L^d$- represents —$(CH_2)_q$—, —$(CH(OH))_q$—, —$(CF_2)_q$—, —$(CH_2$—$CH_2$—$O)_q$—$C_2H_4$—, or —$(CH_2$—$CH_2$—$O)_q$—$CH_2$—;

-$L^e$- represents —$(CH_2)_{p1}$—, —$(CF_2)_{p1}$—, —$C_2H_4$—(O—$CH_2$—$CH_2)_{p1}$—, —$CH_2$—(O—$CH_2$—$CH_2)_{p1}$— or —$(CH_2)_{p1}$—O—$(CH_2)_{p2}$—; and o, q, p1 and p2 are independently of each other an integer selected from 1, 2, 3, 4, 5, and 6; preferably an integer selected from 1, 2, 3, and 4.

An especially preferred intermediate is an intermediate of formula (I2a), (I2b), (I2c), (I2d), (I2e), (I2f), (I2g), (I2h), (I3a), (I3b), (I3c), (I3d), (I3e), (I3f), (I3g), (I3h), (I3i), (I3j), (I3k), (I3l), (I3m), (I3n), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i) or (I5j), wherein -L-represents —$(CH_2)_o$— and o is an integer selected from 2, 5 and 6.

$P^1$, $P^2$, $P^3$, $P^4$, $P^5$, $P^6$, $P^7$, $P^8$, $P^9$, $P^{10}$, $P^{11}$ and $P^{12}$ are suitable protecting groups for hydroxyl groups, more preferably different suitable protecting groups for hydroxyl groups capable of being removed subsequently one after another by a suitable sequence of deprotection reactions. Preferred protecting groups for hydroxyl groups are acetyl, phenyl, benzyl, isopropylidene, benzylidene, benzoyl, p-methoxybenzyl, p-methoxybenzylidene, p-methoxyphenyl, p-bromobenzyledene, p-nitrophenyl, allyl, acetyl, isopropyl, p-bromobenzyl, dimethoxytrityl, trityl, 2-naphthylmethyl, pivaloyl, (2-nitrophenyl)acetyl, triisopropylsilyl, tert-butyldimethylsilyl, tert-butyldiphenylsilyl, tert-butylmethoxyphenylsilyl, triethylsilyl, trimethylsilyl, 2-trimethylsilylethoxymethyl, 9-fluorenylmethoxycarbonyl, benzyloxymethyl, methyloxymethyl, tert-butyloxymethyl, methoxyethyloxymethyl, levulinoyl.

Thus, intermediates (I2a), (I2b), (I2c), (I2d), (I2e), (I2f), (I2g), (I2h), (I3a), (I3b), (I3c), (I3d), (I3e), (I3f), (I3g), (I3h), (I3i), (I3j), (I3k), (I3l), (I3m), (I3n), (I4a), (I4b), (I4c), (I4d), (I4e), (I4f), (I4g), (I4h), (I4i), (I4j), (I5a), (I5b), (I5c), (I5d), (I5e), (I5f), (I5g), (I5h), (I5i) or (I5j), are especially preferred when protecting groups $P^1$, $P^2$, $P^5$, $P^7$, $P^8$ and $P^9$ are benzyl groups, protecting group, $P^3$, $P^6$, $P^{10}$ and $P^{11}$ are 9-fluorenylmethoxycarbonyl or levulinoyl groups, $P^4$ and $P^{12}$ are benzoyl groups, protecting group $P^{13}$ is a benzyl group and protecting group $P^{14}$ is a benzyloxycarbonyl group (Cbz).

Glycoconjugates

Another aspect of the present invention refers to a conjugate comprising an oligosaccharide of general formula (I) covalently bound or covalently linked to an immunogenic carrier through the terminal group E of the —O-L-E group. In other words, another aspect of the present invention is directed to an oligosaccharide of any of the general formulae (I), (II), (II-a)-(II-k), (III), (III-a)-(III-j) or (III-k) conjugated with an immunogenic carrier through the terminal group E of the —O-L-E group. A conjugate comprising a synthetic oligosaccharide of the general formula (I), (II), (II-a)-(II-k), (III), (III-a)-(III-j) or (III-k), covalently bound or covalently linked to an immunogenic carrier through the terminal group E of the —O-L-E group is also defined as a conjugate obtained by reacting an oligosaccharide of any of the general formulae (I), (II), (II-a)-(II-k), (III), (III-a)-(III-j) or (III-k) with an immunogenic carrier. Surprisingly, said conjugate proved to be efficient as a vaccine for immunization against diseases associated with *Klebsiella pneumoniae* serotype O3, O3b and/or O5 bacteria.

Oligosaccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated and neither isotype switching from IgM to other IgG subclasses, nor B cells affinity maturation occurs. Moreover, oligosaccharides are known poor immunogens in humans due to the structural homology to human glycolipids and glycoproteins. Due to their poor immunogenic properties, oligosaccharides manifest poor ability to produce both antibody production by B cells, as well as the formation of memory cells, features which are essential for the production of potent vaccines.

Therefore, to produce a potent oligosaccharide-based vaccine, the oligosaccharides of general formulae (I), (II), (II-a)-(II-k), (III), (III-a)-(III-j) or (III-k) are conjugated to an immunogenic carrier to provide conjugates, which present increased immunogenicity in comparison with the oligosaccharide. Hence, under the scope of the present application is covered also a conjugate comprising a oligosaccharide fragment

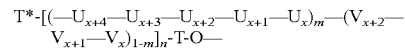

wherein m, n, x, $U_{x+1}$, $U_{x+2}$, $U_{x+3}$, $U_{x+4}$, $V_x$, $V_{x+1}$, $V_{x+2}$, T and T* have the meanings defined herein, covalently linked through the O atom to an immunogenic carrier.

Said conjugate comprises at least one synthetic oligosaccharide of the general formula (I) and an immunogenic carrier to which the at least one oligosaccharide (I) is covalently bound.

Surprisingly it was found that immunization with a conjugate comprising a oligosaccharide of general formula (I) covalently linked to an immunogenic carrier results in the production of high titers of antibodies specific to the carbohydrate part of the oligosaccharide of general formula (I). Said antibodies are cross-reacting with the natural *Klebsiella pneumoniae* serotype O3, O3b and/or O5 lipopolyoligosaccharides and present opsonophagocytosis and bactericidal activity, thus conferring protection against *Klebsiella pneumoniae* serotype O3, O3b and/or O5 bacteria.

In this context the term "immunogenic carrier" is defined as a structure, which is conjugated to the oligosaccharide to form a conjugate that presents an increased immunogenicity in comparison with the oligosaccharide per se. Thus, the conjugation of the oligosaccharides of the general formulae (I), (II), (II-a)-(II-k), (III), (III-a)-(III-j) or (III-k) to the immunogenic carrier has as effect the stimulation of the immune response against the oligosaccharide of general formula (I) without inducing an immune response against said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, non-lipidated cell-surface liporotein (protein D) of non-typeable *Haemophilus influenzae*, outer membrane protein (OMP) complex of *Neisseria meningitidis*, bovine serum albumin (BSA), keyhole limpet hemocyanine (KLH), recombinant non-toxic form of *Pseudomonas aeruginosa* exotoxin A (rEPA) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP) (see FIG. 2).

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the oligosaccharides of general formula I are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Said functional group X of the interconnecting molecules is selected of the group comprising or consisting of maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 3).

Preferably, the oligosaccharide of general formula I is conjugated to the non-toxic mutated diphtheria toxin $CRM_{197}$, which is modified by maleimide. In yet another preferred embodiment, the oligosaccharide of general formula I is conjugated to the non-toxic mutated diphtheria toxin $CRM_{197}$, which is modified by α-bromoacetamide. In the most preferred embodiment, the oligosaccharide of general formula I is conjugated to the non-toxic mutated diphtheria toxin $CRM_{197}$, which is modified by N-hydroxysuccinimide adipate.

Preferred is a conjugate of general formula (IV)

$$[T^*\text{-}((—U_{x+4}—U_{x+3}—U_{x+2}—U_{x+1}—U_x)_m—(V_{x+2}—V_{x+1}—V_x)_{1-m})_n\text{-}T\text{-}O\text{-}L\text{-}E_1\text{-}W]_c\text{-}CP \quad (IV)$$

wherein c is comprised between 2 and 18;

$-E_1-$ represents a covalent bond, —NH—, —O—NH—, —O—, —S—, —CO—, —CH═CH—, —CONH—, —CO—NHNH—,

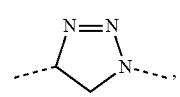

,

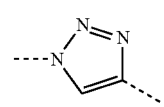

,

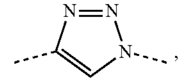

, or

;

—W— is selected from:

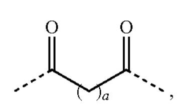

,

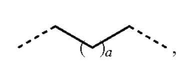

, and

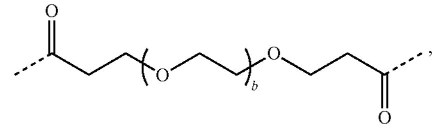

, a represents an integer selected from 1, 2, 3, 4, 5, 6, 7, 8, 9 and 10, b represents an integer selected from 1, 2, 3 and 4, CP is a carrier protein; and m, n, x, L, $U_{x+1}$, $U_{x+2}$, $U_{x+3}$, $U_{x+4}$, $V_x$, $V_{x+1}$, $V_{x+2}$, T and T* have the meanings as defined herein.

Preferably $E_1$ is a covalent bond, —NH—, —CH=CH—, —CONH—,

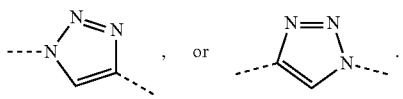

Preferably CP is $CRM_{197}$. Thus, in one embodiment of the present invention the conjugate is of general formula (IV), wherein CP is $CRM_{197}$ and c, $-E_1-$, W, m, n, x, L, $U_{x+1}$, $U_{x+2}$, $U_{x+3}$, $U_{x+4}$, $V_x$, $V_{x+1}$, $V_{x+2}$, T and T* have the meanings as defined herein.

Preferably, in general formula (IV) the linker -L- is selected from: $-L^a-$, $-L^a-L^e-$, $-L^a-L^b-L^e-$, and $-L^a-L^d-L^e-$;

$-L^a-$ is selected from: —$(CH_2)_o$—, —$(CH_2$—$CH_2$—$O)_o$—$C_2H_4$—, —$(CH_2$—$CH_2$—$O)_o$—$CH_2$;

$-L^b-$ represents —O—, —NH—CO—NH—, —NH—CO—$CH_2$—NH—, —NH—CO—;

$-L^d-$ is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

$-L^e-$ is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

and o, q, p1 and p2 are independently of each other an integer selected from 1, 2, 3, 4, 5, and 6; preferably an integer selected from 1, 2, 3, and 4.

Also a conjugate of general formula (IV), wherein —W— represents

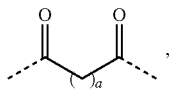

and a is an integer selected from 2, 3, 4, 5 and 6 is preferred.

A conjugate of general formula (IV), wherein the linker -L- is selected from: $-L^a-$, $-L^a-L^e-$, $-L^a-L^b-L^e-$, and $-L^a-L^d-L^e-$;

$-L^a-$ is selected from: —$(CH_2)_o$—, —$(CH_2$—$CH_2$—$O)_o$—$C_2H_4$—, —$(CH_2$—$CH_2$—$O)_o$—$CH_2$;

$-L^b-$ represents —O—, —NH—CO—NH—, —NH—CO—$CH_2$—NH—, —NH—CO—;

$-L^d-$ is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

$-L^e-$ is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

o, q, p1 and p2 are independently of each other an integer selected from 1, 2, 3, 4, 5, and 6; preferably an integer selected from 1, 2, 3, and 4;

—W— represents

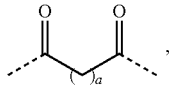

and a is an integer selected from 2, 3, 4, 5 and 6 is especially preferred.

Even more preferred is a conjugate of general formula (IV), wherein x represents 1, V*- represents H—, the linker -L- is selected from: $-L^a-$, $-L^a-L^e-$, $-L^a-L^b-L^e-$, and $-L^a-L^d-L^e-$;

$-L^a-$ is selected from: —$(CH_2)_o$—, —$(CH_2$—$CH_2$—$O)_o$—$C_2H_4$—, —$(CH_2$—$CH_2$—$O)_o$—$CH_2$;

$-L^b-$ represents —O—, —NH—CO—NH—, —NH—CO—$CH_2$—NH—, —NH—CO—;

$-L^d-$ is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;

$-L^e-$ is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— and —$(CH_2)_{p1}$—O—$(CH_2)_{p2}$—;

o, q, p1 and p2 are independently of each other an integer selected from 1, 2, 3, 4, 5, and 6; preferably an integer selected from 1, 2, 3, and 4;

—W— represents

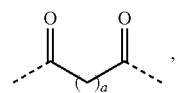

and a is an integer selected from 2, 3, 4, 5 and 6.

Particularly preferred is a conjugate of general formula (IV), wherein the linker -L-represents —$(CH_2)_o$—, o is an integer selected from 2, 3, 4, 5 and 6;

—W— represents

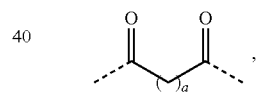

and a is an integer selected from 2, 3, 4, 5 and 6.

Also preferred is a conjugate of general formula (IV), wherein x represents 1,

V*- represents H—, the linker -L- represents —$(CH_2)_o$—, o is an integer selected from 2, 3, 4, 5 and 6;

—W— represents

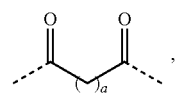

and a is an integer selected from 2, 3, 4, 5 and 6.

Preferably c is comprised between 2 and 18, more preferably between 5 and 15, even more preferably between 8 and 12. It is also preferred that n represents 1.

Preferred is also a conjugate of general formula (V)

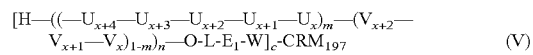

[H—((—$U_{x+4}$—$U_{x+3}$—$U_{x+2}$—$U_{x+1}$—$U_x$)$_m$—($V_{x+2}$—$V_{x+1}$—$V_x$)$_{1-m}$)$_n$—O-L-$E_1$-W]$_c$-$CRM_{197}$ (V)

wherein
c is comprised between 2 and 18;
-$E_1$- represents a covalent bond, —NH—, —O—NH—, —O—, —S—, —CO—, —CH=CH—, —CONH—, —CO—NHNH—,

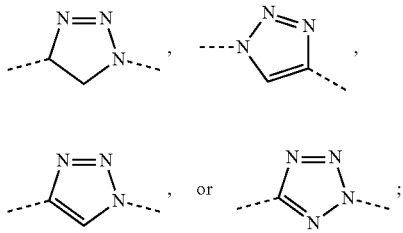

—W— is selected from:

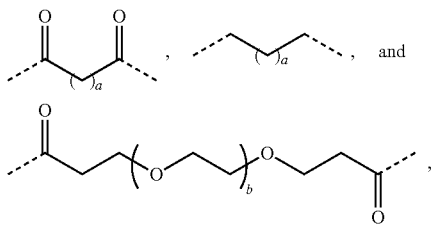

a represents an integer selected from 1, 2, 3, 4, 5, 6, 7, 8, 9 and 10,
b represents an integer selected from 1, 2, 3 and 4; and m, n, x, L, $U_{x+1}$, $U_{x+2}$, $U_{x+3}$, $U_{x+4}$, $V_x$, $V_{x+1}$ and $V_{x+2}$ have the meanings as defined herein.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci.* USA, 1998, 95, 5690).

The conjugates of the oligosaccharides of general formula I with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the oligosaccharides of general formula I to provide conjugates of the oligosaccharides of general formula I, or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the oligosaccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride.

A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected of the group comprising or consisting of maleimide, α-iodoacetyl, α-bromoacetyl, N-hydroxysuccinimide ester (NHS), aldehyde, carboxylic acid, epoxide, alkyl sulfonate, sulfonyl chloride, anhydride, carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

Vaccines containing at least one conjugate of the present invention cause fewer side effects and/or non-protective immune responses in comparison to vaccines containing isolated (and not synthesized) mixtures of oligosaccharides obtained by non-selective cleavage of the capsular poly-, oligosaccharide of *Klebsiella pneumoniae* or conjugates thereof. Moreover the inventive vaccines can be easier manufactured in accordance with the GMP regulations than the vaccines containing isolated mixtures of non-selectively cleaved capsular poly-,oligosaccharides and are easier characterized, which makes stability and purity control easier as well as detection of kind and amount of impurities.

More preferred is a conjugate of any one of the formulae (V-1)-(V-11):

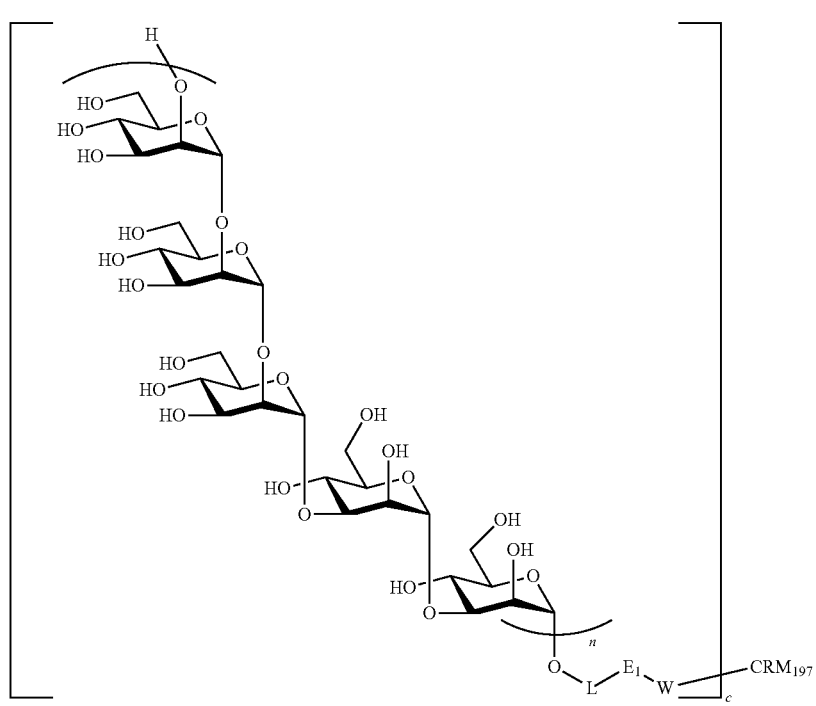
(V-1)
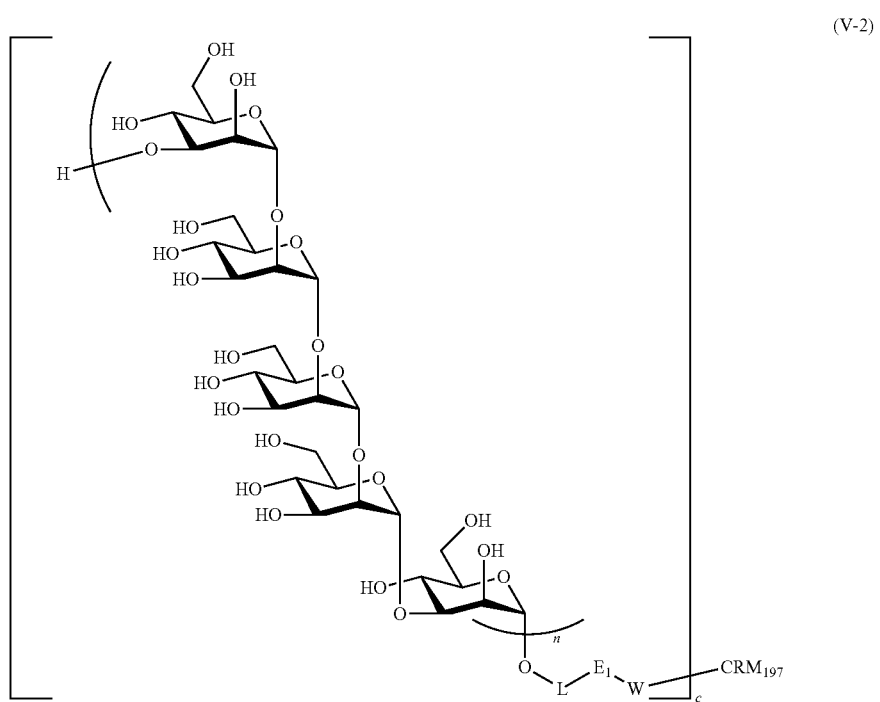
(V-2)

(V-3)
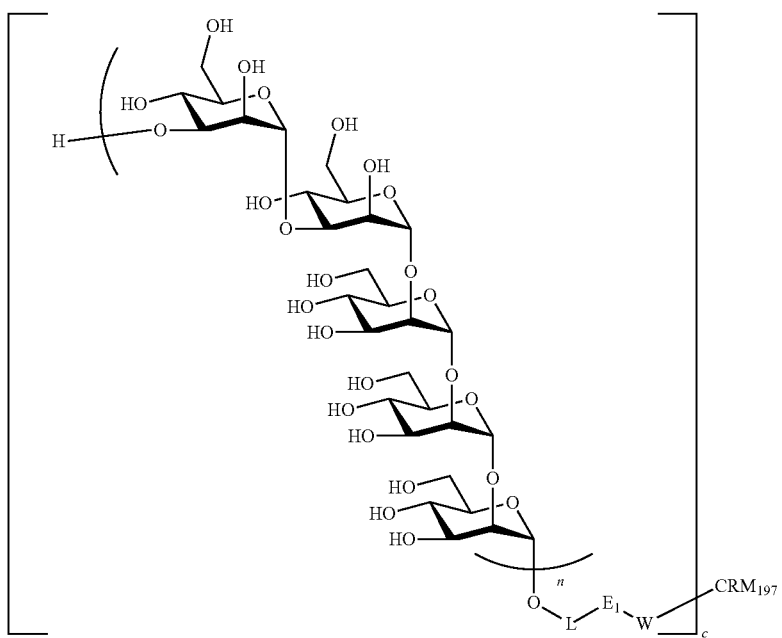
(V-4)
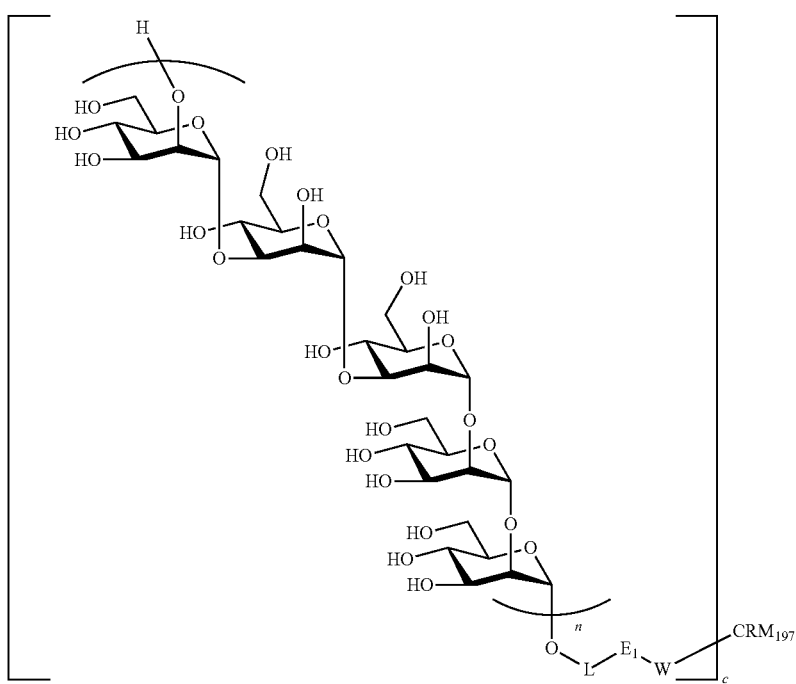

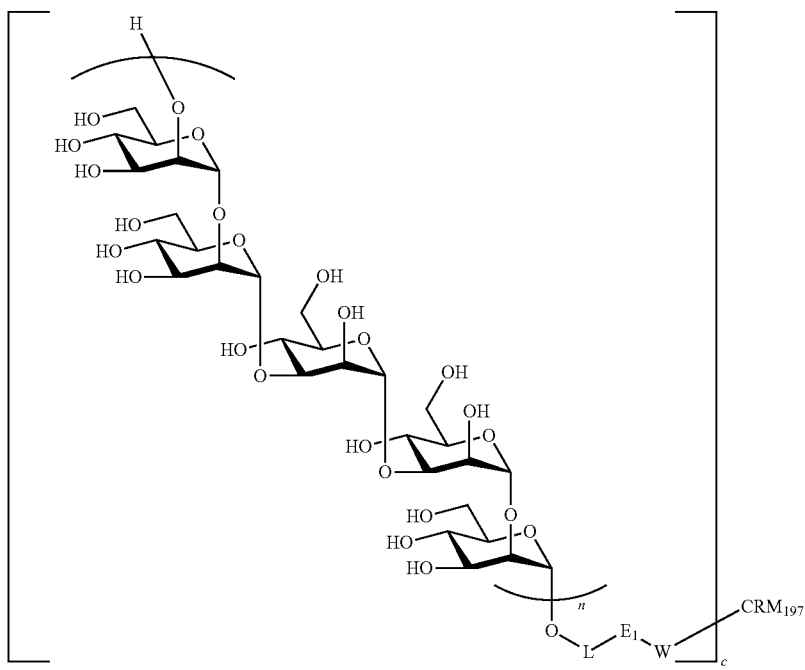
(V-5)
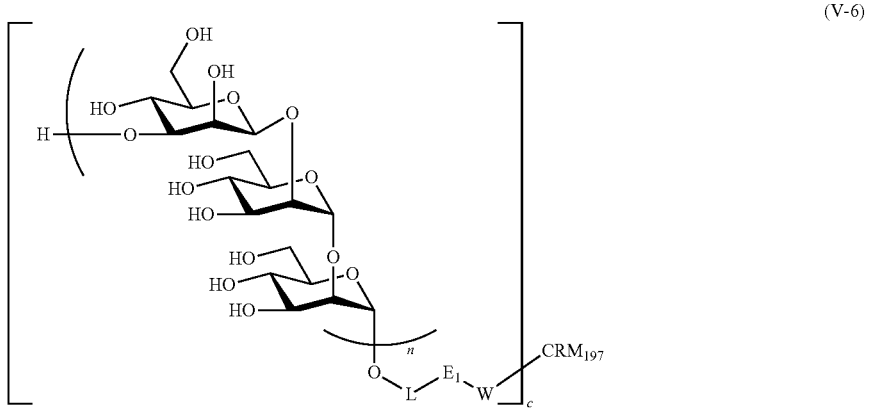
(V-6)
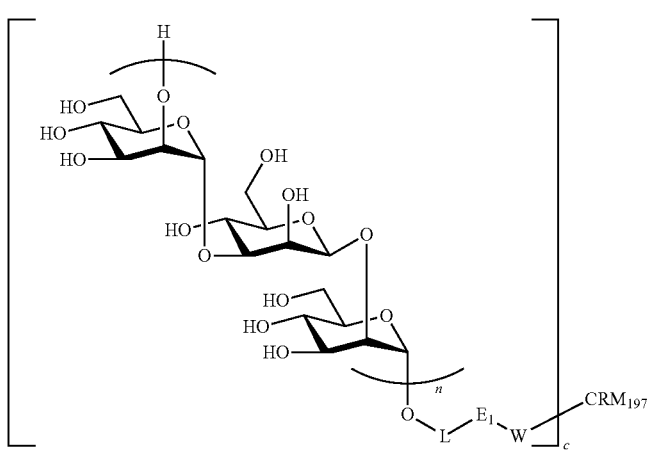
(V-7)

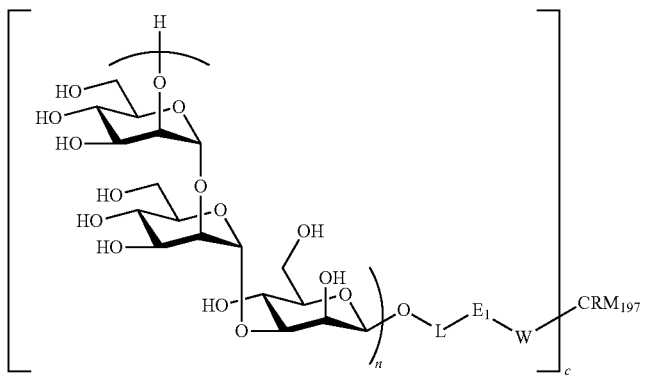
(V-8)
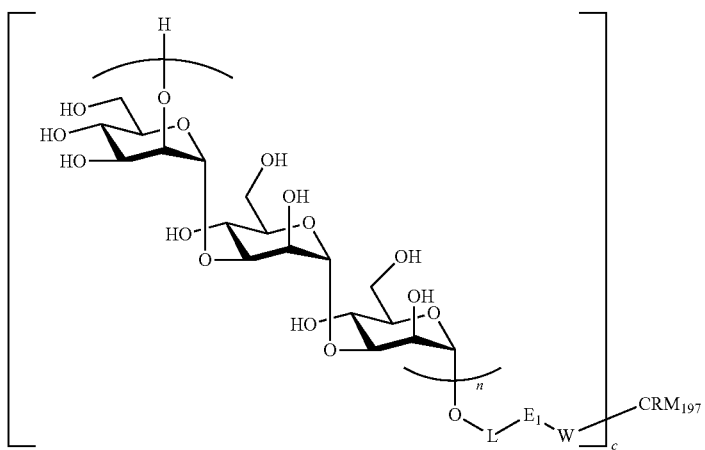
(V-9)
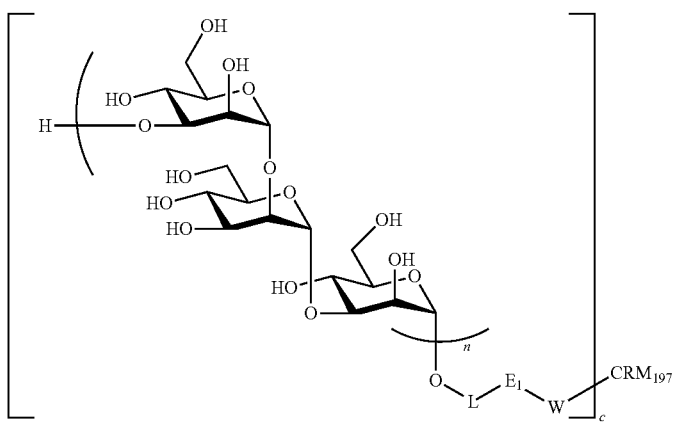
(V-10)

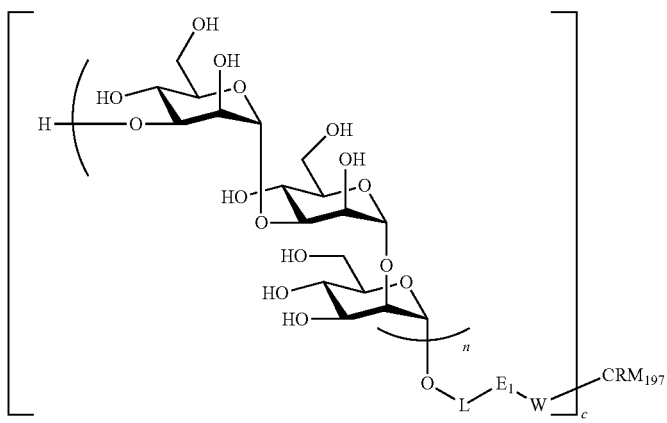

(V-11)

wherein L, $E_1$, W, c, and n have the same meanings as defined above.

More preferred is a conjugate of any one of the formulae (IV), (V) and (V-1)-(V-11), wherein n is an integer from 2 to 10.

More preferred the conjugate of any one of the formulae (IV), (V) and (V-1)-(V-11), wherein c is selected from 4 to 10.

Preferably —W— represents

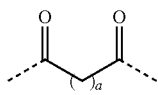

and a is an integer selected from 2, 3, 4, 5 and 6.

Thus, a conjugate of general formula (IV), (V) and (V-1)-(V-11), wherein —W— represents

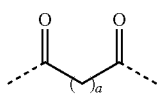

and a is an integer selected from 2, 3, 4, 5 and 6 is especially preferred.

Preferably, the linker -L- represents -$L^a$-, -$L^a$-$L^e$-, -$L^a$-$L^b$-$L^e$-, or -$L^a$-$L^d$-$L^e$-;

-$L^a$- represents —$(CH_2)_o$—, —$(CH_2$—$CH_2$—$O)_o$—$C_2H_4$—, or —$(CH_2$—$CH_2$—$O)_o$—$CH_2$;

-$L^b$- represents —O—, —NH—CO—NH—, —NH—CO—$CH_2$—NH—, —NH—CO—;

-$L^d$- represents —$(CH_2)_q$—, —$(CH(OH))_q$—, —$(CF_2)_q$—, —$(CH_2$—$CH_2$—$O)_q$—$C_2H_4$—, or —$(CH_2$—$CH_2$—$O)_q$—$CH_2$—;

-$L^e$- represents —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$— or —$(CH_2)_{p1}$—O—$(CH_2)_{p2}$—; and o, q, p1 and p2 are independently of each other an integer selected from 1, 2, 3, 4, 5, and 6; preferably an integer selected from 1, 2, 3, and 4.

In the most preferred embodiment, $E_1$ is a covalent bond, —NH—, —CH=CH—, —CONH—,

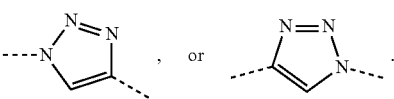

It was found that a conjugate comprising a oligosaccharide of any one of general formulae (I), (II), (II-a)-(II-k), (III), (III-a)-(III-j) or (III-k), and particularly a conjugate of any one of general formulae (IV), (V) and (V-1)-(V-11), elicits a protective immune response in a human and/or animal host, and therefore is useful for prevention and/or treatment of diseases associated with Klebsiella pneumoniae serotype O3, O3b and/or O5 bacteria. Thus, the conjugates comprising the oligosaccharides of general formula (I) conjugated to an immunogenic carrier are useful for prevention and/or treatment of diseases associated with Klebsiella pneumoniae bacteria containing in their lipopolysaccharide one of the following oligosaccharide fragments:

2)-α-D-Man-(1, 2)-α-D-Man-(1, 2)-α-D-Man-(1, 3)-α-D-Man-(1, 3)-α-D-Man-(1-;

3)-α-D-Man-(1, 2)-α-D-Man-(1, 2)-α-D-Man-(1, 2)-α-D-Man-(1, 3)-α-D-Man-(1-;

3)-α-D-Man-(1, 3)-α-D-Man-(1, 2)-α-D-Man-(1, 2)-α-D-Man-(1, 2)-α-D-Man-(1-;

2)-α-D-Man-(1, 3)-α-D-Man-(1, 3)-α-D-Man-(1, 2)-α-D-Man-(1, 2)-α-D-Man-(1-;

2)-α-D-Man-(1, 2)-α-D-Man-(1, 3)-α-D-Man-(1, 3)-α-D-Man-(1, 2)-α-D-Man-(1-;

3)-β-D-Man-(1, 2)-α-D-Man-(1, 2)-α-D-Man-(1-;

2)-α-D-Man-(1, 3)-β-D-Man-(1, 2)-α-D-Man-(1-;

2)-α-D-Man-(1, 2)-α-D-Man-(1, 3)-β-D-Man-(1-;

2)-α-D-Man-(1, 3)-α-D-Man-(1, 3)-α-D-Man-(1-;

3)-α-D-Man-(1, 2)-α-D-Man-(1, 3)-α-D-Man-(1-;

3)-α-D-Man-(1, 3)-α-D-Man-(1, 2)-α-D-Man-(1-.

Preferably, the bacterium containing in the lipopolysaccharide one of the above mentioned oligosaccharide fragments is Klebsiella pneumoniae serotype O3, O3b and/or O5.

In a preferred embodiment, the conjugates comprising the oligosaccharides of general formula I conjugated to an immunogenic carrier are useful for prevention and/or treatment of diseases associated with bacteria, and particularly with diseases associated with bacteria containing in their O-polysaccharide one of the following oligosaccharide fragments: -2)-α-D-Man-(1, 2)-α-D-Man-(1, 2)-α-D-Man-(1, 3)-α-D-Man-(1, 3)-α-D-Man-(1-; -3)-α-D-Man-(1, 2)-α-D-

Man-(1, 2)-α-D-Man-(1, 2)-α-D-Man-(1, 3)-α-D-Man-(1-; -3)-α-D-Man-(1, 3)-α-D-Man-(1, 2)-α-D-Man-(1, 2)-α-D-Man-(1, 2)-α-D-Man-(1-; -2)-α-D-Man-(1, 3)-α-D-Man-(1, 3)-α-D-Man-(1, 2)-α-D-Man-(1, 2)-α-D-Man-(1-; -2)-α-D-Man-(1, 2)-α-D-Man-(1, 3)-α-D-Man-(1, 3)-α-D-Man-(1, 2)-α-D-Man-(1-; -3)-β-D-Man-(1, 2)-α-D-Man-(1, 2)-α-D-Man-(1-; -2)-α-D-Man-(1, 3)-β-D-Man-(1, 2)-α-D-Man-(1-; -2)-α-D-Man-(1, 2)-α-D-Man-(1, 3)-β-D-Man-(1-; -2)-α-D-Man-(1, 3)-α-D-Man-(1, 3)-α-D-Man-(1-; -3)-α-D-Man-(1, 2)-α-D-Man-(1, 3)-α-D-Man-(1-; -3)-α-D-Man-(1, 3)-α-D-Man-(1, 2)-α-D-Man-(1-, and preferably with *Klebsiella pneumoniae* serotype O3, O3b and/or O5, wherein said diseases include pneumonia, bronchitis, meningitis, urinary tract infection, wound infection, osteomyelitis, bacteremia, septicemia and ankylosing spondylitis.

Pharmaceutical Compositions

Another aspect of the present invention is directed to a pharmaceutical composition or a vaccine comprising at least one conjugate that comprises an oligosaccharide of general formula (I) conjugated to an immunogenic carrier and/or at least one oligosaccharide of general formula (I) together with at least one pharmaceutically acceptable adjuvant and/or excipient. Said pharmaceutical composition can be used for raising a protective immune response in a human and/or animal host. Ideally, the pharmaceutical composition is suitable for use in humans.

In another aspect of the present invention, said pharmaceutical composition or vaccine further comprises at least one of capsular polysaccharides, O-polysaccharides and/or capsular polysaccharides, O-polysaccharide fragments and/or protein conjugates thereof of *Klebsiella pneumoniae* bacteria selected from the group comprising or consisting of *Klebsiella pneumoniae* serotypes O1, O2 (O2a, O2ac, . . . ), O4, O7, O8, O12 and carbapenem-resistant *Klebsiella pneumoniae* ST258 Galactan-III.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant), saponins, aluminum or calcium salts (e.g. alum), non-ionic block polymer surfactants, and many others.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg.

Pharmaceutical compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile and gluten free.

Pharmaceutical compositions are suitable for administration to animal (and, in particular, human) patients, and thus include both human and veterinary uses. They may be used in a method of raising an immune response in a patient, comprising the step of administering the composition to the patient.

The pharmaceutical compositions of the present invention may be administered before a subject is exposed to a *Klebsiella pneumoniae* serotype O3, O3b and/or O5 and/or after a subject is exposed to a *Klebsiella pneumoniae* serotype O3, O3b and/or O5.

In another aspect of the present invention, the present invention is directed to the use of at least one conjugate that comprises at least one oligosaccharide of general formula (I) conjugated to an immunogenic carrier and/or at least one oligosaccharide of general formula (I) for the manufacture of said pharmaceutical composition or said vaccine for prevention and/or treatment of diseases associated with *Klebsiella pneumoniae* serotype O3, O3b or 05 bacteria, particularly, diseases associated with *Klebsiella pneumoniae* serotype O3, O3b or O5 bacteria is selected from the group comprising or consisting of pneumonia, bronchitis, meningitis, urinary tract infection, wound infection, osteomyelitis, bacteremia, septicemia and ankylosing spondylitis.

Preferred, the present invention refers to the use of at least one oligosaccharide of any one of general formulae (I), (II), (II-a)-(II-k), (III), (III-a)-(III-j) or (III-k) and/or at least one of the conjugates comprising at least one oligosaccharide of any one of general formulae (I), (II), (II-a)-(II-k), (III), (III-a)-(III-j) or (III-k) for the manufacture of said pharmaceutical composition or said vaccine.

More preferred, the present invention refers to the use of at least one of the oligosaccharides I'a-1-I'a-11, I'a-1-I'b-11, I'b-1-I'c-11, I'c-1-I'c-11, I'd-1-I'd-11, I'e-1-I'e-11 and I'f-1-I'f-11 and/or at least one of the conjugates comprising at least one of the oligosaccharides I'a-1-I'a-11, I'a-1-I'b-11, I'b-1-I'c-11, I'c-1-I'c-11, I'd-1-I'd-11, I'e-1-I'e-11 and I'f-1-I'f-11 for the manufacture of said pharmaceutical composition or said vaccine.

Particularly, the present invention refers to the use of at least one conjugate of any one of general formulae (IV), (V) and (V-1)-(V-11) for the manufacture of said pharmaceutical composition or said vaccine.

Pharmaceutical compositions may be prepared in unit dose form. Preferably, the dose of the inventive conjugate is between 0.1 and 10 μg, preferably 1 and 10 μg, preferably 0.2 and 9 μg, more preferably 0.5 and 9 μg, preferably 1 and 6 μg, and most preferably 1 and 5 μg. In some embodiments a unit dose may have a volume of between 0.1-1.0 mL e.g. about 0.5 mL.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered *Klebsiella pneumoniae* serotype O3, O3b and/or O5 antigen.

This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton PA A therapeutically effective dosage of one conjugate according to the present invention or of one oligosaccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgment of the prescribing physician.

Another aspect of the present invention is directed to a method of inducing immune response against *Klebsiella pneumoniae* serotype O3, O3b and/or O5 in a human and/or animal host, said method comprising administering of the oligosaccharide of general formula (I) and/or salt thereof and/or a conjugate thereof or pharmaceutical composition thereof to said human and/or animal host. A method of treating or preventing diseases caused by *Klebsiella pneumoniae* serotype O3, O3b and/or O5, in a human and/or animal host according to the present invention comprises administering of at least one oligosaccharide of general formula (I) and/or salt thereof and/or a conjugate thereof or pharmaceutical composition thereof to said human and/or animal host.

Immunological Assays

Yet another aspect of the present invention refers to oligosaccharide of general formula (I) for use as marker in immunological assays for detection of antibodies against bacteria containing in their O-poly-,oligosaccharide one of the following oligosaccharide fragments:

2)-α-D-Man-(1, 2)-α-D-Man-(1, 2)-α-D-Man-(1, 3)-α-D-Man-(1, 3)-α-D-Man-(1-;
3)-α-D-Man-(1, 2)-α-D-Man-(1, 2)-α-D-Man-(1, 2)-α-D-Man-(1, 3)-α-D-Man-(1-;
3)-α-D-Man-(1, 3)-α-D-Man-(1, 2)-α-D-Man-(1, 2)-α-D-Man-(1, 2)-α-D-Man-(1-;
2)-α-D-Man-(1, 3)-α-D-Man-(1, 3)-α-D-Man-(1, 2)-α-D-Man-(1, 2)-α-D-Man-(1-;
2)-α-D-Man-(1, 2)-α-D-Man-(1, 3)-α-D-Man-(1, 3)-α-D-Man-(1, 2)-α-D-Man-(1-;
3)-β-D-Man-(1, 2)-α-D-Man-(1, 2)-α-D-Man-(1-;
2)-α-D-Man-(1, 3)-β-D-Man-(1, 2)-α-D-Man-(1-;
2)-α-D-Man-(1, 2)-α-D-Man-(1, 3)-β-D-Man-(1-;
2)-α-D-Man-(1, 3)-α-D-Man-(1, 3)-α-D-Man-(1-;
3)-α-D-Man-(1, 2)-α-D-Man-(1, 3)-α-D-Man-(1-;
3)-α-D-Man-(1, 3)-α-D-Man-(1, 2)-α-D-Man-(1-.

Such assays comprise, for instance, microarray and ELISA useful for detection of antibodies against bacteria containing in their O-poly-,oligosaccharide one of the above mentioned oligosaccharide fragments, such as *Klebsiella pneumoniae* serotype O3, O3b and/or O5.

The O-antigens of *K. pneumoniae* O3, O3b and O5 are shared respectively by *E. coli* O9, and O8. The O5-antigen is shared by *Burkholderia cepacia* O2 and E, and *Serratia marcescens* O28. Therefore, O-poly-,oligosaccharide one of the above mentioned oligosaccharide fragments can be used for detection of antibodies against *E. coli* O8, and O9. *Burkholderia cepacia* O2 and E and *Serratia marcescens* O28.

The oligosaccharides of the present invention can be easily conjugated to solid supports for providing immunological assays useful for detection of antibodies against *Klebsiella pneumoniae* serotype O3, O3b and/or O5. Said solid supports present on their surface a functionality that is prone to react with the amino group of oligosaccharides of general formula (I) or with the functional group Y of the interconnecting molecule to provide modified solid supports, presenting on their surface the functional group X of the interconnecting molecule that can further react with the amino group of oligosaccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Examples of such microarray slides include, but are not restricted to Corning® epoxide coated slides or Corning® GAPS™ II coated slides.

In a preferred embodiment the solid supports are microarray slides presenting on their surface a functionality that is prone to react with the amino group of oligosaccharides of general formula (I), and more preferably an N-hydroxysuccinimide (NHS) activated ester. Such microarray slides are for example CodeLink® NHS slides.

DESCRIPTION OF THE FIGURES

FIG. 1 shows the chemical structure of the repeating unit of *Klebsiella pneumoniae* serotype O3, O3b and O5 LPS O-polysaccharide.

FIG. 2 provides examples of functional group X of the interconnecting molecule according to the present invention.

FIG. 3 provides examples of functional group X of the interconnecting molecule according to the present invention.

FIG. 4(A) shows a $CRM_{197}$ conjugate of the present invention; (B) structure of 21*-$CRM_{197}$; and (C) 69*-$CRM_{197}$.

Figure 5A:
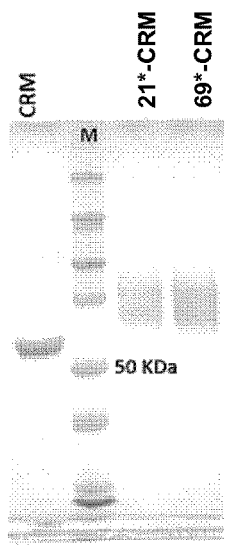

FIG. 5(A) shows SDS-PAGE of glycoconjugates (2.5 µg/well) 21*-$CRM_{197}$ and 69*-$CRM_{197}$ used in immunization experiments resolved using a 10% polyacrylamide gel; (B) SEC Chromatograms of KPC glycoconjugates 21*-$CRM_{197}$ and 69*-$CRM_{197}$.

Figure 6:
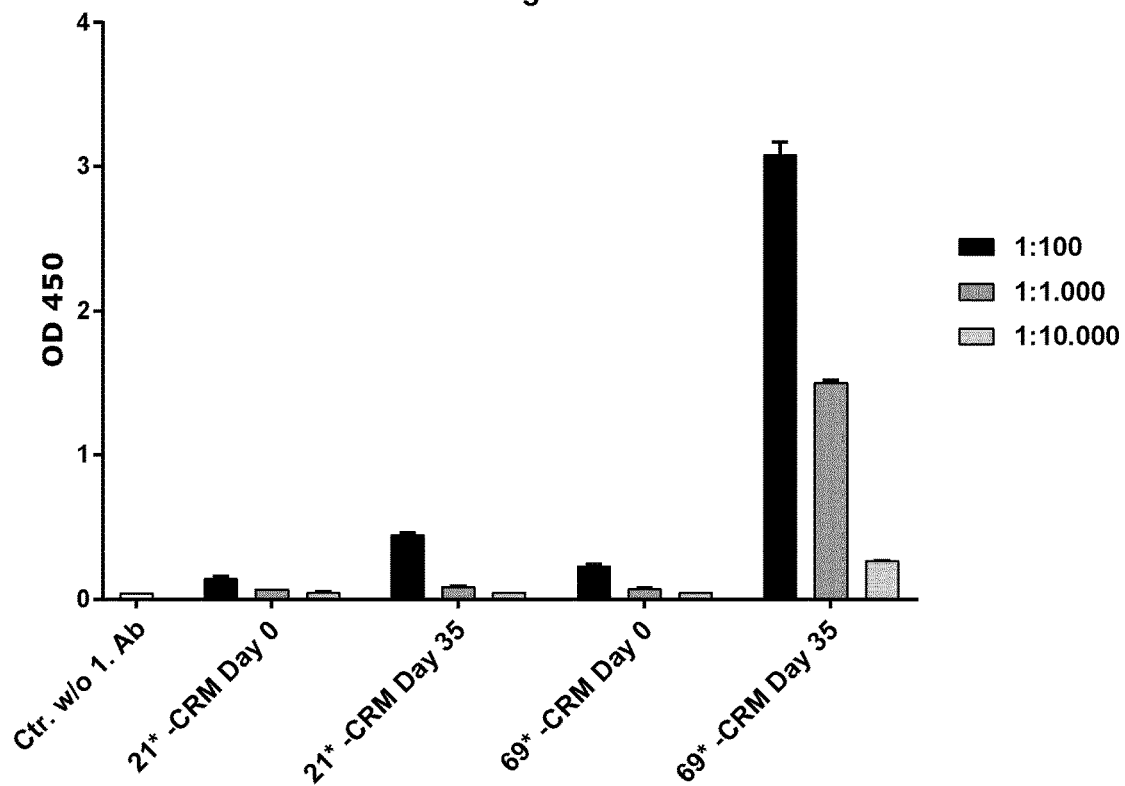

FIG. 6 shows ELISA titers of Day-0 and Day-35 pooled sera from mice (n=6) immunized with 21*-$CRM_{197}$ or 69*-$CRM_{197}$ formulation. Sera of 21*-$CRM_{197}$ and 69*-$CRM_{197}$ formulations were tested against corresponding O-antigen BSA conjugates 21*-BSA and 69*-BSA. In both cases, sera were diluted 1:100, 1000 and 10,000 with 1% BSA-PBS. Diluted sera (100 µL) were added per well of the microtiter plate which was coated with 0.5 µg of the corresponding BSA conjugate. Detection was done using a HRP conjugated goat anti-mouse secondary antibody diluted to 1:10000 and developed using the TMB substrate. Absorbance was measured at 450 nm and the data were plotted using the GraphPad prism software.

Figure 7:
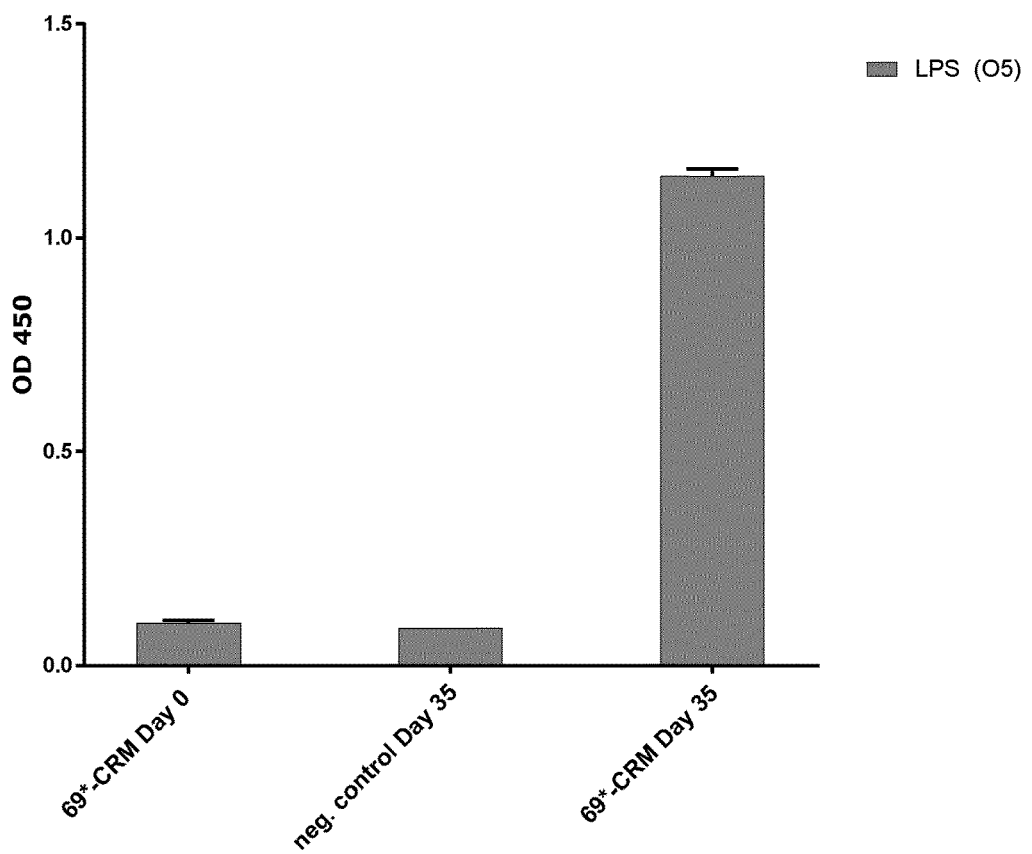

FIG. 7 shows cross-reactivity of Day-0 and Day-35 pooled sera from mice (n=6) immunized with 69*-$CRM_{197}$ formulation. Sera of 69*-$CRM_{197}$ formulation were tested against LPS isolated from the corresponding strain, i.e. LPS (O5). The sera were diluted 1:200 with 1% BSA-PBS. Diluted sera (100 µL) was added per well of the microtiter plate which was coated with 1.0 µg of the corresponding LPS. Detection was done using a HRP conjugated goat anti-mouse secondary antibody diluted to 1:10000 and developed using the TMB substrate. Absorbance was measured at 450 nm and the data were plotted using the GraphPad prism software.

Figure 8:
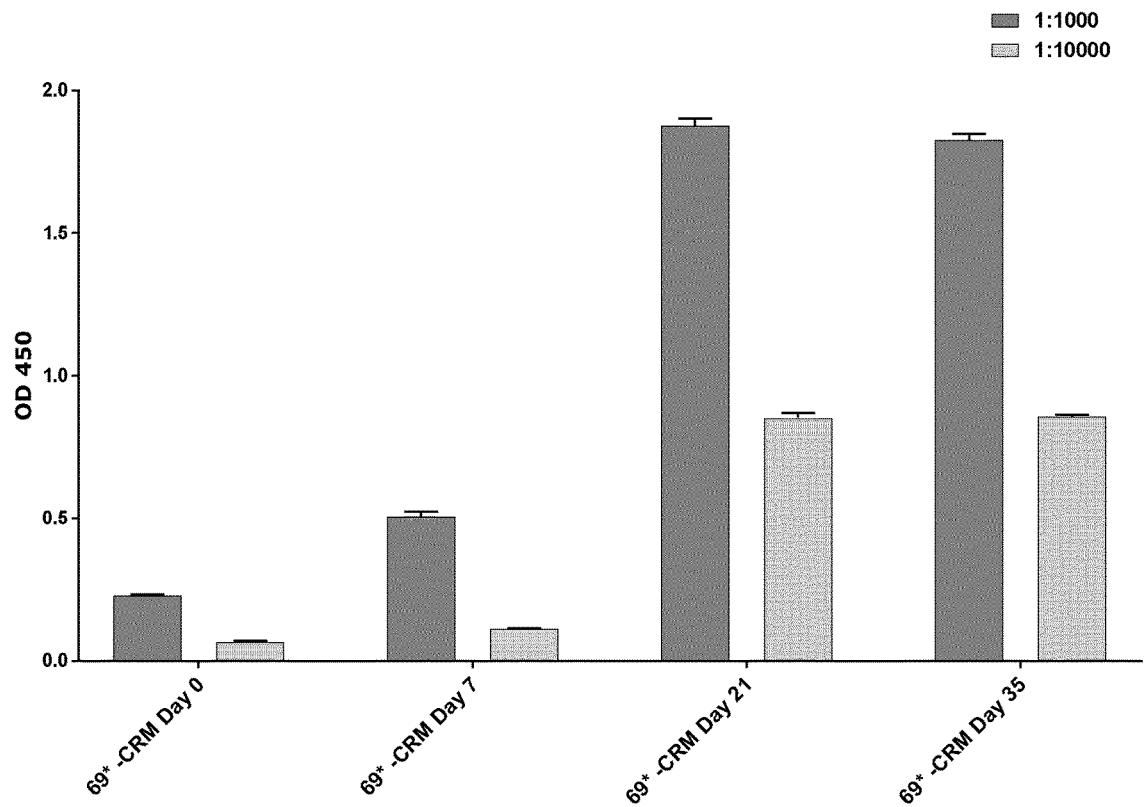

FIG. 8 shows ELISA titers of Day-0 Day-7, Day-21, and Day-35 pooled sera from rabbits (n=4) immunized with 69*-$CRM_{197}$ formulation. Sera of 69*-$CRM_{197}$ formulation were tested against corresponding O-antigen BSA conjugate 69*-BSA. The sera were diluted 1:1000 and 10,000 with 1% BSA-PBS. Diluted sera (100 µL) were added per well of the microtiter plate which was coated with 0.5 µg of the corresponding 69*-BSA. Detection was done using a HRP conjugated goat anti-rabbit secondary antibody diluted to 1:10000 and developed using the TMB substrate. Absorbance was measured at 450 nm and the data were plotted using the GraphPad prism software.

Figure 9:
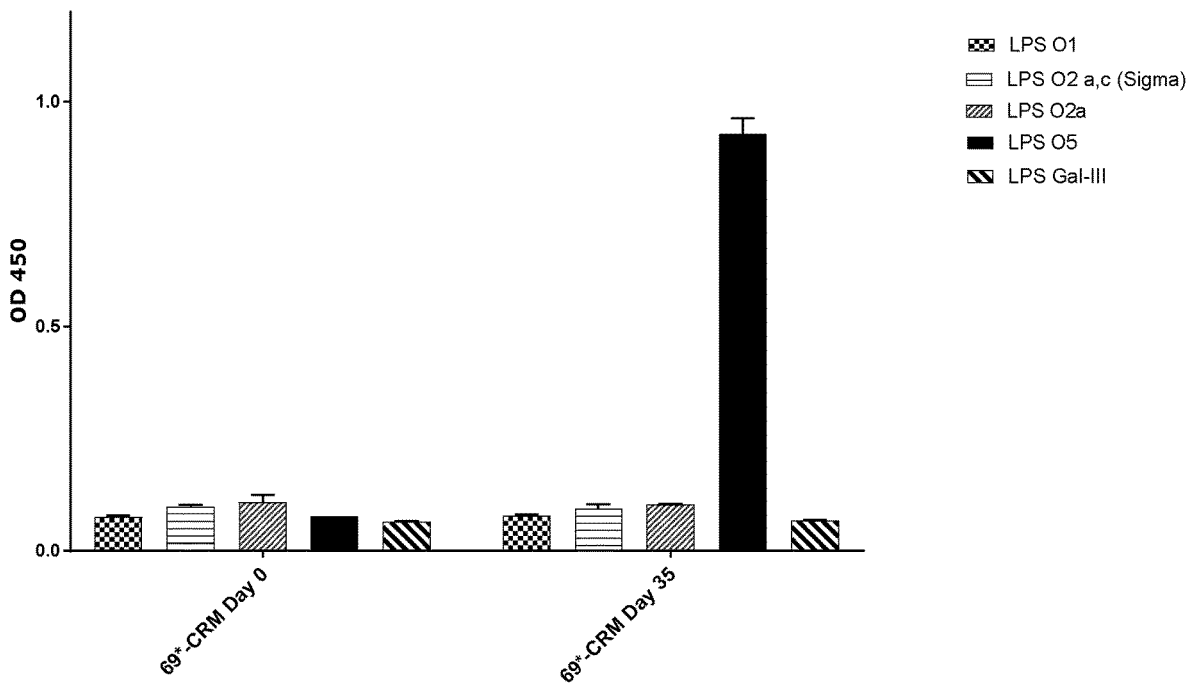

FIG. 9 shows cross-reactivity of Day-0 and Day-35 pooled sera from rabbit (n=4) immunized with 69*-$CRM_{197}$ formulation. Sera of 69*-$CRM_{197}$ formulation was tested against LPS isolated from different KPC strains #1-#4. In both cases, the sera was tested against the LPS (O1), Commercial-LPS (O2 a,c), LPS (O2a), LPS (O5) and LPS (Gal III). Sera were diluted 1:200 with 1% BSA-PBS and 100 µL of the diluted sera was added per well of the microtiter plate which was coated with 1.0 µg of the corresponding LPS. Detection was done using a HRP conjugated goat anti-rabbit secondary antibody diluted to 1:10000 and developed using the TMB substrate. Absorbance was measured at 450 nm and the data were plotted using the GraphPad prism software.

EXAMPLES

A. Chemical Synthesis

General Information:

Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka Kieselgel 60 (230-400 mesh). $^{1}H$, $^{13}C$ and two-dimensional NMR spectra were measured with a Varian 400-MR spectrometer at 296 K. Chemical shifts (d) are reported in parts per million (ppm) relative to the respective residual solvent peaks ($CDCl_3$: d 7.26 in $^{1}H$ and 77.16 in $^{13}C$ NMR; $CD_3OD$: d 3.31 in $^{1}H$ and 49.15 in $^{13}C$ NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). Optical rotation (OR) measurements were carried out with a Schmidt & Haensch UniPol L1000 polarimeter at λ=589 nm and a concentration (c) expressed in g/100 mL in the solvent noted in parentheses. High resolution mass spectrometry (HRMS) was performed at the Free University Berlin, Mass Spectrometry Core Facility, with an Agilent 6210 ESI-TOF mass spectrometer. Infrared (IR) spectra were measured with a Perkin Elmer 100 FTIR spectrometer at applicant's facility.

ABBREVIATIONS

AcOH Acetic acid
Alloc Allyloxycarbonyl
aq. aqueous
$BH_3$ borane
$BBr_3$ boron tribromide
Boc tert-Butoxycarbonyl
br. broad
CAS CAS Registry Number (CAS=Chemical Abstracts Service)
$CHCl_3$ chloroform
cHex cyclohexane
d doublet
dd doublet of doublets
DCM dichloromethane
DEAD diethyl azodicarboxylate
DIPEA N,N-diisopropyl-ethylamine
DME dimethoxyethane
DMF dimethylformamide
DMSO dimethylsulfoxide
DPPA diphenylphosphoryl azide
EDC•HCl N1-((ethylimino)methylene)-N3,N3-dimethyl-propane-1,3 diamine hydrochloride
ES electrospray
$Et_2O$ diethyl ether
EtOAc ethyl acetate
h hour
HCl hydrochloric acid H₂O water
HOBt.H₂O 1H-benzo[d][1,2,3]triazol-1-ol hydrate
K₂CO₃ potassium carbonate
m multiplet
MeCN acetonitrile
MeOH methanol
MeI methyl iodide
MgSO₄ magnesium sulphate
min minutes
MS mass spectrometry
Na₂CO₃ sodium carbonate
NaCNBH₃ sodium cyanoborohydride
NaHCO₃ sodium hydrogencarbonate
NaH sodium hydride
NaOH sodium hydroxide
Na₂SO₄ sodium sulphate
NCS N-chlorosuccinimide
NIS N-iodosuccinimide
NMR nuclear magnetic resonance
PBS phosphate-buffered saline
Pd/C palladium on carbon
PPh₃ triphenylphosphine
q quartet
rt room temperature
s singlet
sat. saturated
sep septet
t triplet
TFA trifluoroacetic acid
THF tetrahydrofuran
TsOH tosic acid
Wt weight.

Example 1: Synthesis of Monosaccharide Building Blocks

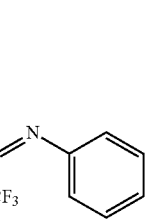

Compound 1*

Compound 1* was prepared according to a procedure described in *Carb. Res.*, 2010, 345, 10, 1316-1323.

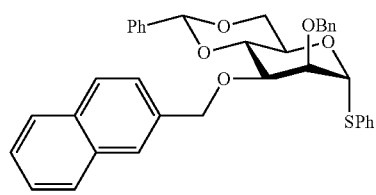

Compound 2*

Compound 2* was prepared according to a procedure described in *Chemistry—A European Journal*, 2010, 16(44), 13163-13175.

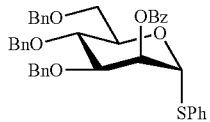

Compound 3*

Compound 3* was prepared according to a procedure described in *Org. Biomol. Chem.*, 2018, (16) 13, 2277-2288.

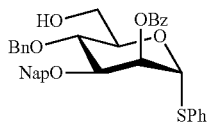

Compound 4*

Compound 4* was prepared according to a procedure described in *J. Org. Chem.*, 2012, 77 (1), 108-125.

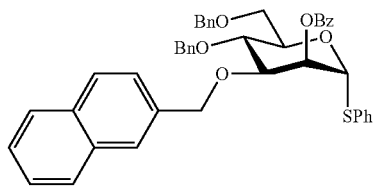

Compound 5*

Compound 4* (2 g, 3.30 mmol) was dissolved in anhydrous DCM (33 mL). Benzyl bromide (1.4 g, 8.24 mmol) and Ag₂O (7.64 g, 33 mmol) were added and the reaction mixture was vigorously stirred at room temperature overnight. The reaction was filtered through celite and concentrated under reduced pressure to give crude product. The crude was charged on isolute® and purified using an automated purification system on silica (ethyl acetate/cyclohexane) to give the product (1.43 g, 62%). HRMS (ESI⁺) Calcd for $C_{44}H_{40}O_6SNa^+$ [M+Na]⁺ 719.2443, found 719.2390.

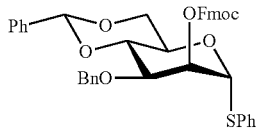

Compound 6*

Compound 6* was prepared according to a procedure described in *J. Am. Chem. Soc.*, 2017, 139 (2), 1011-1018 starting from compound 9*: Compound 9* (400 mg, 1.068 mmol) was dissolved in anhydrous pyridine (5 mL). FmocCl (431 mg, 1.666 mmol) and DMAP (19.58 mg, 0.160 mmol) were added and the reaction mixture was stirred at room temperature overnight. The reaction was diluted with ethyl acetate and washed with sat. NaHCO₃ and brine. The organic layer was dried using Na₂SO₄ and the solvent evaporated to give the crude product. The crude was charged on isolute® and purified using an automated purification system using silica (ethyl acetate/cyclohexane) to give the product (360 mg, 56%). HRMS (ESI⁺) Calcd for $C_{35}H_{32}O_7SNa^+$ [M+Na]⁺ 597.1947, found 597.1857.

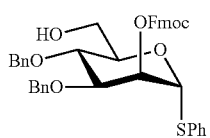

Compound 7*

Compound 6* (1.7 g, 2.274 mmol) was dissolved in BH$_3$.THF (27 mL, 27 mmol) and TMSOTf (0.41 mL, 2.274 mmol) was added. The solution was stirred at room temperature for 1.5 h. The reaction was quenched with methanol (cooling with an ice/water bath) and concentrated under reduced pressure to give crude product. The crude was charged on isolute® and purified using an automated purification system with ethyl acetate/cyclohexane to give the product (930 mg, 61%). HRMS (ESI$^+$) Calcd for C$_{41}$H$_{38}$O$_7$SNa$^+$ [M+Na]$^+$ 697.2236, found 697.2188.

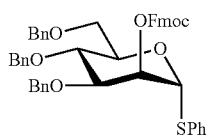

Compound 8*

Compound 7* (930 mg, 1.37 mmol) was dissolved in anhydrous DCM (14 mL). Benzyl bromide (589 mg, 3.45 mmol) and Ag$_2$O (3.19 g, 13.78 mmol) were added and the reaction mixture was vigorously stirred at room temperature overnight. The reaction was filtered through Celite® and concentrated under reduced pressure to give crude product. The crude was charged on isolute® and purified using the automated purification system using silica (ethyl acetate/cyclohexane) to give the product 8* (680 mg, 65%). HRMS (ESI$^+$) Calcd for C$_{48}$H$_{44}$O$_7$SNa$^+$ [M+Na]$^+$ 787.2705, found 787.2653.

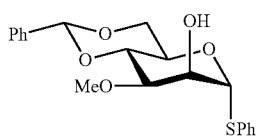

Compound 9*

Compound 9* was prepared according to a procedure described in *Chem. Eur. J.* 2014, 20, 3578-3583.

Example 2: Synthesis of *K. pneumoniae* Serotype O3 Oligosaccharides

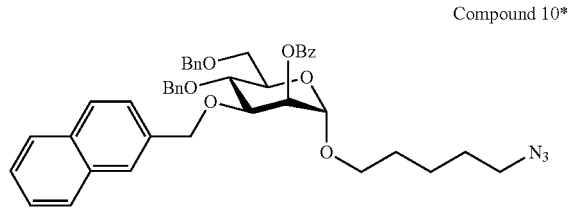

Compound 10*

To a solution of compound 5* (550 mg, 0.789 mmol) and 5-azidopentanol (306 mg, 2.368 mmol) in anhydrous DCM (2.9 mL) was added 4 Å molecular sieves and the mixture let stir at room temperature for 30 min. Then, NIS (213 mg, 0.947 mmol) was added and the reaction mixture cooled to −20° C. TMSOTf (14 μL, 0.079 mmol) was added and the reaction mixture stirred for 1.5 h at 0° C. Reaction mixture was filtered and washed with DCM, and the filtrate was washed with sat. Na$_2$S$_2$O$_3$ solution (15 mL) and extracted with CH$_2$Cl$_2$ (2×25 mL). Combined organic layers were washed with sat. NaHCO$_3$ solution (15 mL) and Brine (10 mL). Dried over anhydr. Na$_2$SO$_4$, filtered and concentrated under reduced pressure. Purification by an automated purification system using silica (ethyl acetate/cyclohexane) afforded the product 10* after evaporation of the solvent as a colorless thick gel (51 mg, 49%).

HRMS (ESI+) Calcd for C$_{43}$H$_{45}$N$_3$O$_7$Na$^+$ [M+Na]$^+$ 738.3155, found 738.3147.

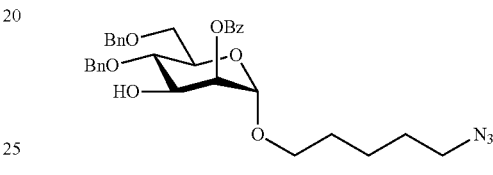

Compound 11*

To a solution of compound 10* (361 mg, 0.504 mmol) in DCM:PBS (2:1, 16.81 mL) was added 2,3-dichloro-5,6-dicyano-1,4-benzoquinone (229 mg, 1.01 mmol) at 0° C. The reaction mixture was stirred for 2.5 h at room temperature. Reaction was monitored by TLC (EtOAc in cyclohexane, 2:1). Reaction was quenched with sat. NaHCO$_3$ (50 mL) and extracted with DCM (2×50 mL). The combined organic layers were washed with brine (50 mL) and dried over Na$_2$SO$_4$, filtered, and the filtrate was concentrated under reduced pressure to obtain the crude product. The crude product was purified by automated flash chromatography using silica (ethyl acetate/cyclohexane) to obtain a colorless oil of compound 11* (210 mg, 72%).

HRMS (ESI+) Calcd for C$_{32}$H$_{37}$N$_3$O$_7$Na$^+$ [M+Na]$^+$ 599.2563, found 599.2555.

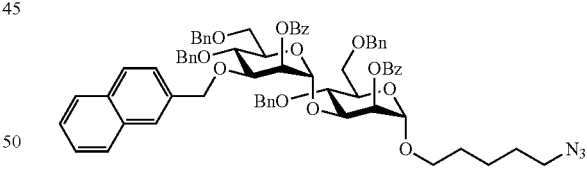

Compound 12*

To a solution of compound 5* (276 mg, 0.396 mmol) and compound 11* (190 mg, 0.330 mmol) in anhydrous DCM (8.4 mL) was added 4 Å MS and the mixture was letting stirred at room temperature for 30 min. Then, NIS (89 mg, 0.396 mmol) was added and the reaction mixture was cooled to −20° C. TMSOTf (6 μL, 0.03 mmol) was added and the reaction mixture stirred for 1 h at 0° C. Reaction mixture was filtered, the filtrate was washed with sat. Na$_2$S$_2$O$_3$ solution (15 mL) and extracted with CH$_2$Cl$_2$ (2×25 mL). Combined organic layers were washed with sat. NaHCO$_3$ solution (15 mL) and brine (10 mL). After drying over anhydr. Na$_2$SO$_4$, the layers were concentrated under reduced pressure. Purification by automated purification system using silica (ethyl acetate/cyclohexane) afforded the product 12* after evaporation of the solvent as a cloudy thick gel (300 mg, 78%).

HRMS (ESI+) Calcd for $C_{70}H_{71}N_3O_{13}Na^+$ [M+Na]$^+$ 1184.4885, found 1184.4902.

Compound 13*

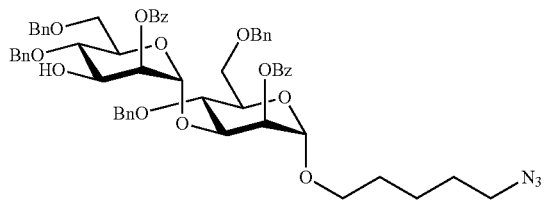

To a solution of compound 12* (290 mg, 0.294 mmol) in DCM:PBS (2:1, 8.3 mL) was added 2,3-dichloro-5,6-dicyano-1,4-benzoquinone (113 mg, 0.499 mmol) at 0° C. The reaction mixture was stirred for 2.5 h at room temperature and monitored by TLC (EtOAc in cyclohexane, 2:1). Reaction was quenched with sat. NaHCO$_3$ (40 mL) and extracted with DCM (2×40 mL). The combined organic layers were washed with brine (20 mL), dried over Na$_2$SO$_4$ and concentrated under reduced pressure to obtain the crude product. The crude product was purified by automated flash chromatography using silica (ethyl acetate/cyclohexane) to obtain compound 13* as a colorless oil (136 mg, 53%).

HRMS (ESI+) Calcd for $C_{59}H_{63}N_3O_{13}Na^+$ [M+Na]$^+$ 1044.4259, found 1044.4252.

Compound 14*

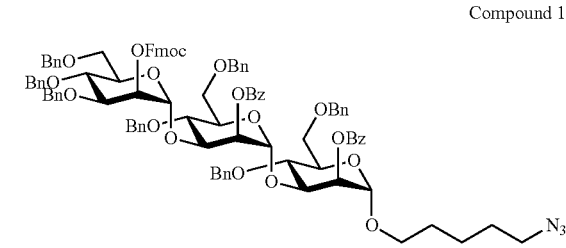

To a solution of compound 8* (135 mg, 0.176 mmol) and 13* (150 mg, 0.147 mmol) in anhydrous DCM (3.8 mL) was added 4 Å MS and the mixture was stirred at room temperature for 30 min. Then, NIS (40 mg, 0.176 mmol) was added and the reaction mixture cooled to −20° C. TMSTOf (2.6 μL, 0.015 mmol) was added and the reaction mixture stirred for 1.5 h at 0° C. Reaction mixture was filtered and washed with sat. Na$_2$S$_2$O$_3$ solution (15 mL) and extracted with CH$_2$Cl$_2$ (2×25 mL). Combined organic layers were washed with sat. NaHCO$_3$ solution (15 mL) and brine (10 mL). After drying over anhydr. Na$_2$SO$_4$, the crude product were purified by automated purification system using silica (ethyl acetate/cyclohexane) which afforded the product 14* after evaporation of the solvent as a cloudy thick gel (184 mg, 75%).

HRMS (ESI+) Calcd for $C_{101}H_{101}N_3O_{20}Na^+$ [M+Na]$^+$ 1699.6910, found 1699.6886.

Compound 15*

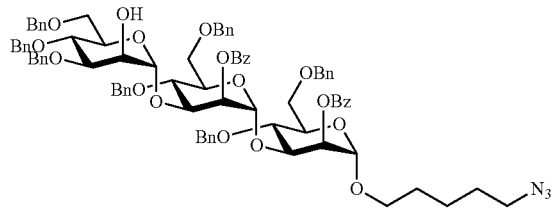

To a solution of compound 14* (180 mg, 0.107 mmol) in DCM (2 mL) triethylamine (208 μL, 1.491 mmol) was added at room temperature and stirred for 1 h. Volatiles were removed under reduced pressure. Purification by automated purification system using silica (ethyl acetate/cyclohexane) afforded the product 15* after evaporation of the solvent as a cloudy thick gel (138 mg, 88%).

HRMS (ESI+) Calcd for $C_{85}H_{91}N_3O_{18}Na^+$ [M+Na]$^+$ 1476.6195, found 1476.6198.

Compound 16*

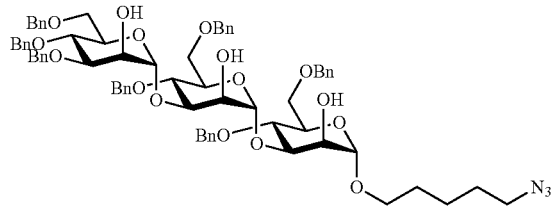

Sodium methoxide solution in MeOH (0.5M) (0.075 mL, 0.330 mmol) was added to a solution of compound 15* (24 mg, 0.016 mmol) in a mixture of MeOH:THF (2:1, 1.5 mL). The reaction was stirred at the same temperature for 20 h. The reaction was quenched by the addition of H$_2$O (2 mL) and diluted with brine (5 mL). Reaction mixture extracted with EtOAc (2×10 mL). Combined organic layers were dried over anhydr. Na$_2$SO$_4$, and concentrated under reduced pressure. Purification by automated purification system using silica (ethyl acetate/cyclohexane) afforded the product after evaporation of the solvent as a colorless thick gel (18 mg, 88%).

HRMS (ESI+) Calcd for $C_{99}H_{90}O_{22}Na^+$ [M+Na]$^+$ 1268.5671, found 1268.5813.

Compound 17*

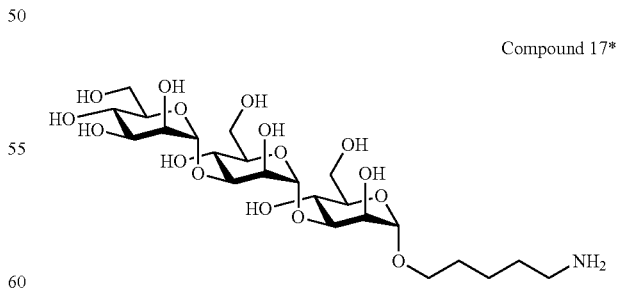

Compound 16* (8.6 mg, 6.90 μmol) was taken in solvent mixture DCM (1 mL), tert-butanol (1 mL) and two drops of water. Pd/C was added to it and hydrogenated for 24 h at 7 bar pressure of H$_2$ at rt. The reaction mixture was filtered through PTFE filter and the residue washed with methanol (6 mL), (50% methanol-water (6 mL). The filtrate was evaporated under vacuum to get the crude product. Crude product was clean by 1H NMR, sample recovered and freeze dried to obtain compound 17* as a white crystalline solid (3.8 mg, 93%).

HRMS (ESI+) Calcd for $C_{23}H_{43}NO_{16}H^+$ $[M+H]^+$ 590.2694, found 590.2683.

$^1$H NMR (400 MHz, $D_2O$) δ 5.15 (d, J=1.7 Hz, 1H), 5.11 (d, J=1.8 Hz, 1H), 4.85 (d, J=1.8 Hz, 1H), 4.24 (dd, J=3.3, 1.8 Hz, 1H), 4.06-4.12 (m, 2H), 4.03 (dd, J=9.1, 3.3 Hz, 1H), 3.86-3.97 (m, 5H), 3.71-3.86 (m, 8H), 3.61-3.71 (m, 2H), 3.51-3.61 (m, 1H), 3.01 (t, J=7.6 Hz, 2H), 1.61-1.78 (m, 4H), 1.39-1.54 (m, 2H).

mmol) was added and the reaction mixture cooled to −20° C. TMSTOf (0.8 μL, 4.47 μmol) was added and the reaction mixture stirred for 35 min at 0° C. Reaction monitored by TLC until no starting material was left. Triethylamine (250 μl) was added and the mixture was warmed to room temperature gradually over 1 h. Reaction mixture was filtered and washed sat. $Na_2S_2O_3$ solution (15 mL) and extracted with $CH_2Cl_2$ (2×25 mL). Combined organic layers were washed with sat. $NaHCO_3$ solution (15 mL) and brine (10 mL), subsequently dried over anhydr. $Na_2SO_4$ and concentrated under reduced pressure. Purification by automated purification system using silica (ethyl acetate/cyclohexane) afforded the product after evaporation of the solvent as a cloudy thick gel (46 mg, 54%).

HRMS (ESI+) Calcd for $C_{113}H_{119}N_3O_{23}H^+$ $[M+H]^+$ 1909.8166, found 1909.8160.

Compound 19*

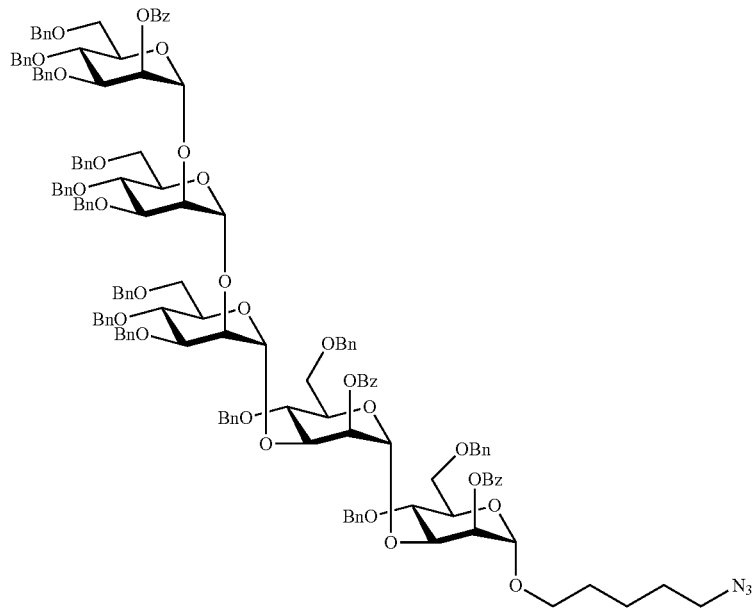

Compound 18*

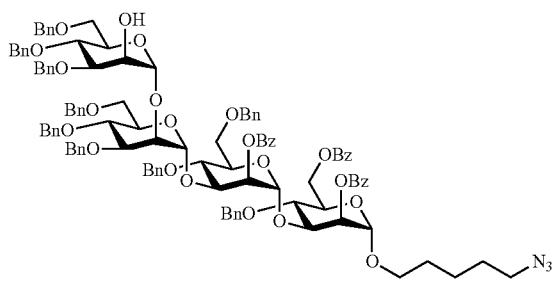

To a solution of compound 8* (43 mg, 0.056 mmol) and compound 15* (65 mg, 0.045 mmol) in anhydrous DCM (1.94 mL) was added 4 Å MS and the mixture was stirred at room temperature for 30 min. Then, NIS (12 mg, 0.054

To a solution of compound 3* (16.8 mg, 0.026 mmol) and compound 18* (28 mg, 0.015 mmol) in mixture of anhydrous toluene (0.9 mL) and anhydrous dioxane (0.3 mL) was added 4 Å MS and the mixture was stirred at room temperature for 1 h. Then, NIS (4 mg, 0.018 mmol) was added and the reaction mixture cooled to −20° C. TMSTOf (0.27 μL, 1.484 μmol) was added and the reaction mixture stirred for 2 h allowing to warm to room temperature. Reaction mixture was filtered and washed with sat. $Na_2S_2O_3$ solution (15 mL) and extracted with $CH_2Cl_2$ (2×25 mL). Combined organic layers were washed with sat. $NaHCO_3$ solution (15 mL) and brine (10 mL), subsequently dried over anhydr. $Na_2SO_4$ and concentrated under reduced pressure. Purification by automated purification system using silica (ethyl acetate/cyclohexane) afforded the product after evaporation of the solvent as a cloudy thick gel (32 mg, 89%).

HRMS (ESI+) Calcd for $C_{147}H_{151}N_3O_{29}Na^+$ $[M+Na]^+$ 2445.0331, found 2445.9951.

Compound 20*

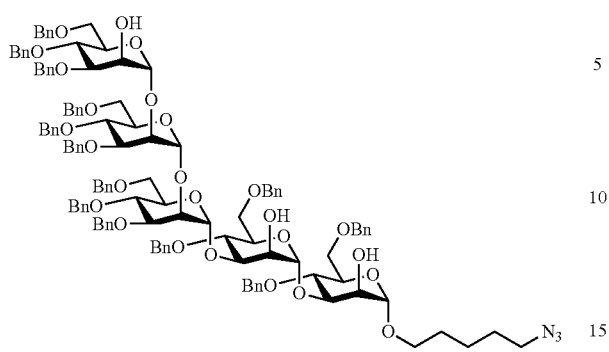

Sodium methoxide solution in MeOH (25% w/w) (0.051 mL, 0.223 mmol) was added to a solution of the pentasaccharide 19* (27 mg, 0.011 mmol) in a mixture of MeOH: THF (2:1, 1.5 mL). The reaction was stirred at the same temperature for 16 h. The reaction was quenched by the addition of H$_2$O (3 mL) and diluted with brine (5 mL). Reaction mixture extracted with EtOAc (2×10 mL). Combined organic layers were dried over anhydr. Na$_2$SO$_4$ and concentrated under reduced pressure. Purification by automated purification system using silica (ethyl acetate/cyclohexane) afforded the product after evaporation of the solvent as a colorless thick gel (17 mg, 72%).

HRMS (ESI+) Calcd for C$_{126}$H$_{139}$N$_3$O$_{26}$Na$^+$ [M+Na]$^+$ 2133.9578, found 2133.9517.

Compound 21*

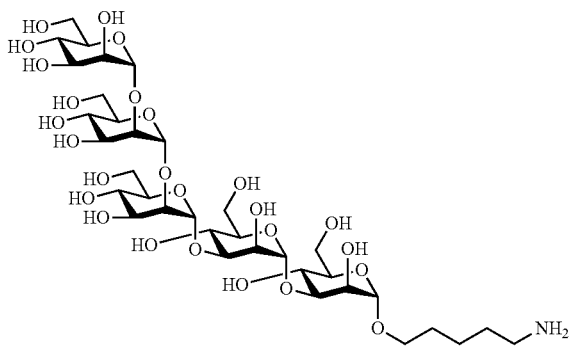

Compound 20* (17 mg, 8.05 μmol) was taken in a solvent mixture of DCM (1 mL), tert-butanol (1 mL) and two drops of water. Pd/C was added and hydrogenated for 24 h under H$_2$ balloon at rt. The reaction mixture was filtered through PTFE filter, washed the residue with methanol (6 mL), (50% methanol-water (6 mL). The filtrate was evaporated under vacuum to get the crude product. 1H NMR analysis showed the completion of the reaction and the presence of product. So, crude product was purified through the C18 Sepak column using water (3 mL×2, fr1), 20% acetonitrile-water (3 mL×2, fr2) and acetonitrile (3 mL, fr3). All the fractions were frozen and lyophilized for 24 h to get one pure fraction fr1 of compound 21* (white solid, 6.4 mg, 87%), and two impure fractions white fluffy solid (fr2, 0.4 mg) a white fluffy solid (fr.3, 0.6 mg).

HRMS (ESI+) Calcd for C$_{35}$H$_{63}$NO$_{26}$H$^+$ [M+H]$^+$ 914: 3717, found 914:3725.

$^1$H NMR (400 MHz, D$_2$O) δ 5.35 (d, J=1.7 Hz, 1H), 5.28 (d, J=1.8 Hz, 1H), 5.08 (d, J=1.8 Hz, 1H), 5.02 (d, J=1.8 Hz, 1H), 4.82 (d, J=1.8 Hz, 1H), 4.20 (dd, J=3.3, 1.8 Hz, 1H), 4.02-4.11 (m, 4H), 3.92-4.01 (m, 3H), 3.80-3.92 (m, 8H), 3.50-3.80 (m, 18H), 2.93-3.04 (m, 2H), 1.58-1.76 (m, 4H), 1.37-1.58 (m, 2H).

Compound 22*

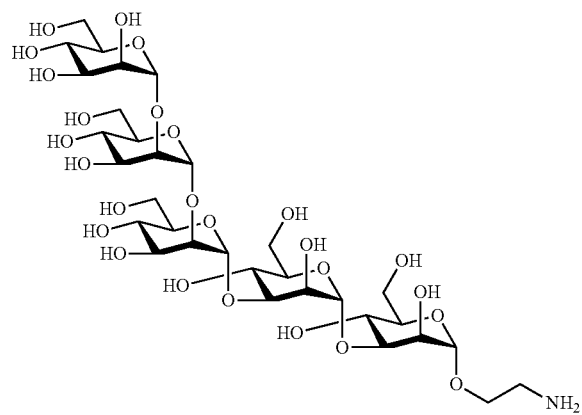

Compound 22* is prepared similarly to compound 21* starting from compound 5* and azidoethanol.

Compound 23*

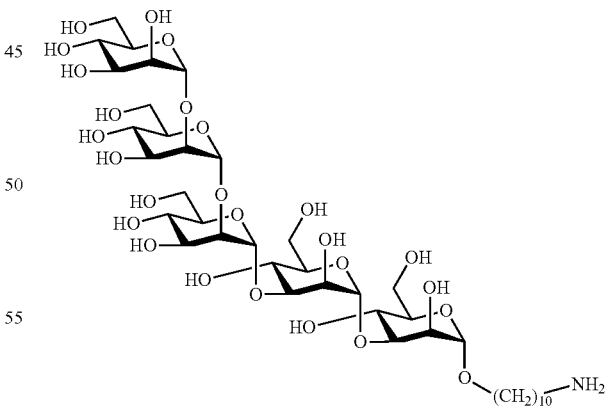

Compound 23* is prepared similarly to compound 21* starting from compound 5* and azidodecanol.

Compound 24*
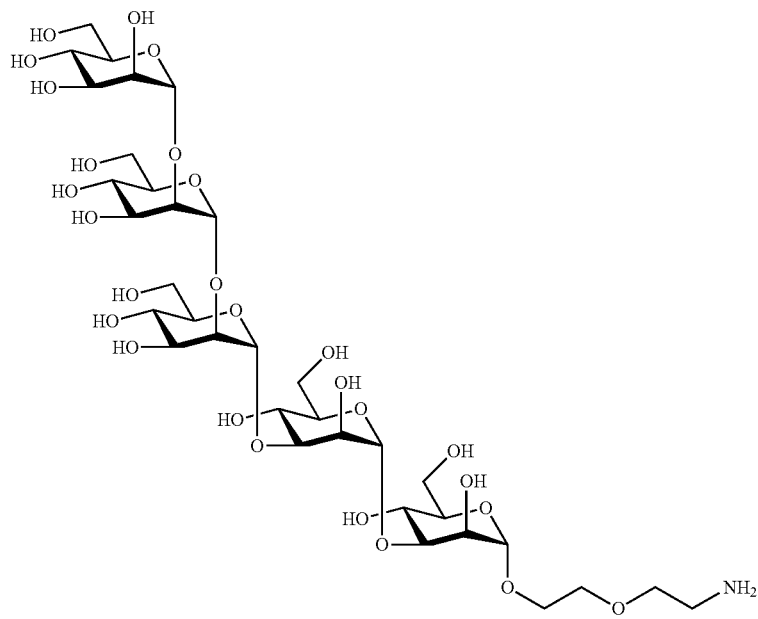
Compound 24* is prepared similarly to compound 21* starting from compound 5* and 2-(2-azidoethoxy)ethanol.
Compound 25*
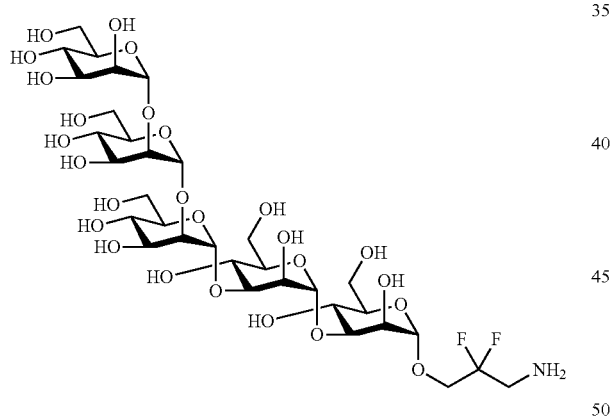
Compound 25* is prepared similarly to compound 21* starting from compound 5* and 3-azido-2,2-difluoropropanol.

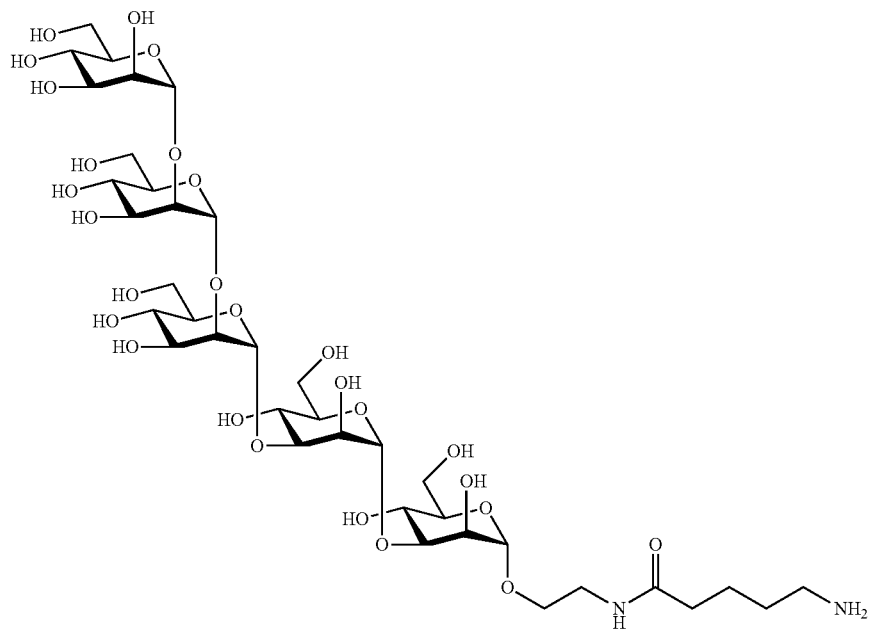
Compound 26*
Compound 26* is prepared similarly to compound 21* starting from compound 5* and the corresponding azido alcohol.
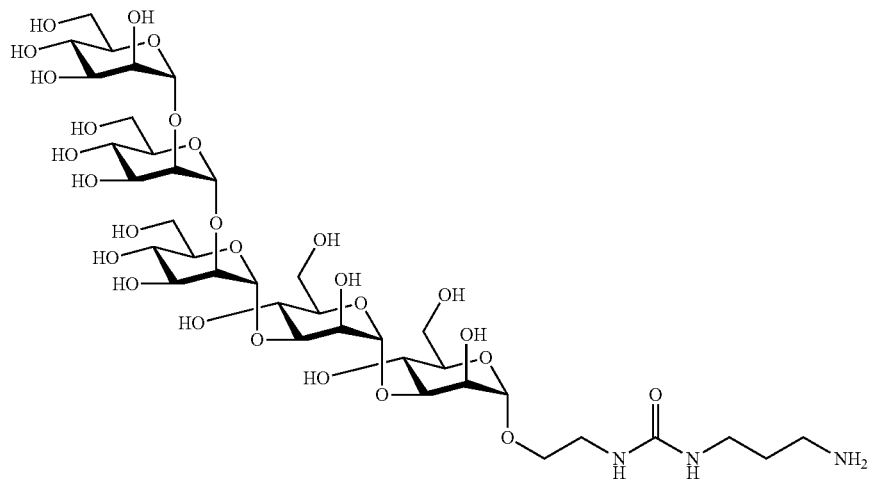
Compound 27*
Compound 27* is prepared similarly to compound 21* starting from compound 5* and the corresponding azido alcohol.

Compound 28*

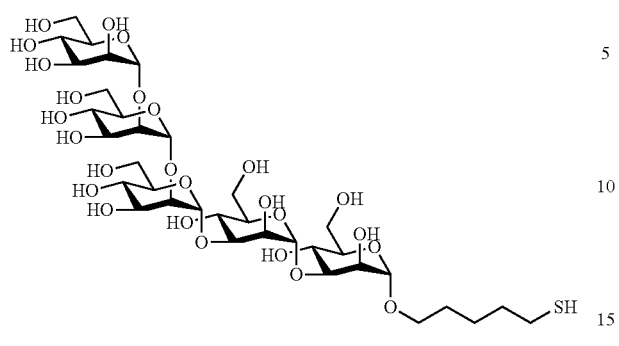

Compound 28* is prepared similarly to compound 21* starting from compound 5* and the corresponding S-benzylthio alcohol.

Compound 29*

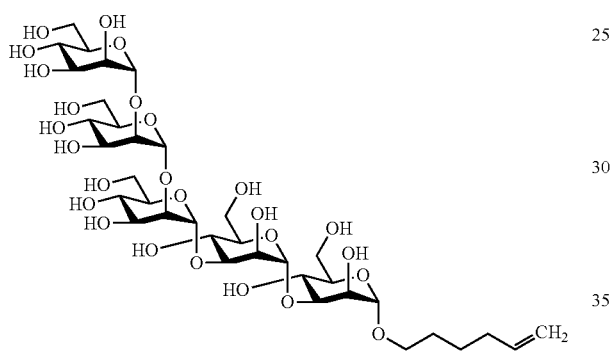

Compound 29* is prepared similarly to compound 21* starting from compound 5* and 5-hexenol.

Compound 30*

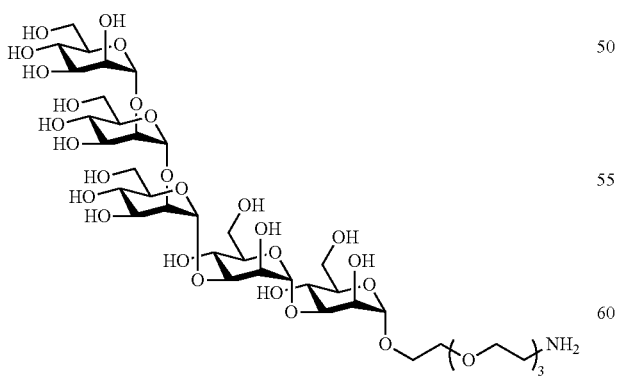

Compound 30* is prepared similarly to compound 21* starting from compound 5* and 11-azido-3,6,9-trioxaundecanol.

Compound 31*

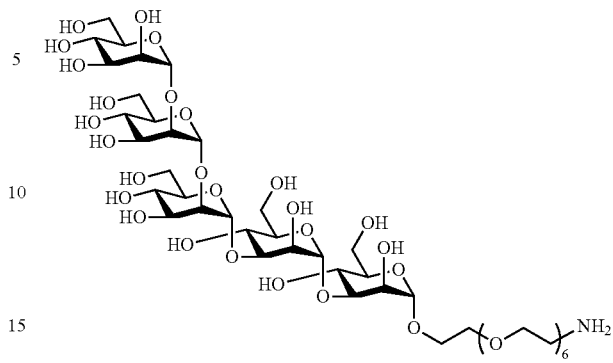

Compound 31* is prepared similarly to compound 21* starting from compound 5* and azido-PEG7-alcohol.

Compound 32*

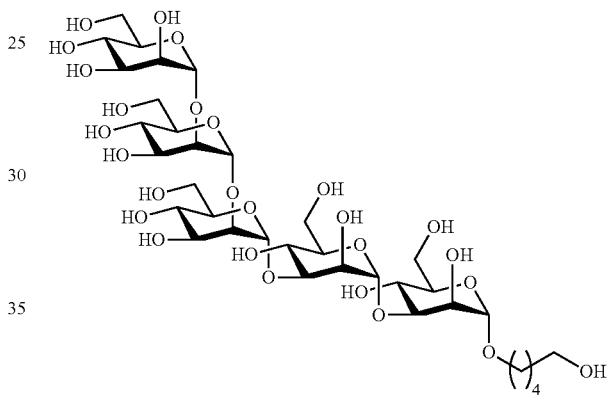

Compound 32* is prepared similarly to compound 21* starting from compound 5* and 5-benzyloxypentanol.

Compound 33*

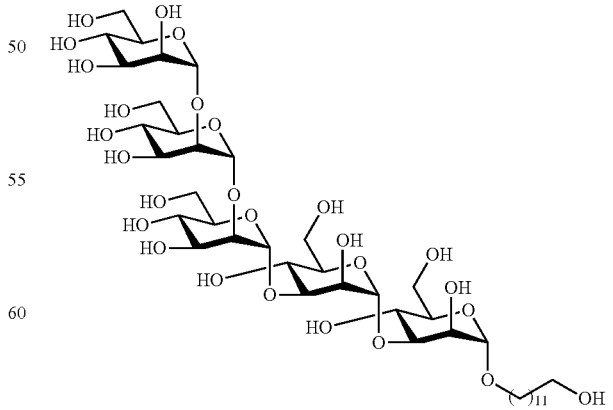

Compound 33* is prepared similarly to compound 21* starting from compound 5* and 12-benzyloxydecanol.

Compound 34*

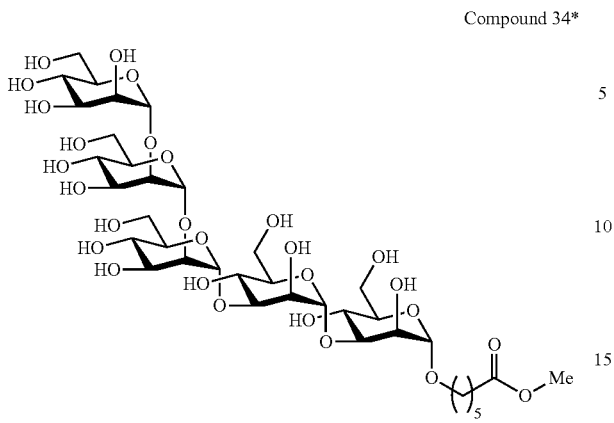

Compound 34* is prepared similarly to compound 21* starting from compound 5* and methyl 6-hydroxydecanoic acid.

Compound 34a*

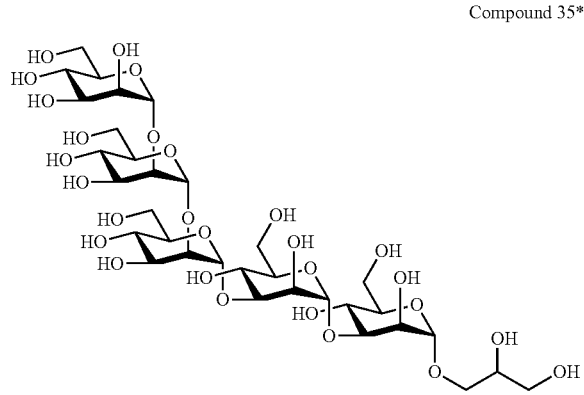

Compound 34a* is prepared similarly to compound 21* starting from compound 5* and methyl 6-hydroxydecanoic acid.

Compound 35*

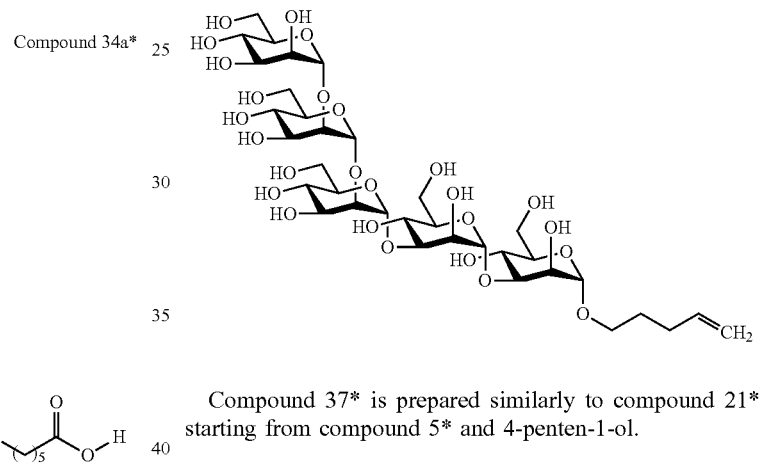

Compound 35* is prepared similarly to compound 21* starting from compound 5* and 1,2-dibenzyl glycerol or acetonide protected glycerol.

Compound 36*

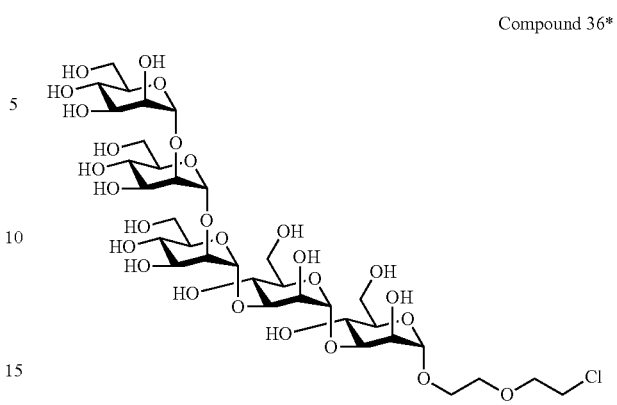

Compound 36* is prepared similarly to compound 21* starting from compound 5* and 2-(chloroethoxy)ethanol.

Compound 37*

Compound 37* is prepared similarly to compound 21* starting from compound 5* and 4-penten-1-ol.

Example 3: Synthesis of *K. pneumoniae* Serotype O5 Trisaccharide

Compound 38*

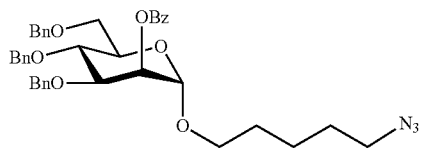

To a solution of compound 3* (490 mg, 0.758 mmol) and 5-azidopropanol (294 mg, 2.273 mmol) in a mixture of anhydrous toluene (11.4 mL) and anhydrous dioxane (3.76 mL) was added 4 Å MS and the mixture was stirred at room temperature for 30 min. Then, NIS (205 mg, 0.909 mmol) was added and the reaction mixture cooled to 0° C. TfOH (11.4 mg, 0.076 mmol) was added and the reaction mixture stirred for 2 h at 0° C. Reaction mixture was filtered and washed with sat. $Na_2S_2O_3$ solution (25 mL) and extracted with $CH_2Cl_2$ (2×40 mL). Combined organic layers were washed with sat. $NaHCO_3$ solution (25 mL) and brine (10 mL) and dried over anhydr. $Na_2SO_4$, and concentrated under reduced pressure. Purification by automated purification system using silica (ethyl acetate/cyclohexane) afforded the product 38* after evaporation of the solvent as a colorless thick gel (420 mg, 83%).

HRMS (ESI+) Calcd for $C_{39}H_{43}N_3O_7Na^+$ [M+Na]$^+$ 688.2999, found 688.3009.

Compound 39*

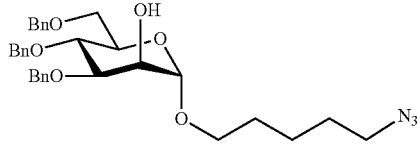

Sodium methoxide solution in MeOH (25% w/w) (0.41 mL, 1.802 mmol) was added to a solution of the monosaccharide 38* (400 mg, 0.601 mmol) in a mixture of MeOH:THF (2:1, 12 mL). The reaction was stirred at the same temperature for 20 h. The reaction was quenched by the addition of H$_2$O (15 mL) and diluted with brine (20 mL). Reaction mixture extracted with EtOAc (2×60 mL). Combined organic layers were dried over anhydr. Na$_2$SO$_4$ and concentrated under reduced pressure. Purification by automated purification system using silica (ethyl acetate/cyclohexane) afforded the product after evaporation of the solvent as a colorless thick gel (300 mg, 89%).

HRMS (ESI+) Calcd for $C_{32}H_{39}N_3O_6Na^+$ [M+Na]$^+$ 584.2737, found 584.2738.

Compound 40*

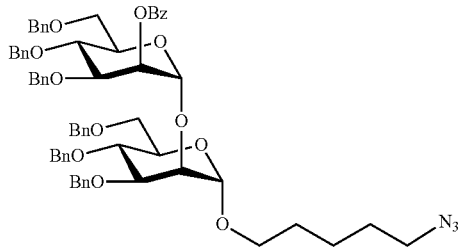

To a solution of compound 3* (355 mg, 0.548 mmol) and compound 39* (280 mg, 0.499 mmol) in a mixture of anhydrous toluene (10 mL) and anhydrous dioxane (3.3 mL) was added 4 Å MS and the mixture was stirred at room temperature for 30 min. Then, NIS (135 mg, 0.598 mmol) was added and the reaction mixture cooled to 0° C. TfOH (7.5 mg, 0.05 mmol) was added and the reaction mixture stirred for 1 h at 0° C. Reaction mixture was filtered and washed with sat. Na$_2$S$_2$O$_3$ solution (15 mL) and extracted with CH$_2$Cl$_2$ (2×25 mL). Combined organic layers were washed with sat. NaHCO$_3$ solution (15 mL) and brine (10 mL), subsequently dried over anhydr. Na$_2$SO$_4$ and concentrated under reduced pressure. Purification by automated purification system using silica (ethyl acetate/cyclohexane) afforded the product after evaporation of the solvent as a cloudy thick gel (350 mg, 64%) and starting compound 39* (62 mg, 22%).

HRMS (ESI+) Calcd for $C_{66}H_{71}N_3O_{12}Na^+$ [M+Na]$^+$ 1120.4935, found 1120.4922.

Compound 41*

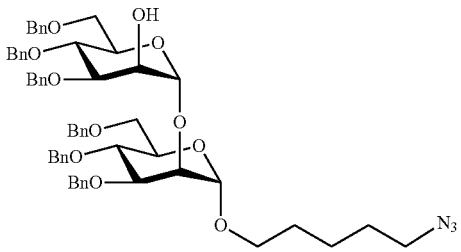

Sodium methoxide solution in MeOH (25% w/w) (0.8 mL, 3.19 mmol) was added to a solution of compound 40* (350 mg, 0.319 mmol) in a mixture of MeOH:THF (2:1, 7.5 mL). The reaction was stirred at the same temperature for 20 h. The reaction was quenched by the addition of H$_2$O (15 mL) and diluted with brine (20 mL). Reaction mixture was extracted with EtOAc (2×60 mL). Combined organic layers were dried over anhydr. Na$_2$SO$_4$, and concentrated under reduced pressure. Purification by automated purification system using silica (ethyl acetate/cyclohexane) afforded the product after evaporation of the solvent as a colorless thick gel (278 mg, 88%).

HRMS (ESI+) Calcd for $C_{59}H_{67}N_3O_{11}Na^+$ [M+Na]$^+$ 1016.4673, found 1016.4686.

Compound 42*

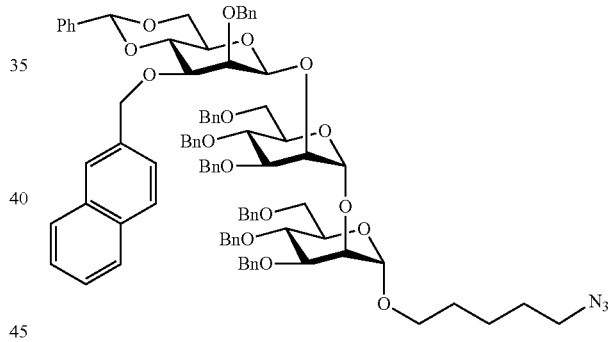

To a solution of compound 2* (180 mg, 0.304 mmol) in anhydrous DCM (11 mL) was added 4 Å MS and the mixture was stirred at room temperature for 30 min. Then, 1-(phenylsulfinyl)piperidine (69.7 mg, 0.333 mmol) and 2,4,6-tri-tert-butylpyrimidine (150 mg, 0.606 mmol) was added, reaction mixture cooled to −65° C. and stirred for 30 min. Triflic anhydride (61 µL, 0.362 mmol) was added and the reaction mixture stirred for 20 min at −65° C. Reaction mixture was then cooled to −78° C. and compound 41* (275 mg, 0.277 mmol) in DCM (5 mL) was added dropwise and stirred for 6 h at −78° C. and then warmed to 0° C. over 1 h. The reaction mixture was filtered and washed with sat. NaHCO$_3$ solution (25 mL) and extracted with CH$_2$Cl$_2$ (2×35 mL). Combined organic layers were washed with brine (10 mL) and dried over anhydr. Na$_2$SO$_4$. Purification by automated purification system using silica (ethyl acetate/cyclohexane) afforded the product after evaporation of the solvent as a cloudy thick gel (220 mg, 54%).

HRMS (ESI+) Calcd for $C_{99}H_{95}N_3O_{16}Na^+$ [M+Na]$^+$ 1496.6610, found 1496.6623.

Compound 43*

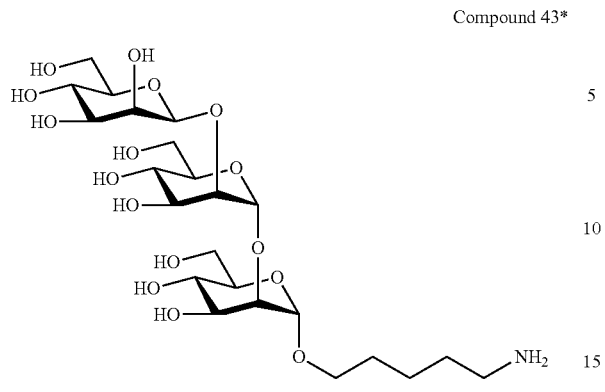

Compound 45*

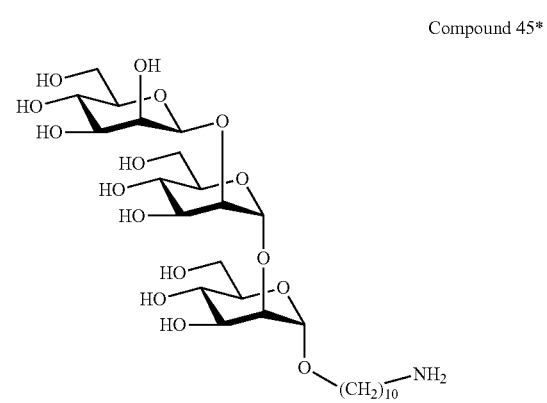

Compound 45* is prepared similarly to compound 43* starting from compound 5* and azidodecanol.

Compound 42* (8 mg, 5.99 µmol) was taken in solvent mixture DCM (1 mL), tBuOH (1 mL) and two drops of water. Pd/C was added and hydrogenated under $H_2$ balloon at rt. The reaction mixture was filtered through PTFE filter, washed the residue with methanol (6 mL), (50% methanol-water (6 mL). The filtrate was evaporated in vacuum to get the crude product. Crude product was clean by $^1$H NMR, sample recovered and freeze dried to obtain a white crystalline solid (3.53 mg, quantitative).

HRMS (ESI+) Calcd for $C_{23}H_{43}NO_{16}H^+$ [M+H]$^+$ 590.2660, found 590.2814.

$^1$H NMR (400 MHz, $D_2O$) δ 5.12 (d, J=1.8 Hz, 1H), 5.07 (d, J=1.7 Hz, 1H), 4.77 (s, 1H), 4.28 (dd, J=3.4, 1.8 Hz, 1H), 4.02 (d, J=3.2 Hz, 1H), 3.81-4.00 (m, 6H), 3.48-3.81 (m, 11H), 3.36 (ddd, J=9.4, 6.7, 2.3 Hz, 1H), 2.98 (t, J=7.6 Hz, 2H), 1.58-1.74 (m, 4H), 1.36-1.51 (m, 2H).

Compound 46*

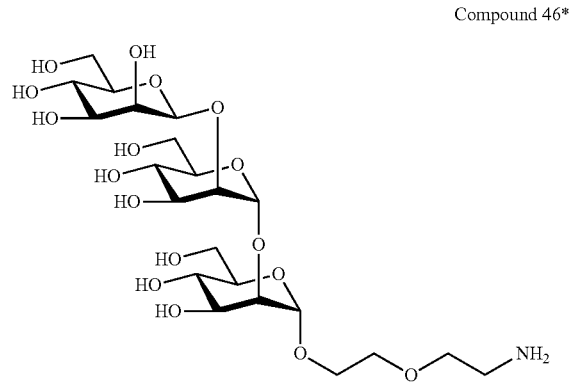

Compound 46* is prepared similarly to compound 43* starting from compound 5* and 2-(2-azidoethoxy)ethanol.

Compound 44*

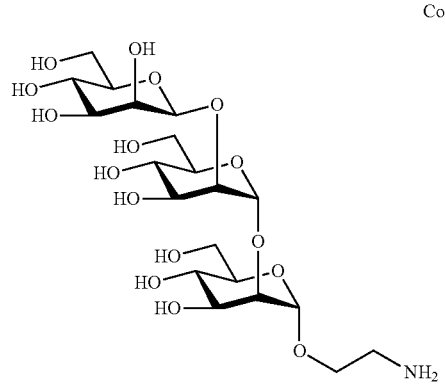

Compound 47*

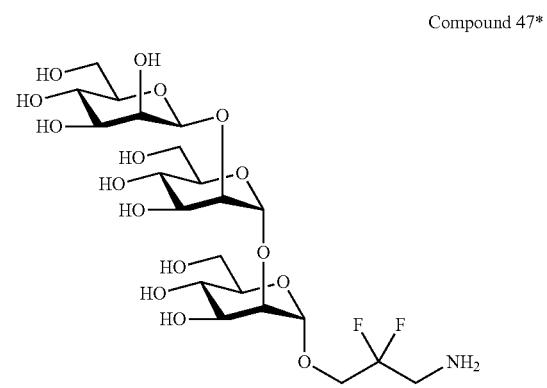

Compound 44* is prepared similarly to compound 43* starting from compound 3* and azidoethanol.

Compound 47* is prepared similarly to compound 43* starting from compound 5* and 3-azido-2,2-difluoropropanol.

Compound 48*

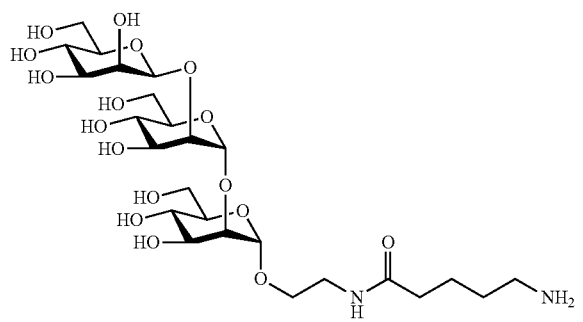

Compound 48* is prepared similarly to compound 43* starting from compound 5* and the corresponding azido alcohol.

Compound 51*

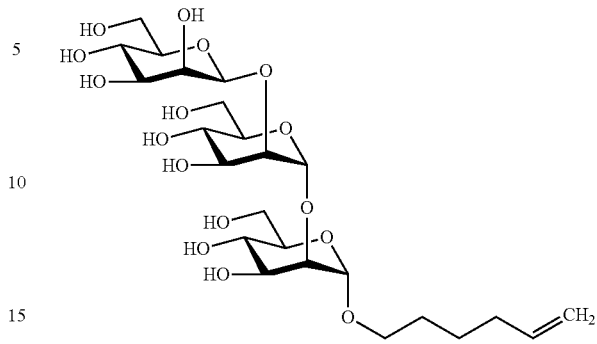

Compound 51* is prepared similarly to compound 43* starting from compound 5* and 5-hexenol.

Compound 49*

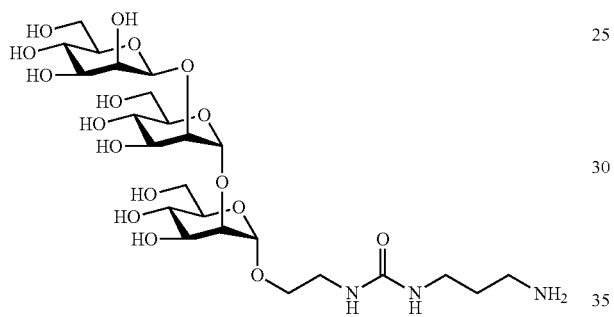

Compound 49* is prepared similarly to compound 43* starting from compound 5* and the corresponding azido alcohol.

Compound 52*

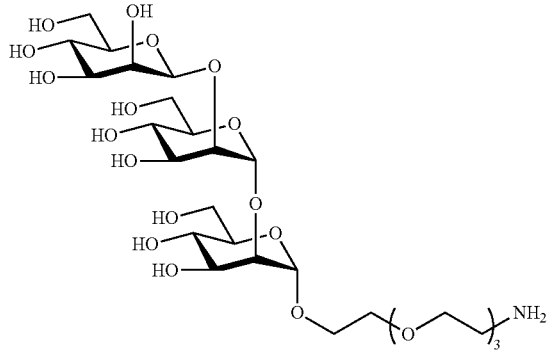

Compound 52* is prepared similarly to compound 43* starting from compound 5* and 11-azido-3,6,9-trioxaundecanol.

Compound 50*

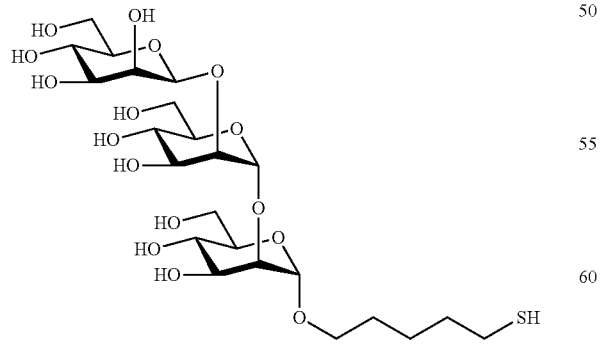

Compound 50* is prepared similarly to compound 43* starting from compound 5* and the corresponding S-benzylthio alcohol.

Compound 53*

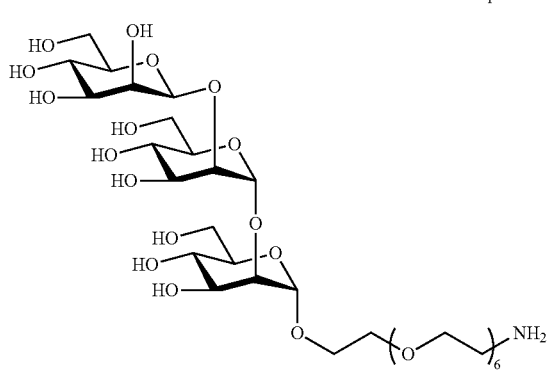

Compound 53* is prepared similarly to compound 43* starting from compound 5* and azido-PEG7-alcohol.

Compound 54*

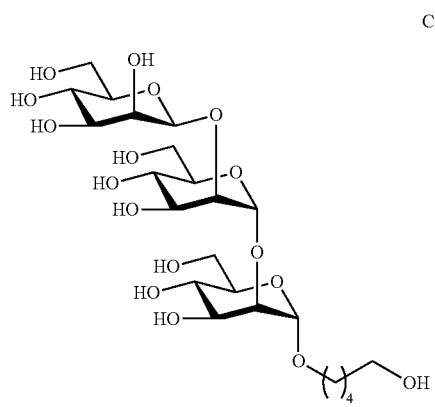

Compound 54* is prepared similarly to compound 43* starting from compound 5* and 5-benzyloxypentanol.

Compound 55*

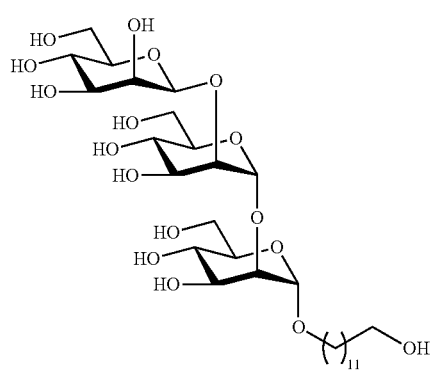

Compound 55* is prepared similarly to compound 43* starting from compound 5* and 12-benzyloxydecanol.

Compound 56*

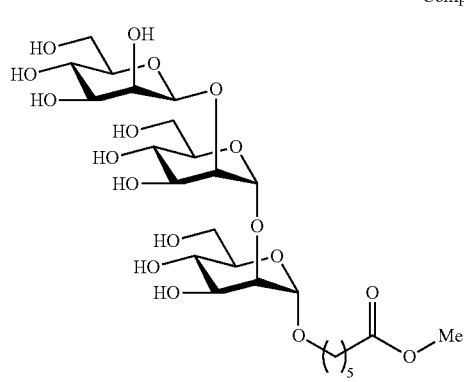

Compound 56* is prepared similarly to compound 43* starting from compound 5* and methyl 6-hydroxydecanoic acid.

Compound 56a*

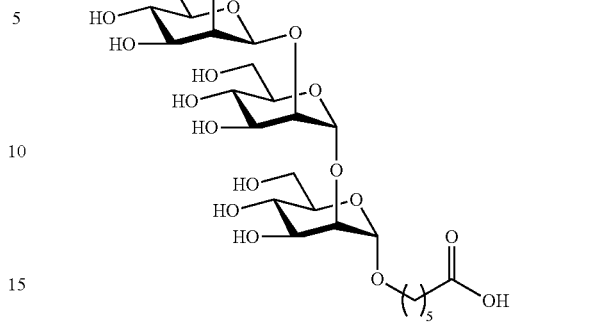

Compound 56a* is prepared similarly to compound 43* starting from compound 5* and methyl 6-hydroxydecanoic acid.

Compound 57*

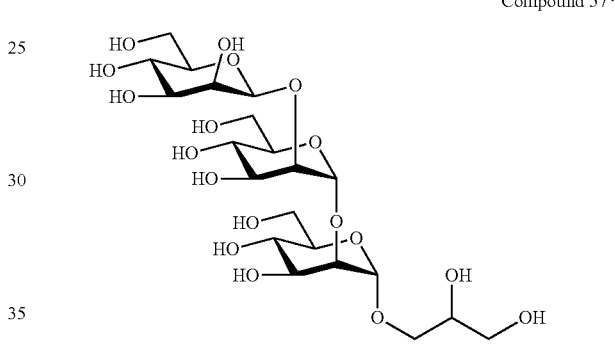

Compound 57* is prepared similarly to compound 43* starting from compound 5* and 1,2-dibenzyl glycerol.

Compound 58*

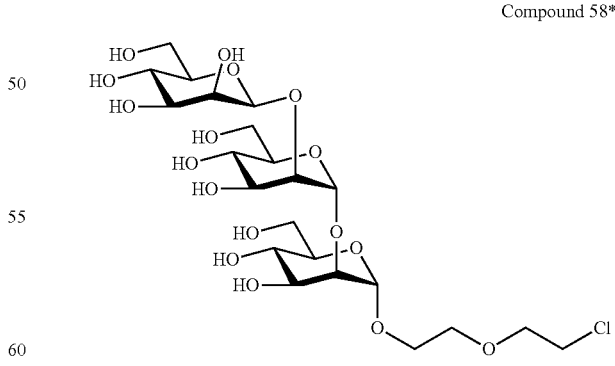

Compound 58* is prepared similarly to compound 43* starting from compound 5* and 2-(chloroethoxy)ethanol.

Compound 59*

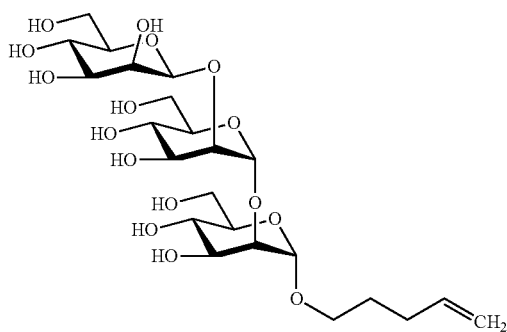

Compound 59* is prepared similarly to compound 43* starting from compound 5* and 4-penten-1-ol.

Example 4: Synthesis of *K. pneumoniae* Serotype O5 Hexasaccharide

Compound 60*

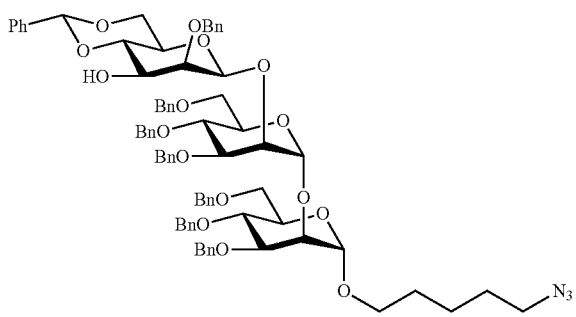

To a solution of compound 42* (220 mg, 0.149 mmol) in DCM:PBS (2:1, 7.4 mL) was added 2,3-dichloro-5,6-dicyano-1,4-benzoquinone (67.7 mg, 0.298 mmol) at 0° C. The reaction mixture was stirred for 4 h at room temperature and monitored by TLC (EtOAc in cyclohexane, 2:1). Reaction was quenched with sat. NaHCO$_3$ (50 mL) and extracted with DCM (2×50 mL). The combined organic layers were washed with brine (25 mL) and dried over Na$_2$SO$_4$ to obtain the crude product. The crude product was purified by automated flash chromatography using silica (ethyl acetate/cyclohexane) to obtain compound 60* as colorless oil (125 mg, 63%).

HRMS (ESI+) Calcd for $C_{79}H_{87}N_3O_{16}Na^+$ [M+Na]$^+$ 1356.5984, found 1356.5983.

Compound 61*

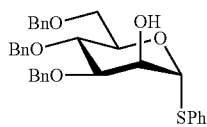

To a solution of compound 8* (160 mg, 0.209 mmol) in DCM (3 mL) was added triethylamine (0.2 mL, 1.435 mmol) at 0° C. The reaction mixture was stirred for 1 h at room temperature. Reaction mixture was concentrated under reduced pressure to obtain the crude product. The crude product was purified by automated flash chromatography using silica (ethyl acetate/cyclohexane) to obtain a colorless oil (96 mg, 85%).

HRMS (ESI+) Calcd for $C_{33}H_{34}O_5SNa^+$ [M+Na]$^+$ 566.2025, found 566.2065.

Compound 62*

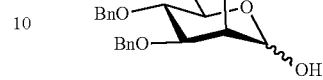

To compound 61* (1.05 g, 1.623 mmol) in DCM (10 mL) and H$_2$O (1 mL) was added N-iodosuccinimide (365 mg, 1.623 mmol) and trifluoroacetic acid (124 µL, 1.623 mmol) at 0° C. and stirred for 2 h. The reaction mixture was partitioned between sat. aqu. NaHCO$_3$ (50 mL) solution and DCM (50 mL). The organic layer was washed with sat. Na$_2$S$_2$O$_3$ solution (50 mL) and dried over Na$_2$SO$_4$. The crude product was purified by column chromatography using EtOAc and cyclohexane as solvents to afford the desired product (730 mg, 81%) as colorless oil.

HRMS (ESI+) Calcd for $C_{34}H_{34}O_7Na^+$ [M+Na]$^+$ 577.2202, found 577.2208.

Compound 63*

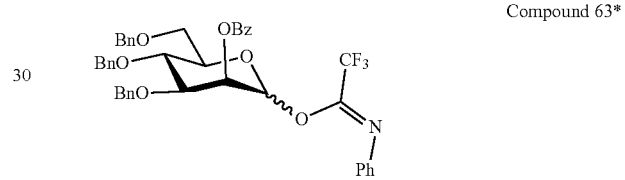

Cs$_2$CO$_3$ (141 mg, 0.433 mmol) and 2,2,2-trifluro-N-phenyl-acetimidoyl chloride (135 mg, 0.649 mmol) were added to a solution of lactol 62* (120 mg, 0.216 mmol) in DCM (2.2 mL). The reaction mixture was stirred at room temperature and monitored by TLC. After 2 hours all the starting material was consumed, the reaction was filtered through Celite® and washed with DCM (10 mL). The solvent was evaporated and the crude product (157 mg, quantitative) was used in the next step without any purification.

Compound 64*

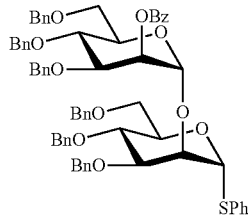

To a solution of compound 63* (157 mg, 0.216 mmol) and compound 61* (117 mg, 0.216 mmol) in anhydrous toluene (4.6 mL) and dioxane (1.5 mL) was added 4 Å MS and the mixture was stirred at room temperature for 30 min. TMSOTf (3.92 µL, 0.022 mmol) was added and the reaction mixture stirred at −10° C. for 1 h. The reaction was quenched with sat. NaHCO$_3$ solution (25 mL) and extracted with DCM (2×20 mL). The organic layer was dried over Na$_2$SO$_4$ and evaporated to give crude product. The residue was purified by column chromatography using EtOAc and cyclohexane as solvents to afford the desired product (193 mg, 83%) as colorless oil.

HRMS (ESI+) Calcd for $C_{67}H_{66}O_{11}SNa^+$ [M+Na]$^+$ 1101.4224, found 1101.4073.

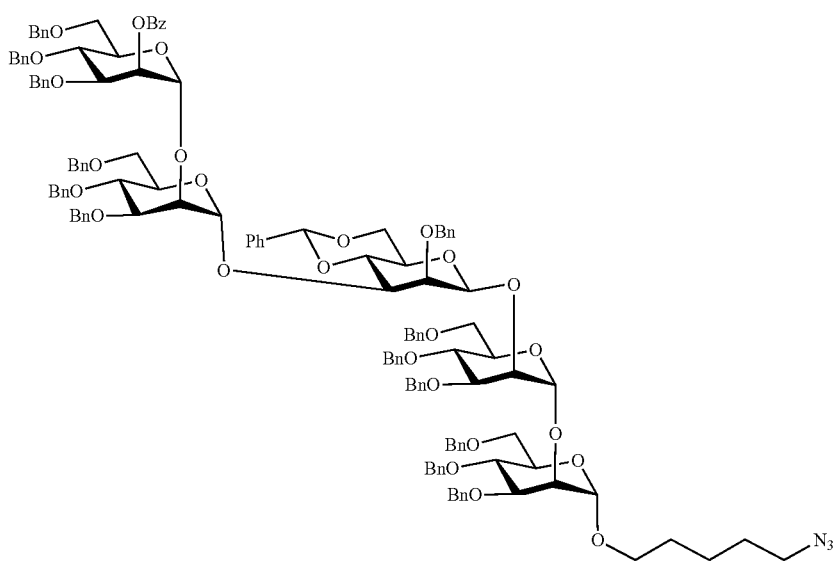

Compound 65*

To a solution of compound 64* (116 mg, 0.108 mmol) and compound 60* (120 mg, 0.090 mmol) in a mixture of anhydrous toluene (4.5 mL) and anhydrous dioxane (1.5 mL) was added 4 Å MS and the mixture was stirred at room temperature for 30 min. Then, NIS (26.3 mg, 0.117 mmol) was added and the reaction mixture cooled to 0° C. TfOH (1.35 mg, 8.99 µmol) was added and the reaction mixture stirred for 3 h and gradually warmed to room temp. Reaction mixture was filtered and washed with sat. $Na_2S_2O_3$ solution (15 mL) and extracted with $CH_2Cl_2$ (2×25 mL). Combined organic layers were washed with sat. $NaHCO_3$ solution (15 mL) and brine (10 mL) and dried over anhydr. $Na_2SO_4$. Purification by automated purification system using silica (ethyl acetate/cyclohexane) afforded the product after evaporation of the solvent as a cloudy thick gel (110 mg, 53%).

HRMS (ESI+) Calcd for $C_{140}H_{147}N_3O_{27}Na^+$ [M+Na]$^+$ 2326.0153, found 2326.0177.

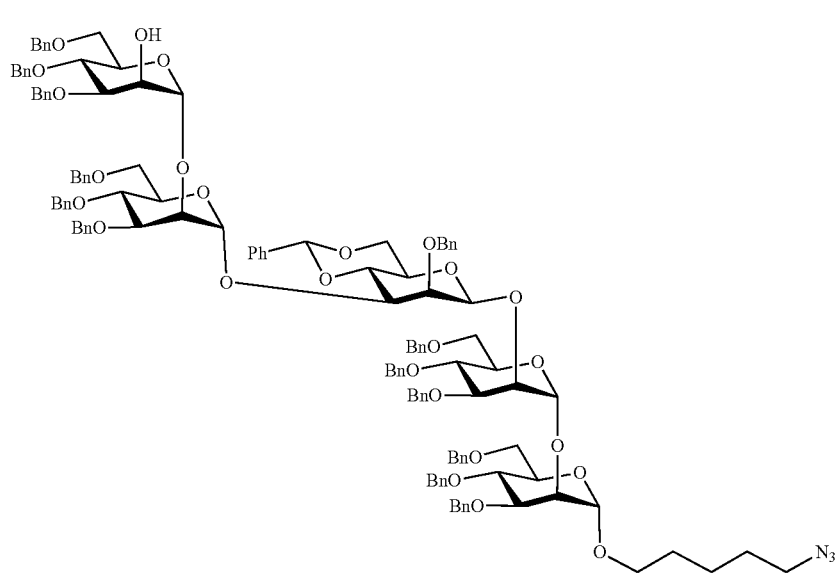

Compound 66*

Sodium methoxide solution in MeOH (25% w/w) (0.051 mL, 0.239 mmol) was added to a solution of the pentasaccharide 65* (110 mg, 0.048 mmol) in a mixture of MeOH:THF (2:1, 3 mL). The reaction was stirred at the same temperature for 16 h. The reaction was quenched by the addition of $H_2O$ (5 mL) and diluted with brine (10 mL). Reaction mixture extracted with EtOAc (2×20 mL). Combined organic layers were dried over anhydr. $Na_2SO_4$, filtered and concentrated under reduced pressure. Purification by automated purification system using silica (ethyl acetate/cyclohexane) afforded the product 66* after evaporation of the solvent as a colorless thick gel (95 mg, 90%).

HRMS (ESI+) Calcd for $C_{140}H_{147}N_3O_{27}Na^+$ [M+Na]$^+$ 2221.9891, found 2221.9960.

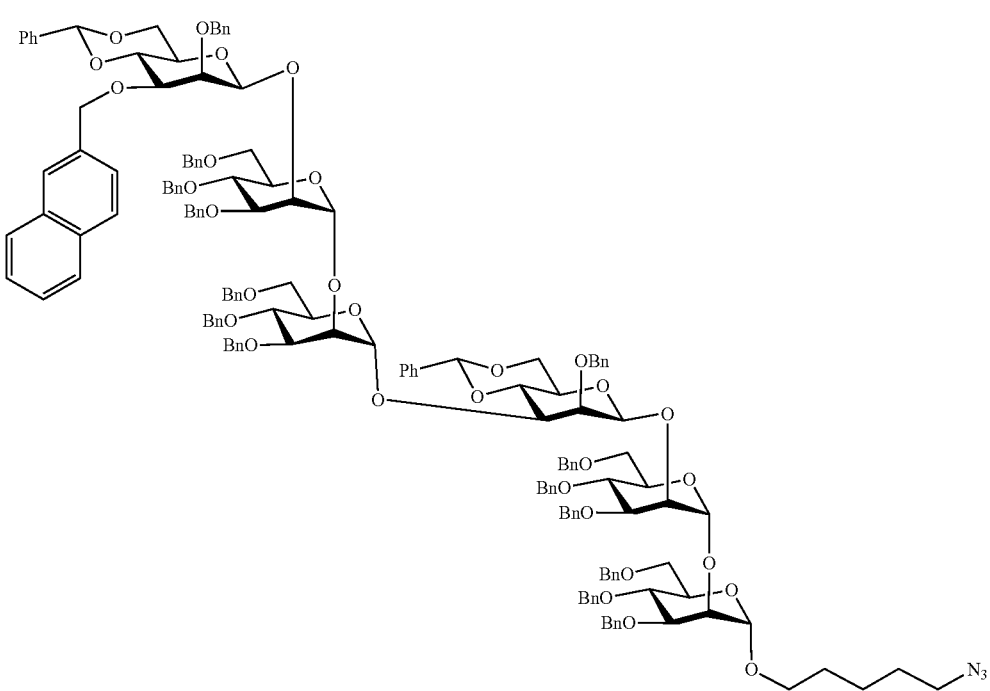

Compound 67*

To a solution of compound 2* (23.16 mg, 0.039 mmol) in anhydrous DCM (2 mL) was added 4 Å MS and the mixture was stirred at room temperature for 10 min. Then, 1-(phenylsulfinyl)piperidine (8.59 mg, 0.041 mmol) and 2,4,6-tri-tert-butylpyrimidine (18.55 mg, 0.075 mmol) were added. The reaction mixture was cooled to −65° C. and stirred for 30 min. Triflic anhydride (7.55 µL, 0.045 mmol) was added and the reaction mixture stirred for 15 min at −65° C. Reaction mixture was then cooled to −78° C. and compound 66* (75 mg, 0.034 mmol) in DCM (1.5 mL) was added dropwise and stirred for 6 h at −78° C. and then warmed to −25° C. within 1 h. Reaction mixture was filtered and washed with sat. NaHCO$_3$ solution (15 mL) and extracted with CH$_2$Cl$_2$ (2×25 mL). Combined organic layers were washed with brine (10 mL) and dried over anhydr. Na$_2$SO$_4$. Purification by automated purification system using silica (ethyl acetate/cyclohexane) afforded the product (as α/β mixture) after evaporation of the solvent as a cloudy thick gel (35 mg, 38%).

HRMS (ESI+) Calcd for $C_{164}H_{171}N_3O_{31}Na^+$ [M+Na]$^+$ 2702.1828, found 2702.1783.

Compound 68*

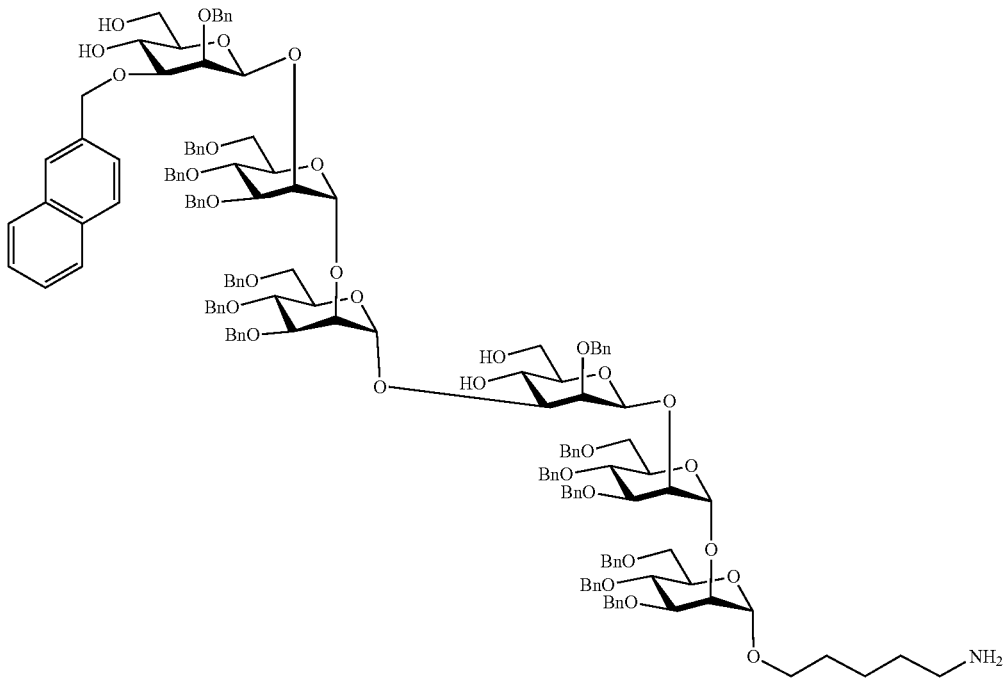

To compound 67* (35 mg, 0.013 mmol) in DCM (2.5 mL) was added ethane thiol (9.66 µL, 0.131 mmol) and p-toluene sulfonic acid monohydrate (1.24 mg, 6.53 µmol) at room temperature and the mixture was stirred for 1.5 h. Reaction mixture was quenched with triethylamine (1 mL) and concentrated under vacuum, the residue was purified by column chromatography using EtOAc and cyclohexane as solvents to afford the desired product as pure desired β-isomer (16 mg, 49%) as colorless oil.

HRMS (ESI+) Calcd for $C_{150}H_{163}N_3O_{31}Na^+$ [M+Na]$^+$ 2526.1202, found 2526.1152.

Compound 69*

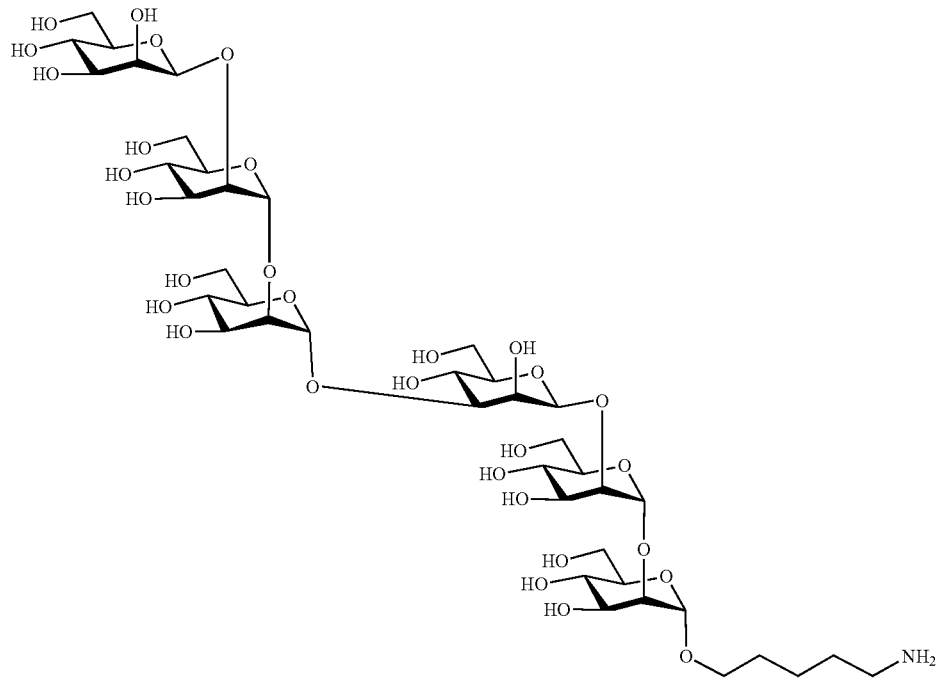

Compound 68* (15 mg, 5.99 µmol) was taken in solvent mixture DCM (1 mL), tBuOH (1 mL) and two drops of water. Pd/C was added and hydrogenated for 24 h under H$_2$ balloon at r.t. The reaction mixture was filtered through PTFE filter, and the residue was washed with methanol (6 mL), (50% methanol-water (6 mL). The filtrate was evaporated under vacuum to get the crude product. $^1$H NMR analysis showed the completion of the reaction and the presence of product. So, crude product was purified through the C18 Sepak column using water (3 mL×2, fr1), 20% acetonitrile-water (3 mL×2, fr2) and acetonitrile (3 mL, fr3). All the fractions were frozen and lyophilized for 24 h to get one pure fraction fr1 of compound 69* (white solid, 5.64 mg, 87%), and two impure fractions white fluffy solid (fr2, 0.2 mg) a white fluffy solid (fr.3, 0.2 mg).

HRMS (ESI+) Calcd for C$_{41}$H$_{73}$NO$_{31}$H$^+$ [M+H]$^+$ 1076.4244, found 1076.4245.

$^1$H NMR (400 MHz, Deuterium Oxide) δ 5.33 (d, J=1.8 Hz, 1H), 5.14 (d, J=1.8 Hz, 1H), 5.10 (d, J=1.7 Hz, 1H), 5.06 (d, J=1.7 Hz, 1H), 4.65-4.68 (m, 2H), 4.27 (dt, J=3.2, 1.4 Hz, 2H), 4.14-4.20 (m, 1H), 4.09 (dd, J=3.4, 1.7 Hz, 1H), 3.82-4.04 (m, 12H), 3.47-3.82 (m, 23H), 3.32-3.43 (m, 2H), 2.94-3.02 (m, 2H), 1.59-1.73 (m, 4H), 1.35-1.53 (m, 2H).

Example 5: Synthesis of *K. pneumoniae* Serotype O5 Nonasaccharide

Compound 70*

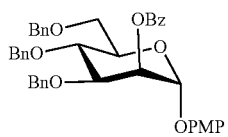

To a solution of compound 63* (720 mg, 0.978 mmol) and 4-methoxyphenol (121 mg, 0.978 mmol) in anhydrous toluene (7.3 mL) and dioxane (2.5 mL) was added 4 Å MS and the mixture was stirred at room temperature for 30 min. TMSOTf (18 µL, 0.098 mmol) was added and the reaction mixture stirred at −10° C. for 1 h. The reaction was quenched with sat. NaHCO$_3$ solution (35 mL) and extracted with DCM (2×50 mL). The organic layer was dried over Na$_2$SO$_4$ and evaporated to give crude product. The residue was purified by column chromatography using EtOAc and cyclohexane as solvents to afford the desired product (540 mg, 84%) as colorless oil.

HRMS (ESI+) Calcd for C$_{41}$H$_{40}$O$_8$Na$^+$ [M+Na]$^+$ 683.2621, found 683.2643.

Compound 71*

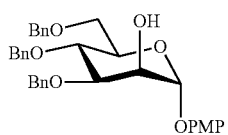

Sodium methoxide solution in MeOH (25% w/w) (0.52 mL, 2.406 mmol) was added to a solution of the benzoate 70* (530 mg, 0.802 mmol) in a mixture of MeOH:THF (4:1, 7.5 mL). The reaction was stirred at the same temperature for 16 h. The reaction was quenched by the addition of H$_2$O (3 mL) and diluted with brine (25 mL). Reaction mixture was extracted with EtOAc (2×50 mL). Combined organic layers were dried over anhydr. Na$_2$SO$_4$ and concentrated under reduced pressure. Purification by automated purification system using silica (ethyl acetate/cyclohexane) afforded the product after evaporation of the solvent as a colorless thick gel (430 mg, 96%).

HRMS (ESI+) Calcd for C$_{34}$H$_{36}$O$_7$Na$^+$ [M+Na]$^+$ 579.2359, found 579.2395.

Compound 72*

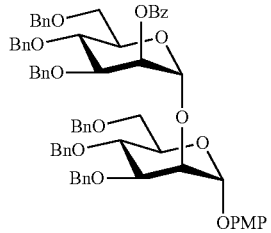

To a solution of compound 3* (100 mg, 0.155 mmol) and compound 71* (86 mg, 0.155 mmol) in a mixture of anhydrous toluene (2.3 mL) and anhydrous dioxane (0.8 mL) was added 4 Å MS and the mixture let stir at room temperature for 30 min. Then, NIS (41.7 mg, 0.186 mmol) was added and the reaction mixture cooled to −10° C. TfOH (2.32 mg, 0.015 mmol) was added and the reaction mixture stirred for 1 h and gradually warmed to room temp. Reaction mixture was filtered and washed with sat. Na$_2$S$_2$O$_3$ solution (25 mL) and extracted with CH$_2$Cl$_2$ (2×30 mL). Combined organic layers were washed with sat. NaHCO$_3$ solution (15 mL) and brine (10 mL), dried over anhydr. Na$_2$SO$_4$, and concentrated under reduced pressure. Purification by automated purification system using silica (ethyl acetate/cyclohexane) afforded the product after evaporation of the solvent as a cloudy thick gel (132 mg, 78%).

HRMS (ESI+) Calcd for C$_{66}$H$_{68}$O$_{13}$Na$^+$ [M+Na]$^+$ 1115.4558, found 1115.4595.

Compound 73*

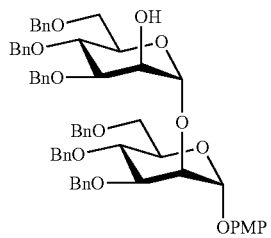

Sodium methoxide solution in MeOH (25% w/w) (0.074 mL, 0.343 mmol) was added to a solution of the benzoate 72* (125 mg, 0.114 mmol) in a mixture of MeOH:THF (4:1, 2.3 mL). The reaction was stirred at the same temperature for 16 h. The reaction was quenched by the addition of H$_2$O (3 mL) and diluted with brine (25 mL). Reaction mixture extracted with EtOAc (2×25 mL). Combined organic layers were dried over anhydr. Na$_2$SO$_4$, and concentrated under reduced pressure. Purification by automated purification system using silica (ethyl acetate/cyclohexane) afforded the product after evaporation of the solvent as a colorless thick gel (108 mg, 95%).

HRMS (ESI+) Calcd for C$_{61}$H$_{64}$O$_{12}$Na$^+$ [M+Na]$^+$ 1011.4295, found 1011.4326.

Compound 74*

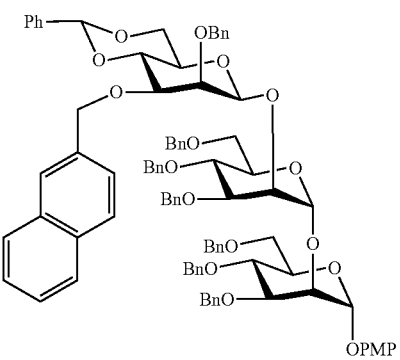

To a solution of compound 2* (197 mg, 0.334 mmol) in anhydrous DCM (6 mL) was added 4 Å MS and the mixture was stirred at room temperature for 30 min. Then, 1-(phenylsulfinyl)piperidine (76 mg, 0.365 mmol) and 2,4,6-tri-tert-butylpyrimidine (165 mg, 0.664 mmol) were added, reaction mixture cooled to −65° C. and stirred for 30 min. Triflic anhydride (67 µL, 0.397 mmol) was added and the reaction mixture stirred for 20 min at −65° C. Reaction mixture was then cooled to −78° C. and compound 73* (300 mg, 0.303 mmol) in DCM (4 mL) was added dropwise and stirred for 6 h at −78° C. and then warmed to 0° C. within 1 h. Reaction mixture was filtered and washed with sat. NaHCO$_3$ solution (25 mL) and extracted with CH$_2$Cl$_2$ (2×25 mL). Combined organic layers were washed with brine (10 mL), dried over anhydr. Na$_2$SO$_4$, and concentrated under reduced pressure. Purification by automated purification system using silica (ethyl acetate/cyclohexane) afforded the product after evaporation of the solvent as a cloudy thick gel (300 mg, 67%).

HRMS (ESI+) Calcd for C$_{92}$H$_{95}$O$_{17}$Na$^+$ [M+Na]$^+$ 1492.6266, found 1492.6232.

Compound 75*

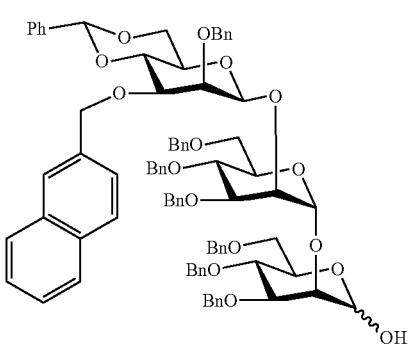

To trisaccharide 74*(289 mg, 0.197 mmol) in acetonitrile (8.7 mL) and H$_2$O (1.1 mL) was added ceric ammonium nitrate (172 mg, 0.315 mmol) at 0° C. and stirred for 2 h. Reaction mixture was monitored by TLC, another portion of ceric ammonium nitrate (172 mg, 0.315 mmol) was added and stirred for 2 h. The reaction mixture was partitioned between sat. aq. NaHCO$_3$ (25 mL) solution and DCM (35 mL). The aqueous layer was extracted with DCM (25 mL), combined organic layers were dried over Na$_2$SO$_4$ and evaporated to give crude product. The residue was purified by column chromatography using EtOAc and cyclohexane as solvents to afford the desired product (125 mg, 46%) as light-yellow oil.

HRMS (ESI+) Calcd for C$_{85}$H$_{86}$O$_{16}$Na$^+$ [M+Na]$^+$ 1385.5814, found 1385.5885.

Compound 76*

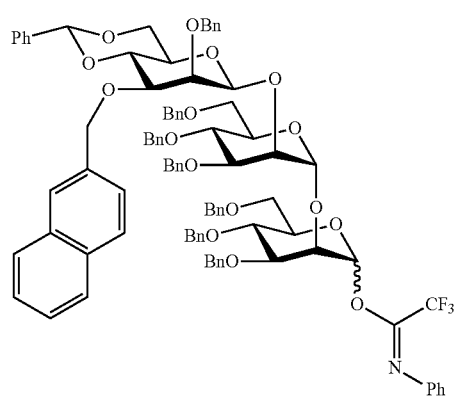

Cs$_2$CO$_3$ (38.2 mg, 0.117 mmol) and 2,2,2-trifluro-N-phenyl-acetimidoyl chloride (36.5 mg, 0.176 mmol) were added to a solution of lactol 75* (80 mg, 0.059 mmol) in DCM (8 mL). The reaction mixture was stirred at room temperature and monitored by TLC. After 2 hours all the starting material was consumed, the reaction was filtered through celite and washed with DCM (20 mL). The solvent was evaporated and the crude product (90 mg, quantitative) was used in the next step without any purification.

Compound 77*

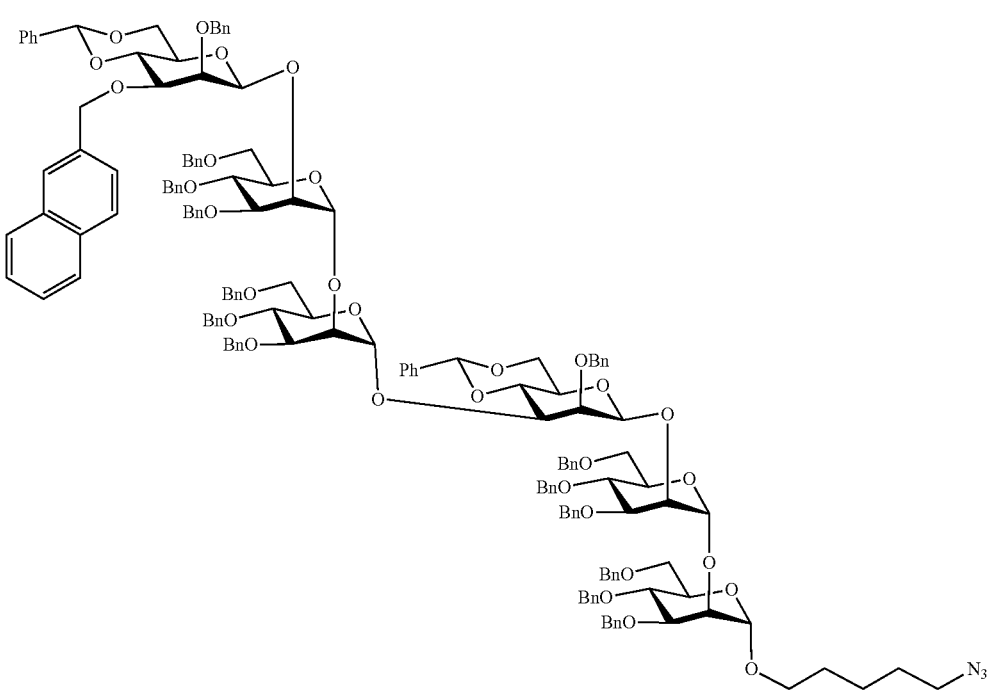

To a solution of compound 76* (80 mg, 0.052 mmol) and compound 60* (69.6 mg, 0.052 mmol) in anhydrous toluene (2 mL) and dioxane (0.66 mL) was added 4 Å MS and the mixture was stirred at room temperature for 30 min. TMSOTf (1 µL, 5.21 µmol) was added and the reaction mixture stirred at −10° C. for 1 h. The reaction was quenched with sat. NaHCO$_3$ solution (20 mL) and extracted with DCM (2×25 mL). The organic layer was dried over Na$_2$SO$_4$ and evaporated to give crude product. The residue was purified by column chromatography using EtOAc and cyclohexane as solvents to afford the desired product (70 mg, 50%) as colorless oil.

HRMS (ESI+) Calcd for C$_{164}$H$_{171}$N$_3$O$_{31}$Na$^+$ [M+Na]$^+$ 2702.1828, found 2702.1853.

Compound 78*

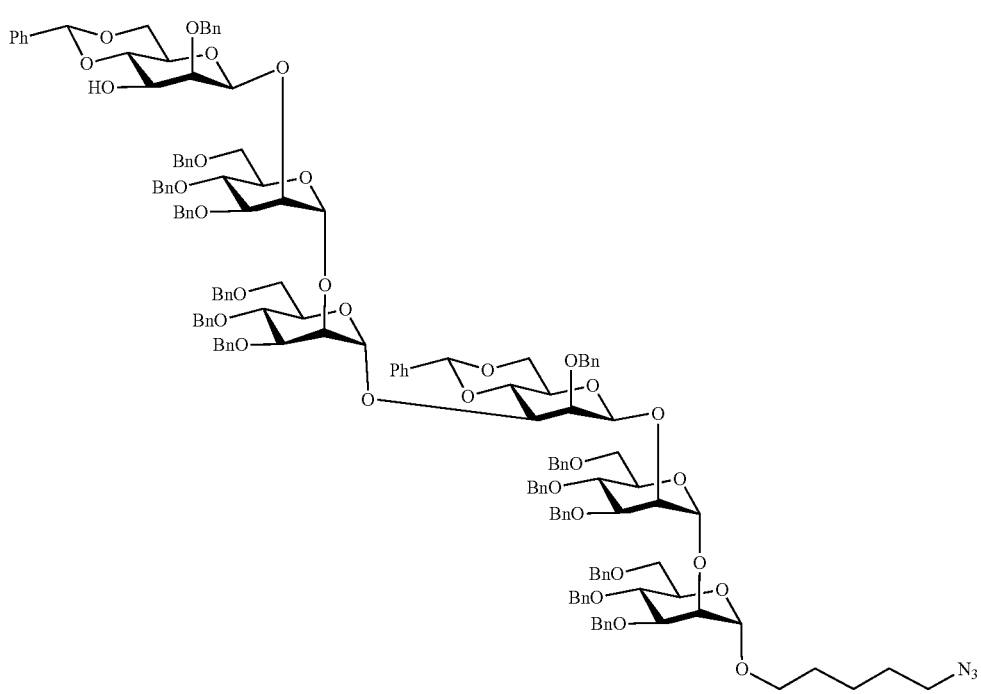

To a solution of compound 77* (60 mg, 0.022 mmol) in DCM:PBS (2:1, 5.1 mL) was added 2,3-dichloro-5,6-dicyano-1,4-benzoquinone (10.2 mg, 0.045 mmol) at 0° C. The reaction mixture was stirred for 2 h at room temperature and monitored by TLC (EtOAc in cyclohexane, 2:1). A portion of 2,3-dichloro-5,6-dicyano-1,4-benzoquinone (5 mg) was added again and the mixture was stirred at room temp for 2 h. Reaction was quenched with sat. NaHCO$_3$ (25 mL) and extracted with DCM (2×25 mL). The combined organic layers were washed with brine (15 mL) and dried over Na$_2$SO$_4$, and the filtrate was concentrated under reduced pressure to obtain the crude product. The crude product was purified by automated flash chromatography using silica (ethyl acetate/cyclohexane) to obtain a colorless oil (30 mg, 53%).

HRMS (ESI+) Calcd for C$_{153}$H$_{163}$N$_3$O$_{31}$Na$^+$ [M+Na]$^+$ 2562.1202, found 2562.1219.

Compound 79*

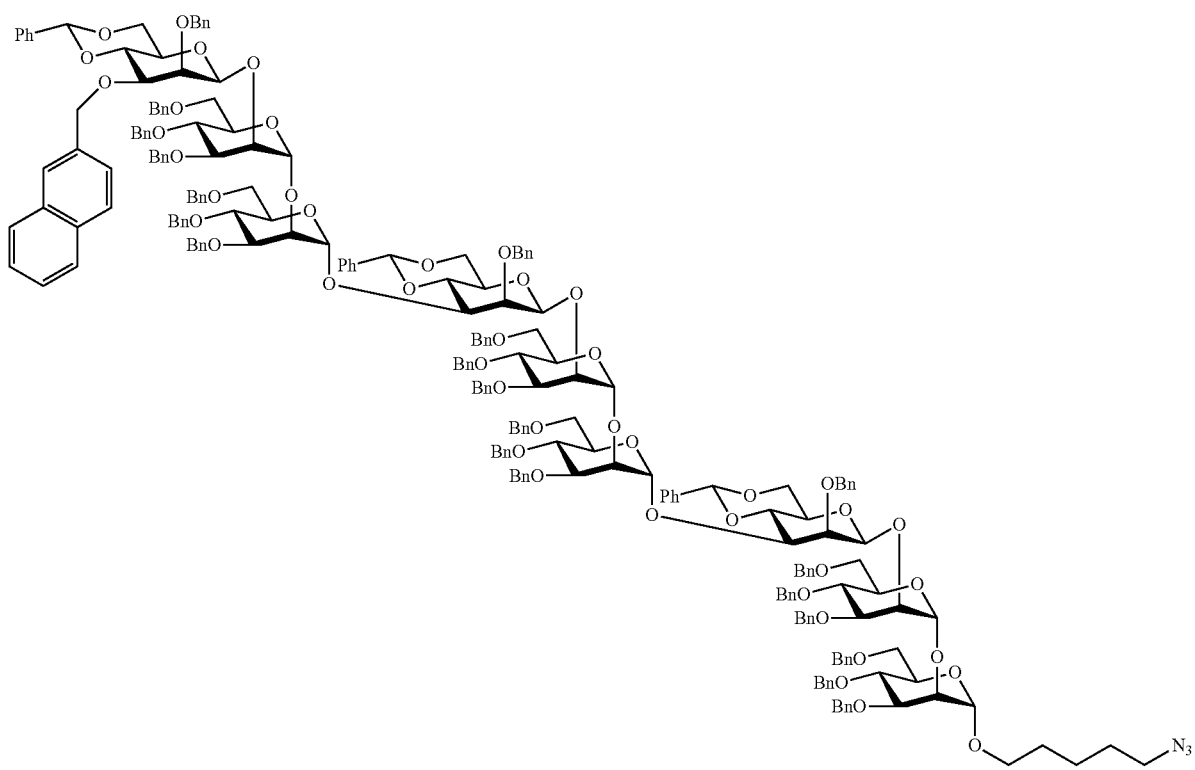

To a solution of compound 76* (35 mg, 0.023 mmol) and compound 78* (29 mg, 0.011 mmol) in anhydrous toluene (3 mL) and dioxane (1 mL) was added 4 Å MS and the mixture was stirred at room temperature for 30 min. TMSOTf (0.2 μL, 1.142 μmol) was added and the reaction mixture stirred at −10° C. for 1 h. The reaction was quenched with sat. NaHCO$_3$ solution (20 mL) and extracted with DCM (2×25 mL). The organic layer was dried over Na$_2$SO$_4$ and evaporated to give crude product. The residue was purified by column chromatography using EtOAc and cyclohexane as solvents to afford the desired product (28 mg, 63%) as yellow oil.

MALDI-TOF: Calcd for C$_{238}$H$_{247}$N$_3$O$_{46}$H$^+$ [M+H]$^+$ 3885.722, found 3885.105.

Compound 80*

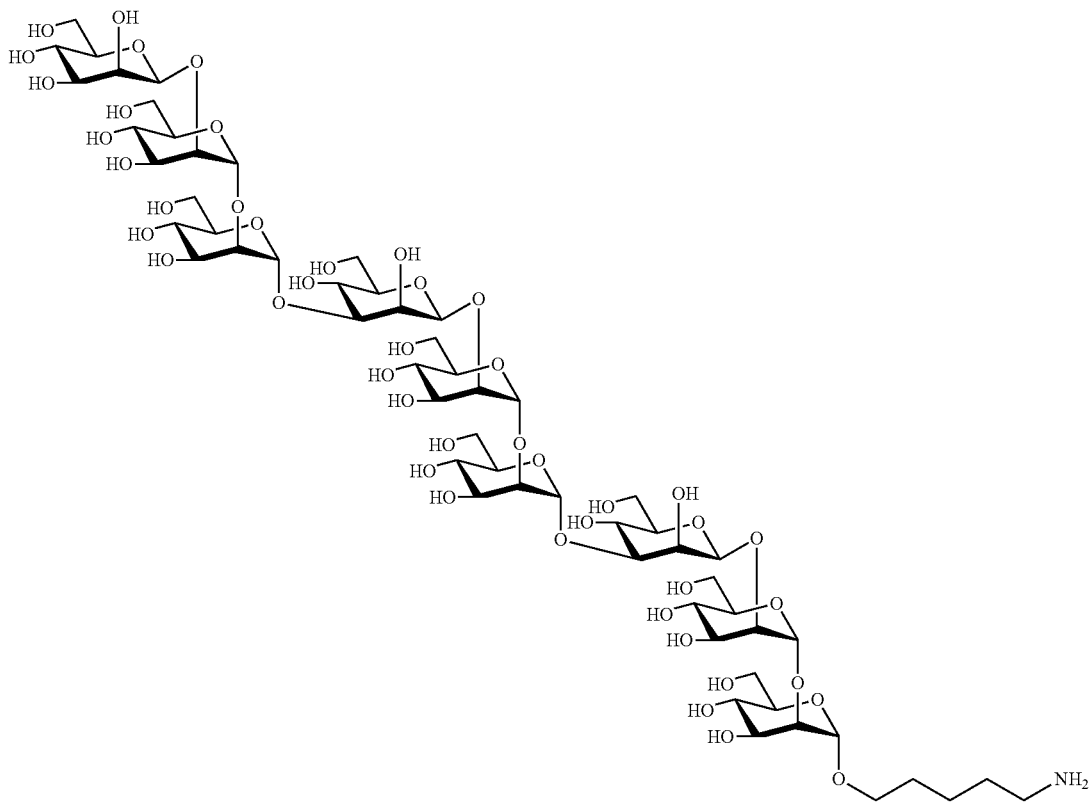

Compound 79* (6.0 mg, 1.415 μmol) was taken in solvent mixture DCM (1 mL), tBuOH (1 mL) and two drops of water. Pd/C was added to it and hydrogenated for 24 h under H$_2$ balloon at rt. The reaction mixture was filtered through PTFE filter, the residue was washed with methanol (6 mL), (50% methanol-water (6 mL). The filtrate was evaporated under vacuum to get the crude product. $^1$H NMR analysis showed the completion of the reaction and the presence of product. So, crude product was purified through the C18 Sepak column using water (3 mL×2, fr1), 20% acetonitrile-water (3 mL×2, fr2) and acetonitrile (3 mL, fr3). All the fractions were frozen and lyophilized for 24 h to get one pure fraction of compound 80* fr1 (white solid, 2.4 mg, 99%), and two impure fractions white fluffy solid (fr2, 0.03 mg) a white fluffy solid (fr.3, 0.4 mg).

HRMS (ESI+) Calcd for $C_{59}H_{103}NO_{46}H^+$ [M+H]$^+$ 1562.5829, found 1562.5815.

Example 5: Automated Synthesis of *K. pneumoniae* Serotype O3 Oligosaccharides

General Methods and Materials

Anhydrous* solvents used to prepare building block as well as activator, TMSOTf and capping stock solutions were taken from a solvent drying system (JC Meyer solvent systems). HPLC Grade DCM was used for washing. All other washing solvents (DMF, THF, dioxane and MeOH) were reagent grade.

Building blocks are dried by co-evaporation with toluene (3×) and drying under high vacuum for approximately 1 to 2 hours.

All synthesis were carried out on a scale of 0.0125 mmol using a Merrifield resin modified with a photocleavable linker (loading=0.41 mmol/g). The structure of the linker loaded resin is as follows—

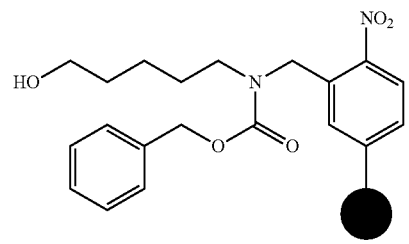

The polymer matrix is Copoly(styrol-1% divinylbenzol) 100-200 mesh.

Stock Solutions

Activator solution: 150 mM NIS/15 mM TfOH in DCM*: dioxane*
Acid wash solution: 62 mM TMSOTf in DCM*
Capping solution: 10% (v/v) Ac$_2$O/2% (v/v) MeSO$_3$H in DCM*
pyridine "pre-wash" solution: 10% (v/v) pyridine in DMF
Fmoc deprotection solution: 20% (v/v) piperidine in DMF

AUTOMATION MODULES

Module A: Initial Resin Swelling/Beginning of Synthesis Wash

The resin is washed with DCM, DMF and THF (3×, 2 mL, 25 s each) before swelling in DCM (2 mL) for 30 mins with occasional mixing using pulsed Argon bubbling.

Module B: Acidic Wash with 62 mM TMSOTf

DCM (2 mL) is delivered into the reaction vessel, and the temperature is adjusted to −20° C. The DCM is drained and replaced by another 2 mL of DCM before TMSOTf solution (1 mL) is added dropwise. The mixture is incubated for 1.5 mins under Ar bubbling before draining washing with 2 mL DCM for 25 s.

| Action | Cycles | Reagent | Amount | T (° C.) | Incubation Time |
|---|---|---|---|---|---|
| Cooling | — | — | — | −20 | — |
| Deliver | 2 | DCM | 2 mL | −20 | — |
| Deliver | | TMSOTf | 1 mL | −20 | 1.5 min |
| Wash | | DCM | 2 mL | −20 | 25 s |

Module C: Thioglycoside Coupling

Building Block Stocks and Glycosylation Parameters:

| | Structure | Excess | c (mM) | T1 (° C.) | T2 (° C.) |
|---|---|---|---|---|---|
| A 81* | BnO, OBz, BnO, FmocO, SPh | 6.5 eq. | ~81 | 0 | 10 |
| B 82* | AcO, OFmoc, BnO, BnO, STol | 10 eq. | ~125 | 0 | 20 |

Glycosylation Cycle:

DCM (2 mL) is added to the resin and the temperature is set to the activation temperature T1—2 K. While cooling down, the building block solution is delivered to the reaction vessel. After the set temperature has stabilized at T1—2 K, the reaction is started by adding 1 mL of activator solution. The mixture is kept at T1 for 5 minutes before a second 20 minute incubation cycle is started during which the temperature is raised to a temperature T2. Upon completion of the incubation cycle the reaction mixture is drained and the resin is washed once each with DCM:Dioxane 1:1 (2 mL) and DCM (2 mL). The module finishes by raising the temperature to 25° C. while performing two additional DCM washes (2 mL).

| Action | Cycles | Solution | Amount | T (° C.) | Incubation Time |
|---|---|---|---|---|---|
| Cooling | — | — | — | T1-2 | — |
| Deliver | 2 for A | BB Solution | 1 mL | | |
| Deliver | 1 for B | Activator Solution | 1 mL | | |
| Incubation | | | | T1 | 5 min |
| Incubation | | | | T2 | 20 min |
| Wash | 1 | DCM:Dioxane 1:1 | 2 mL | T2 | 25 s |
| Wash | 1 | DCM | 2 mL | 0 | 25 s |
| Heating | — | — | — | 25 | — |
| Wash | 2 | DCM | 2 mL | 25 | 25 s |

Module D: Capping

The resin is washed with DMF (2×, 25 s) and the temperature of the reaction vessel was set to 25° C. 2 mL of 10% Pyridine in DMF is delivered into the reaction vessel. After 1 min, the solution is drained and the resin is washed with DCM (3×, 2 mL, 25 s). Then, 4 mL of capping solution is delivered into the reaction vessel and incubated for 20 mins under Argon bubbling. The cycle concludes by draining the reaction mixture washing the resin with DCM (3×, 2 mL, 25 s).

| Action | Cycles | Solution | Amount | T (° C.) | Incubation Time |
|---|---|---|---|---|---|
| Heating | — | — | — | 25 | |
| Wash | 2 | DMF | 2 mL | 25 | 25 s |
| Deliver | 1 | 10% Py in DMF | 2 mL | 25 | 1 min |
| Wash | 3 | DCM | 2 mL | 25 | 25 s |
| Deliver | 1 | Capping solution | 4 mL | 25 | 20 mins |
| Wash | 3 | DCM | 2 mL | 25 | 25 s |

Module E: FMOC Deprotection

The resin is washed with DMF (3×, 2 mL, 25s) and the temperature of the reaction vessel is adjusted to 25° C. 2 mL of FMOC deprotection solution is delivered into the reaction vessel. After 5 mins, the solution was drained through the UV-sensor and the resin is washed with DMF (3×, 2 mL) and DCM (5×, 2 mL, 60 s each). The temperature of the reaction vessel was decreased to −20° C. in preparation of the next cycle.

| Action | Cycles | Solution | Amount | T (° C.) | Incubation Time |
|---|---|---|---|---|---|
| Heating | — | — | — | 25 | |
| Wash | 3 | DMF | 2 mL | 25 | 25 s |
| Deliver | 1 | FMOC deprotection Solution | 2 mL | 25 | 5 mins |
| Wash | 1 | DMF | 2 mL | | |
| Cooling | — | — | — | −20 | — |
| Wash | 3 | DMF | 2 mL | | 25 s |
| Wash | 5 | DCM | 2 mL | | 25 s |

Post-Automation Steps

Cleavage from Solid Support

After automated synthesis, the oligosaccharides were cleaved from solid support using a continuous flow photoreactor. The sample (resin loaded with target oligosaccharide) is taken up in 20 mL DCM (stabilized with amylene, LC-MS grade) and injected into the reactor (Wavelength=300 nm) at the rate of 1.0 mL/min. When all of the resin is inside the reactor, fresh DCM (20 mL) is injected to retrieve the photocleaved resin. The filtrate so obtained is concentrated in-vacuo and subjected to further analysis and purification.

Purification and HPLC Analysis

The crudes were dissolved in 1:1 hexane: ethyl acetate and analyzed using analytical HPLC (YMC-Diol-300 column, 150×4.6 mm, ELSD Detector and DAAD, 280 nm). Method—(Stop Time—60.0 mins)

| Time (min) | % Ethyl Acetate | % Hexane | Flow (mL/min) |
|---|---|---|---|
| 0.00 | 20 | 80 | 1.000 |
| 5.00 | 20 | 80 | 1.000 |
| 40.00 | 55 | 45 | 1.000 |
| 45.00 | 100 | 0 | 1.000 |
| 50.00 | 100 | 0 | 1.000 |

LIST OF OLIGOSACCHARIDES OBTAINED

| Amount | Structure |
|---|---|
| 22 mg | 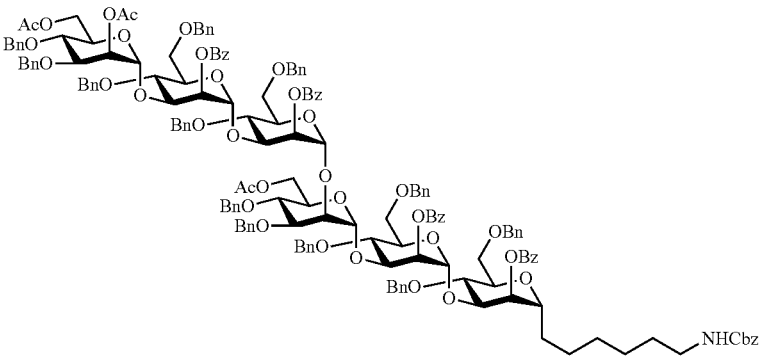 83* |
| 38 mg | 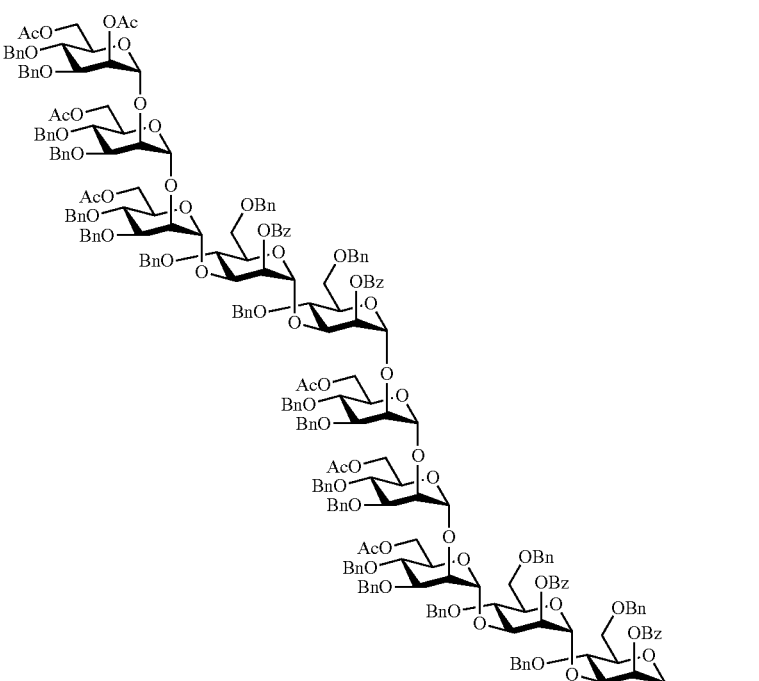 84* |

| Amount | Structure |
|---|---|
| 31 mg | 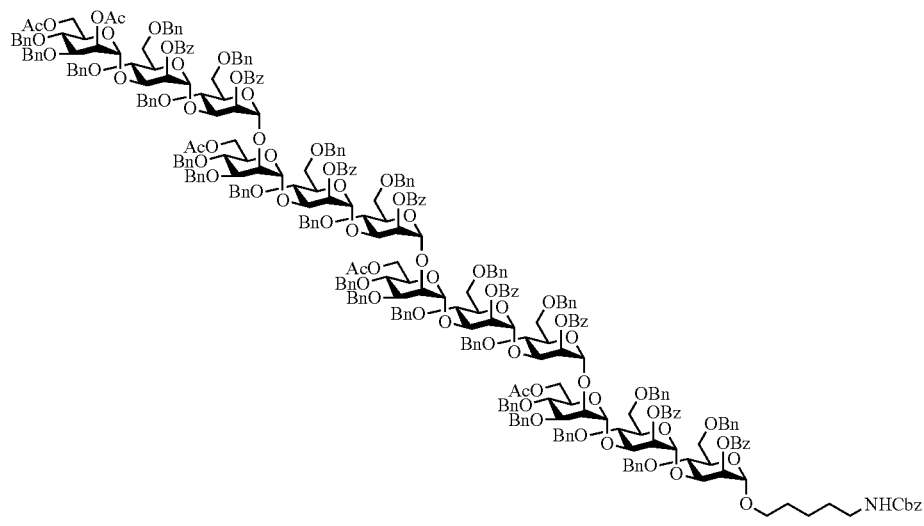 85* |
| 38 mg |  86* |

| Amount | Structure |
|---|---|
| 42 mg | 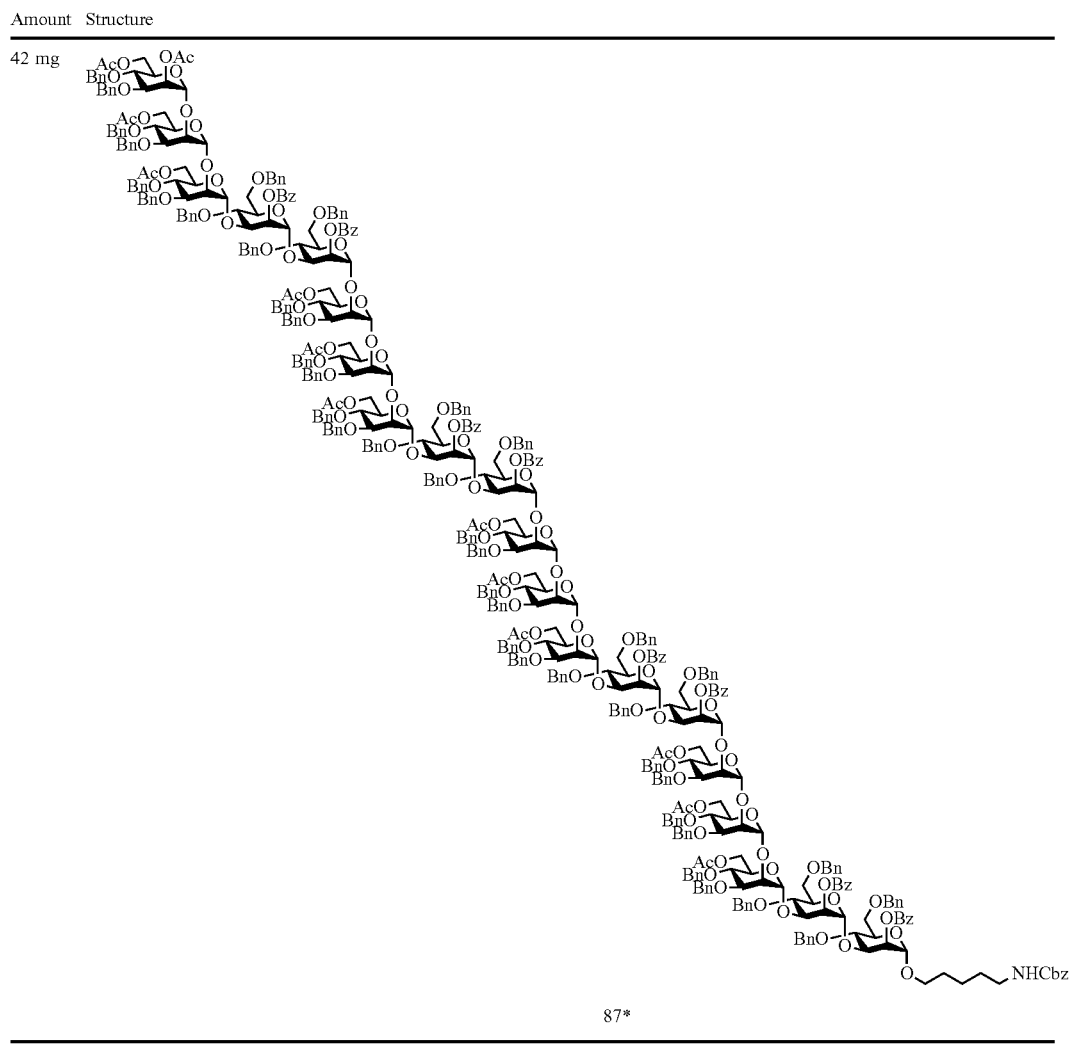 87* |

Experimental Procedures for the Deprotection of Fully Protected Oligosaccharides from Automation Steps in Solution Phase Synthesis Benzoyl and Acetate Deprotection:

Sodium methoxide solution in MeOH (25% w/w) (30-45 eq.) was added to a solution of benzoate 83*-87* (1 eq.) in a mixture of MeOH:THF (2:1). The reaction was stirred at the same temperature for 16 h. The reaction was quenched by the addition of $H_2O$ (1 mL) and diluted with brine (5 mL). The reaction mixture extracted with EtOAc (2×10 mL). Combined organic layers were dried over anhydr. $Na_2SO_4$ and concentrated under reduced pressure. Crude product 83a*-87a* after evaporation of the solvent obtained as a yellow thick gel which was used in next step without any further purification.

Benzyl Deprotection:

83a*-87a* (1 eq.) was taken in solvent mixture DCM (2 mL), tBuOH (2 mL) and two drops of water. Pd/C was added and hydrogenated for 24 h under $H_2$ balloon at r.t. The reaction mixture was filtered through PTFE filter and the residue washed with methanol (6 mL), (50% methanol-water (6 mL). The filtrate was evaporated under vacuum to get the crude product. $^1H$ NMR analysis showed the completion of the reaction and the presence of product. So, crude product was purified through the C18 Sepak column using water (3 mL×2, fr1), 50% acetonitrile-water (3 mL×2, fr2) and acetonitrile (3 mL, fr2). All the fractions were frozen and lyophilized for 24 h to get one pure fraction of compound 83b*-87b* fr1, and impure fraction fr2.

Thus, hexasaccharide 83b*, decasaccharide 84b*, dodecasaccharide 85b* and pentadecasaccharide 86b* have been obtained using the protocol stated above. Following the similar protocol, the fully deprotected Icosasaccharide 87b* can be achieved from compound 87a*.

| Compound structure | Amount | Mass |
|---|---|---|
| 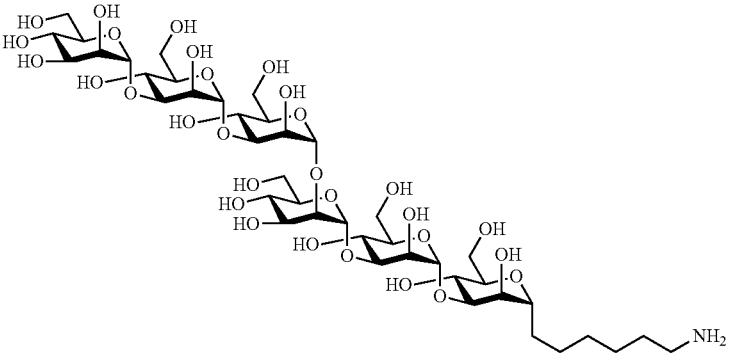
83b* | 5.2 mg | HRMS (ESI+) Calcd for $C_{41}H_{73}NO_{31}H^+$ [M + H]$^+$ 1076.4245, found 1076.4241. |
| 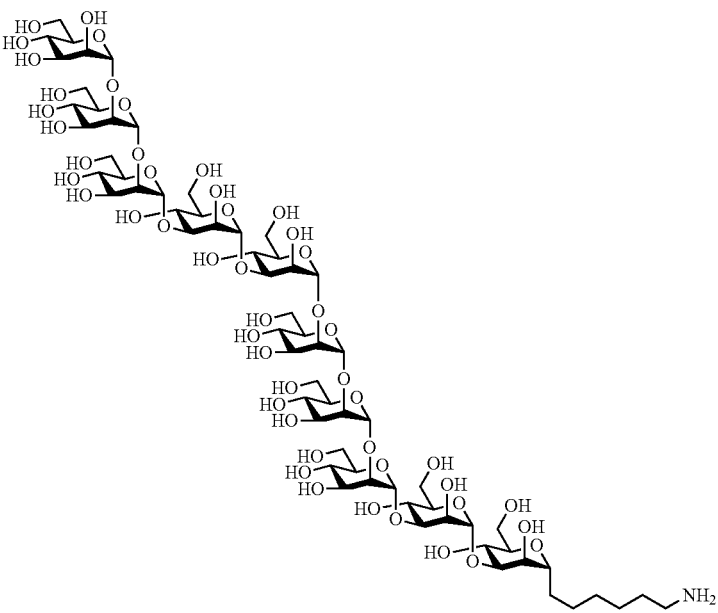
84b* | 10.2 mg | HRMS (ESI+) Calcd for $C_{65}H_{113}NO_{51}H^+$ [M + H]$^+$ 724.6358, found 1724.6328. |
| 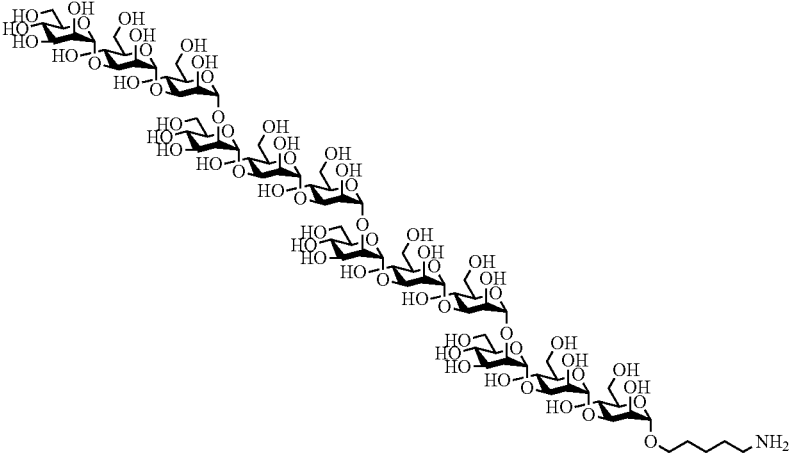
85b* | 11.1 mg | HRMS (ESI+) Calcd for $C_{77}H_{133}NO_{61}H^+$ [M + H]$^+$ 2048.7414, found 2048.7329. |

-continued

| Compound structure | Amount | Mass |
|---|---|---|
| 86b* (structure) | 13.7 mg | MALDI-TOF Calcd for $C_{95}H_{163}NO_{76}Na^+$ $[M + Na]^+$ 2557.8852, found 2560.363. |
| 87b* (structure) | | MALDI-TOF Calcd for $C_{95}H_{163}NO_{76}Na^+$ $[M + Na]^+$ 2557.8852, found 2560.363. |

B Immunization Studies of *K. pneumoniae* Serotype O3 and O5 Oligosaccharides

Materials:
ELISA plates (high-binding, EIA/RIA Plate, 96 well, flat bottom with low evaporation lid, company: Costar® 3361)
Detection antibody: Goat anti rabbit IgG peroxidase conjugate (Sigma, #A4914) and Goat anti-Mouse IgG (H+L) peroxidase conjugate (Dianova Code: 115-035-068).
Blocking solution: 1% FCS (v/v) in PBS.
Antibody diluent: PBS+1% BSA (w/v).
Wash Buffer: PBS+0.1% Tween 20 (PBS-T)
Developing solution: 1 Step™ Ultra TMB-ELISA developer. (ThermoScientific, Cat #: 34028)
Stop solution—2M sulphuric acid ($H_2SO4$).
Plate reader: Anthos HT 2.
Software: WinRead 2.36 for absorbance measurements and GraphPad Prism 7 for data plotting and analysis.
Alum: Aluminium Hydroxide Gel Adjuvant (Alhydrogel® 2%), Brenntag, Batch #: 5447 Exp Dt: February 2020.
Incomplete Freund's Adjuvant (IFA). InvivoGen; Cat: vac-ifa-10, Batch #: IFA-39-03; Exp Dt: September 2019
QuantiPro™ BCA Assay Kit (SIGMA) Product: QPBCA-1KT; Lot #: SLBR7451V; Pcode: 1002296464
Mini-PROTEAN® TGX™ Gels- 10%, 10 well (30 μL/well) Control Nr:64175708,
Precision Plus Dual Color, Cat: 1610374; Control Nr: 641798899
GelCode™ Blue Safe Protein Stain; ThermoScientific; Ref: 1860957; Lot #: TA260266
*Klebsiella pneumoniae* LPS. SIGMA- L4268; Lot #: 116 M 4057 V Methods:
1. Bacterial Strains and LPS.

*Klebsiella pneumoniae* (KPC) strains differing in their LPS (O-antigen) with/without the capsule were used to isolate and purify the corresponding LPS. The purified LPS were used as coating antigen in Enzyme Linked Immunosorbent Assay (ELISA). The O2a,c LPS was procured from Sigma-Aldrich.

TABLE 1

*Klebsiella pneumoniae* strains used for LPS isolation.

| # | LPS/O-antigen |
|---|---|
| 1 | O1 |
| 2 | O2a |
| 3 | O2a,c |
| 4 | Galactan-III |

2. Production of Glycoconjugate and Characterization.

The KPC synthetic antigens were 21* and 69* conjugated to the carrier protein $CRM_{197}$ (21*-$CRM_{197}$ and 69*-$CRM_{197}$) for immunization experiments and to Bovine Serum Albumin (BSA; (21*-$CRM_{197}$ and 69*-$CRM_{197}$)) as coating antigen for ELISA according to the procedure described below.

General Conjugation Protocol

Step 1: PNP-Ester Synthesis

Compound 21* or 69* (1 eq) was dissolved in DMSO or DMSO—$H_2O$ at room temperature in a 8 mL vial. Activated bis-(4-nitrophenyl) adipate (20 eq) was added to it and stirred for 5 minutes. Triethylamine (50 eq) was added and the reaction mixture was allowed to stir at room temperature for 3-5 h. The reaction mixture was frozen using liquid nitrogen and then lyophilized for 18 h to dryness to afford pale yellow colored crude product along with the excess of the reagent. The crude product was washed thoroughly with sufficient $CHCl_3$ followed by DCM to remove excess reagent. The solid para-nitrophenyl (PNP) ester was dried and taken for the next step.

Step 2: Conjugation to the Protein

Conjugation procedure: The PNP ester of 21* or 69* in 50 μL of 0.15 M NaCl in NaPi buffer was added dropwise to the reaction vial containing $CRM_{197}$ or BSA in buffer (~150 μL). The vial was finally rinsed with 50 μL of buffer solution and transferred to the reaction vial completely. Thus making the volume of the reaction in the vial ~200 μL. The reaction mixture became yellow in colour and stirred the reaction mixture at r.t. for 24h. The conjugate solution (21*-$CRM_{197}$, 69*-$CRM_{197}$, 21*-$CRM_{197}$ or 69*-$CRM_{197}$) was transferred to an Amicon® Ultra-0.5 mL centrifugal filter, centrifuged for 6 minutes at 2-8° C. 300 μL of buffer were added to the reaction vial, rinsed and transferred to the filter and centrifuged again. Additional washings were done using 1×PBS solution and centrifuging till the yellow colour was gone and the conjugate became clear solution. After the final wash the conjugate was stored in 1×PBS solution at 2-8° C.

The conjugates were analyzed by SDS-PAGE, SEC chromatography, and MALDI analysis. The loading of the sugar on the carrier was specifically calculated by subtracting the mass between the conjugated and unconjugated protein using MALDI analysis. The protein content was estimated using the micro BCA method following manufacture protocol.

2.1 SDS-PAGE Analysis

The samples were mixed in a microfuge tube and heated for 5 min at 95° C. on a thermocycler. After cooling to room temperature for 5 min, the samples at approximately 2.5 μg were loaded onto the respective wells of a 10% polyacrylamide gel along with 10 μL of the marker. The samples were run at a constant voltage of 120V for 1 h. Staining was done using the GelCode™ Blue Safe Protein Stain as per manufacture instructions. The gels were washed with deionized water overnight and scanned using the gel documentation system.

2.2 Size Exclusion Chromatography (SEC) of Glycoconjugates

The glycoconjugates (21*-$CRM_{197}$ and 69*-$CRM_{197}$) used for immunization studies were analyzed by SEC to observe a mass difference between the conjugated and unconjugated CRM protein. The samples were diluted in 50 mM Tris, 20 mM NaCl, pH 7.2 and run on a Agilent 1100 HPLC system fitted with Tosoh TSK G2000 column (SWxl, 7.8 mm×30 cm, 5 μm) and a Tosoh TSKgel® Guard Column (SWxl 6.0 mm×4 cm, 7 μm). The flow rate was kept at 1 mL/min.

3. Formulation of Vaccines for Immunization

The glycoconjugates were formulated in aluminum hydroxide (alum) adjuvant for mice studies, and in Incomplete Freund's Adjuvant (IFA) for immunization in rabbits.

3.1 Formulation in Alum

All the formulations were prepared under sterile conditions. The glycoconjugates (DS) and PBS were mixed in the appropriate pre-calculated ratio in a 50 mL Falcon™ tube corresponding to the final formulation volume leaving out the volume of alum (0.25 mg/mL) required. This formed the DS-PBS mixture. The antigen/DS dose per animal was kept at 5 μg/100 μL/animal. The DS-PBS mixture was gently mixed (5×) using a serological pipette. To the DS-PBS mixture, the corresponding volume of stock alum (10 mg/mL) was added to give a final alum ratio of 1:40 or 0.250 mg/mL. The mixture was immediately mixed by gentle pipetting (20×) using a 5 mL serological pipette. The Falcon™ tube was capped, wrapped with Parafilm® and allowed to mix on a shaker at 250 rpm for 2 h at room temperature (RT). After the incubation time of 2 h, the formulations were brought under the clean bench, aliquoted, and further stored at 4° C. till further use.

3.2 Formulation in IFA

Incomplete Freund's Adjuvant (IFA) from InvivoGen was used for formulating the vaccines for rabbit immunization studies. Protocol was followed as per manufacture. Antigen: IFA concentration was kept at 1:1. The antigen dose per animal was kept at 5 μg/200 μL/animal (100 μL of antigen +100 μL IFA). IFA at the desired calculated volume (50% of the final immunization volume) was taken in a 15 mL sterile Falcon™ tube. The calculated amount of the diluted antigen solution (volume adjusted with PBS to 50% of the final immunization volume) was taken in a 3 mL sterile syringe, fitted with a 20 G needle. The DS solution was added into the Falcon™ tube containing the IFA and immediately vortexed for 15 sec (5×). The color of the formulation changes from pale-yellow to milky-white on vortexing which indicates the formation of stable emulsion. The resulting vaccine formulation was briefly vortexed and aliquoted into 2 mL sterile tubes with the desired dose volumes. Prior to immunizations, the tubes containing the vaccine formulations were vortexed and then injected into animals.

3.3 Characterization of Alum Formulations

The glycoconjugates formulated in alum were characterized to determine the final alum concentration and the pH of the formulations.

4. Immunization Schedule

Mice and rabbit immunizations were performed under specific pathogen-free conditions and were provided food and water ad libitum. Mice (n=6) and rabbits (n=4) were immunized sub cutaneous with the vaccine formulations (Table 2) at an injection volume of 100 μL/mice, and 200 μL/rabbit. The antigen dose for mice was kept at 5 μg/animal except for the antigen-7 (2.5 μg each of antigen 1, and -2). The antigen dose for rabbit was kept at 5 μg/animal. Mice and rabbits were immunized on day 0, 14 and 28. Blood was drawn on day −1, 7, and 22 for mice and day 0, 7 and 21 for rabbits respectively, for the determination of antibody titers. On day 35, the animals were sacrificed, and blood collected.

TABLE 2

Immunization schedule of mice (n = 6) and rabbits (n = 4).

| group | glycoconjugate | mice per group | rabbits per group |
|---|---|---|---|
| 1 | 21*-CRM$_{197}$ (O3) | 6 | 0 |
| 2 | 69*-CRM$_{197}$ (O5) | 6 | 4 |

*All values for mice sera analysis were subtracted using the values from PBS (negative control).

5. Enzyme Linked Immunosorbent Assay (ELISA) of Sera Using In-House Antigen Coated Plates Coating of Plates with Antigen:

Conjugates 21*-BSA and 69*-BSA, and LPS #1-#4 were used as the coating antigen. LPS was dissolved in isopropanol at a concentration of 10/20 μg/mL. 100 μL was used for coating each well resulting in a coating concentration of 1-2 μg/well. The LPS solutions were loaded into the well and subjected to overnight evaporation at r.t. inside the sterile bench. For conjugates 21*-BSA and 69*-BSA, the respective conjugates were dissolved at a concentration of 5 μg/mL in phosphate buffered saline (PBS) pH 7.4. 100 μL were coated per well and incubated overnight at 4° C. to get an antigen concentration of 0.5 μg/well.

Washing:

After overnight adsorption of the antigen, the plates were washed 1× with PBS-T (200 μL/well) and the excess fluid per well was removed by inverting the plate and tapping on a clean dry tissue towel.

Blocking:

The plates were blocked using 200 μL of the commercial blocking solution and incubated for 2 h at RT.

Washing:

After blocking, the plates were washed 3× with PBS-T (200 μL/well) and the excess fluid per well was removed by inverting the plate and by tapping on a clean dry tissue towel.

Dilution of Sera and Incubations:

Pooled sera (n=4 rabbits or n=6 mice/group) from different time-points of the different experimental groups were diluted to their respective dilutions in the antibody diluent (PBS+1% BSA). 100 μL of the diluted sera samples of the different experimental groups were added in duplicates to the corresponding wells and incubated on a shaker set at 250 rpm for 2h at RT. 100 μL/well of the antibody diluent (PBS+1% BSA) formed the experimental blank. After incubation with sera, the plates were washed 4× with PBS-T (200 μL/well) and the excess fluid per well was removed by inverting the plate and by tapping on a clean dry tissue towel.

Incubation (Detection Antibody):

The corresponding detection antibody, anti-rabbit or anti-mouse IgG HRP conjugate was diluted 1:10,000 in the antibody diluent (PBS+1% BSA) and 100 μL/well was added and incubated on a shaker at 250 rpm for 1h at RT. After the incubation with detection antibody, the plates were washed 5× with PBS-T (200 μL/well) and the excess fluid per well was removed by inverting the plate and by tapping on a clean dry tissue towel.

Substrate Addition:

To each well, 100 μL of the ready to use TMB (3,3,',5, 5'-tetramethylbenzidine) substrate (normalized to r.t. from 4° C.) was added and incubated in dark for 15 min. The blue color of the enzymatic reaction was stopped by adding 50 μL/well of 2M $H_2SO_4$ solution resulting in a yellow colored solution. The absorption of the yellow colored solution was measured at 450 nm using a plate reader.

Results:

The absorption values were analyzed by plotting a graph using the GraphPad Prism software.

Results.

Characterization of Glycoconjugates 21*-CRM$_{197}$ and 69*-CRM$_{197}$.

The KPC antigen glycoconjugates 21*-CRM$_{197}$ and 69*-CRM$_{197}$ used for the immunization studies were analyzed for the conjugation efficiency and antigen content. MALDI analysis of the glycoconjugates revealed a very good conjugation efficiency. The mass differences between the conjugated and unconjugated CRM$_{197}$ protein yielded a loading from 2-15, preferably from 3-10 antigens/CRM$_{197}$ molecule for the different glycoconjugates.

Figure 5B:
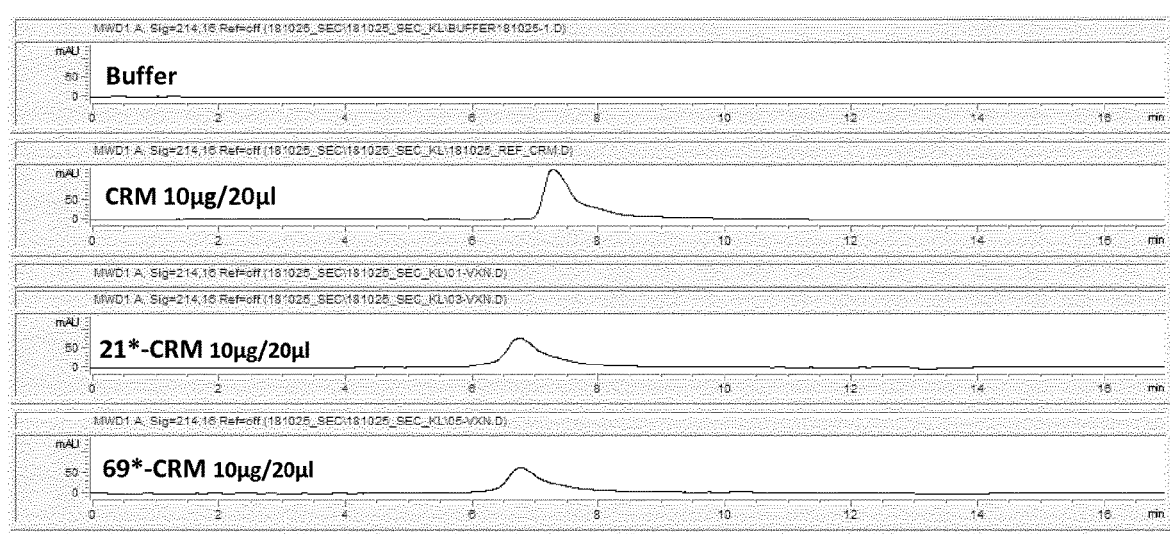

The glycoconjugates were also analyzed by a 10% SDS-PAGE and SEC that revealed a clear mass shift as compared to the unconjugated CRM$_{197}$ protein (FIG. 5A and FIG. 5B).

ELISA Data.

Sera from 21*-CRM$_{197}$/69*-CRM$_{197}$ immunized mice recognize the corresponding antigens (see FIG. 6). The sera also cross-react with the corresponding K. pneumoniae LPS (see FIG. 7). Sera from 21*-CRM$_{197}$/69*-CRM$_{197}$ immunized rabbits recognize the corresponding O-antigens in the related BSA conjugates 21*-BSA and 69*-BSA, respectively (see FIG. 8). Sera from 21*-CRM$_{197}$/69*-CRM$_{197}$ immunized mice recognize selectively the corresponding K. pneumoniae LPS (see FIG. 9).

The herein provided data demonstrate that after immunization with a conjugate of the present invention, functional antibodies against oligosaccharides of the present invention as well as against the natural O-polysaccharides of K. pneumoniae serotypes O3, O3b and O5 were elicited in rabbits and mice. The Antibodies do cross-react with the natural O-polysaccharides (LPS) of K. pneumoniae serotypes O3, O3b and O5 indicating the potential of these antibodies to bind to K. pneumoniae bacteria and to confer protection against K. pneumoniae infection.

The ELISA data further proves that the conjugates of the present invention are immunogenic and induce high antibody titers. Hence, ELISA analysis shows that the oligosaccharides of formula (I) of the present invention are immunogenic in rabbits and mice and generate cross reactive antibodies.

The invention claimed is:

1. An oligosaccharide of general formula (II)

$$T^*\text{-}[(\text{—}U_{x+4}\text{—}U_{x+3}\text{—}U_{x+2}\text{—}U_{x+1}\text{—}U_x)_m\text{—}(V_{x+2}\text{—}V_{x+1}\text{—}V_x)_{1-m}]_n\text{—}O\text{-}L\text{-}E \quad (II)$$

wherein
m is an integer selected from 0 and 1;
x is 1;
n is an integer selected from 2, 3, 4, 5, 6, 7, and 8;

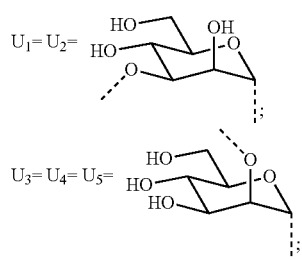

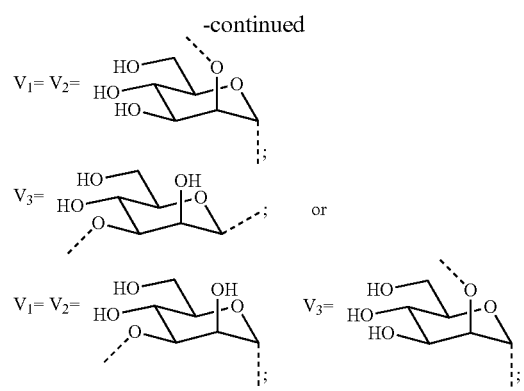

T*- represents H—;
-L- represents $-L^a$-, $-L^a$-$L^e$-, $-L^a$-$L^b$-$L^e$-, or $-L^a$-$L^d$-$L^e$-;
$-L^a$- represents —(CH$_2$)$_o$—, —(CH$_2$—CH$_2$—O)$_o$—C$_2$H$_4$—, or —(CH$_2$—CH$_2$—O)$_o$—CH$_2$;
$-L^b$- represents —O—, —NH—CO—NH—, —NH—CO—CH$_2$—NH—, —NH—CO—;
$-L^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;
$-L^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and o, q, p1 and p2 are independently of each other an integer selected from 1, 2, 3, 4, 5, and 6;

E represents —NH$_2$, —N$_3$, —CN, —O—NH$_2$, —CH═CH$_2$, —C≡CH, —Br, —Cl, —I, —CO$_2$R', —COR', —CONH—NH$_2$, —SH, or —SAc;

R' represents —H, -Me, -Et, 4-nitrophenyl, pentafluorophenyl, —N-hydroxysuccinimidyl, -(3-sulfo-N-hydroxysuccinimidyl), or -(dibenzocyclooctyne-sulfo-N-hydroxysuccinimidyl);

or a pharmaceutically acceptable salt thereof.

2. The oligosaccharide according to claim 1, wherein
-L- represents —(CH$_2$)$_o$—; and
o is an integer selected from 2, 3, 4, 5, and 6,
or a pharmaceutically acceptable salt thereof.

3. The oligosaccharide according to claim 1, wherein —O-L-E is selected from the group consisting of:

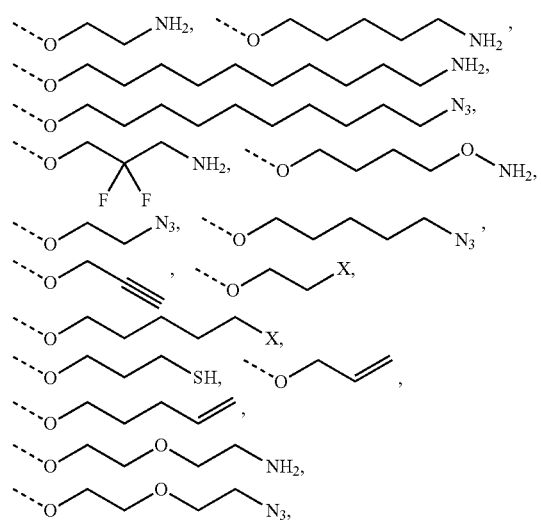

171
-continued
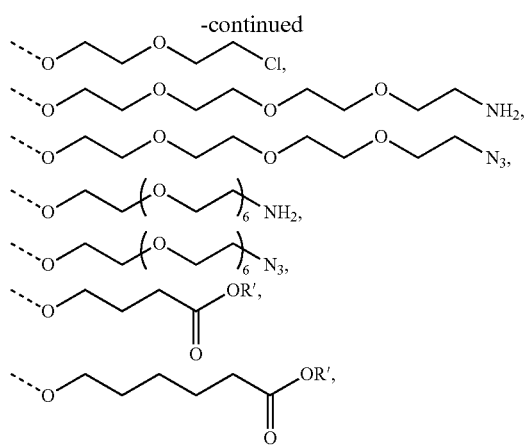
172
-continued
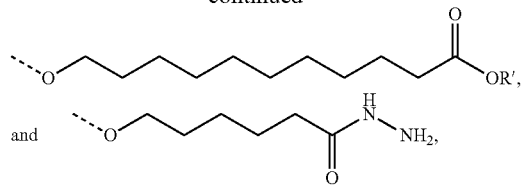
wherein R' represents —H, -Me, -Et, 4-nitrophenyl, pentafluorophenyl, —N-hydroxysuccinimidyl, —(3- sulfo-N-hydroxysuccinimidyl), or -(dibenzocyclooctyne-sulfo-N-hydroxy succinimidyl);
X represents —Br, —Cl, —I, —CO₂H, or —SAc,
or a pharmaceutically acceptable salt thereof.
4. The oligosaccharide according to claim 1 selected from the group consisting of:
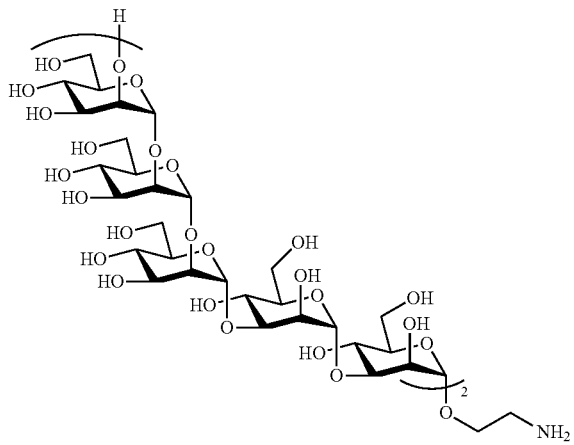
(I'd-1)
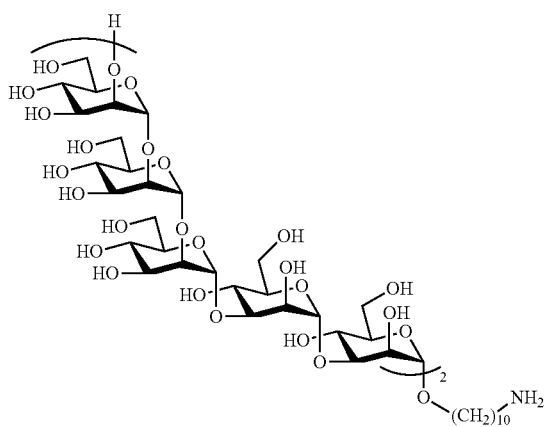
(I'd-2)

(I'd-3)
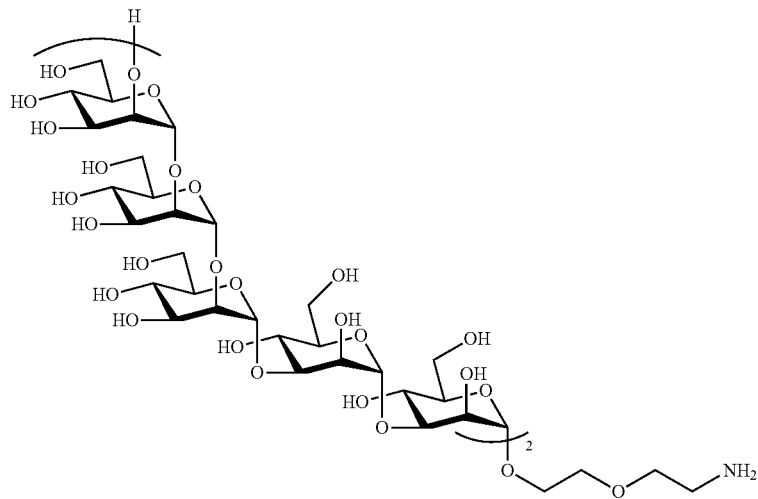
(I'd-4)
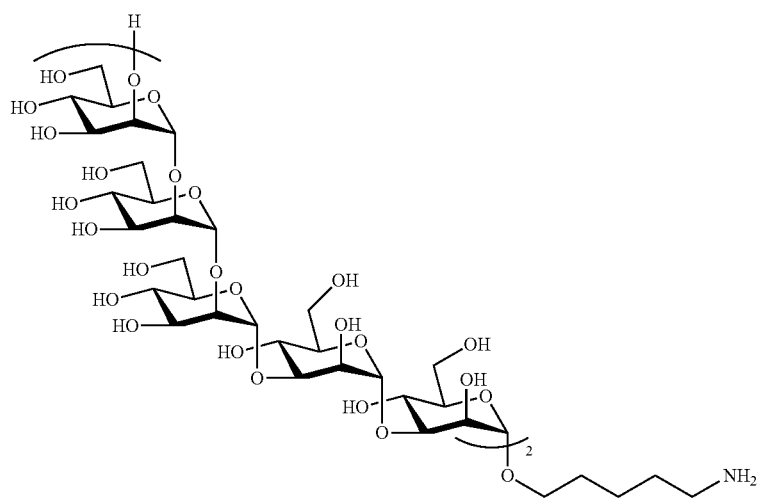
(I'd-5)
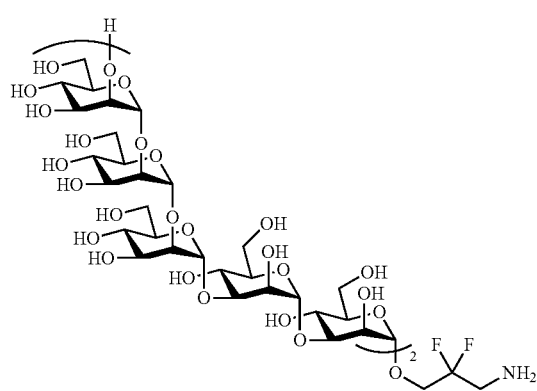

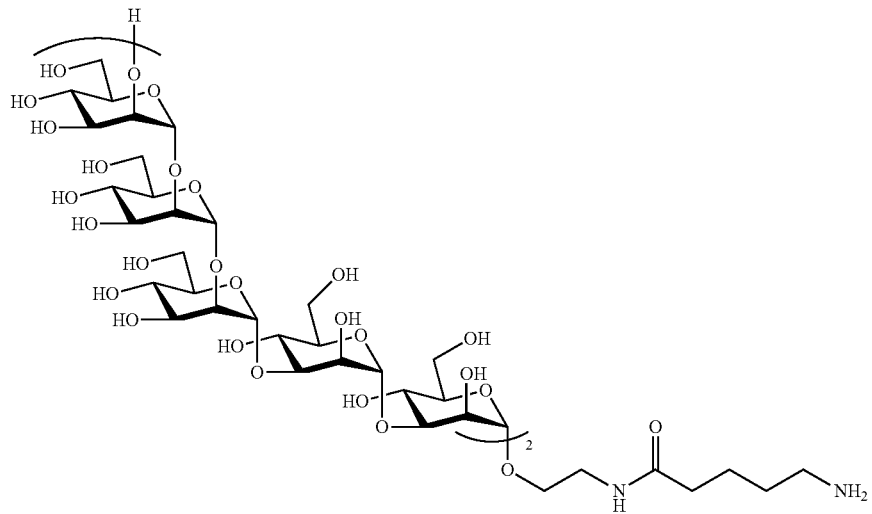
(I'd-6)
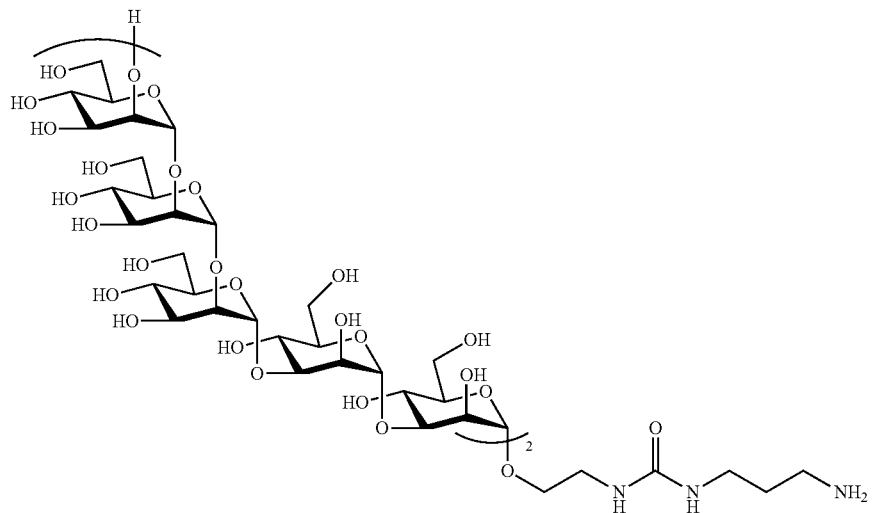
(I'd-7)
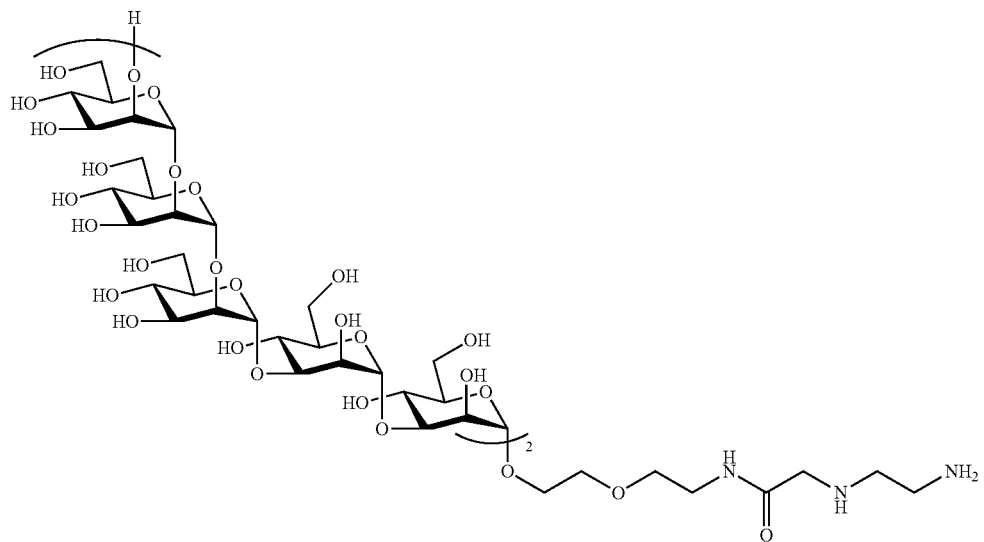
(I'd-8)

(I'd-9)
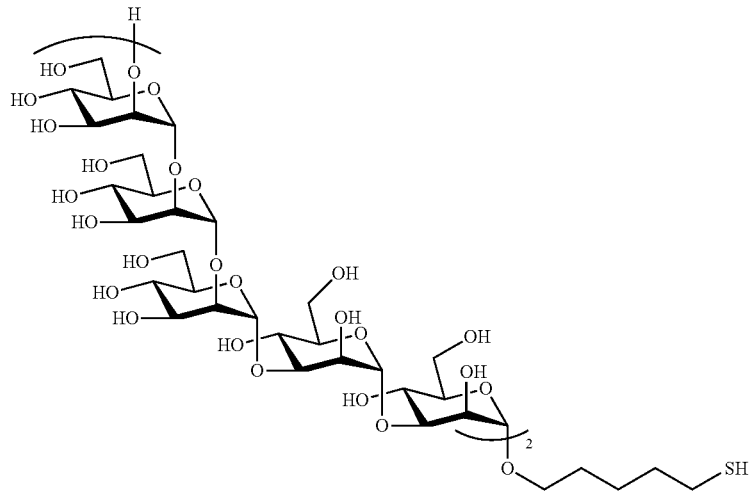
(I'd-10)
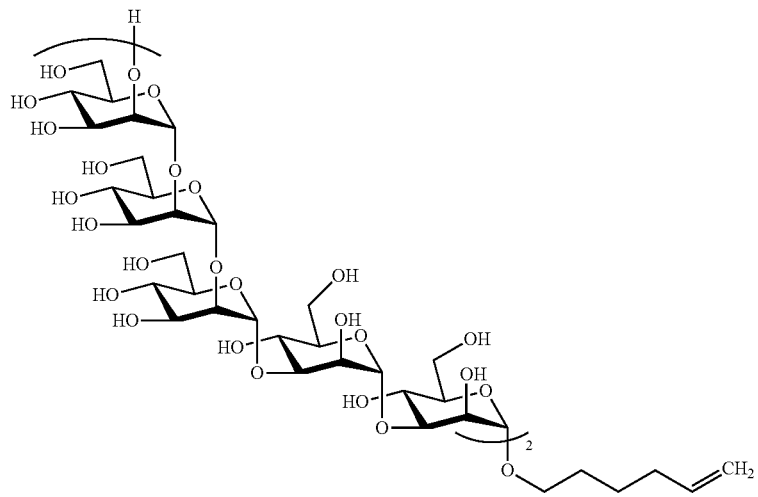
(I'd-11)
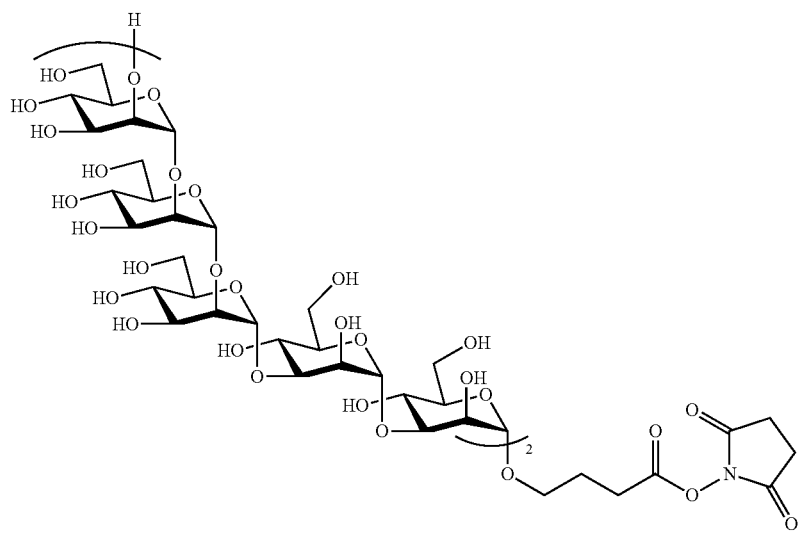

-continued
(I'e-1)
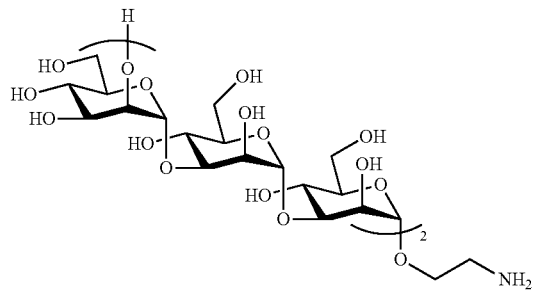
(I'e-2)
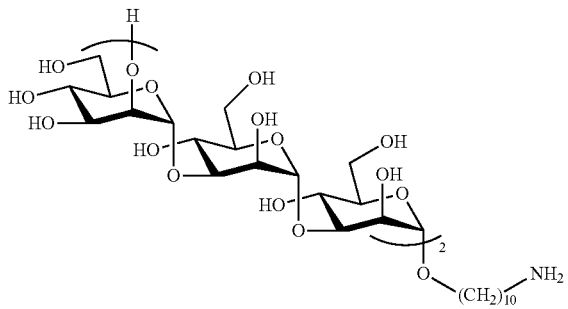
(I'e-3)
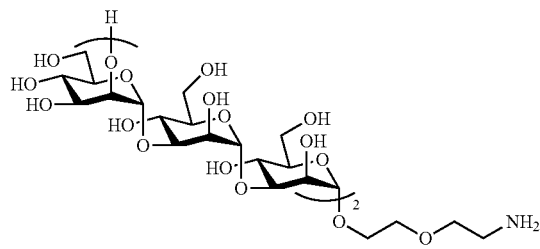
(I'e-4)
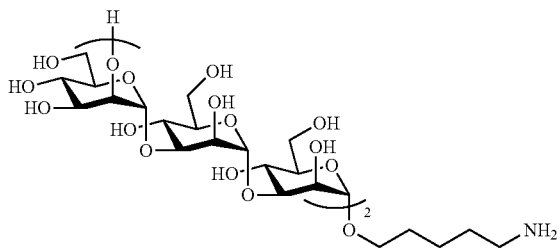
(I'e-5)
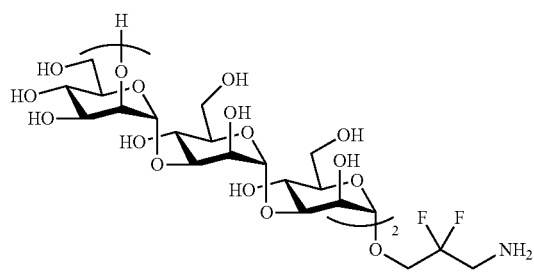
(I'e-6)
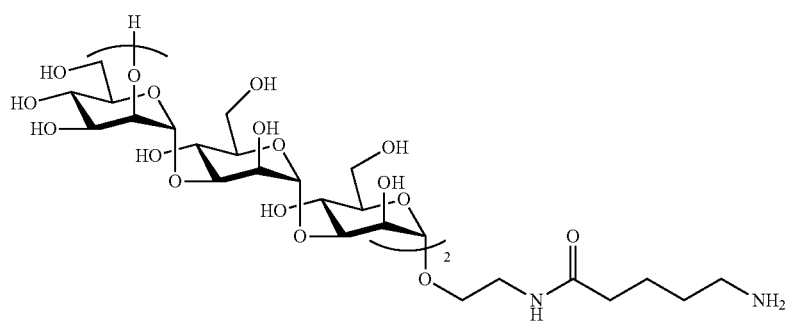
(I'e-7)
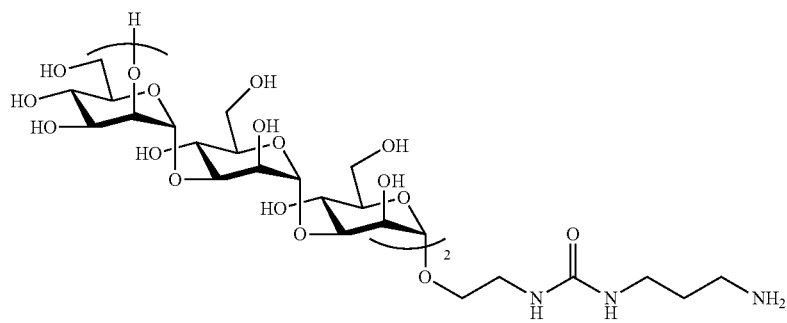

-continued
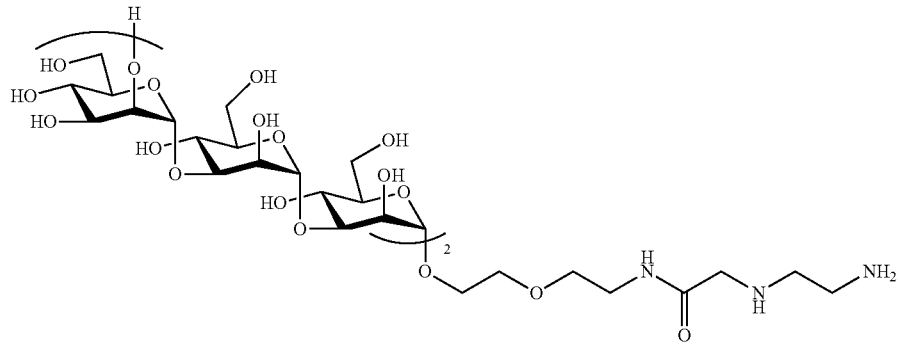
(I'e-8)
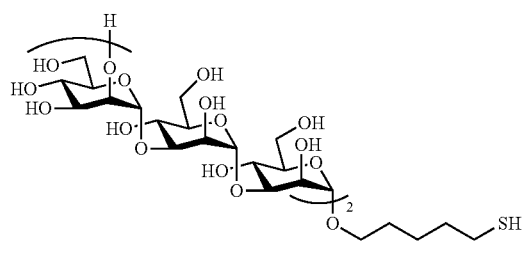
(I'e-9)
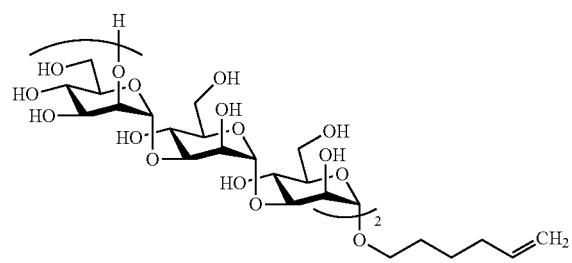
(I'e-10)
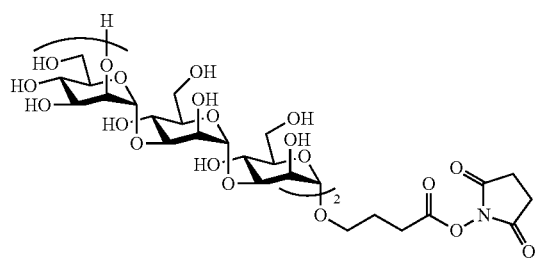
(I'e-11)
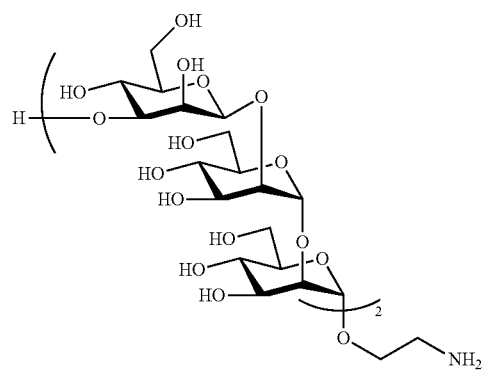
(I'f-1)
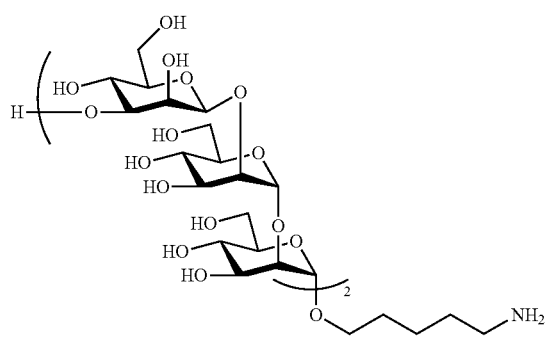
(I'f-2)
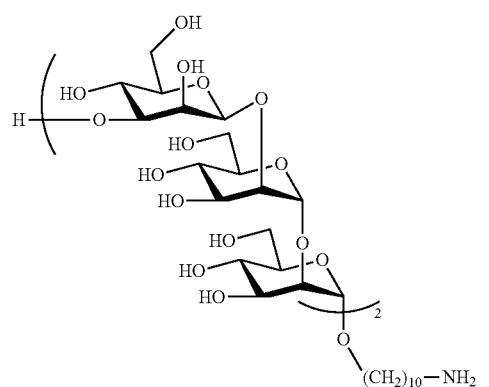
(I'f-3)

-continued
(I'f-4)
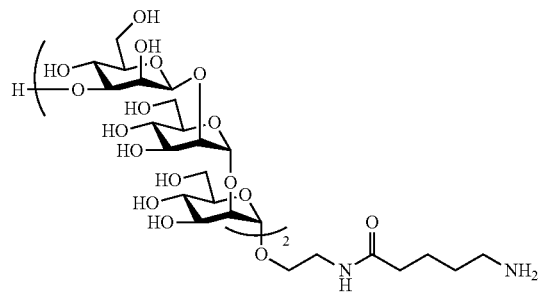
(I'f-5)
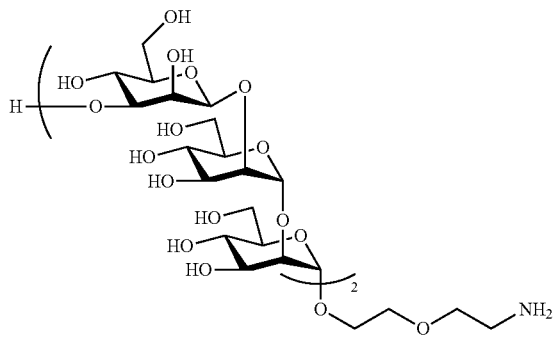
(I'f-6)
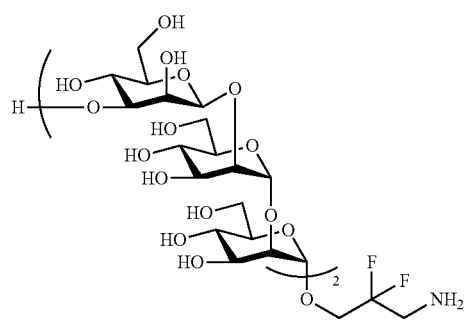
(I'f-7)
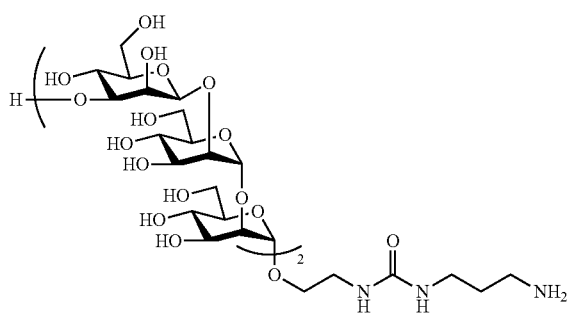
(I'f-8)
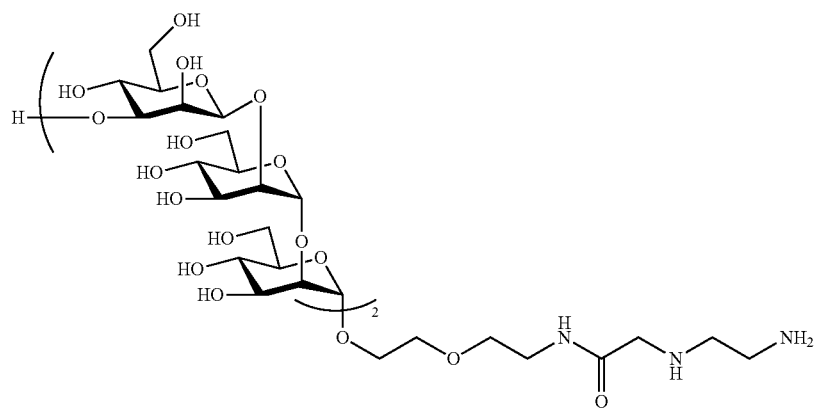
(I'f-9)
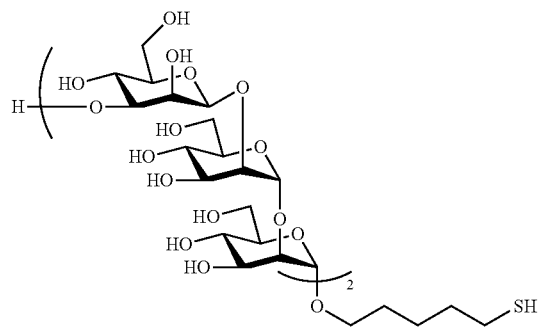
(I'f-10)
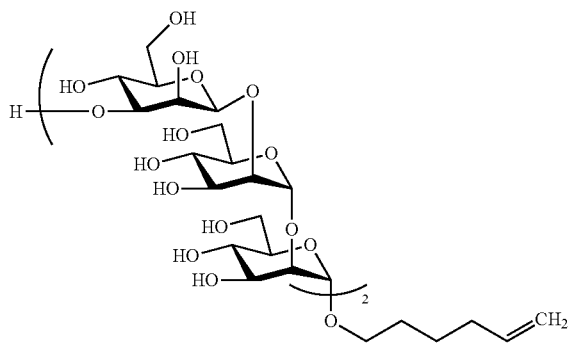

and

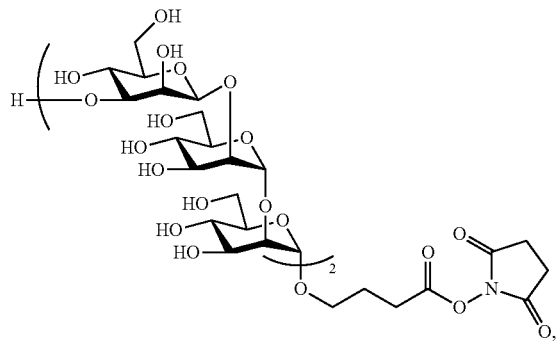

(I'f-11)

or a pharmaceutically acceptable salt thereof.

5. The oligosaccharide according to claim 1 selected from the group consisting of:

II-a

II-f

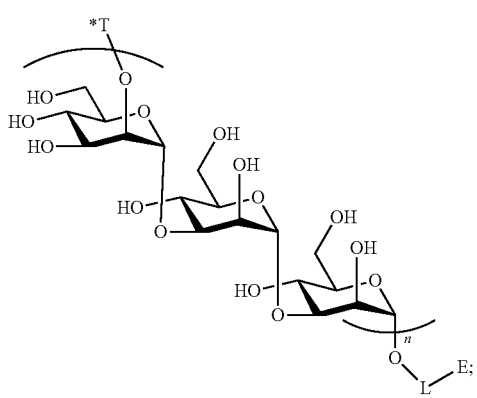

or a pharmaceutically acceptable salt thereof.

6. The oligosaccharide according to claim 5, wherein n is an integer selected from 2, 3, 4, 5, and 6, or a pharmaceutically acceptable salt thereof.

7. The oligosaccharide according to claim 1, wherein E represents an amino group, or a pharmaceutically acceptable salt thereof.

8. The oligosaccharide according to claim 6, wherein E represents an amino group, or a pharmaceutically acceptable salt thereof.

9. A pharmaceutical composition comprising the oligosaccharide according to claim 1 together with at least one pharmaceutically acceptable adjuvant and/or excipient.

10. A conjugate comprising an oligosaccharide according to claim 1 covalently linked to an immunogenic carrier through the residue E of the —O-L-E group, wherein the immunogenic carrier is a carrier protein selected from the group consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, non-lipidated cell-surface liporotein (protein D) of non-typeable *Haemophilus influenzae*, outer membrane protein (OMP) complex of *Neisseria meningitidis*, bovine serum albumin (BSA), keyhole limpet hemocyanine (KLH), recombinant non-toxic form of *Pseudomonas aeruginosa* exotoxin A (rEPA) or cholera toxoid (CT).

11. A pharmaceutical composition comprising the conjugate according to claim 10 together with at least one pharmaceutically acceptable adjuvant and/or excipient.

12. A method for raising a protective immune response in a human and/or animal host, said method comprising administering at least one conjugate according to claim 10 to said human or animal host.

13. A method of treatment of a disease associated with *Klebsiella pneumonia* serotype O3, O3b and/or O5 bacteria in a human and/or animal host comprising administering at least one conjugate according to claim 10 to said human or animal host.

14. The method according to claim 13, wherein the disease associated with *Klebsiella pneumonia* serotype O3, O3b and/or O5 bacteria is pneumonia, bronchitis, meningitis, urinary tract infection, wound infection, osteomyelitis, bacteremia, septicemia or ankylosing spondylitis.

15. A conjugate of general formula (IV)

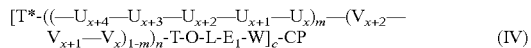
$$[T^*-((-U_{x+4}-U_{x+3}-U_{x+2}-U_{x+1}-U_x)_m-(V_{x+2}-V_{x+1}-V_x)_{1-m})_n\text{-}T\text{-}O\text{-}L\text{-}E_1\text{-}W]_c\text{-}CP \quad (IV)$$

wherein
m is an integer selected from 0 and 1;
x is 1;
n is an integer selected from 2, 3, 4, 5, 6, 7, and 8;

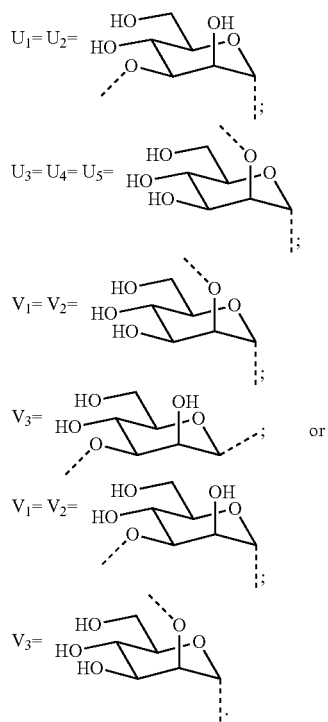

T*- represents H—;
-L- represents -$L^a$-, -$L^a$-$L^e$-, -$L^a$-$L^b$-$L^e$-, or -$L^a$-$L^d$-$L^e$-;
-$L^a$- represents —(CH$_2$)$_o$—, —(CH$_2$—CH$_2$—O)$_o$—C$_2$H$_4$—, or —(CH$_2$—CH$_2$—O)$_o$—CH$_2$;
-$L^b$- represents —O—, —NH—CO—NH—, —NH—CO—CH$_2$—NH—, —NH—CO—;
-$L^d$- represents —(CH$_2$)$_q$—, —(CH(OH))$_q$—, —(CF$_2$)$_q$—, —(CH$_2$—CH$_2$—O)$_q$—C$_2$H$_4$—, or —(CH$_2$—CH$_2$—O)$_q$—CH$_2$—;
-$L^e$- represents —(CH$_2$)$_{p1}$—, —(CF$_2$)$_{p1}$—, —C$_2$H$_4$—(O—CH$_2$—CH$_2$)$_{p1}$—, —CH$_2$—(O—CH$_2$—CH$_2$)$_{p1}$— or —(CH$_2$)$_{p1}$—O—(CH$_2$)$_{p2}$—; and
o, q, p1 and p2 are independently of each other an integer selected from 1, 2, 3, 4, 5, and 6;
T represents a bond;
c is comprised between 2 and 18;
-$E_1$- represents a covalent bond, —NH—, —O—NH—, —O—, —S—, —CO—, —CH=CH—, —CONH—, —CO—NHNH—,

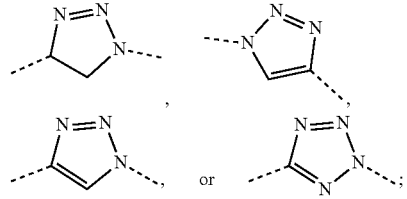

—W— is selected from:

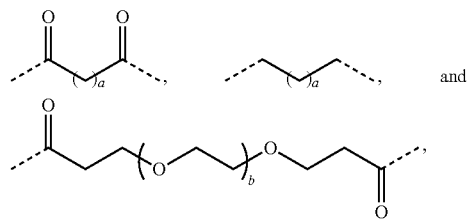

a represents an integer selected from 1, 2, 3, 4, 5, 6, 7, 8, 9 and 10,
b represents an integer selected from 1, 2, 3 and 4; and
CP is a carrier protein selected from the group consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, non-lipidated cell-surface liporotein (protein D) of non-typeable *Haemophilus influenzae*, outer membrane protein (OMP) complex of *Neisseria meningitidis*, bovine serum albumin (BSA), keyhole limpet hemocyanine (KLH), recombinant non-toxic form of *Pseudomonas aeruginosa* exotoxin A (rEPA) or cholera toxoid (CT).

16. The conjugate according to claim 15 of general formula (V)

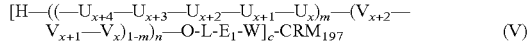
$$[H-((-U_{x+4}-U_{x+3}-U_{x+2}-U_{x+1}-U_x)_m-(V_{x+2}-V_{x+1}-V_x)_{1-m})_n-O\text{-}L\text{-}E_1\text{-}W]_c\text{-}CRM_{197} \quad (V)$$

17. The conjugate according to claim 15, wherein -$E_1$- represents a covalent bond, —NH—, —CH=CH—, —CONH—, —CO—NHNH—,

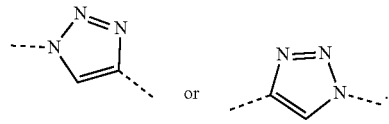

18. The conjugate according to claim 16, wherein -$E_1$- represents a covalent bond, —NH—, —CH=CH—, —CONH—, —CO—NHNH—,

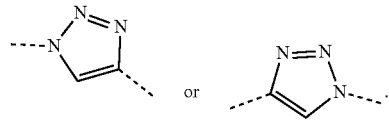

19. The conjugate according to claim 17, wherein —W— represents
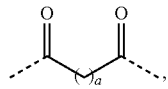
and a represents an integer selected from 2, 3, 4, 5, and 6.
20. The conjugate according to claim 18, wherein —W— represents
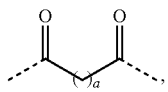
and a represents an integer selected from 2, 3, 4, 5, and 6.
21. The conjugate according to claim 15, wherein the conjugate has any one of the following formula (V-1), (V-6) or (V-9)
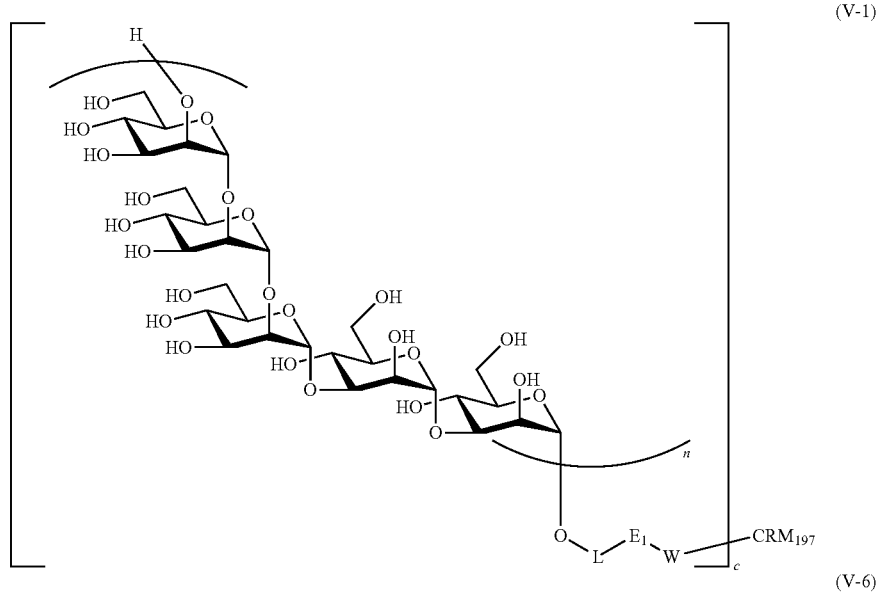
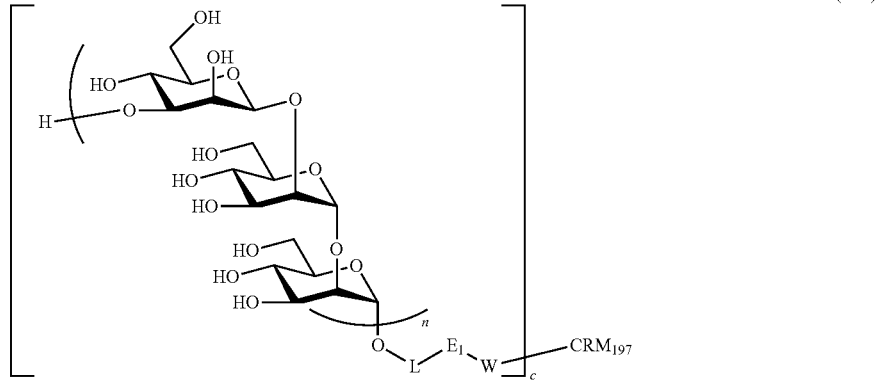
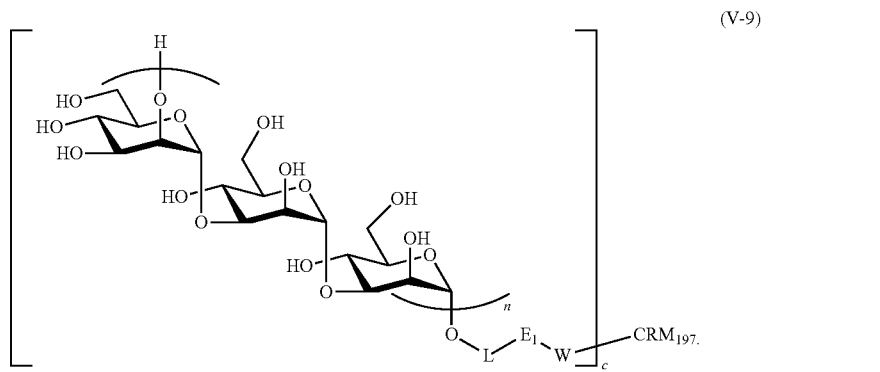

22. The conjugate according to claim 21, wherein the conjugate has the following formula (V-6)

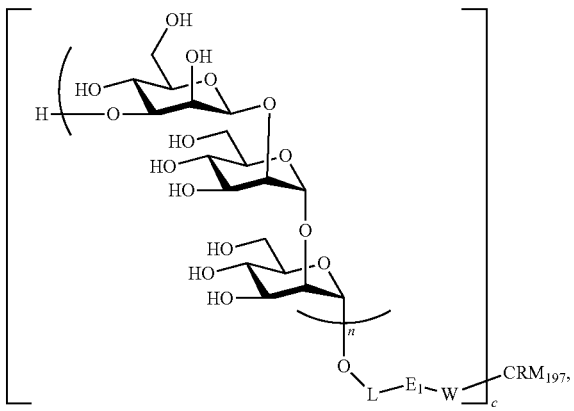

wherein -L- represents —$(CH_2)_o$— and o is an integer selected from 2, 3, 4, 5, and 6;
—W— represents

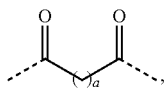

and a represents an integer selected from 2, 3, 4, 5, and 6.

23. The conjugate according to claim 22, wherein -$E_1$- is —NH—.

24. The conjugate according to claim 23, wherein c is between 5 and 15.

25. A pharmaceutical composition comprising the conjugate according to claim 15 together with at least one pharmaceutically acceptable adjuvant and/or excipient.

26. A pharmaceutical composition comprising at least one conjugate according to claim 21 together with at least one pharmaceutically acceptable adjuvant and/or excipient.

27. A method for raising a protective immune response in a human and/or animal host, said method comprising administering at least one conjugate according to claim 15 to said human or animal host.

28. A method of treatment of a disease associated with *Klebsiella pneumonia* serotype O3, O3b and/or O5 bacteria in a human and/or animal host comprising administering at least one conjugate according to claim 15 to said human or animal host.

29. The method according to claim 28, wherein the disease associated with *Klebsiella pneumonia* serotype O3, O3b and/or O5 bacteria is pneumonia, bronchitis, meningitis, urinary tract infection, wound infection, osteomyelitis, bacteremia, septicemia or ankylosing spondylitis.

30. A method for raising a protective immune response in a human and/or animal host, said method comprising administering at least one conjugate according to claim 21 to said human or animal host.

31. A method of treatment of a disease associated with *Klebsiella pneumonia* serotype O3, O3b and/or O5 bacteria in a human and/or animal host comprising administering at least one conjugate according to claim 21 to said human or animal host.

32. The method according to claim 31, wherein the disease associated with *Klebsiella pneumonia* serotype O3, O3b, and/or O5 bacteria is pneumonia, bronchitis, meningitis, urinary tract infection, wound infection, osteomyelitis, bacteremia, septicemia or ankylosing spondylitis.

* * * * *